US007550484B2

(12) United States Patent
Bridger et al.

(10) Patent No.: US 7,550,484 B2
(45) Date of Patent: Jun. 23, 2009

(54) CHEMOKINE RECEPTOR BINDING HETEROCYCLIC COMPOUNDS WITH ENHANCED EFFICACY

(75) Inventors: Gary J. Bridger, Bellingham, WA (US); Ernest J. McEachern, White Rock (CA); Renato Skerlj, Vancouver (CA); Dominique Schols, Herent (BE); Ian Baird, West Abbotsford (CA); Al Kaller, Vancouver (CA); Curtis Harwig, Vancouver (CA); Yongbao Zhu, Coquitlam (CA); Gang Chen, Langley (CA); Krystyna Skupinska, New Westminister (CA); Markus Metz, Delta (CA)

(73) Assignee: Genzyme Corporation, Cambridge, MA (US)

( * ) Notice: Subject to any disclaimer, the term of this patent is extended or adjusted under 35 U.S.C. 154(b) by 221 days.

(21) Appl. No.: 10/831,098

(22) Filed: Apr. 22, 2004

(65) Prior Publication Data
US 2005/0059702 A1    Mar. 17, 2005

Related U.S. Application Data

(60) Provisional application No. 60/505,230, filed on Sep. 22, 2003, provisional application No. 60/464,858, filed on Apr. 22, 2003.

(51) Int. Cl.
*A61K 31/445* (2006.01)
*C07D 401/04* (2006.01)

(52) U.S. Cl. .................. 514/318; 514/235.5; 544/124; 546/193; 546/194

(58) Field of Classification Search .............. 514/235.5, 514/318; 544/124; 546/193, 194
See application file for complete search history.

(56) References Cited

U.S. PATENT DOCUMENTS

| | | | |
|---|---|---|---|
| 5,021,409 A | 6/1991 | Murrer et al. ............... 514/183 |
| 5,235,056 A | 8/1993 | Cunkle et al. | |
| 5,582,823 A | 12/1996 | Souza ....................... 424/85.2 |
| 5,583,131 A | 12/1996 | Bridger et al. .............. 514/183 |
| 5,698,546 A | 12/1997 | Bridger et al. .............. 514/183 |
| 5,817,807 A | 10/1998 | Bridger et al. .............. 540/474 |
| 6,001,826 A | 12/1999 | Murrer et al. ............... 514/183 |
| 6,365,583 B1 | 4/2002 | MacFarland et al. ........ 514/183 |
| 2004/0110304 A1* | 6/2004 | Canary et al. ................. 436/81 |

FOREIGN PATENT DOCUMENTS

| WO | WO 00/56729 | 9/2000 |
|---|---|---|
| WO | WO 02/22599 | 3/2002 |
| WO | WO 02/22600 | 3/2002 |
| WO | WO 02/34745 | 5/2002 |
| WO | WO-02/076948 | 10/2002 |
| WO | WO-2006/138259 | 12/2006 |

OTHER PUBLICATIONS

Khorline et al. "Preparation of 3' . . . " CA112:56585 (1990).*
Dai et al. "Stereochemical control . . . " CA 137:256911 (2002).*
Exhibit I "CAS-abstract and structure" (2002).*
Haller "Synthesis of 2,6-disubstituted . . . " CA 64:27414 (1966).*
Cohen et al. "Cytokine function . . . " CA 135:31527 (1996).*
Hendrix et al. "Pharmacokinetics and . . . " CA 133:99145 (2000).*
Bundgaard "Design of produrgs" p. 1 (1985).*
Silverman "The organic chemistry of . . . " p. 73 (1993).*
Pike et al. "Nutrition an integrated approach" p. 538-539 (1984).*
Dai et al. "Stereochemical control . . . " Chem Commun. p. 1414-1415 (2002).*
Kirkland et al. "Quantitation of . . . " Blood, v.87 (9) p. 2983-3969 (1996).*
Haanstra et al. "Transition metal complexes . . . " CA 116:206551 (1992).*
Comba et al., Eur. J. Inorg. Chem. (2003) 1711-1718.
Database CAPLUS on STN, No. 52:25483, Potts et al., (1957), see RN 77898-87-4.
Database CAPLUS on STN, No. 134:326532, Sircar et al., PCT (2001), see RN 336813-07-1.
Diaz et al., Spectrochimica Acta Part A (2000) 56:2191-2201.
Haller, Archiv. Pharmaz. (1967) 300:119-125.
International Search Report for PCT/US04/12627, mailed on Jan. 13, 2005, 3 pages.
Potts and Smith, J. Chem. Soc. (1957) 4018-4022.
Samhammer et al., Arch. Pharm. (Weinheim) (1989) 322:551-555.
Zhao et al., J. Chem. Research (S) (1999), 312-313.
Abi-Younes, et al., Circ. Res. (2000) 86:131-138.
Alkhatib, et al., Science (1996) 272:1955-1958.
Arai, et al., Eur. J. Haematol. (2000) 64:323-332.
Auiti, et al., J. Exp. Med. (1997) 185:111-120.
Blaak, et al., Proc. Natl. Acad. Sci. (2000) 97:1269-1274.
Blanco, et al., Antimicrobial Agents and Chemother. (2000) 44:51-56.
Bleul, et al., J. Exp. Med. (1998) 187:753-762.
Bleul, et al., Nature (1996) 382:829-833.
Bradstock, et al., Leukemia (2000) 14:882-888.
Bridger, et al., J. Med. Chem. (1999) 42:3971-3981.
Broxmeyer, et al., Exp. Hematol. (1995) 23:335-340.
Broxmeyer, et al., Blood Cells, Molecules and Diseases (1998) 24:14-30.
Burger, et al., Blood (1999) 94:3658-3667.
Carroll, et al., Science (1997) 276:273-276.
Cocchi, et al., Science (1995) 270:1811-1815.
Connor, J. Virol. (1994) 68:4400-4408.
Dale et al., Am J Hematol (1998) 57:7-15.
Deng. et al., Nature (1996) 381:661-666.
Donzella, et al., Nature Medicine (1998) 4:72-77.

(Continued)

*Primary Examiner*—Celia Chang
(74) *Attorney, Agent, or Firm*—Morrison & Foerster LLP

(57) ABSTRACT

Compounds that interact with the CXCR4 receptor are described. These compounds are useful in treating, for Example, HIV infection and inflammatory conditions such as rheumatoid arthritis, as well as asthma or cancer, and are useful in methods to elevate progenitor and stem cell counts as well as methods to elevate white blood cell counts.

11 Claims, 2 Drawing Sheets

OTHER PUBLICATIONS

Dragic, et al., Nature (1996) 381:667-673.
Egberink, et al., J. Virol. (1999) 73:6346-6352.
Eitner, et al., Transplantation (1998) 66:1551-1557.
Fedyk, et al., J. Leukocyte Biol. (1999) 66:667-673.
Feng, et al., Science (1996) 272:872-877.
Glaspy, et al., Cancer Chemother. Pharmacol. (1996) 38 (suppl): S53-S57.
Glaspy, et al., Blood (1997) 90:2939-2951.
Gonzalo, et al., J. Immunol. (2000) 165:499-50.
Gupta, et al., J. Biolog. Chem. (1998) 273(7):4282-4287.
Ishii, et al., J. Immunol. (1999) 163:3612-3620.
King, et al., Blood (2001) 97:1534-1542.
Lataillade, et al., Blood (2000) 95:756-768.
Liu, et al., Cell (1996) 86:367-377.
Ma, et al., Immunity (1999) 10:463-471.
Maekawa, et al., Internal Medicine (2000) 39:90-100.
Michael, et al., Nature Med. (1997) 3:338-340.
Michael, et al., J. Virol. (1998) 72:6040-6047.
Miedema, et al., Immune. Rev. (1994) 140:35-72.
Moore, et al., J. Invest. Med. (1998) 46:113-120.
Moore, et al., Trends Cardiovasc. Med. (1998) 8:51-58.
Nagasawa, et al., Nature (1996) 382:635-638.
Nagase, J. Immunol. (2000) 164:5935-5943.
Nanki, et al., J. Immunol. (2000) 164:5010-5014.
Oberlin, et al., Nature (1996) 382:833-835.
O'Brien, et al., Lancet (1997) 349:1219.
Peled, et al., Science (1999) 283:845-848.
Peled, et al., Blood (2000) 95:3289-3296.
Ponath, Exp. Opin. Invest. Drugs (1998) 7:1-18.
Pruijt, et al., Cur. Op. in Hematol. (1999) 6:152-158.
Rana, et al., J. Virol. (1997) 71:3219-3227.
Rosenfeld, et al., Bone Marrow Transplantation (1996) 17:179-183.
Salcedo, et al., Am. J. Pathol. (1999) 154:1125-1135.
Samson, et al., Nature (1996) 382:722-725.
Schols, et al., J. Exp. Med. (1997) 186:1383-1388.
Schols, et al., Antiviral Research (1997) 35:147-156.
Schuitemaker, et al., J. Virol. (1992) 66:1354-1360.
Seghal, et al., J. Surg. Oncol. (1998) 69:99-104.
Simmons, et al. J. Virol. (1996) 70:8355-8360.
Simmons, et al., J. Virol. (1988) 72:8453-8457.
Tachibana, et al., Nature (1998) 393:591-594.
Tersmette, et al., J. Virol. (1988) 62:2026-2032.
Theodorou, et al., Lancet (1997) 349:1219-1220.
Vadhanm-Raj, et al., Ann. Intern. Med. (1997) 126:673-681.
Viardot, et al., Ann. Hematol. (1998) 77:193-197.
Wyatt, et al., Science (1998) 280:1884-1888.
Xia, et al., J. Neurovirology (1999) 5:32-41.
Yssel, et al., Clinical and Experimental Allergy (1998) 28:104-109.
Zhang, et al., AIDS Res. Hum. Retroviruses (1997) 13:1357-1366.
Zhang, et al., J. Virol. (1998) 72:9307-9312.
Zhang, et al., J. Virol. (1999) 73:3443-3448.
Database CAPLUS on STN, No. 83:58606, Ram et al. (1974).
Database CAPLUS on STN, No. 50:1538, Baliah et al. (1954).
Database CAPLUS on STN, No. 120:191489, Pillay et al. (1993).
Database CAPLUS on STN, No. 140:16629, Mamutova et al. (2003).
Database CAPLUS on STN, No. 112:7331, Mobio et al. (1989).
Database CAPLUS on STN, No. 80:36962, Azerbaev et al. (1973).
Database CAPLUS on STN, No. 94:103485, Abiyurov et al. (1980).
Database CAPLUS on STN, No. 115:192267, Rajanarayanan et al. (1991).
Database CAPLUS on STN, No. 137:125068, Kim et al. (2002).
Database CAPLUS on STN, No. 88:62271, Abdullaev et al. (1977).
Database CAPLUS on STN, No. 79:42294, Radhakrisha et al. (1973).
Database CAPLUS on STN, No. 55:38053, Merz et al. (1960).
International Search Report for PCT/US05/34950, mailed on Oct. 4, 2006, 4 pages.
Written Opinion of the International Searching Authority for PCT/US05/34950, mailed on Oct. 4, 2006, 3 pages.
Supplementary Partial European Search Report for EP 04814091.7, mailed Mar. 10, 2008, 4 pages.
Daintith, Dictionary of Chemistry, 3rd ed., Oxford: New York (1996) p. 144.
Greene and Wuts, Protective Groups in Organic Synthesis, 3rd ed., Wiley: New York (1999) p. 601.
Dorwald, Side Reactions in Organic Synthesis, Wiley: VCH, Weinheim (2005) p. IX of preface, pp. 1-15, 41.
Seiner et al., J. Med. Chem. (2000) 43:3746-3751.
Supplementary Partial European Search Report for EP 04760161.2, mailed Jun. 10, 2008, 3 pages.

* cited by examiner

CHEMOKINE RECEPTOR BINDING HETEROCYCLIC COMPOUNDS WITH ENHANCED EFFICACY

CROSS-REFERENCE TO RELATED APPLICATIONS

This application claims priority to U.S. provisional patent application Ser. No. 60/505,230, filed Sep. 22, 2003, and Ser. No. 60/464,858, filed Apr. 22, 2003, which are incorporated by reference in this application.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV), as well as enhance the population of progenitor and/or stem cells, stimulate the production of white blood cells, and/or to effect regeneration of cardiac tissue.

BACKGROUND ART

Approximately 40 human chemokines have been described, that function, at least in part, by modulating a complex and overlapping set of biological activities important for the movement of lymphoid cells and extravasation and tissue infiltration of leukocytes in response to inciting agents (See, for example: Ponath, P., *Exp. Opin. Invest. Drugs* (1998) 7:1-18). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR."

Chemokines are considered to be principal mediators in the initiation and maintenance of inflammation (see *Chemokines in Disease* published by Humana Press (1999), Edited by C. Herbert; Murdoch, et al., *Blood* (2000) 95:3032-3043). More specifically, chemokines have been found to play an important role in the regulation of endothelial cell function, including proliferation, migration and differentiation during angiogenesis and re-endothelialization after injury (Gupta, et al., *J. Biolog. Chem.* (1998) 7:4282-4287). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR5 (Wyatt, et al., *Science* (1998) 280:1884-1888). HIV-1 isolates arising subsequently in the infection bind to the CXCR4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll, et al., *Science* (1997) 276:273-276; Feng, et al., *Science* (1996) 272:872-877; Bleul, et al., *Nature* (1996) 382:829-833; Oberlin, et al., *Nature* (1996) 382:833-835; Cocchi, et al., *Science* (1995) 270:1811-1815; Dragic, et al., *Nature* (1996) 381:667-673; Deng. et al., *Nature* (1996) 381:661-666; Alkhatib, et al., *Science* (1996)272:1955-1958). During the course of infection within a patient, it appears that a majority of HIV particles shift from the M-tropic to the more aggressive pathogenic T-tropic viral phenotype (Miedema, et al., *Immune. Rev.* (1994) 140:35; Blaak, et al., *Proc. Natl. Acad. Sci.* (2000) 97:1269-1274; Simmonds, et al. *J. Virol.* (1996) 70:8355-8360; Tersmette, et al., *J. Virol.* (1988) 62:2026-2032; Connor, R. I., Ho, D. D., *J. Virol.* (1994) 68:4400-4408; Schuitemaker, et al., *J. Virol.* (1992) 66:1354-1360). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinically observations suggest that patients who possess genetic mutations in the CCR5 or CXCR4 appear resistant or less susceptible to HIV infection (Liu, et al., *Cell* (1996) 86:367-377; Samson, et al., *Nature* (1996) 382:722-725; Michael, et al., *Nature Med.* (1997) 3:338-340; Michael, et al., *J. Virol.* (1998) 72:6040-6047; Obrien, et al., *Lancet* (1997) 349:1219; Zhang, et al., *AIDS Res. Hum. Retroviruses* (1997) 13:1357-1366; Rana, et al., *J. Virol.* (1997) 71:3219-3227; Theodorou, et al., *Lancet* (1997) 349:1219-1220). Despite the number of chemokine receptors which have been reported to HIV mediate entry into cells, CCR5 and CXCR4 appear to be the only physiologically relevant coreceptors used by a wide variety of primary clinical HIV-1 strains (Zhang, et al., *J. Virol.* (1998) 72:9307-9312; Zhang, et al., *J. Virol.* (1999) 73:3443-3448; Simmonds, et al., *J. Virol.* (1988) 72:8453-8457). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou, et al., *Nature* (1998) 393:591-594; Tachibana, et al., *Nature* (1998)393:591-594; Nagasawa, etal., *Nature* (1996)382:635-638). CXCR4-deficient mice also display hematopoietic defects (Nagasawa, et al., *Nature* (1996) 382:635-638); the migration of CXCR4 expressing leukocytes and hematopoietic progenitors to SDF-1 appears to be important for maintaining B-cell lineage and localization of CD34$^+$ progenitor cells in bone marrow (Bleul, et al., *J. Exp. Med.* (1998) 187:753-762; Viardot, et al., *Ann. Hematol.* (1998) 77:195-197; Auiti, et al., *J. Exp. Med.* (1997) 185:111-120; Peled, et al., *Science* (1999) 283:845-848; Qing, et al., *Immunity* (1999) 10:463-471; Lataillade, et al., *Blood* (1999) 95:756-768; Ishii, et al., *J. Immunol.* (1999) 163:3612-3620;

Maekawa, et al., *Internal Medicine* (2000) 39:90-100; Fedyk, et al., *J. Leukocyte Biol.* (1999) 66:667-673; Peled, et al., *Blood* (2000) 95:3289-3296).

Blood cells play a crucial part in maintaining the health and viability of animals, including humans. White blood cells include neutrophils, macrophage, eosinophils and basophils/mast cells as well the B and T cells of the immune system. White blood cells are continuously replaced via the hematopoietic system, by the action of colony stimulating factors (CSF) and various cytokines, in particular on stem cells and progenitor cells in hematopoietic tissues. The nucleotide sequences encoding a number of these growth factors have been cloned and sequenced. Perhaps the most widely known of these is granulocyte colony stimulating factor (G-CSF) which has been approved for use in counteracting the negative effects of chemotherapy by stimulating the production of white blood cells and progenitor cells (peripheral blood stem cell mobilization). A discussion of the hematopoietic effects of this factor can be found, for example, in U.S. Pat. No. 5,582,823, incorporated herein by reference.

Several other factors have been reported to increase white blood cells and progenitor cells in both human and animal subjects. These agents include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin and growth related oncogene, as single agents or in combination (Dale, D., et al., *Am. J. of Hematol.* (1998) 57:7-15; Rosenfeld, C., et al., *Bone Marrow Transplantation* (1997) 17:179-183; Pruijt, J., et al., *Cur. Op. in Hematol.* (1999) 6:152-158; Broxmeyer, H., et al., *Exp. Hematol.* (1995) 23:335-340; Broxmeyer, et al., *Blood Cells, Molecules and Diseases* (1998) 24:14-30; Glaspy, J., et al., *Cancer Chemother. Pharmacol.* (1996) 38 (suppl): S53-S57; Vadhan-Raj, S., et al., *Ann. Intern. Med* (1997) 126:673-681; King, A., et al., *Blood* (2001) 97:1534-1542; Glaspy, J., et al., *Blood* (1997) 90:2939-2951).

While endogenous growth factors are pharmacologically effective, the well known disadvantages of employing proteins and peptides as pharmaceuticals underlies the need to add to the repertoire of such growth factors with agents that are small molecules. In another aspect, such small molecules are advantageous over proteins and peptides where production in large quantities are desired.

The signal provided by SDF-1 on binding to CXCR4 may also play an important role in tumor cell proliferation and regulation of angiogenesis associated with tumor growth (See "*Chemokines and Cancer*" published by Humana Press (1999), Edited by B. J. Rollins; Arenburg, et al., *J. Leukocyte Biol.* (1997) 62:554-562; Moore, et al., *J. Invest. Med.* (1998) 46:113-120; Moore, et al., *Trends Cardiovasc. Med* (1998) 8:51-58; Seghal, et al., *J. Surg. Oncol.* (1998) 69:99-104); the known angiogenic growth factors VEG-F and bFGF, up-regulate levels of CXCR4 in endothelial cells, and SDF-1 can induce neovascularization in vivo (Salcedo, et al., *Am. J. Pathol.* (1999) 154:1125-1135); leukemia cells that express CXCR4 migrate and adhere to lymph nodes and bone marrow stromal cells that express SDF-1 (Burger, et al., *Blood* (1999) 94:3658-3667; Arai, et al., *Eur. J. Haematol.* (2000) 64:323-332; Bradstock, et al., *Leukemia* (2000) 14:882-888).

The binding of SDF-1 to CXCR4 has also been implicated in the pathogenesis of atherosclerosis (Abi-Younes, et al., *Circ. Res.* (2000) 86:131-138), renal allograft rejection (Eitner, et al., *Transplantation* (1998) 66:1551-1557), asthma and allergic airway inflammation (Yssel, et al., *Clinical and Experimental Allergy* (1998) 28:104-109; *J. Immunol.* (2000) 164:5935-5943; Gonzalo, et al., *J. Immunol.* (2000) 165:499-508), Alzheimer's disease (Xia, et al., *J. Neurovirology* (1999) 5:32-41) and arthritis (Nanki, et al., *J. Immunol.* (2000) 164:5010-5014).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols, et al., *J. Exp. Med.* (1997) 186:1383-1388; Schols, et al., *Antiviral Research* (1997) 35:147-156; Bridger, et al., *J. Med. Chem.* (1999) 42:3971-3981; Bridger, et al., "Bicyclam Derivatives as HIV Inhibitors" in *Advances in Antiviral Drug Design* (1999) Volume 3:161-229, published by JAI press, Edited by E. De Clercq). Small molecules, such as bicyclams, appear to specifically bind to CXCR4 and not CCR5 (Donzella, et al., *Nature Medicine* (1998) 4:72-77). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink, et al., *J. Virol.* (1999) 73:6346-6352).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco, et al., *Antimicrobial Agents and Chemother.* (2000) 44:51-56).

U.S. Pat. Nos. 5,583,131; 5,698,546; 5,817,807; 5,021,409; and 6,001,826, which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Pat. No. 6,365,583 that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in PCT WO 00/56729, PCT WO 02/22600, PCT WO 02/22599, and PCT WO 02/34745 a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR4 has been found to be essential for the vascularization of the gastrointestinal tract (Tachibana, et al., *Nature* (1998) 393:591-594) as well as hematopoietic and cerebellar development (Zou, et al., *Nature* (1998) 393:591-594). Interference with any of these important functions served by the binding of pre-B-cell growth-stimulating factor/stromal derived factor (PBSF/SDF-1) to the CXCR4 chemokine receptor results in lethal deficiencies in vascular development, hematopoietic and cardiogenesis. Similarly, fetal cerebellar development appears to rely upon the effective functioning of CXCR4 in neuronal cell migration and patterning in the central nervous system. This G-protein-coupled chemokine receptor appears to play a critical role in ensuring the necessary patterns of migration of granule cells in the cerebellar anlage.

Herein, we disclose compounds that have unique chemical attributes and that exhibit protective effects against HIV infection of target cells by binding to chemokine receptor CXCR4 or CCR5 in a similar manner to the previously disclosed macrocyclic compounds. In addition, these compounds antagonize the binding, signaling and chemotactic effects of the natural ligand for CXCR4, the chemokine stromal cell-derived factor 1α (SDF-1) and/or the natural ligand for CCR5 (the chemokine RANTES).

Further, the compounds of the invention have the effect of increasing progenitor cells and/or stem cells. Even further, the compounds have the effect of enhancing production of white blood cells as well as exhibiting antiviral properties. Thus, these agents are useful where treatment affects the activities within the bone marrow resulting in leukopenia, thus controlling the side-effects of chemotherapy, radiotherapy, enhancing the success of bone marrow transplantation, enhancing wound healing and burn treatment, as well as combating bacterial infections in leukemia. Further, the compounds of the invention effect regeneration of cardiac tissue.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that bind chemokine receptors and interfere with the binding of the natural ligand thereto. The compounds of the present invention are useful as agents demonstrating protective effects on target cells from HIV infection, and which are useful to treat rheumatoid arthritis. Embodiments of the present invention are compounds that act as antagonists or agonists of chemokine receptors, which are useful as agents capable of reconstituting the immune system by increasing the level of $CD4^+$ cells; as antagonist agents of apoptosis in immune cells, such as $CD8^+$ cells, and neuronal cells; as antagonist agents of migration of human bone marrow B lineage cells to stromal-derived factor 1, as well as other biological activities related to the ability of these compounds to inhibit the binding of chemokines to their receptors.

In addition, the invention is directed to methods of treating animal subjects, in particular, veterinary and human subjects, to enhance the number of progenitor cells and/or stem cells. The progenitor and/or stem cells may be harvested and used in cell transplantation. In one embodiment, bone marrow progenitor and/or stem cells are mobilized for myocardial repair. Further, the invention is directed to methods of treating animal subjects, in particular, veterinary and human patients, who are defective in white blood cell (WBC) count, or who would benefit from elevation of WBC levels using the compounds disclosed herein. Moreover, the invention is directed to methods of effecting regeneration of cardiac tissue in a subject in need of such regeneration using the disclosed compounds.

In one aspect, the invention is directed to compounds of the formula

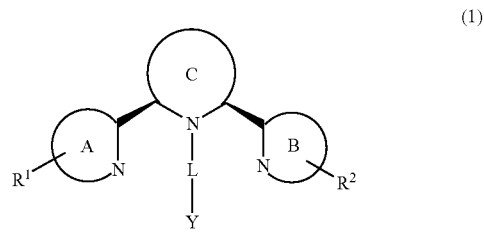

(1)

wherein each of rings A and B is independently an optionally substituted 5-6 membered monocyclic heteroaryl;

ring C is a saturated or partially saturated ring of 5-8 members which is optionally substituted;

Y is H, a $C_{1-6}$ alkyl containing one or more heteroatoms, or a cyclic moiety, each of which is optionally substituted;

L is $(CR^3{}_2)_l$ or $NR(CR^3{}_2)_l$ wherein an alkyl bond may be replaced with an alkenyl or alkynyl bond;

where each $R^3$ is independently H or a non-interfering substituent;

l is 1-6;

$R^1$ and $R^2$ are independently H or a non-interfering substituent; wherein at least one of $R^1$ and $R^2$ is not H when ring C is piperidinyl or 1,2,3,6-tetrahydropyridinyl and rings A and B are pyridinyl; and $R^1$ and $R^2$ are not both naphthalenyl when ring C is piperidinyl and rings A and B are pyridinyl;

provided that if L-Y is $CH_3$, ring C is not 4-oxo-piperidine-3,5-dicarboxylic acid; and if L-Y is benzyl, ring C is not 4-hydroxy-1,2,5,6-tetrahydro-pyridine-3-carboxylic acid ester.

In the above Formula 1, the substituents on optionally substituted rings may be inorganic moieties, alkyl $(C_{1-10})$, alkenyl $(C_{2-10})$, alkynyl $(C_{2-10})$, aryl (5-12 members), arylalkyl arylalkenyl, or arylalkynyl, each of which may optionally contain one or more heteroatoms selected from O, S, and N and each of which may further be substituted.

The substituents on rings A, B and C are non-interfering substituents. In general, a "noninterfering substituent" is a substituent whose presence does not destroy the ability of the compound of formula I to behave as a chemokine receptor antagonist. Specifically, the presence of the substituent does not destroy the effectiveness of the compound. Because the compounds of the present invention have been shown to inhibit HIV replication, and specifically to interact with the CXCR4 receptor, the compounds of the invention are shown to be effective in treating conditions which require modulation of CXCR4 and CCR5 mediated activity.

Suitable noninterfering substituents include alkyl $(C_{1-10})$, alkenyl $(C_{2-10})$, alkynyl $(C_{2-10})$, aryl ("C"$_{5-12}$), arylalkyl, arylalkenyl, or arylalkynyl, each of which may optionally contain one or more heteroatoms selected from O, S, and N and each of which may further be substituted; or optionally substituted forms of acyl, arylacyl, alkyl- alkenyl-, alkynyl- or arylsulfonyl and forms thereof which contain heteroatoms in the alkyl, alkenyl, alkynyl or aryl moieties. Other noninterfering substituents include OR, SR, NR$_2$, COOR, CONR$_2$, where R is H or alkyl, alkenyl, alkynyl or aryl as defined above. Where the substituted atom is C, the substituents may include, in addition to the substituents listed above, halo, OOCR, NROCR, where an R is H or a substituent set forth above, or may be =O, or may be NO$_2$, SO$_2$R, SOR, CN, CF$_3$, OCF$_3$ or =NOR.

In the above Formula 1, R$^1$ and R$^2$ may be H or a non-interfering substituent as defined above. Furthermore, each optionally substituted moiety in the above Formula I may be substituted with inorganic moieties, alkyl (C$_{1-10}$), alkenyl (C$_{2-10}$), alkynyl (C$_{2-10}$), aryl (5-12 members), arylalkyl, arylalkenyl, or arylalkynyl, each of which may optionally contain one or more heteroatoms selected from O, S, and N and each of which may further be substituted.

In the above Formula 1, R$^3$ may be H or a non-interfering substituent as defined above. In particular examples, R$^3$ is H.

In the above Formula 1, each of rings A and B may independently be pyridine, pyrimidine, pyrazine, pyridazine, 1,2,3-triazine, 1,2,4-triazine, 1,3,5-triazine, 1,2,4,5-tetrazine, pyrrole, imidazole, pyrazole, 1,2,3-triazole, 1,2,4-triazole, tetrazole, thiazole, oxazole, isothiazole, isoxazole, 1,2,3-thiadiazole, 1,3,4-thiadiazole, 1,2,3-oxadiazole, 1,3,4-oxadiazole, quinoline, isoquinoline, quinoxaline, quinazoline, pthalazine, cinnoline, 1,2,3-benzotriazine, 1,2,4-benzotriazine, indole, benzimidazole, 1H-indazole, benzoxazole, benzthiazole, benz[d]isoxazole, benz[d]isothiazole, or purine. In particular examples, each of rings A and B is independently pyridine, pyrimidine, imidazole or benzimidazole. In some examples, rings A and B may be identical.

In the above Formula 1, ring C may be pyrrolidine, piperidine, hexahydro-1 H-azepine, piperazine, morpholine, thiomorpholine, azepane, azocane, 2,3,4,7-tetrahydro-1 H-azepine, 2,3,6,7-tetrahydro-1H-azepine, 3-pyrroline, 1,2,3,6-tetrahydropyridine, isoindoline, 1,2,3,4-tetrahydroisoquinoline, 2,3,4,5-tetrahydro-1H-benzo[d]azepine, 2,3,4,5-tetrahydro-1H-benzo[c]azepine, cyclobutane, cyclopentane, cyclohexane, cycloheptane, cyclooctane, cyclopentene, cyclohexene, cycloheptene, cyclooctene, tetrahydropyran, tetrahydrothiopyran, oxepane, thiepane, oxocane, or thiocane. In some examples, ring C is pyrrolidine, piperidine, piperazine or hexahydro-1H-azapine.

In the above Formula 1, Y may be an aromatic, heteroaromatic, or a heterocyclic moiety. In particular examples, Y is phenyl, imidazole, pyridine, thiophene, pyrrolidine, pyrazole, piperidine, azetidine, benzimidazole, benzo[d]isoxazole, or thiazole. In other examples, Y is optionally substituted with halo; cyano; nitro; hydroxy optionally substituted with alkyl or halogenated alkyl; substituted carbonyl; a cyclic moiety; or an alkyl, alkenyl, or a heteroalkyl moiety optionally containing one or more N, O, S, each of which is optionally in the form of oxides.

In the above Formula 1, Y may optionally be substituted with a cyclic moiety optionally containing one or more N, O or S. The cyclic moiety may be an optionally substituted aromatic or heteroaromatic moiety of 5-12 ring members. Examples of cyclic moieties include but are not limited to pyridine, phenyl, piperidine or 2H-tetrazole.

In the above Formula 1, Y may be phenyl or imidazole. In other examples, Y may be selected from the group consisting of:

—(CR$_2$)$_m$NR$_2$,
—(CR$_2$)$_m$NR$_2$(CR$_3$),
—(CR$_2$)$_m$NR(CR$_2$)$_m$NR$_2$,
—(CR$_2$)$_m$NR(CR$_2$)$_m$NR(CR$_2$)$_m$NR$_2$,
—(CR$_2$)$_m$OR,
—(CR$_2$)$_m$CO(CR$_2$)$_m$OR,
—(CR$_2$)$_m$CO(CR$_2$)$_m$NR$_2$,
—(CR$_2$)$_m$CO(CR$_2$)$_m$NR(CR$_2$)$_m$NR$_2$,
—(CR$_2$)$_m$NRCO(CR$_2$)$_m$NR$_2$,
—(CR$_2$)$_m$NR(CR$_2$)$_m$CO$_2$R,
—(CR$_2$)$_m$NR(CR$_2$)$_m$COR,
—(CR$_2$)$_m$NR(CR$_2$)$_m$SO$_2$R,
—(CR$_2$)$_m$NRCO(CR$_2$)$_m$NR(CR$_2$)$_m$NR$_2$,
—(CR$_2$)$_m$NRCO(CR$_2$)$_m$NR(CR$_2$)$_m$NR(CR$_2$)$_m$NR(CR$_2$)$_m$NR$_2$,
—(CR$_2$)$_m$NR(CR$_2$)$_m$OR,
—(CR$_2$)$_m$CR=NOH,
—(CR$_2$)$_m$CONR(CR$_2$)$_m$OR,
—(CR$_2$)$_m$N[(CR$_2$)$_m$CO$_2$R]$_2$,
—(CR$_2$)$_m$ONRCONR$_2$,
—(CR$_2$)$_m$-Z
—(CR$_2$)$_m$NR—(CO)$_m$Z,
—(CR$_2$)$_m$NR—(CR$_2$)$_m$Z, and
—(CR$_2$)$_m$—CR=N=Z;

each R is independently H or an non-interfering substituent, each m is independently 0-4; and Z is an optionally substituted aromatic or heteroaromatic moiety containing 5-12 ring members.

In one example, Y is (CH$_2$)$_l$NR$_2$ where R is H or a non-interfering substituent and l is 1-10.

In the above Formula 1, each of rings A and B may contain a single substituent at the position adjacent to the bond linking the rings to ring C. In one example, the substituents are identical on rings A and B.

In the above Formula 1, R$^1$ and R$^2$ may independently be unsubstituted alkyl. In one example, R$^1$ and R$^2$ are at positions adjacent the bonds to ring C.

In the above Formula 1, ring C may be saturated or contains one double bond.

Various embodiments of the present invention are set forth in the Examples. The present invention encompasses other compounds having Formula 1, with substituents independently selected from compounds in the Examples. Thus, the present invention is not limited to the specific combination of substituents described in various embodiments below.

In other aspects, the invention is directed to pharmaceutical compositions containing at least one compound of Formula I, and to methods of ameliorating conditions that are modulated by the CXCR4 receptor or the CCR5 receptor. Such conditions include, HIV infection, diseases associated with inflammation, diseases that are associated with immunosuppression and certain tumors. Such conditions also include those benefited by enhancing stem cell and progenitor cell populations and elevating white blood cell counts.

MODES OF CARRYING OUT THE INVENTION

Figure 1:
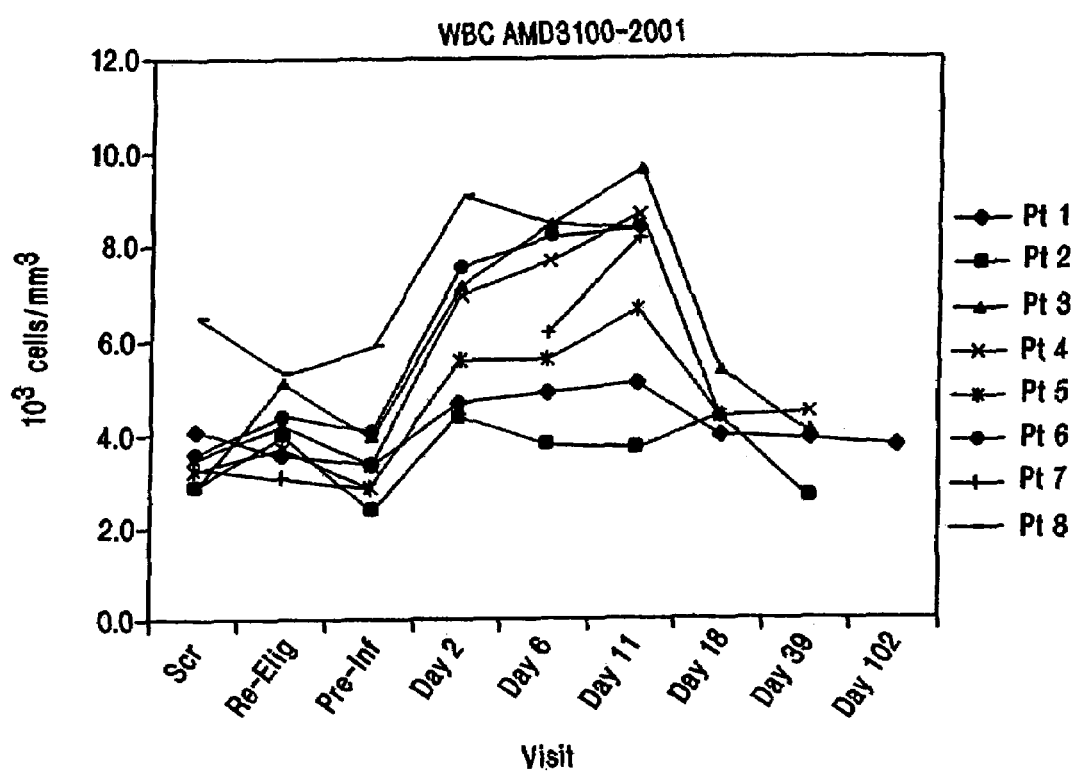
FIG. 1 is a graph shows the response of individual human patients to intravenous administration of AMD3100 (1,1'-[1,4-phenylenebis(methylene)]-bis-1,4,8,11-tetra-azacyclotetradecane).

The invention provides compounds described above of Formula I which are chemokines and thus modulators of chemokine receptors.

In more detail, the compounds bind chemokine receptors and interfere with the binding of the natural ligand thereto, and demonstrate protective effects on target cells from HIV infection. The compounds are also useful as antagonists or agonists of chemokine receptors, and are thus capable of reconstituting the immune system by increasing the level of CD4+ cells; as antagonist agents of apoptosis in immune cells, such as CD8+ cells, and neuronal cells; as antagonist agents of migration of human bone marrow B lineage cells to stromal-derived factor 1, as well as other biological activities related to the ability of these compounds to inhibit the binding of chemokines to their receptors.

The compounds also inhibit the binding and signaling induced by the natural ligand, the chemokine SDF-1. While not wishing to be bound by any theory, the compounds of formula I which inhibit the binding of SDF-1 to CXCR4 effect an increase in stem and/or progenitor cells by virtue of such inhibition. Enhancing the stem and/or progenitor cells in blood is helpful in treatments to alleviate the effects of protocols that adversely affect the bone marrow, such as those that result in leukopenia. These are known side-effects of chemotherapy and radiotherapy. The compounds of formula I also enhance the success of bone marrow transplantation, enhance wound healing and burn treatment, and aid in restoration of damaged organ tissue. They also combat bacterial infections that are prevalent in leukemia. The compounds of formula I are used to mobilize and harvest CD34+ cells via apheresis with and without combinations with other mobilizing factors. The harvested cells are used in treatments requiring stem cell transplantations.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, "stem" cells are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

Chemokine antagonists that interfere in the binding of a chemokine to its receptor are also useful to reconstitute the immune system by increasing the level of CD4+ cells (Biard-Piechaczyk, et al., *Immunol. Lett.* (1999) 70:1-3); as antagonist agents of apoptosis in immune cells, such as CD8+ cells (Herbin, et al., *Nature* (1998) 395:189-193), and as antagonist agents of apoptosis in neuronal cells (Ohagen, et al., *J. of Virol.* (1999) 73:897-906; and Hesselgesser, et al., *Curr. Biol.* (1998) 8:595-598). Chemokine receptor antagonist agents also inhibit the migration of human bone marrow B lineage cells to stromal-derived factor 1 (See, for example: E. Fedyk, et al., *J. of Leukocyte Biol.* (1999) 66:667-783).

The invention includes pharmaceutical compositions comprising a therapeutically effective amount of a compound of Formula I along with at least one excipient, and methods of treating diseases of the human body or the bodies of other mammals with such compositions. The invention provides a method for blocking or interfering with the binding by a chemokine receptor with its natural ligand, comprising contacting of said chemokine receptor with an effective amount of the compound according to Formula I. Also included is a method of protecting target cells possessing chemokine receptors, the binding to which by a pathogenic agent results in disease or pathology, comprising administering to a mammalian subject a pharmaceutical composition comprising a therapeutically effective amount of the compound according to Formula I. The invention includes the use of a compound of Formula I in the manufacture of a medicament for the treatment of a disease in which blocking or interfering with binding of a chemokine receptor with its natural ligand is advantageous. The compound is formulated into a composition in amount corresponding to a therapeutically effective amount of a compound of Formula I.

The Invention Compounds

The compounds may be supplied as "pro-drugs", that is, protected forms, which release the compound after administration to a subject; For example, the compound may carry a protective group which is split off by hydrolysis in body fluids, e.g., in the bloodstream, thus releasing active compound or is oxidized or reduced in body fluids to release the compound. A discussion of pro-drugs may be found in "*Smith and Williams' Introduction to the Principles of Drug Design,*" H. J. Smith, Wright, Second Edition, London 1988.

The compounds may also be supplied as salts with organic or inorganic acids or bases that are nontoxic. Non-toxic in the present sense has to be considered with reference to the prognosis for the infected patient without treatment. Examples of inorganic bases with alkali met al hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases include trimethylamine, triethylamine, pyridine, picoline, ethanolamine, diethanolamine, triethanolamine, dicyclohexylamine, N,N'-dibenzylethylenediamine, etc. Examples of inorganic acids include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, omithine, etc., and salts with acidic amino acids such as aspartic acid, glutamic acid, etc.

The compounds of the invention may contain additional chiral centers besides those for which chirality is shown. The invention includes mixtures of stereoisomers, individual stereoisomers, and enantiomeric mixtures, and mixtures of multiple stereoisomers with respect to these additional centers.

The invention compounds are described generally by Formula I which is reproduced below for purposes of the present discussion.

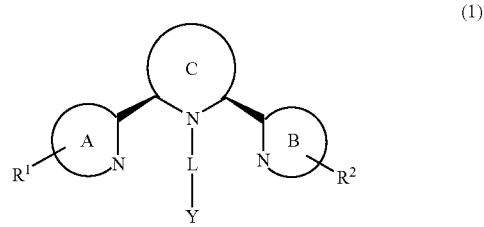

(1)

wherein each of rings A and B is independently an optionally substituted 5-6 membered monocyclic heteroaryl;

ring C is a saturated or partially saturated ring of 5-8 members which is optionally substituted;

Y is H, a $C_{1-6}$ alkyl containing one or more heteroatoms, or a cyclic moiety, each of which is optionally substituted;

L is $(CR^3_2)_l$ or $NR(CR^3_2)_l$ wherein an alkyl bond may be replaced with an alkenyl or alkynyl bond;

where each $R^3$ is independently H or a non-interfering substituent;

l is 1-6;

$R^1$ and $R^2$ are independently H or a non-interfering substituent; wherein at least one of $R^1$ and $R^2$ is not H when C is piperidinyl or 1,2,3,6-tetrahydropyridinyl and rings A and B are pyridinyl; and $R^1$ and $R^2$ are not both naphthalenyl when C is piperidinyl and rings A and B are pyridinyl;

provided that if L-Y is $CH_3$, C is not 4-oxo-piperidine-3,5-dicarboxylic acid; and if L-Y is benzyl, C is not 4-hydroxy-1,2,5,6-tetrahydropyridine-3-carboxylic acid ester.

Illustrative embodiments of rings A and B include pyridine, pyrimidine, pyrazine, pyridazine, 1,2,3-triazine, 1,2,4-triazine, 1,3,5-triazine, 1,2,4,5-tetrazine, pyrrole, imidazole, pyrazole, 1,2,3-triazole, 1,2,4-triazole, tetrazole, thiazole, oxazole, isothiazole, isoxazole, 1,2,3-thiadiazole, 1,3,4-thiadiazole, 1,2,3-oxadiazole, 1,3,4-oxadiazole, quinoline, isoquinoline, quinoxaline, quinazoline, pthalazine, cinnoline, 1,2,3-benzotriazine, 1,2,4-benzotriazine, indole, benzimidazole, 1H-indazole, benzoxazole, benzthiazole, benz[d]isoxazole, benz[d]isothiazole, and orpurine.

Embodiments wherein rings A and B are pyridine, pyrimidine, imidazole, and/or benzimidazole are preferred. Also preferred are compounds of Formula I wherein A and B are identical.

Illustrative embodiments of C include pyrrolidine, piperidine, hexahydro-1H-azepine, piperazine, morpholine, thiomorpholine, azepane, azocane, 2,3,4,7-tetrahydro-1H-azepine, 2,3,6,7-tetrahydro-1H-azepine, 3-pyrroline, 1,2,3,6-tetrahydropyridine, isoindoline, 1,2,3,4-tetrahydroisoquinoline, 2,3,4,5-tetrahydro-1H-benzo[d]azepine, 2,3,4,5-tetrahydro-1H-benzo[c]azepine, cyclobutane, cyclopentane, cyclohexane, cycloheptane, cyclooctane, cyclopentene, cyclohexene, cycloheptene, cyclooctene, tetrahydropyran, tetrahydrothiopyran, oxepane, thiepane, oxocane, and thiocane.

Preferred embodiments of ring C are pyrrolidine, piperidine, piperazine and hexahydro-1H-azepine.

In one example, Y is selected from the group consisting of:

—$(CR_2)_m NR_2$,
—$(CR_2)_m NR_2(CR_3)$,
—$(CR_2)_m NR(CR_2)_m NR_2$,
—$(CR_2)_m NR(CR_2)_m NR(CR_2)_m NR_2$,
—$(CR_2)_m OR$,
—$(CR_2)_m CO(CR_2)_m OR$,
—$(CR_2)_m CO(CR_2)_m NR_2$,
—$(CR_2)_m CO(CR_2)_m NR(CR_2)_m NR_2$,
—$(CR_2)_m NRCO(CR_2)_m NR_2$,
—$(CR_2)_m NR(CR_2)_m CO_2 R$,
—$(CR_2)_m NR(CR_2)_m COR$,
—$(CR_2)_m NR(CR_2)_m SO_2 R$,
—$(CR_2)_m NRCO(CR_2)_m NR(CR_2)_m NR_2$,
—$(CR_2)_m NRCO(CR_2)_m NR(CR_2)_m NR(CR_2)_m NR(CR_2)_m NR_2$,
—$(CR_2)_m NR(CR_2)_m OR$,
—$(CR_2)_m CR=NOH$,
—$(CR_2)_m CONR(CR_2)_m OR$,
—$(CR_2)_m N[(CR_2)_m CO_2 R]_2$,
—$(CR_2)_m ONRCONR_2$,
—$(CR_2)_m$-Z
—$(CR_2)_m NR—(CO)_m Z$,
—$(CR_2)_m NR—(CR_2)_m Z$, and
—$(CR_2)_m —CR=N=Z$;

each R is independently H or an non-interfering substituent, each m is independently 0-4; and Z is an optionally substituted aromatic or heteroaromatic moiety containing 5-12 ring members.

In addition, an embodiment for Y includes, for example, an inorganic moiety. As used herein, "inorganic moiety" refers to a moiety that does not contain carbon. Examples include, but are not limited to, halo, hydroxyl, SH, $NO_2$ or $NH_2$.

Preferred embodiments of Z include partially saturated nitrogen containing rings.

Particularly preferred are compounds of the invention which contain substituents on rings A and B at the position adjacent to the bond linking these rings to ring C. Especially preferred are embodiments wherein these substituents are identical on rings A and B.

Particularly preferred embodiments of Y include $(CH_2)_l$—$NR_2$, where R is as defined above and l is 1-10.

Also preferred are embodiments wherein the substituents on any of rings A, B or C or rings contained in Y, including ring Z are fused to additional ring systems.

Examples of optionally substituted alkyl groups include methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc.; $C_{1-6}$ alkyl and alkenyl are preferred.

Examples of halogen include fluorine, chlorine, bromine, iodine, etc., with fluorine and chlorine preferred.

Examples of optionally substituted hydroxyl and thiol groups include optionally substituted alkyloxy or alkylthio (e.g., $C_{1-10}$ alkyl) such as methyl, ethyl, propyl, isopropyl, butyl, isobutyl, sec-butyl, tert-butyl, pentyl, cyclopropyl, cyclobutyl, cyclopentyl, cyclohexyl, cycloheptyl, etc.); an optionally substituted arylalkyloxy or arylalkylthio (e.g., phenyl-$C_{1-4}$ alkyl, e.g., benzyl, phenethyl, etc.). Where there are two adjacent hydroxyl or thiol substituents, the heteroatoms may be connected via an alkylene group such as $O(CH_2)_n O$ and $S(CH_2)_n S$ (where n=1-5). Examples include methylenedioxy, ethylenedioxy, etc. Oxides of thio-ether groups such as sulfoxides and sulfones are also envisioned.

Examples of optionally substituted hydroxyl groups also include optionally substituted $C_{2-4}$alkanoyl (e.g., acetyl, propionyl, butyryl, isobutyryl, etc.), $C_{1-4}$ alkylsulfonyl (e.g., methanesulfonyl, ethanesulfonyl, etc.) and an optionally substituted aromatic and heterocyclic carbonyl group including benzoyl, pyridinecarbonyl, etc.

Substituents on optionally substituted amino groups may bind to each other to form a cyclic amino group (e.g., 5- to 6-membered cyclic amino, etc., such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, trifluoromethoxy, trifluoroethoxy, etc.), $C_{2-4}$ alkanoyl (e.g., acetyl, propionyl, etc.), $C_{1-4}$ alkylsulfonyl (e.g., methanesulfonyl, ethanesulfonyl, etc.) the number of preferred substituents are 1 to 3.

An amino group may also be substituted once or twice (to form a secondary or tertiary amine) with a group such as an optionally substituted alkyl group including $C_{1-10}$ alkyl (e.g., methyl, ethyl propyl, etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g., phenyl$C_{1-4}$ alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl, e.g., acetyl, propionyl, butyryl, isobutyryl etc., or a $C_{1-4}$ alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl, etc. The heterocycles are as defined above.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as defined above.

Utility and Administration

The invention is directed to compounds of Formula I that modulate chemokine receptor activity. Chemokine receptors include but are not limited to CCR1, CCR2, CCR3, CCR4, CCR5, CXCR3 and CXCR4.

In one embodiment, the invention provides compounds of Formula I that demonstrate protective effects on target cells from HIV infection by binding specifically to the chemokine receptor thus affecting the binding of a natural ligand to the CCR5 and/or CXCR4 of a target cell.

In another embodiment, the compounds of the present invention are useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors and tumors of prostate, lung or haematopoetic tissues. Thus, a compound that modulates the activity of such chemokine receptors is useful for the treatment or prevention of such diseases.

The term "modulators" as used herein is intended to encompass antagonist, agonist, partial antagonist, and or partial agonist, i.e., inhibitors, and activators. In one embodiment of the present invention, compounds of Formula I demonstrate a protective effect against HIV infection by inhibiting the binding of HIV to a chemokine receptor such as CCR5 and/or CXCR4, of a target cell. Such modulation is obtained by a method which comprises contacting a target cell with an amount of the compound which is effective to inhibit the binding of the virus to the chemokine receptor.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

The compounds of the invention also have a use for preparation of a medicament for a therapy such as for the treatment of HIV, for treating a condition mediated by a chemokine receptor, for the treatment of an inflammatory condition, such as rheumatoid arthritis, or for the treatment of a tumor condition.

In addition compounds that activate or promote chemokine receptor function are used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); *Trichuriasis, Enterobiasis, Ascariasis*, Hookworm, *Strongyloidiasis, Trichinosis*, filariasis; trematodes; visceral worms, visceral larva migtrans (e.g., *Toxocara*), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

Typical conditions which may be ameliorated or otherwise benefited by the method of the invention include hematopoietic disorders, such as aplastic anemia, leukemias, drug-induced anemias, and hematopoietic deficits from chemotherapy or radiation therapy. The method of the invention is also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the invention targets a broad spectrum of conditions characterized by a deficiency in white blood cell count, or which would benefit from elevation of said WBC count.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith* and *Williams Introduction to the Principles of Drug Design*, Smith, H. J.; Wright, 2$^{nd}$ ed., London (1988).

The compounds of the invention may be administered as sole active ingredients, as mixtures of various compounds of formula I, and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The compounds of the invention may be formulated for administration to animal subject using commonly understood formulation techniques well known in the art. Formulations which are suitable for particular modes of administration and for compounds of the type represented by those of formula I may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula I vary according to these considerations, but in general, the compounds are administered in the range of about 0.1 μg/kg-5 mg/kg of body weight; preferably the range is about 1 μg/kg-300 μg/kg of body weight; more preferably about 10 μg/kg-100 μg/kg of body weight. For a typical 70-kg human subject, thus, the dosage range is from about 0.7 μg-350 mg; preferably about 700 μg-21 mg; most preferably about 700 μg-7 mg. Dosages may be higher when the compounds are administered orally or transdermally as compared to, for example, i.v. administration.

The compounds may be administered as a single bolus dose, a dose over time, as in i.v. or transdermnal administration, or in multiple dosages.

In addition to direct administration to the subject, the compounds of formula I can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of formula I alone or in combination with other agents, such as macrophage inflammatory protein is a matter of routine optimization.

Compounds of the present invention further may be used in combination with any other active agents or pharmaceutical compositions where such combined therapy is useful to modulate chemokine receptor activity and thereby prevent and treat inflammatory and immunoregulatory diseases.

The compounds may further be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D, and SCH350634; TAK779; UK 427, 857 and TAK 449;

(6) Integrase inhibitors such as L-870,810; GW-810781 (S-1360); and (7) Budding inhibitors such as PA-344; and PA-457.

Combinations of compounds of the present invention with HIV agents is not limited to (1), (2), and/or (3), but includes combination with any agent useful for the treatment of HIV. Combinations the compounds of the invention and other HIV agents may be administered separately or in conjunction. The administration of one agent may be prior to, concurrent to, or subsequent to the administration of other agent(s).

Like the compounds of the present invention, AMD3100 is an antagonist with the CXCR4 chemokine receptor (Gerlach, et al., *J. Biol. Chem.* (2001) 276:14153-14160). These compounds interfere with the binding of bone marrow stromal cell derived SDF-1 with CXCR4 on stem cells which leads to the release of hematopoietic stem cells from bone marrow into the circulation (Broxmeyer, et al., *Blood* (2001) 98:811a (Abstract)). In a Phase 1 study at the University of Washington, Seattle, a single dose of 80 μg/kg of AMD3100 resulted in a WBC count of 17,000/μl and a peak 6-fold increase in circulating CD34$^+$ progenitor/stem cells at the 6 hour time point (Liles, et al., *Blood* (2001) 98:737a (Abstract)). In another recent study mice were injected with rhG-CSF and recombinant rat Stem Cell Factor (rrSCF) in order to mobilize large numbers of bone marrow stem cells into the circulation and then we induced a heart attack. The combination of rrSCF and rhG-CSF provides a peak number of circulating stem cells after 5 daily injections. At 27 days post surgery there was a 68% improvement in survival in the treated group versus the controls. At this time the dead tissue was replaced with regenerating myocardium and all functional parameters tested were improved compared with controls (Orlic, et al., *PNAS* (2001) 98:10344-10349).

Thus, the compounds of the invention are useful to stimulate the production and proliferation of stem cells and progenitor cells.

The compounds of the invention may be prepared in the form of prodrugs, i.e., protected forms which release the compounds of the invention after administration to the subject. Typically, the protecting groups are hydrolyzed to body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, $2^{nd}$ ed., London (1988).

The compounds of the invention, as they are polyamines, may be administered prepared in the forms of their acid addition salts or met al complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be administered as sole active ingredients, as mixtures of various compounds of formula (1), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like.

The compounds of the invention may be formulated for administration to animal subject using commonly understood formulation techniques well known in the art. Formulations which are suitable for particular modes of administration and for compounds of the type represented by those of formula (1) may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula (1) vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds of formula (1) can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of formula (1) alone or in combination with other agents, such as macrophage inflammatory protein is a matter of routine optimization.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by stimulation of hematopoiesis, include hematopoietic disorders, such as aplastic anemia, leukemias, drug-induced anemias, and hematopoietic deficits from chemotherapy or radiation therapy. The compounds of the invention are also useful in enhancing the success of transplantation during and following immunosuppressive treatments as well as in effecting more efficient wound healing and treatment of bacterial inflammation, and for treating subjects who are immuno-compromised or whose immune system is otherwise impaired. Typical conditions which are ameliorated or otherwise benefited by hematopoiesis stimulation include those subjects who are infected with a retrovirus and more specifically who are infected with human immunodeficiency virus (HIV). The compounds of the invention thus target a broad spectrum of conditions for which elevation of progenitor cells and/or stem cells in a subject would be beneficial or, where harvesting of progenitor cells and/or stem cell for subsequent stem cell transplantation or transfusion would be beneficial.

The invention compounds are also administered to regenerate myocardium by mobilizing bone marrow stem cells.

A broad range of routes of administration are contemplated. Thus, the compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention are used to treat animals, including mice, rats, horses, cattle, sheep, dogs, cats, and monkeys, and avians such as chickens and the like. The compounds of the invention are also effective for use in humans. In general, any subject who would benefit from an elevation of progenitor cells and/or stem cells, or whose progenitor cells and/or stem cells are desirable for stem cell transplantation are appropriate for administration of the invention method and/or any subject who has a WBC deficiency or, more generally, who would profit from the elevation of white blood cell count, or who would benefit from the regeneration of cardiac tissue is appropriate for administration of the invention method.

The invention also relates to a pharmaceutical composition comprising a pharmaceutically acceptable carrier or diluent and an effective amount of compound of Formula I. The compounds may be administered alone or as an admixture with a pharmaceutically acceptable carrier (e.g., solid formulations such as tablets, capsules, granules, powders, etc.; liquid formulations such as syrups, injections, etc.) may be orally or non-orally administered. Examples of non-oral formulations include injections, drops, suppositories, pessaryies.

In the treatment or prevention of conditions which require chemokine receptor modulation an appropriate dosage level will generally be about 0.01 to 500 mg per kg subject body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

Experimental

The intermediate N-(4-hydroxymethyl-benzyl)-2-nitro-N-pyridin-2 -ylmethyl-benzenesulfonamide was prepared according to the procedures described in Bridger, et al., U.S. Pat. No. 6,506,770. The intermediate 2-bromomethyl-5-cyano-benzoic acid methyl ester was prepared according to the procedures described in WO 02/34745, both incorporated herein by reference.

General Procedures

General Procedure A: N-Alkylation of hexahydro-[2,2';6'2"]terpyridines

To a solution of the substituted-hexahydro-[2,2';6'2"]terpyridine] (1 equiv) in DMF or $CH_3CN$ (concentration ~0.1-0.2 M) was added the alkyl halide (1-1.4 equivalents), KI (0.05-0.16 equiv), and N,N-diisopropylethylamine (DIPEA) (1.5-2 equiv) and the mixture stirred at 60° C. overnight. The reaction mixture was cooled, diluted with $CH_2Cl_2$ (10 mL/mmol amine) and poured into either saturated aqueous $NaHCO_3$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was purified by chromatography to afford the desired N-alkylated product.

General Procedure B: Salt Formation Using Saturated HBr(g) in HOAc

To a solution of the free base in glacial HOAc (2 mL) was added, a saturated solution of HBr(g) in HOAc (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification, the solid was dissolved in MeOH and re-precipitated with a large volume of ether. Washing the solid with ether by decantation, followed by drying of the solid in vacuo (0.1 Torr) gave the desired compound.

General Procedure C: Direct Reductive Amination with $NaBH(OAc)_3$ or $NaBH_4$

To a stirred solution of the amine (1 equivalent) in $CH_2Cl_2$ (concentration ~0.2 M), at room temperature, was added the carbonyl compound (~1-2 equivalents), glacial HOAc (0-2 equivalents) and $NaBH(OAc)_3$ (~1.5-3 equivalents) and the resultant solution stirred at room temperature. The reaction mixture was poured into either saturated aqueous $NaHCO_3$ or 1.0 M aqueous NaOH (10 mL/mmol amine). The phases separated and the aqueous phase extracted with $CH_2Cl_2$ (3×10 mL/mmol amine). The combined organic phases were dried ($Na_2SO_4$) and concentrated under reduced pressure. The crude material was purified by chromatography.

General Procedure D: Double-Step Mannich Condensation

To a solution of the appropriate pyridinecarboxaldehyde (2 equivalents) in MeOH (concentration ~0.1-1 M) at 0° C. was added $NH_4OAc$ (1.1 equivalents) followed by the slow addition (a period of approx. 15 minutes) of 1,3-acetonedicarboxylic acid (1 equivalents). After the vigorous bubbling subsided, the solution was allowed to stir for 1 hour while warming to room temperature. The solvent was then removed under reduced pressure and $CH_2Cl_2$ (10 mL/mmol amine) and saturated aqueous $Na_2CO_3$ (10 mL/mmol amine) were added. The layers were separated and the aqueous phase extracted with $CH_2Cl_2$ (2×10 mL/mmol amine). The combined organic extracts were dried ($Na_2SO_4$) and concentrated under reduced pressure. The crude product was purified by chromatography on silica gel.

General Procedure E: Wolff-Kishner Reduction

The following reaction was carried out under a flow of nitrogen in a 3-necked round bottom flask equipped with a condenser heated using a sand-filled Variac controlled heating mantle. To a solution of the appropriate substituted-tetrahydro-1'H-[2,2';6',2"]terpyridin-4'-one (1 equivalent) in diethylene glycol (concentration ~0.1-0.2 M) was added hydrazine monohydrate (40 equivalents) and potassium hydroxide pellets (20 equivalents) and the reaction stirred at 80° C. for 1-2 hours. The excess hydrazine was then distilled off (bath temperature of ~200° C.) by use of a short-path distillation apparatus and the remaining mixture was allowed to cool to room temperature. The reaction was diluted with $CH_2Cl_2$ (10 mL/mmol amine) and $H_2O$ (10 mL/mmol amine) and the layers separated. The aqueous phase was extracted with $CH_2Cl_2$ (10 mL/mmol amine) and the combined organic extracts dried ($Na_2SO_4$) and concentrated under reduced pressure. The crude product was purified by column chromatography on silica gel to afford the desired substituted-tetrahydro-1'H-[2,2';6',2"]terpyridine.

General Procedure F: Reaction of Alcohols with Methanesulfonyl Chloride

To a stirred solution of the alcohol (1 equivalent) and $Et_3N$ (1.5-2 equivalents) in $CH_2Cl_2$ (or THF) (concentration ~0.1 M) at room temperature (or 0° C.) was added methanesulfonyl chloride (MsCl) (~1.5 equivalents) and the reaction stirred at room temperature for 0.5-1 h. The reaction mixture was poured into either saturated aqueous $NaHCO_3$ or saturated $NH_4Cl$ (10 mL/mmol alcohol). The phases were separated and the aqueous phase extracted with $CH_2Cl_2$ (3×10 mL/mmol amine). The combined organic phases were dried ($Na_2SO_4$) and concentrated under reduced pressure. The crude material was either purified by chromatography or used without further purification in the N-alkylation step.

General Procedure G: EDCI Coupling

To a stirred solution of a 1° or 2° amine (0.1-0.3 mmol), 1-[3-(dimethylamino)propyl]-3-ethylcarbodiimide hydrochloride (EDCI) (1.5 equiv.), 1-hydroxy-benzotriazole hydrate (HOBT) (1.5 equiv.), and DIPEA (2.0 equiv.) in $CH_2Cl_2$ or DMF (0.05 M), was added a carboxylic acid (1.0-2.0 equiv). The solution was stirred for 16 h at ambient temperature. The reaction was quenched with saturated $NaHCO_3$ solution and extracted three times with $CH_2Cl_2$. The combined organic layers were dried over $Na_2SO_4$, filtered, and concentrated. The resultant crude material was purified on a silica gel column (5% $MeOH/CH_2Cl_2$).

EXAMPLE 1

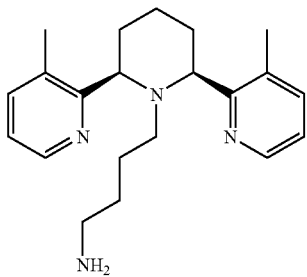

COMPOUND 1: 4-(3,3"-Dimethyl-3',4',5',6'-tetrahydro-2'H-cis-[2,2';6',2"]terpyridin-1'-yl-butylamine To a cold (−78° C.) solution of N,N,N',N'-tetramethylethylenediamine (TMEDA) (4.06 mL, 26.9 mmol) in dry THF (50 mL) under an atmosphere of Ar was added n-BuLi (2.5 M in hexanes, 10.7 mL, 26.9 mmol). 2-Bromo-3-methylpyridine (3.0 mL, 26.9 mmol) was added dropwise and the temperature was raised to −55° C. for 30 minutes. The reaction mixture turned red. It was then cooled to −78° C. and dimethyl glutarate (1.65 mL, 11.2 mmol) was added. The reaction mixture was stirred at −78° C. for 1 h. Water (200 mL) was added and the mixture was extracted with $CH_2Cl_2$ (3 times 200 mL). The combined organic extracts were washed with brine (200 mL), were dried over $mgSO_4$, filtered and concentrated. The crude material was purified by flash column chromatography on silica gel (1:1 EtOAc:hexanes) to provide 1.5 g (48%) of 1,5-bis-(3-methyl-pyridin-2-yl)-pentane-1,5-dione as a white solid. $^1$H NMR(CDCl$_3$) δ 2.00 (p, 2H, J=7.5 Hz), 2.44 (s, 6H), 3.19 (t, 4H, J=7.5 Hz), 7.18 (dd, 2H, J=7.8, 4.2 Hz), 7.43 (d, 2H, J=7.8 Hz), 8.33 (d, 2H, J=4.2 Hz).

To a solution of 1,5-bis-(3-methyl-pyridin-2-yl)-pentane-1,5-dione (340 mg, 1.20 mmol) mmol) in MeOH (15 mL) was added $NaBH_4$ (100 mg, 2.65 mmol) and the mixture was stirred at room temperature for 2 h. MeOH was removed in vacuo, water (25 mL) was added to the residue and the mixture was extracted with $CH_2Cl_2$ (3 times 25 mL). The organic extracts were dried over $mgSO_4$ and concentrated to give 365 mg (100%) of 1,5-bis-(3-methyl-pyridin-2-yl)-pentane-1,5-diol as a white foam. $^1$H NMR(CDCl$_3$): δ 1.52-1.81 (m, 6H), 2.33 (s, 6H), 4.69 (dd, 2H, J=7.5, 4.5 Hz), 4.79-4.86 (m, 2H), 7.09-7.14 (m, 2H), 7.43-7.45 (m, 2H), 8.36-8.39 (m, 2H).

To a cold (−20° C.) solution of 1,5-bis-(3-methyl-pyridin-2-yl)-pentane-1,5-diol (527 mg, 1.84 mmol) in dry $CH_2Cl_2$ (25 mL) was added $Et_3N$ (0.767 mL, 5.52 mmol) followed by mesyl chloride (0.357 mL, 4.61 mmol). The mixture was stirred for 2 h at −20° C. then was warmed to 0° C. prior to the addition of saturated $NaHCO_3$ solution (20 mL). The layers were separated and the aqueous layer was extracted with $CH_2Cl_2$ (3 times 20 mL). The combined organic extracts were dried ($MgSO_4$), filtered and the solvent volume was reduced to about 5 mL without heating. $^1$H NMR of an aliquot showed complete and clean conversion to the di-mesylate.

To the solution of the di-mesylate above at 0° C. was added allylamine (1.38 mL, 18.4 mmol) and the reaction mixture was warmed to room temperature and stirred for 17 hours. Saturated solution of $NaHCO_3$ (20 mL) was added and the mixture was extracted with $CH_2Cl_2$ (3 times 20 mL). The combined organic extracts were dried ($MgSO_4$), filtered and concentrated to yield a 1:1 mixture of two products (cis and trans). Separation of the two isomers was achieved by flash column chromatography on silica gel (2:1 hexanes:EtOAc then EtOAc then MeOH) to provide 204 mg of less polar isomer (trans) and 194 mg of more polar isomer (cis). The more polar isomer was further subjected to chromatography ($Et_2O$ saturated with $NH_4OH$) and 142 mg (25%) of 1'-allyl-3,3"-dimethyl-1',2',3',4',5',6'-hexahydro-cis-[2,2';6',2"]terpyridine was obtained. $^1$H NMR(CDCl$_3$): δ 1.48-1.75 (br m, 3H), 1.77-2.10 (m, 3H), 2.45 (br s, 6H), 2.80 (d, 2H, J=6.9 Hz), 3.98 (br d, 2H, J=9.9 Hz), 4.28-4.36 (br m, 1H), 4.72 (br s, 1H), 5.64 (br s, 1H), 7.04 (dd, 2H, J=7.8, 4.8 Hz), 7.39 (d, 2H, J=7.8 Hz), 8.35 (br s, 2H); ES-MS m/z 308.3 (M$^+$H).

To a solution of 1'-allyl-3,3"-dimethyl-1',2',3',4',5',6'-hexahydro-cis-[2,2';6',2"]terpyridine (142 mg, 0.462 mmol) in $CH_2Cl_2$ was added 1,3-dimethylbarbaturic acid (361 mg, 2.31 mmol) and Pd(PPh$_3$)$_4$ (53 mg, 0.046 mmol) and the reaction mixture was stirred for 20 h. Saturated solution of $NaHCO_3$ (10 mL) was added and the mixture was extracted with $CH_2Cl_2$ (3 times 20 mL). The organic extracts were dried ($MgSO_4$), filtered and concentrated. The crude material was purified by flash column chromatography on silica gel (9:1: 0.2 $CH_2Cl_2$-MeOH—$NH_4OH$) to provide 105 mg (85%) of the 3,3"-dimethyl-1',2',3',4',5', 6'-hexahydro-cis-[2,2';6',2"] terpyridine as a clear oil. $^1$H NMR(CDCl$_3$) δ 1.51-1.63 (m, 2H), 1.76-1.85 (m, 3H), 2.11-2.15 (m, 1H), 2.37 (s, 6H), 3.10-3.30 (m, 1H), 4.22 (d, 2H, J=10.8 Hz), 7.02 (dd, 2H, J=7.5, 4.5 Hz), 7.38 (d, 2H, J=7.5 Hz), 8.45 (d, 2H, J=4.5 Hz); $^{13}$C NMR (CDCl$_3$) δ 18.68, 25.84, 32.28, 57.60, 121.96, 129.73, 138.04, 147.31, 160.94; ES-MS m/z 269.1 (M$^+$H). Anal. Calcd. for $C_{17}H_{21}N_3$·0.1$CH_2Cl_2$: C, 74.45; H, 7.75; N, 15.23. Found: C, 74.70; H, 7.80; N, 15.18.

To a solution of 3,3"-dimethyl-1',2',3',4',5',6'-hexahydro-cis-[2,2';6',2"]terpyridine (75.4 mg, 0.282 mmol) in DMF (6 mL) were added 2-(4-bromo-butyl)-isoindole-1,3-dione (159 mg, 0.564 mmol), KI (4 mg, 0.03 mmol), DIPEA (0.6 mL) and the mixture was stirred at 60° C. for 17 hours. Volatiles were removed on high vacuum rotary evaporator. Saturated $NaHCO_3$ (10 mL) was added and the mixture was extracted with $CH_2Cl_2$ 3 times (20 mL). The organic extracts were dried ($MgSO_4$), filtered and concentrated. Purification of the crude material by column chromatography on silica gel (1:1 EtOAc: hexanes then EtOAc then 9:1 EtOAc:MeOH) provided 83.6 mg (63%) of 2-[4-(3,3"-dimethyl-3',4',5 ',6'-tetrahydro-2'H-cis-[2,2';6',2"]terpyridin-1'-yl)-butyl]-isoindole-1,3-dione as a white foam. $^1$H NMR(CDCl$_3$) δ 0.75 (br s, 1H), 0.91-0.97 (m, 2H), 1.56-1.66 (m, 3H), 1.94-2.04 (m, 2H), 2.15-2.29 (m, 2H), 2.41 (s, 6H), 2.50-2.72 (m, 2H), 3.23 (dd, 2H, J=6.9, 7.2 Hz), 4.0 (br s, 2H), 6.99 (dd, 2H, J=7.5, 4.5 Hz), 7.31 (d, 2H, J=7.5 Hz), 7.68-7.71 (m, 2H), 7.75-7.81 (m, 2H), 8.41 (br s, 2H).

To a solution of 2-[4-(3,3"-dimethyl-3',4',5',6'-tetrahydro-2'H-cis-[2,2';6',2"]terpyridin-1'-yl)-butyl]-isoindole-1,3-dione (83 mg, 0.1771 mmol) in EtOH (25 mL) was added hydrazine monohydrate (0.3 mL), and the reaction mixture was stirred at room temperature for 17 h. The reaction mixture was concentrated, and purification of the crude material by radial chromatography on silica gel (1 mm plate, 9:1:0.1 $CH_2Cl_2$—MeOH—$NH_4OH$) provided 37 mg (62%) of COMPOUND 1 as a colorless oil. $^1$H NMR(CDCl$_3$) δ 0.66-0.80 (m, 3H), 1.57-1.66 (m, 3H), 1.97-2.22 (br m, 7H), 2.52 (br s, 6H), 2.50-2.54 (br s, 1H), 4.02 (d, 2H, J=10.8 Hz), 7.08 (dd, 2H, J=4.5, 7.2 Hz), 7.42 (d, 2H, J=7.2 Hz), 8.45 (br s, 2H); $^{13}$C NMR (CDCl$_3$) δ 19.2, 23.3, 30.6, 31.1, 41.6, 49.8, 64.1, 71.4, 122.2, 138.7, 139.8, 147.0, 160.7; ES-MS m/z 339.3 (M+H). Anal. Calcd. for C$_{22}$H$_{31}$N$_5$O.0.5H$_2$O.0.5CH$_2$Cl$_2$: C, 66.22; H, 8.27; N, 14.37. Found: C, 65.82; H, 8.24; N, 14.20.

EXAMPLE 2

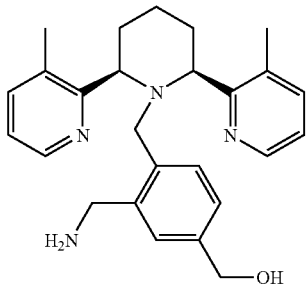

COMPOUND 2: [3-Aminomethyl-4-meso-(3,3''-dimethyl-3',4',5',6'-tetrahydro-2'H-cis-[2,2';6',2'']terpyridin-1'-ylmethyl)-phenyl]-methanol To a solution of 3-methylpyridinecarbaldehyde (43.27 g, 357 mmol) in MeOH (179 mL) at 0° C. was added NH$_4$OAc (151.14 g, 197 mmol). 1,3-Acetonedicarboxylic acid (26.10 g, 178.6 mmol) was then slowly added to the reaction over a period of 15 minutes. After vigorous bubbling subsided, the solution was allowed to stir for 1 hour while warming to room temperature. The solvent was then removed under reduced pressure and CH$_2$Cl$_2$ (500 mL) was added. The solution was washed with saturated aqueous Na$_2$CO$_3$ (350 mL) and separated. The aqueous phase was then extracted with CH$_2$Cl$_2$ (2×400 mL) and the combined organic components dried (Na$_2$SO$_4$) and concentrated under reduced pressure to give, after flash chromatography through a plug of silica gel (2:0.5: 97.5 MeOH/NH$_4$OH/CH$_2$Cl$_2$), meso-3,3''-Dimethyl-2',3',5', 6'-tetrahydro-1'H-cis-[2,2';6',2'']terpyridin-4'-one as a yellow solid (30.1 g, 60%). $^1$H NMR(CDCl$_3$) δ 2.37 (s, 6H), 2.55 (m, 2H), 2.82 (m, 2H), 3.37 (m, 1H, NH), 4.50 (t, 2H, J=9.0 Hz), 7.10 (m, 2H), 7.45 (d, 2H, J=7.5 Hz), 8.47 (d, 2H, J=4.5 Hz).

A solution of the above ketone (20.00 g, 71.1 mmol) in diethylene glycol (350 mL) was prepared in a 1L 3-neck round bottom flask. The vessel was purged under a flow of N$_2$ gas and also fitted with a condenser. Hydrazine monohydrate (138 mL, 2.84 mol) and KOH pellets (79.77 g, 1.42 mol) were added to the solution and an overhead mechanical stirrer was equipped to the flask. The reaction mixture was then stirred and heated to 80° C. for 2 hours using a Variac controlled heating mantle filled with sand in tin foil. The excess hydrazine was then distilled from the reaction at a bath temperature of ~200° C. Once all the hydrazine had been collected, the solution was allowed to slowly cool to room temperature. CH$_2$Cl$_2$ (500 mL) and H$_2$O (400 mL) were added and the organic phase separated. The aqueous phase was then extracted with CH$_2$Cl$_2$ (2×500 mL) and the combined organic components dried (Na$_2$SO$_4$) and concentrated under reduced pressure to afford, after column chromatography (NH$_3$/Et$_2$O ramping to 5% and then 10% MeOH in NH$_3$/Et$_2$O) meso-3,3 ''-dimethyl-1',2',3',4',5',6'-hexahydro-cis-[2,2';6',2'']terpyridine as a pale yellow solid (15.0 g, 79%). $^1$H NMR(CDCl$_3$) δ 1.59 (dq,2H, J=12.4, 3.6 Hz), 1.80 (m, 2H), 2.13 (m, 1H),2.37 (s, 6H),3.09 (br, 1H, NH), 4.20 (br d, 2H, J=11.1 Hz), 7.03 (m, 2H), 7.39 (d, 2H, J=7.5 Hz), 8.46 (d, 2H, J=4.5 Hz).

A solution of 4-methyl-3-nitrobenzoic acid (27.95 g, 154 mmol) in MeOH (550 mL) was treated with concentrated H$_2$SO$_4$ (10 mL, 188 mmol) and heated to reflux for 17 hours. The reaction was cooled and concentrated under reduced pressure. EtOAc (300 mL) and brine (400 mL) were added and the solution cooled to 0° C. 10N NaOH solution (40 mL) was slowly added until the acid content was neutralized and the solution basic. The organic phase was separated and the aqueous was then extracted with EtOAc (2×400 mL), and the combined organic phases dried (MgSO$_4$), filtered, and concentrated under reduced pressure to give 4-Methyl-3-nitrobenzoic acid methyl ester as a white solid (29.37 g, 98%).

The ester from above (29.37 g, 150 mmol) was added to a 2 L Parr hydrogenation flask and dissolved in anhydrous MeOH (200 mL) plus EtOAc (25 mL). The solution was then treated with 10% Pd/C (2.25 g, 50% wet) and fitted to a hydrogenator apparatus. After purging the flask 3 times with hydrogen gas, the mixture was shaken for 1 hour at 30 psi. The flask was then removed, and filtered through a celite pad washing with MeOH. The solvent was then removed under reduced pressure to afford 3-amino-4-methyl-benzoic acid methyl ester as a white solid (25.0 g, 100%). $^1$H NMR (CDCl$_3$) δ 2.21 (s, 3H), 3.70 (br s, 2H, NH2), 3.88 (s, 3H), 7.10 (d, 1H, J=7.5 Hz), 7.35 (s, 1H), 7.37 (d, 1H, J=8.4 Hz).

The above amine (25.00 g, 150 mmol) was suspended in water (140 mL) and treated with hydrochloric acid (41 mL) at 0° C. Upon dissolution, another portion of water (33 mL) was added. The substrate solution was then treated with NaNO$_2$ (11.39 g, 165 mmol) in water (26 mL) and stirred for half an hour. After neutralizing the acid content with K$_2$CO$_3$ (~20 g), the mixture was transferred via cannula to a solution of NaCN (17.64 g, 360 mmol) and CuCN (16.12 g, 180 mmol) in water (65 mL) at 60° C. The mixture was then heated to reflux for 1 hour. Upon cooling to room temperature, the mixture was partitioned between saturated aqueous NaHCO$_3$ solution (200 mL) and CH$_2$Cl$_2$ (400 mL) and the organic phase separated. The aqueous phase was the extracted with CH$_2$Cl$_2$ (3×300 mL) and the combined organic components dried (Na$_2$SO$_4$), filtered, and concentrated under reduced pressure to afford, after column chromatography with silica gel (5% EtOAc/hexanes) 3-cyano-4-methyl-benzoic acid methyl ester as a peach-colored solid (15.8 g, 60%). $^1$H NMR (CDCl$_3$) δ 2.62 (s, 3H), 3.94 (s, 3H), 7.41 (d, 1H, J=7.5 Hz), 8.13 (d, 1H, J=7.5 Hz), 8.27 (s, 1H).

To a solution of the above nitrile (5.08 g, 29.0 mmol) in CCl$_4$ (90 mL) was added N-bromosuccinimide (5.68 g, 32.0 mmol), and 1,1'-azobis(cyclohexanecarbonitrile) (1.06 g, 4.3 mmol). The solution was stirred at reflux for 2 hours and then a second portion of 1,1'-azobis(cyclohexanecarbonitrile) (0.35 g, 1.4 mmol) was added. After an additional 16 hours stirring at reflux the solution was allowed to cool, filtered through a medium glass fritted funnel, and concentrated under reduced pressure. This gave, after column chromatography with silica gel (5% EtOAc/hexanes ramping to 20% EtOAc/hexanes), 4-bromomethyl-3-cyano-benzoic acid methyl ester as pale orange solid. (3.94 g, 53%). $^1$H NMR (CDCl$_3$) δ 3.96 (s, 3H), 4.65 (s, 2H), 7.65 (d, 1H, J=7.5 Hz), 8.23 (d, 1H, J=7.5 Hz), 8.33 (s, 1H).

A solution of meso-3,3''-dimethyl-1',2',3',4',5',6'-hexahydro-cis-[2,2';6',2'']terpyridine (1.01 g, 3.8 mmol), 4-bromomethyl-3-cyano-benzoic acid methyl ester (1.25 g, 4.9 mmol), and KI (126 mg, 0.76 mmol) in anhydrous DMF (19 mL) was treated with DIPEA (1.32 mL, 7.6 mmol) and stirred at 60° C. for 16 hours. The mixture was then concentrated under reduced pressure and the residue dissolved in EtOAc (25 mL). The organic solution was washed with brine (5×20 mL), dried (MgSO$_4$), and concentrated under reduced pressure. This afforded, after purification by column chromatography with silica gel (2:0.5:97.5 MeOH/NH$_4$OH/CH$_2$Cl$_2$), 3-cyano-4-(meso-3,3''-dimethyl-3',4',5',6'-tetrahydro-2'H-cis-[2,2';6', 2'']terpyridin-1'-ylmethyl)-benzoic acid methyl ester as a light beige-colored solid (1.52 g, 91%). $^1$H NMR(CDCl$_3$) δ 1.70 (m, 3H), 2.05 (m, 1H), 2.33 (m, 2H), 2.49 (s, 6H), 3.73 (s, 2H), 3.85 (s, 3H), 4.15 (br d, 2H, J=10.5 Hz), 6.85 (m, 2H), 7.25 (d, 2H, J=7.5 Hz), 7.67 (s, 1H), 7.77 (d, 1H, J=7.5 Hz), 7.85 (d, 1H, J=7.5 Hz), 8.25 (d, 2H, J=4.5 Hz).

The alkylated product from above (1.52 g, 3.45 mmol) was dissolved in THF (30 mL) and MeOH (30 mL), cooled to 0° C., and treated with solid LiBH₄ (0.90 g, 41.4 mmol). After vigorous bubbling subsided, the mixture was let warm to room temperature over 1 hour while stirring. The excess LiBH₄ was quenched with 1N NaOH solution (10 mL) plus brine (30 mL). The aqueous phase was then extracted with $CH_2Cl_2$ (3×60 mL), dried ($Na_2SO_4$), and concentrated under reduced pressure to give 2-(meso-3,3"-dimethyl-3',4',5',6'-tetrahydro-2'H-cis-[2,2';6',2"]terpyridin-1'-ylmethyl)-5-hydroxymethyl-benzonitrile as a fluffy white solid (1.42 g, 100%).

A solution of the above alcohol (0.69 g, 1.67 mmol) in MeOH (20 mL) was prepared in a 250 mL Parr hydrogenation flask and anhydrous solid Raney Nickel (~1 g) was added. The mixture was then saturated with ammonia gas and transferred to a hydrogenator apparatus. After purging the reaction vessel (flushing three times with hydrogen gas), the flask was pressurized to 50 psi $H_2$ and shaken for 16 hours. The flask was then removed from the hydrogenator, filtered through a celite pad (washing several times with MeOH), and the filtrate concentrated under reduced pressure to give a lightly green-colored solid that did not give a proper ¹H NMR spectrum. The nickel impurity was then removed by dissolving the solid in MeOH (5 mL) and water (5 mL) and treating with NaCN (0.33 g, 6.7 mmol) at 50° C. for half an hour. After cooling, the solution was extracted with $CH_2Cl_2$ (3×15 mL), dried ($Na_2SO_4$), and concentrated under reduced pressure to give, after column chromatography with silica gel (1:1:10 MeOH: $NH_4OH$:$CH_2Cl_2$), COMPOUND 2 as a white solid (0.46 g, 65%). ¹H NMR ($CDCl_3$) δ 1.67 (m, 3H), 2.04 (m, 1H), 2.26 (m, 2H), 2.42 (s, 6H), 2.58 (br, 3H), 3.48 (br s, 2H), 3.59 (s, 2H), 4.13 (br d, 2H, J=11.4 Hz), 4.40 (s, 2H), 6.75 (d, 1H, J=7.5 Hz), 6.86 (m, 3H), 7.00 (m, 1H), 7.18 (d, 2H, J=4.8 Hz), 8.29 (d, 2H, J=4.2 Hz). ¹³C NMR($CDCl_3$) δ 18.87 (2C), 25.26 (2C), 28.79, 42.51, 53.43, 64.69 (2C), 66.34, 121.85 (2C), 124.41, 125.96, 129.24, 131.72 (2C), 137.47, 137.86 (2C), 138.71, 139.06, 146.35 (2C), 159.66 (2C). ES-MS m/z 417 ($M^+H$). Anal. Calcd. for $C_{26}H_{32}N_4O·0.5CH_2Cl_2$: C, 69.34; H, 7.25; N, 12.21. Found: C, 69.63; H, 7.54; N, 12.30.

EXAMPLE 3

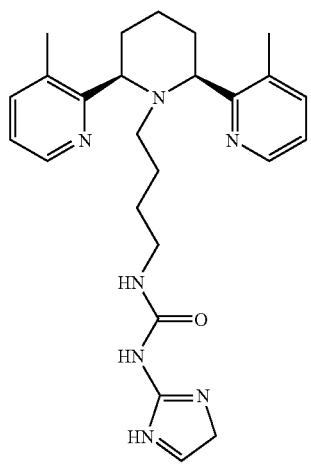

COMPOUND 3: The (1-[4-((2'S,6'R)-3,3"-dimethyl-3',4',5',6'-tetrahydro-2'H-[2,2';6',2"]terpyridin-1'-yl)-butyl]-3-(1H-imidazol-2-yl)-urea A mixture of 2-aminoimidazole sulfate (0.100 g, 0.757 mmol), 1,1'-carbonyldiimidazole (0.129 g, 0.796 mmol) and DIPEA (0.293 g, 2.27 mmol) in $CH_2Cl_2$ (10 mL) was stirred for 5 h, and then the solvent was removed. The residue was dissolved in DMF (6 mL), and 4-((2'S,6'R)-3,3"-dimethyl-3',4',5',6'-tetrahydro-2'H-[2,2';6',2"]terpyridin-1'-yl)-butylamine (0.130 g, 0.384 mmol) and DIPEA (0.293 g, 2.27 mmol) were added. The mixture was heated at 75° C. for 16 h, and then cooled to room temperature. Saturated aqueous $NaHCO_3$ (20 mL) was added, and the mixture was extracted with $CH_2Cl_2$ (3×30 mL). The extracts were combined and dried over $Na_2SO_4$. After filtration the solvent was removed by evaporation under vacuum, and the residue was purified by flash chromatography on a silica gel column (100:5:2 $CH_2Cl_2/CH_3OH/NH_4OH$), affording a pale yellow solid (0.115 g, 67%) after precipitation from $CH_2Cl_2$/hexanes by evaporation under vacuum. ¹H NMR($CDCl_3$) δ 0.70-0.85 (m, 4H), 1.46-1.66 (m, 3H), 1.90-2.00 (m, 2H), 2.15-2.19 (m, 2H), 2.41 (s, 6H), 2.53-2.70 (m, 1H), 2.75-2.83 (m, 2H), 3.95-4.00 (m, 2H), 6.69 (s, 2H), 6.90-7.02 (m, 2H), 7.30-7.40 (m, 2H), 8.34-8.42 (m, 2H); ¹³C NMR($CDCl_3$) δ 18.96, 22.82, 25.22, 27.67, 31.30, 39.41, 50.56, 63.61, 122.03, 131.12, 138.63, 144.22, 146.85, 155.71, 160.40. ES-MS m/z 448 ($M^+H$). Anal. Calcd. for $C_{25}H_{33}N_7O·0.1CH_2Cl_2·0.1C_6H_{14}$: C, 66.43; H, 7.50; N, 21.10. Found: C, 66.41; H, 7.46; N, 20.87.

EXAMPLE 4

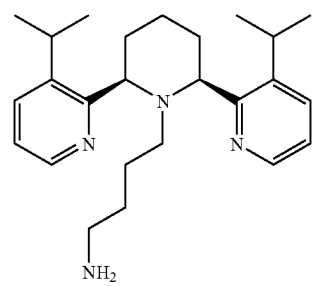

COMPOUND 4: 4-(3,3"-Diisopropyl-3'4',5',6'-tetrahydro-2'H-cis-[2,2';6',2"]terpyridin-1'-yl)-butylamine (HBr salt)

A 50% solution of hydrogen peroxide (24.89 mL) was slowly added to a solution of 3-isopropyl-2-methyl-pyridine (24.5 g, 183 mmol) (Ishiguro, et al., *Yakugaku Zasshi* (1958) 78:220) in HOAc (280 mL). The mixture was warmed to 70° C. and stirred for 18 h, then cooled to room temperature and concentrated in vacuo to remove the majority of HOAc. The mixture was basified with a saturated solution of $NaHCO_3$ to pH 12 and extracted with $CH_2Cl_2$ (3×150 mL). The combined organic layers were dried over $Na_2SO_4$ and concentrated in vacuo to afford 3-isopropyl-2-methyl-pyridine 1-oxide (26.05 g, 94%) as a yellow oil. ¹H NMR($CDCl_3$) δ 1.24 (d, 6H, J=7.0 Hz), 2.56 (s, 3H), 3.13 (sep, 1H, J=7.0 Hz), 7.06-7.17 (m, 2H), 8.17 (d, 1H, J=6.6 Hz).

To a stirred solution of 3-isopropyl-2-methyl-pyridine 1-oxide (26.05 g, 173 mmol) in $CH_2Cl_2$ (690 mL) was added dropwise TFAA (51.83 mL) over 30 min. under $N_2$ then stirred for an additional 3 h. Caution: exothermic reaction on addition of TFAA. The mixture was concentrated in vacuo to a minimum volume. Brine (200 mL) was added, basified to pH 9 with solid $K_2CO_3$ slowly, then the aqueous mixture was extracted with $CH_2Cl_2$ (3×100 mL). The combined organic layers were dried over $Na_2SO_4$ and concentrated in vacuo to afford (3-isopropyl-pyridin-2-yl)-methanol (26 g, 99%) as an orange oil. $^1$H NMR(CDCl$_3$) δ 1.24 (d, 6H, 7.0 Hz), 2.92 (sep, 1H, J=6.6 Hz), 4.79 (s, 2H), 7.02-7.25 (m, 1H), 7.61 (d, 1H, J=7.9 Hz), 8.41 (d, 1H, J=4.8 Hz).

To a vigorously stirred solution of (3-isopropyl-pyridin-2-yl)-methanol (26 g, 170 mmol) in CH$_2$Cl$_2$ (575 mL) was added MnO$_2$ (105 g, 1.20 mol) under N$_2$. The mixture was stirred for 18 h then filtered through a celite pad and concentrated in vacuo. Purification by column chromatography on silica gel (EtOAc/hexanes, 1:3) afforded 3-isopropyl-pyridine-2-carbaldehyde (15.65 g, 61%) as an orange oil. $^1$H NMR(CDCl$_3$) δ 1.26 (d, 6H, J=7.0 Hz), 4.17 (sep, 1H, J=6.6 Hz) 7.45 (dd, 1H, J=7.9, 4.4 Hz), 7.84 (d, 1H, J=7.9 Hz), 8.56 (dd, 1H, J=4.4, 1.3 Hz), 10.2 (s, 1H).

To a solution of 3-isopropyl-pyridine-2-carbaldehyde (235 mg, 1.57 mmol) in MeOH (10 mL) was added NH$_4$OAc (67 mg, 0.866 mmol) and 1,3-acetonedicarboxylic acid (115 mg, 0.787 mmol), and the mixture was stirred at room temperature for 2 h. The mixture was concentrated in vacuo and saturated NaHCO$_3$ (10 mL) followed by CH$_2$Cl$_2$ (20 mL) were added. The layers were separated and the aqueous layer was extracted two more times with CH$_2$Cl$_2$ (2 times 20 mL). The organic extracts were dried (MgSO$_4$), filtered and concentrated. Purification of the crude material by flash column chromatography on silica gel (10:1 EtOAc:hexanes) provided 106 mg (40%) of 3,3"-diisopropyl-2',3',5',6'-tetrahydro-1'H-cis-[2,2';6',2"]terpyridin-4'-one as a solid. $^1$H NMR(CDCl$_3$) δ 1.25 (d, 6H, J=9.3 Hz), 2.54 (d, 2H, J=13.5 Hz), 2.88 (dd, 2H, J=12.0, 12.6 Hz), 3.16-3.26 (m, 2H), 3.46-3.55 (m, 1H), 4.59-4.63 (m, 2H), 7.16 (dd, 2H, J=7.8, 4.5 Hz), 7.57 (d, 2H, J=7.8 Hz), 8.48 (d, 2H, J=4.5 Hz).

To a solution of 3,3"-diisopropyl-2',3',5',6'-tetrahydro-1'H-[2,2';6',2"]terpyridin-4'-one (106 mg, 0.314 mmol) in diethylene glycol (3 mL) were added KOH (352 mg, 6.29 mmol) and hydrazine monohydrate (0.61 mL, 12.6 mmol). The reaction mixture was heated to ~100° C. for 1 h using a sand bath. After 1 h the temperature was raised to 200° C. for about 45 minutes. CH$_2$Cl$_2$ (50 mL) was added to the remaining mixture and was washed with water (3 times 50 mL). The organic layer was dried (MgSO$_4$), filtered and concentrated to provide 100 mg (99%) of 3,3"-diisopropyl-1',2',3',4',5',6'-hexahydro-cis-[2,2';6',2"]terpyridine (with some DEG). $^1$H NMR (CDCl$_3$) δ 1.25 (d, 6H, J=9.3 Hz), 1.57-1.65 (m, 2H), 1.68-1.89 (m, 3H), 2.10-2.14 (m, 1H), 3.19-3.30 (m, 3H), 4.33 (br s, 1H), 7.10 (dd, 2H, J=7.8, 4.5 Hz), 7.53 (d, 2H, J=7.8 Hz), 8.46 (d, 2H, J=4.5 Hz).

To a solution of 3,3"-diisopropyl-1',2',3',4',5',6'-hexahydro-icis-[2,2';6',2"]terpyridine (100 mg, 0.3141 mmol) in DMF (3 mL) were added 2-(4-bromo-butyl)-isoindole-1,3-dione (106 mg, 0.376 mmol), KI (4 mg, 0.03 mmol), DIPEA (0.10 mL, 0.62 mmol) and the mixture was stirred at 60° C. for 17 hours. Volatiles were removed on high vacuum rotovap. Saturated NaHCO$_3$ (10 mL) was added and the mixture was extracted with CH$_2$Cl$_2$ (20 mL). The organic extracts were dried (MgSO$_4$), filtered and concentrated. Purification of the crude material by column chromatography on silica gel (Et$_2$O saturated with NH$_4$OH) provided 81.3 mg (49%) of 2-[4-(3,3"-diisopropyl-3',4',5',6'-tetrahydro-2'H-cis-[2,2';6',2"]terpyridin-1'-yl)-butyl]-isoindole-1,3-dione as a white foam. By $^1$H NMR the product appeared to be a mixture of two rotamers in about 2.5:1 ratio. ES-MS m/z 525 (M$^+$H).

To a solution of 2-[4-(3,3"-diisopropyl-3',4',5',6'-tetrahydro-2'H-cis-[2,2';6',2"]terpyridin-1'-yl)-butyl]-isoindole-1,3-dione (80 mg, 0.153 mmol) in EtOH (25 mL) was added hydrazine monohydrate (0.3 mL), and the reaction mixture was stirred at room temperature for 17 h. The reaction mixture was concentrated, and purification of the crude material by radial chromatography on silica gel (1 mm plate, 20:1:1 CH$_2$Cl$_2$—MeOH—NH$_4$OH) provided 56 mg (93%) of 4-(3,3"-diisopropyl-3',4',5',6'-tetrahydro-2'H-cis-[2,2';6',2"]terpyridin-1'-yl)-butylamine as a colorless oil. $^1$H NMR showed that a mixture of isomers (2:1) was obtained which separated on LCMS and had identical mass (m/z 395 (M$^+$H)).

To a solution of 4-(3,3"-diisopropyl-3',4',5',6'-tetrahydro-2'H-cis-[2,2';6',2"]terpyridin-1'-yl)-butylamine (53 mg, 0.134 mmol) in glacial HOAc (1.0 mL) was added HBr saturated HOAc (1.0 mL). The reaction mixture was stirred for 2 minutes then Et$_2$O was added (100 mL). The white precipitate was allowed to settle and the solvent was removed with a pipette. The solid was washed with Et$_2$O (100 mL) two more times. The resultant white powder was dried under reduced pressure to give 79.4 mg (88%) of COMPOUND 4. $^1$H NMR (D$_2$O) δ 1.14-1.23 (m, 3H), 1.32-1.36 (m, 7H), 1.54-1.76 (m, 3H), 1.93-1.96 (m, 1H), 2.05-2.16 (m, 2H), 2.25-2.33 (m, 2H), 2.69-2.75 (m, 2H), 3.45-3.56 (m, 2H), 7.95 (dd, 2H, J=8.4, 5.7 Hz), 8.60 (d, 2H, J=8.4 Hz), 8.67 (d, 2H, J=5.7 Hz); $^{13}$C NMR(D$_2$O) δ 20.2, 22.5, 22.7, 23.5, 25.0, 27.9, 34.0, 39.4, 52.2, 57.6, 126.6, 140.2, 146.0, 146.9, 153.1; ES-MS m/z 395.4 (M$^+$H). Anal. Calcd. for C$_{25}$H$_{38}$N$_4$.3HBr.2.2H$_2$O: C, 44.36; H, 6.76; N, 8.28; Br, 35.41. Found C, 44.67; H, 6.69; N, 8.50; Br, 35.65.

EXAMPLE 5

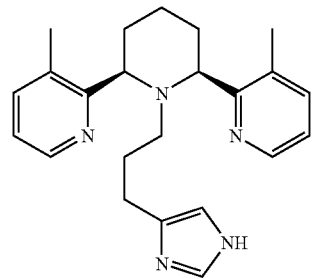

COMPOUND 5: (2'R,6'S)-1'-[3-(1H-Imidazol-4-yl)-propyl]-3,3"-dimethyl-1',2',3',4',5',6'-hexahydro-cis-[2,2';6',2"]terpyridine (HBr salt)

To a solution of 4-(3-hydroxy-propyl)-imidazole-1-carboxylic acid tert-butyl ester (147 mg, 0.648 mmol) in anhydrous CH$_2$Cl$_2$ (5 mL) was added pyridine (0.080 mL, 0.98 mmol) followed byp-toluenesul°fonyl chloride (247 mg, 1.30 mmol) and DMAP (8.0 mg, 0.065 mmol). The resultant mixture was stirred overnight at room temperature. The mixture was diluted with saturated aqueous NaHCO$_3$ (25 mL) and extracted with CH$_2$Cl$_2$ (3×15 mL). The combined organic extracts were dried (Na$_2$SO$_4$), filtered, and concentrated under reduced pressure. Purification by flash chromatography on silica gel (Hexanes/EtOAc, 60:40) afforded a regioisomeric mixture of 4-[3-(toluene-4-sulfonyloxy)-propyl]-imidazole-1-carboxylic acid tert-butyl ester (99 mg, 40%) as a colorless oil. $^1$H NMR(CDCl$_3$) of major regioisomer δ 1.59 (s, 9H), 1.99 (t, 2H, J=7.2 Hz), 2.43 (s, 3H), 2.57 (t, 2H, J=7.4 Hz), 4.04 (t, 2H, J=6.3 Hz), 7.00 (s, 1H), 7.33 (d, 2H, J=8.3 Hz), 7.77 (d, 2H, J=8.4 Hz), 7.93 (s, 1H).

To a solution of 4-[3-(toluene-4-sulfonyloxy)-propyl]-imidazole-1-carboxylic acid tert-butyl ester (99 mg, 0.26 mmol) in dry CH$_3$CN (2.5 mL) was added (2'R,6'S)-3,3"-dimethyl-1',2',3',4',5',6'-hexahydro-cis-[2,2';6',2"]terpyridine (104 mg, 0.389 mmol) and DIPEA (0.14 mL), 0.78 mmol). The resultant solution was heated to 60° C. overnight and then cooled to room temperature. The reaction mixture was concentrated and the residue was partitioned between CH$_2$Cl$_2$ (15 mL) and saturated aqueous NaHCO$_3$ (25 mL). The aqueous phase was separated and extracted with CH$_2$Cl$_2$ (2×15 mL). The combined organic extracts were dried (Na$_2$SO$_4$), filtered, and concentrated under reduced pressure. Purification by flash chromatography on silica gel (CH$_2$Cl$_2$/MeOH/NH$_4$OH, 92:4:

4) afforded a mixture of the desired amine and (2'R,6'S)-3,3"-Dimethyl-1',2',3',4',5',6'-hexahydro-cis-[2,2';6',2"]terpyridine (93 mg). The mixture was dissolved in $CH_2Cl_2$ (2 mL) and treated with TFA (1 mL). The resultant solution was stirred at room temperature for 1.5 h and then concentrated. The residue was partitioned between $CH_2Cl_2$ (15 mL) and saturated aqueous $NaHCO_3$ (40 mL). The aqueous phase was separated and extracted with $CH_2Cl_2$ (2×10 mL). The combined organic extracts were dried ($Na_2SO_4$), filtered, and concentrated under reduced pressure. Purification by radial chromatography on a 1 mm silica gel plate ($CH_2Cl_2$/MeOH/$NH_4OH$, 96:2:2, then 92:4:4) afforded the free base of the title compound (18 mg, 13% over 2 steps).

Using General Procedure B: Conversion of the free base from above (18 mg, 0.049 mmol) to a HBr salt followed by re-precipitation of the crude material from MeOF/ether gave COMPOUND 5 as a cream solid (25 mg, 77%). $^1H$ NMR ($D_2O$) δ 1.43-1.83 (m, 5H), 1.88-2.04 (m, 1H), 2.07-2.19 (m, 2H), 2.19-2.29 (m, 2H), 2.29-2.39 (m, 2H), 2.52 (s, 6H), 4.59 (d, 2H, J=9.2 Hz), 6.90 (s, 1H), 7.80-7.93 (m, 2H), 8.38 (d, 2H, J=7.6 Hz), 8.49 (s, 1H), 8.67 (d, 2H, J=5.0 Hz); $^{13}C$ NMR($D_2O$) δ 17.08, 21.36, 22.22, 22.40, 32.42, 51.43, 58.39, 115.99, 126.03, 132.90, 133.38, 136.65, 140.35, 148.95, 154.36; ES-MS m/z 376 ($M^+H$). Anal. Calcd. for $C_{23}H_{29}N_5$·3.0 HBr·2.7 $H_2O$: C, 41.42; H, 5.65; N, 10.50; Br, 35.94. Found: C, 41.58; H, 5.71; N, 10.45; Br, 35.82.

EXAMPLE 6

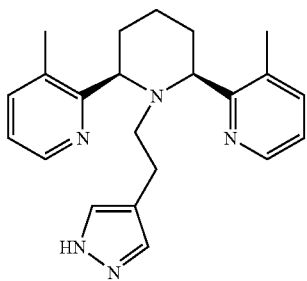

COMPOUND 6: The (2'R,6'S)-3,3"-dimethyl-1'-[2-(1H-pyrazol-4-yl)-ethyl]-1',2',3',4'5',6'-hexahydro-[2,2';6',2"]terpyridine To a suspension of methoxymethyl-triphenyl-phosphonium chloride (2.06 g, 6.00 mmol) in dry THF (20 mL) cooled at −15° C. (ethyl glycol/dry ice) was added LDA (2.0 M in THF, 3.1 mL, 6.2 mmol) slowly. After the addition the mixture was stirred at −15° C. for 30 min, and a solution of 2-benzyl-1H-pyrazole-4-carbaldehyde (1.00 g, 5.37 mmol) (Werner, A., et al., *Tetrahedron* (1995) 51:4779-4800) in THF (15 mL) was added. The reaction mixture was stirred at room temperature for 16 h. Water (30 mL) was added, and the mixture was extracted with EtOAc (30 mL) and $CH_2Cl_2$ (2×30 mL). The extracts were combined and dried over $Na_2SO_4$. After filtration the solvent was removed by evaporation under vacuum, and the residue was purified by flash chromatography on a silica gel column ($CH_2Cl_2$) to afford a colorless oil. The oil was dissolved in THF (3 mL) and aqueous HCl (4 N, 15 mL) was added. After being stirred for 72 h, the mixture was neutralized with saturated aqueous $K_2CO_3$, and extracted with $CH_2Cl_2$ (3×30 mL). The extracts were combined and dried over $Na_2SO_4$. After filtration the solvent was removed by evaporation under vacuum, and the residue was purified by flash chromatography on a silica gel column (2:1 $CH_2Cl_2/Et_2O$), affording (2-benzyl-1H-pyrazol-4-yl)-acet aldehyde as a colorless oil (0.548 g, 51%). $^1H$ NMR (CDCl$_3$) δ 3.56 (d, 2H, J=2.1 Hz), 5.29 (s, 2H), 7.21-7.24 (m, 2H), 7.28-7.39 (m, 4H), 7.45 (s, 1H), 9.70 (t, 1H, J=2.1 Hz).

(2-Benzyl-1H-pyrazol-4-yl)-acet aldehyde (0.548 g, 2.74 mmol) was dissolved in dry EtOH (20 mL) and cooled at 0° C. $NaBH_4$ (0.104 g, 2.74 mmol) was added, and the mixture was stirred at room temperature for 2 h. Water (10 mL) was added, and MeOH was removed by evaporation under vacuum. The aqueous residue was neutralized with HCl (1 N), and then extracted with $CH_2Cl_2$ (3×30 mL). The extracts were combined and dried over $Na_2SO_4$. After filtration the solvent was removed by evaporation under vacuum to provide a pale yellow oil.

At 0° C., to a solution of the oil in $CH_2Cl_2$ (10 mL) was added MsCl (0.345 g, 3.01 mmol) and $Et_3N$ (0.415 g, 4.11 mmol). The mixture was stirred at room temperature for 30 min. Water (10 mL) was added, and the mixture was extracted with $CH_2Cl_2$ (3×20 mL). The extracts were combined and dried over $Na_2SO_4$. After filtration the solvent was removed by evaporation under vacuum, and the residue was purified by flash chromatography on a silica gel column (4:1 $CH_2Cl_2/Et_2O$), affording methanesulfonic acid 2-(2-benzyl-1H-pyrazol-4-yl)-ethyl ester as a pale yellow oil (0.734 g, 96%). $^1H$ NMR(CDCl$_3$) δ 2.84 (s, 3H), 2.87 (t, 2H, J=6.6 Hz), 4.27 (t, 2H, J=6.6 Hz), 5.22 (s, 2H), 7.17-7.20 (m, 2H), 7.27-7.35 (m, 4H), 7.40 (s, 1H).

A mixture of (2'R,6'S)-3,3"-dimethyl-1',2',3',4',5',6'-hexahydro-[2,2';6'2"]terpyridine (0.320 g, 1.20 mmol), methanesulfonic acid 2-(2-benzyl-1 H-pyrazol-4-yl)-ethyl ester (0.540 g, 1.60 mmol) and 2,2,6,6-tetramethylpiperidine (0.255 g, 1.80 mmol) in $CH_3CN$ (5 mL) was stirred and heated at reflux overnight. The solvent was then removed, water (20 mL) was added, and the mixture was extracted with $CH_2Cl_2$ (3×20 mL). The extracts were combined and dried over $Na_2SO_4$. After filtration the solvent was removed by evaporation under vacuum, and the residue was purified by flash chromatography on a silica gel column (500:15:1 $CH_2Cl_2/CH_3OH/NH_4OH$), affording (2'R,6'S)-1'-[2-(2-benzyl-1H-pyrazol-4-yl)-ethyl]-3,3"-dimethyl-1',2',3',4',5',6'-hexahydro-[2,2';6',2"]terpyridine as a pale yellow oil (0.420 g, 93%).

To a solution of (2'R,6'S)-1'-[2-(2-benzyl-1 H-pyrazol-4-yl)-ethyl]-3,3"-dimethyl-1',2',3',4',5',6'-hexahydro-[2,2';6',2"]terpyridine (0.130 g, 0.288 mmol) in dry DMSO (0.70 mL) and THF (12 mL) was added 4 Å molecular sieve (~1 g) pre-heated at 140° C., and KO$^t$Bu (0.600 g, 5.35 mmol). The solution was bubbled with air (pre-dried by passing through a NaOH column) at room temperature for 1 h. Saturated aqueous $NH_4Cl$ (20 mL) was then added. The mixture was filtered through a celite cake and the cake was washed with EtOAc throughout. The organic layer in the filtrate was collected, and the aqueous layer was extracted with $CH_2Cl_2$ (3×30 mL). The extracts were combined and dried over $Na_2SO_4$. After filtration the solvent was removed by evaporation under vacuum, and the residue was purified by flash chromatography on a silica gel column (200:10:1 $CH_2Cl_2/CH_3OH/NH_4OH$), affording a pale yellow solid (0.067 g, 64%) after precipitation from $CH_2Cl_2$/hexanes by evaporation under vacuum. $^1HNMR(CDCl_3)$ δ 1.60-1.85 (4H), 2.00-2.15 (m, 2H), 2.25-2.62 (m, 10H), 4.10-4.20 (m, 2H), 6.73 (s, 2H), 7.07-7.12 (m, 2H), 7.43 (d, 2H, J=7.2 Hz), 8.45 (s, br. 2H); $^{13}C$ NMR ($CD_2Cl_2$) δ 19.02, 21.33, 25.61, 30.31, 50.86, 64.12, 118.85, 122.40, 132.22, 132.65, 138.78, 147.03, 160.46. ES-MS m/z 362 ($M^+H$). Anal. Calcd. for $C_{22}H_{27}N_5$·0.2$H_2O$: C, 72.38; H, 7.56; N, 19.18. Found: C, 72.31; H, 7.70; N, 18.98.

EXAMPLE 7

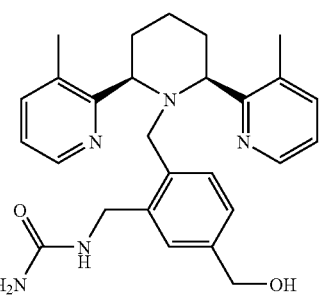

COMPOUND 7: [2-meso-(3,3"-Dimethyl-3'4',5'6'-tetrahydro-2'H-cis-[2,2';6',2]terpyridin-1'-ylmethyl)-5-hydroxymethyl-benzyl]-urea A solution of [3-aminomethyl-4-meso-(3,3"-dimethyl-3', 4',5',6'-tetrahydro-2'H-cis-[2,2';6',2"]terpyridin-1'-ylmethyl)-phenyl]-methanol (0.138 mg, 0.33 mmol) in isopropanol (2.2 mL) was treated with trimethylsilylisocyanate (63 µL, 0.46 mmol) at room temperature. The reaction was stirred 24 hours and concentrated under reduced pressure. This afforded, after column chromatography with silica gel (10:1:1 $CH_2Cl_2$:MeOH:$NH_4OH$), COMPOUND 7 as a white crystalline solid (112 mg, 74%). $^1$H NMR($CDCl_3$) δ 1.64 (m, 3H), 1.98 (m, 1H), 2.19 (m, 2H), 2.45 (s, 6H), 3.51 (s, 2H), 3.88 (br s, 2H), 3.94 (br d, 2H, J=10.5 Hz), 4.35 (s, 2H), 5.00 (br, 3H), 6.65 (d, 1H, J=7.5 Hz), 6.79 (d, 1H, J=7.5 Hz), 6.85 (m, 3H), 7.23 (d, 2H, J=7.5 Hz), 8.22 (d, 2H, J=3.9 Hz). $^{13}$C NMR($CDCl_3$) δ 19.24 (2C), 25.00, 32.01 (2C), 41.64, 57.50, 64.59 (2C), 65.85, 122.21 (2C), 124.59, 126.36, 129.96, 130.96 (2C), 135.74, 138.31, 138.52 (2C), 140.25, 146.79 (2C), 160.41, 160.86 (2C). ES-MS m/z 460 (M$^+$H). Anal. Calcd. for $C_{27}H_{33}N_5O_2 \cdot 0.6CH_2Cl_2$: C, 64.93; H, 6.75; N, 13.72. Found: C, 64.60; H, 6.90; N, 13.74.

EXAMPLE 8

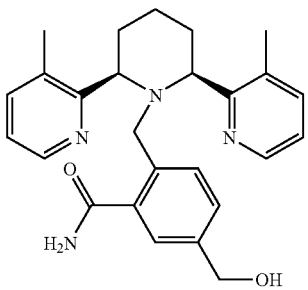

COMPOUND 8: 2-meso-(3,3"-Dimethyl-3',4'5'6'-tetrahydro-2'H-cis-[2,2';6',2"]terpyridin-1'-ylmethyl)-5-hydroxymethyl-benzamide 2-(meso-3,3"-Dimethyl-3',4',5',6'-tetrahydro-2 'H-cis-[2,2';6',2"]terpyridine-1'-ylmethyl)-5-hydroxymethyl-benzonitrile (100 mg, 0.24 mmol) was dissolved in a solution of 50% hydrogen peroxide (0.07 mL), 3N NaOH (0.3 mL), and MeOH (0.75 mL) and heated to 60° C. for 20 hours. Water (5 mL) and $CH_2Cl_2$ (10 mL) were added and the phases separated. The aqueous phase was then extracted with $CH_2Cl_2$ (2×10 mL), and the combined organic components dried ($Na_2SO_4$) and concentrated under reduced pressure. This gave, after radial chromatography with silica gel (5:0.5:94.5 $CH_3OH/NH_4OH/CH_2Cl_2$), COMPOUND 8 as a pale yellow solid (33 mg, 32%). $^1$H NMR($CDCl_3$) δ 1.66 (m, 3H), 2.05 (m, 1H), 2.22 (m, 2H), 2.44 (s, 6H), 3.71 (s, 2H), 4.05 (br d, 2H, J=8.4 Hz), 4.40 (s, 2H), 5.74 (br, 1H, NH), 6.84 (m, 2H), 6.92 (d, 1H, J=7.8 Hz), 7.07 (d, 1H, J=7.5 Hz), 7.18 (m, 3H), 8.25 (d, 2H, J=3.9 Hz), 9.49 (br, 1H, NH). $^{13}$C NMR($CDCl_3$) δ 18.87 (2C), 24.65, 30.37 (2C), 53.45, 64.08, 65.79 (2C), 121.87 (2C), 126.90, 127.37 (2C), 130.53, 130.73, 134.94, 135.32, 138.02 (2C), 139.79, 146.48 (2C), 159.89, 170.53 (2C). ES-MS m/z 431 (M$^+$H). Anal. Calcd. for $C_{26}H_{30}N_4O_2 \cdot 0.7CH_2Cl_2$: C, 65.45; H, 6.46; N, 11.43. Found: C, 65.30; H, 6.54; N, 11.44.

EXAMPLE 9A AND 9B

COMPOUND 9A

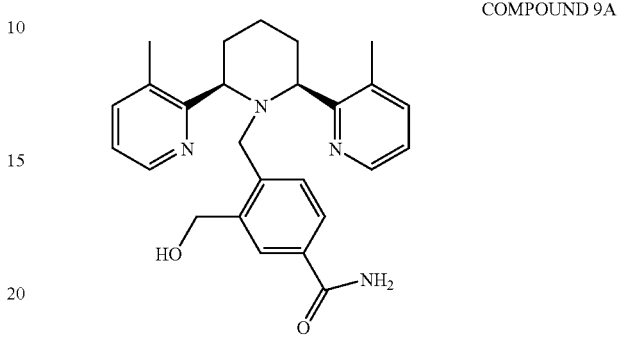

COMPOUND 9B

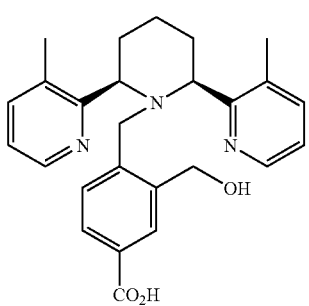

COMPOUND 9A: 4-(3,3"-Dimethyl-3'4',5',6'-tetrahydro-2'H-cis-[2,2';6',2"]terpyridine-1'-ylmethyl)-3-hydroxymethyl-benzamide and COMPOUND 9B: 4-(3,3 "-Dimethyl-3',4',5',6'-tetrahydro-2'H-cis-[2,2';6',2 "]terpyridin-1'-ylmethyl)-3-hydroxymethyl-benzoic acid Using General Procedure A: A solution of 3,3"-dimethyl-1',2',3',4',5',6'-hexahydro-cis-[2,2';6',2"]terpyridine (0.260 g, 0.98 mmol), 2-bromomethyl-5-cyano-benzoic acid methyl ester (0.360 g, 1.42 mmol), KI (37 mg, 0.22 mmol), and DIPEA (0.35 mL, 2.01 mmol) in DMF (5 mL) was heated at 60° C. for 17 hours. Purification of the crude material by column chromatography on silica gel (20:1:1 $CH_2Cl_2$—$CH_3OH$—$NH_4OH$) provided 415 mg (96%) of 5-cyano-2-(3, 3"-dimethyl-3',4',5',6'-tetrahydro-2'H-cis-[2,2';6',2"]terpyridine-1'-ylmethyl)-benzoic acid methyl ester as a tan solid.

To a cold (0° C.) solution of 5-cyano-2-(3,3"-dimethyl-3', 4',5',6'-terpyridine-2'H-cis-[2,2';6',2"]terpyridin-1'-ylmethyl)-benzoic acid methyl ester (0.409 g, 0.937 mmol) in THF (4.5 mL) and MeOH (9 mL) was added LiBH$_4$ (229 mg, 10.52 mmol) and the mixture was allowed to warm to room temperature overnight. The mixture was diluted with 1.0 N NaOH (10 mL) and extracted with $CH_2Cl_2$ (5×25 mL). The combined organic extracts were dried ($Na_2SO_4$) and concentrated. Purification of the crude material by column chromatography on silica gel (20:1:1 $CH_2Cl_2$—$CH_3OH$—$NH_4OH$) provided 0.332 g (87%) of 4-(3,3"-dimethyl-3',4',5',6'-tetrahydro-2'H-cis-[2,2';6',2"]terpyridin-1'-ylmethyl)-3-hydroxymethyl-benzonitrile as a white foam. $^1$H NMR($CDCl_3$) δ 1.61-1.77 (m, 3H), 2.05 -2.14 (m, 1H), 2.30-2.44 (m, 2H), 2.51 (s, 6H), 3.71 (s, 2H), 4.11 (d, 2H, J=10.8 Hz), 4.46 (s, 2H), 4.94 (br s, 1H), 6.87-6.96 (m, 4H), 7.22-7.27 (m, 3H), 8.21 (d, 2H, J=4.2 Hz).

To a solution of the 4-(3,3"-dimethyl-3',4',5',6'-tetrahydro-2'H-cis-[2,2';6',2"]terpyridin-1'-ylmethyl)-3-hydroxymethyl-benzonitrile (0.310 g, 0.75 mmol) in MeOH (4 mL) was added water (4 mL) and solid NaOH (0.315 g, 7.88 mmol). The resultant mixture was heated to reflux overnight then cooled to room temperature. The mixture was adjusted to pH ~4 with 4 N HCl (~2 mL) and extracted with $CH_2Cl_2$ (5×20 mL). The combined organic extracts were dried ($Na_2SO_4$) and concentrated. Purification of the crude material by radial chromatography on silica gel (1 mm plate, 5:1:1 $CH_2Cl_2$—$CH_3OH$—$NH_4OH$ followed by 5:1:1:1 $CH_2Cl_2$—$CH_3CN$—$CH_3OH$—$NH_4OH$) provided 24 mg (6%) of COMPOUND 9A as a pale yellow solid and 171 mg (45%) of COMPOUND 9B as a white solid.

Characterization data for COMPOUND 9A (24 mg, 6%), a pale yellow solid. $^1$H NMR($CDCl_3$) δ 1.60-1.75 (m, 3H), 1.80-2.15 (m, 1H), 2.23-2.43 (m, 2H), 2.51 (s, 6H), 3.68 (s, 2H), 4.06 (d, 2H, J=10.8 Hz), 4.44 (s, 2H), 5.45 (br s, 1H), 5.97 (br s, 1H), 6.83-6.96 (m, 3H), 7.19-7.32 (m, 4H), 8.19 (d, 2H, J=10.2 Hz); $^{13}$C NMR($CDCl_3$) δ 19.43, 25.69, 29.52, 53.39, 62.67, 67.47, 122.38, 126.18, 127.64, 129.20, 131.27, 131.95, 138.53, 139.05, 143.49, 146.83, 159.66,169.56; ES-MS m/z 431 ($M^+H$). Anal. Calcd. For $C_{26}H_{30}N_4O_2 \cdot 1.4CH_2Cl_2$: C, 59.90; H, 6.02; N, 10.20. Found: C, 60.22; H, 5.99; N, 10.38.

Characterization data for COMPOUND 9B (171 mg, 45%), a white solid. $^1$H NMR ($CDCl_3$) δ 1.66-1.77 (m, 3H), 2.00-2.07 (m, 1H), 2.24-2.32 (m, 2H), 2.46 (s, 6H), 3.71 (s, 2H), 4.14 (d, 2H, J=10.8 Hz), 4.39 (s, 2H), 6.86 (dd, 2H, J=4.8, 7.5 Hz), 6.94 (d, 1H, J=7.8 Hz), 7.24 (d, 2H, J=7.5 Hz), 7.46 (d, 1H, J=7.8 Hz), 7.68 (s, 1H), 8.24 (d, 2H, J=4.8 Hz); $^{13}$C NMR($CDCl_3$) δ 19.17, 25.02, 30.39, 54.42, 62.52, 66.71, 122.66, 128.25, 129.40, 130.22, 130.80, 131.93, 138.97, 139.12, 142.19, 146.66, 159.27, 170.67; ES-MS m/z 432 ($M^+H$). Anal. Calcd. For $C_{26}H_{29}N_3O_3 \cdot 0.5H_2O \cdot 0.7CH_2Cl_2$: C, 64.14; H, 6.33; N, 8.40. Found: C, 63.76; H, 6.24; N, 8.60.

EXAMPLE 10

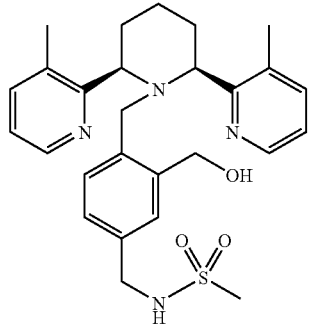

COMPOUND 10: N-[4-(3,3"-Dimethyl-3',4',5',6'-tetrahydro-2'H-cis-[2,2';6',2"]tenpyridin-1'-ylmethyl)-3-hydroxymethyl-benzyl]-methanesulfonamide To a solution of 4-(3,3"-dimethyl-3',4',5',6'-tetrahydro-2'H-cis-[2,2';6'2"]terpyridine-1'-ylmethyl)-3-hydroxymethyl-benzonitrile (0.64 g, 1.55 mmol) in $CH_2Cl_2$ (15 mL) was added 3,4-dihydro-2H-pyran (0.7 mL, 7.67 mmol) followed by p-toluenesulfonic acid monohydrate (1.21 g, 6.35 mmol). The resultant mixture was stirred at room temperature overnight then diluted with $CH_2Cl_2$ (50 mL). The solution was washed with 1.0 N NaOH (15 mL), saturated aqueous $NaHCO_3$ (15 mL), and brine (15 mL), dried ($Na_2SO_4$) and concentrated. Purification of the crude material by column chromatography on silica gel (20:1:1 $CH_2Cl_2$—$CH_3OH$—$NH_4OH$) followed by column chromatography on silica gel ($NH_4OH$ saturated $Et_2O$) gave 0.56 g (72%) of 4-(3,3"-dimethyl-3',4',5',6'-tetrahydro-2'H-cis-[2,2';6',2"]terpyridin-1'-ylmethyl)-3-(tetrahydro-pyran-2-yloxymethyl)-benzonitrile as a tan foam.

The tan foam (0.56 g, 1.12 mmol) was dissolved in $NH_3$ saturated MeOH (8 mL), treated with Raney nickel (500 mg) and placed under 50 psi $H_2$, on a Parr shaker, for 5 h. The mixture was filtered through Celite and the cake was washed with MeOH. The eluant was concentrated under reduced pressure and the thus obtained material was purified by column chromatography on silica gel (20:1:1 $CH_2Cl_2$—$CH_3OH$—$NH_4OH$) and provided 0.405 g (72%) of 4-(3,3"-dimethyl-3',4',5',6'-tetrahydro-2'H-cis-[2,2';6',2"]terpyridin-1'-ylmethyl)-3-(tetrahydro-pyran-2-yloxymethyl)-benzylamine as an orange solid.

To a solution of 4-(3,3"-dimethyl-3',4',5',6'-tetrahydro-2'H-cis-[2,2';6',2"]terpyridin-1'-ylmethyl)-3-(tetrahydro-pyran-2-yloxymethyl)-benzylamine (0.104 g, 0.21 mmol) in $CH_2Cl_2$ (2 mL) was added $Et_3N$ (0.09 mL, 0.65 mmol) followed by MsCl (24 µL, 0.31 mmol). The resultant mixture was stirred at room temperature for 40 minutes then diluted with brine (5 mL) and $CH_2Cl_2$ (20 mL). The phases were separated and the organic phase was washed with brine (3×5 mL), dried ($Na_2SO_4$), and concentrated and provided 105 mg of a white solid. The white solid (105 mg) was dissolved in THF (3.5 mL) and treated with 6 N HCl (3 mL) followed by water (3 mL). The mixture was stirred at room temperature for 2.5 hours. The mixture was saturated with solid $K_2CO_3$ (~3 g) and diluted with $CH_2Cl_2$ (30 mL) and water (10 mL). The phases were separated and the aqueous phase was extracted with $CH_2Cl_2$ (3×10 mL). The combined organic extracts were dried ($Na_2SO_4$), and concentrated. Purification of the crude material by radial chromatography on silica gel (1 mm plate, 20:1:1 $CH_2Cl_2$—$CH_3OH$—$NH_4OH$) gave COMPOUND 10 (59 mg, 59%) as a white solid. $^1$H NMR ($CDCl_3$) δ 1.61-1.71 (m, 3H), 2.01-2.05 (m, 1H), 2.26-2.36 (m, 2H), 2.50 (s, 6H), 2.84 (s, 3H), 3.64 (s, 2H), 4.01 (m, 4H) 4.31 (t, 1H, J=6.0 Hz), 4.37 (s, 2H), 5.10 (br s, 1H), 6.65 (d, 1H, J=7.5 Hz), 6.76 (d, 1H, J=7.5 Hz), 6.83-6.87 (m, 3H), 7.23-7.26 (m, 2H), 8.21 (d, 2H, J=3.3 Hz); $^{13}$C NMR($CDCl_3$) δ 19.42, 25.59, 30.16, 41.19, 47.03, 54.27, 62.46, 67.31, 122.18, 126.13, 128.44, 129.60, 131.75, 134.83, 138.49, 139.78, 146.80, 160.05; ES-MS m/z495 ($M^+H$). Anal. Calcd. For $C_{27}H_{34}N_4O_3S \cdot 0.3H_2O \cdot 1.0CH_2Cl_2$: C, 57.49; H, 6.31; N, 9.58; S, 5.48. Found: C, 57.45; H, 6.35; N, 9.63; S, 5.53.

EXAMPLE 11

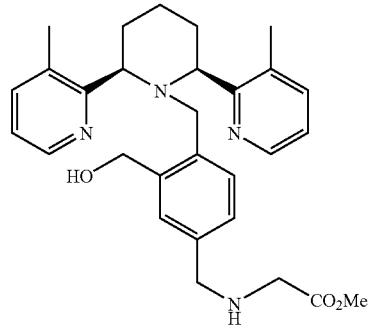

COMPOUND 11: [4-(3,3"-Dimethyl-3',4',5',6'-tetrahydro-2'H-cis-[2,2';6',2"]terpyridin-1'-ylmethyl)-3-hydroxymethyl-benzylamino]-acetic acid methyl ester To a cold (0° C.) solution of 4-(3,3"-dimethyl-3',4',5',6'-tetrahydro-2'H-cis-[2,2';6',2"]terpyridin-1'-ylmethyl)-3-(tetrahydro-pyran-2-yloxymethyl)-benzylamine (0.112 g, 0.22 mmol) in THF (2 mL) was added $Et_3N$ (0.04 mL, 0.28 mmol) followed by methyl bromoacetate (24 µL, 0.25 mmol). The resultant mixture was warmed to room temperature overnight. The mixture was diluted with $CH_2Cl_2$ (20 mL), washed with brine (5×5 mL), dried ($Na_2SO_4$), and concentrated. Purification of the crude material by column chromatography on silica gel (20:1:1 $CH_2Cl_2$—$CH_3OH$—$NH_4OH$) provided 43 mg of a yellow oil. The oil (43 mg) was dissolved in THF (2 mL) and treated with 6 N HCl (2 mL) followed by water (2 mL). The mixture was stirred at room temperature overnight. The mixture was saturated with solid $K_2CO_3$ (~1.8 g) and diluted with $CH_2Cl_2$ (25 mL) and water (5 mL). The phases were separated and the aqueous phase was extracted with $CH_2Cl_2$ (3×10 mL). The combined organic extracts were dried ($Na_2SO_4$), and concentrated. Purification of the crude material by radial chromatography on silica gel (1 mm plate, 20:1:1 $CH_2Cl_2$—$CH_3OH$—$NH_4OH$) gave COMPOUND 11 (27 mg, 24%) as a white solid. $^1$H NMR($CDCl_3$) δ 1.60-1.71 (m, 3H), 1.92-2.06 (m, 1H), 2.28-2.36 (m, 2H), 2.50 (s, 6H), 3.23 (s, 2H), 3.51 (s, 2H), 3.64 (s, 2H), 3.73 (s, 3H), 4.20 (d, 2H, J=10.8 Hz), 4.35 (s, 2H), 6.62 (d, 1H, J=7.5 Hz), 6.73 (d, 1H, J=7.5 Hz), 6.83-6.87 (m, 2H), 8.23 (d, 2H, J=3.6 Hz); $^{13}$C NMR($CDCl_3$) δ 19.45, 25.62, 30.20, 49.90, 52.17, 52.92, 54.90, 62.95, 67.49, 122.08, 126.57, 129.38, 129.59, 131.73, 137.52, 137.87, 138.45, 139.28, 146.86, 160.18, 173.18; ES-MS m/z 489 ($M^+H$). Anal. Calcd. For $C_{29}H_{36}N_4O_3.1.0H_2O$: C, 68.75; H, 7.56; N, 11.06. Found: C, 68.89; H, 7.29; N, 10.82.

EXAMPLE 12

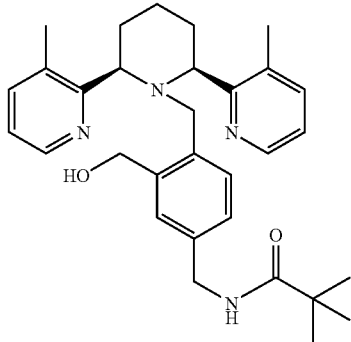

COMPOUND 12: N-[4-(3,3"-Dimethyl-3',4',5',6'-tetrahydro-2'H-cis-[-2,2';6',2"]terpyridin-1'-ylmethyl)-3-hydroxymethyl-benzyl]-2,2-dimethyl-propionamide A solution of 4-(3,3"-dimethyl-3',4',5',6'-tetrahydro-2'H-cis-[2,2';6',2"]terpyridin-1'-ylmethyl)-3-hydroxymethyl-benzonitrile (0.412 g, 1.00 mmol) in $NH_3$ saturated MeOH (20 mL) was treated with Raney nickel (500 mg) and placed under 50 psi $H_2$, on a Parr shaker, for 5 h. The mixture was filtered through Celite and the cake was washed with MeOH. The eluant was concentrated under reduced pressure. Purification of the crude material by column chromatography on silica gel (10:1:1 $CH_2Cl_2$—$CH_3OH$—$NH_4OH$) provided 0.371 g (89%) of [5-aminomethyl-2-(3,3"-dimethyl-3',4',5',6'-tetrahydro-2'H-[2,2';6',2"]terpyridin-1'-ylmethyl)-phenyl]-methanol as a white solid.

To a cold (0° C.) solution of [5-aminomethyl-2-(3,3"-dimethyl-3',4',5',6'-tetrahydro-2'H-cis-[2,2';6',2"]terpyridin-1'-ylmethyl)-phenyl]-methanol (126 mg, 0.30 mmol) in $CH_2Cl_2$ was added $Et_3N$ (0.08 mL, 0.58 mmol) followed by pivaloyl chloride (42 μL, 0.34 mmol). After 30 minutes, the reaction mixture was diluted with $CH_2Cl_2$ (20 mL), washed with brine (3×5 mL), dried ($Na_2SO_4$), and concentrated. Purification of the crude material by column chromatography on silica gel (20:1:1 $CH_2Cl_2$—$CH_3OH$—$NH_4OH$) gave COMPOUND 12 (111 mg, 67%) as a white solid. $^1$H NMR($CDCl_3$) δ 1.18 (s, 9H), 1.60-1.72 (m, 3H), 1.97-2.05 (m, 1H), 2.28-2.37 (m, 2H), 2.50 (s, 6H), 3.63 (s, 2H), 4.02 (d, 2H, J=10.8 Hz), 4.12 (d, 2H, J=5.4 Hz), 4.36 (s, 2H), 5.13 (br s, 1H), 5.58 (br s, 1H), 6.57 (d, 1H, J=7.5 Hz), 6.72 (d, 1H, J=7.5 Hz), 6.81-6.86 (m, 3H), 7.22-7.26 (m, 2H), 8.22 (d, 2H, J=4.2 Hz); $^{13}$C NMR ($CDCl_3$) δ 19.45, 25.70, 27.96, 29.57, 38.99, 43.53, 53.83, 63.01, 67.68, 122.10, 126.16, 128.78, 129.51, 131.92, 136.47, 138.02, 138.41, 139.29, 146.79, 160.01, 178.33; ES-MS m/z 501 ($M^+H$). Anal. Calcd. For $C_{31}H_{40}N_4O_2.0.6H_2O.0.4CH_2Cl_2$: C, 69.14; H, 7.76; N, 10.27. Found: C, 68.85; H, 7.74; N, 10.20.

EXAMPLE 13

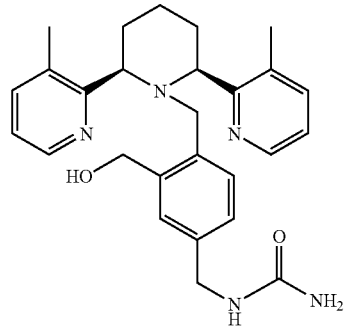

COMPOUND 13: [4-(3,3"-Dimethyl-3',4',5',6'-tetrahydro-2'H-cis-[2,2';6',2"]terpyridin-1'-ylmethyl)-3-hydroxymethyl-benzyl]-urea To a solution of [5-aminomethyl-2-(3,3"-dimethyl-3',4',5',6'-tetrahydro-2'H-cis-[2,2';6',2"]terpyridin-1'-ylmethyl)-phenyl]-methanol (98 mg, 0.24 mmol) in 2-propanol (4 mL) was added trimethylsilyl-isocyanate (30 μL, 0.22 mmol). The resultant solution was stirred at room temperature overnight then concentrated. Purification of the crude material by radial chromatography on silica gel (1 mm plate, 20:1:1 $CH_2Cl_2$—$CH_3OH$—$NH_4OH$) gave COMPOUND 13 (62 mg, 49%) as a white solid. $^1$H NMR($CDCl_3$) δ 1.60-1.71 (m, 3H), 1.99-2.05 (m, 1H), 2.22-2.31 (m, 2H), 2.48 (s, 6H), 3.58 (s, 2H), 3.97 (d, 2H, J=10.8 Hz), 4.06 (d, 2H, J=5.7 Hz), 4.33 (s, 2H), 4.68 (s, 2H), 5.28 (br s, 1H), 6.60 (d, 1H, J=7.8 Hz), 6.64 (d, 1H, J=7.8 Hz), 6.82-6.86 (m, 3H), 7.24 (d, 2H, J=7.8 Hz), 8.19 (d, 2H, J=3.3 Hz); $^{13}$C NMR ($CDCl_3$) δ 19.52, 25.64, 30.82, 43.99, 55.21, 62.78, 67.58, 122.29, 126.06, 128.12, 129.37, 131.60, 137.66, 138.47, 139.16, 146.89, 159.93; ES-MS m/z 460 ($M^+H$). Anal. Calcd. For $C_{27}H_{33}N_5O_2.0.9CH_2Cl_2$: C, 62.52; H, 6.54; N, 13.07. Found: C, 62.81; H, 6.56; N, 13.01.

EXAMPLE 14

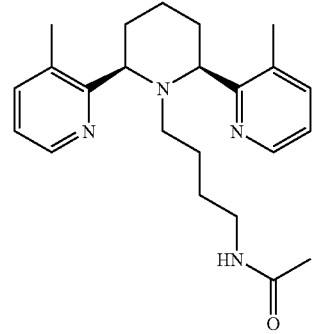

COMPOUND 14: N-[4-(3,3"-Dimethyl-3',4',5',6'-tetrahydro-2'H-cis-[2,2';6',2"]terpyridin-1'-yl)-butyl]-acetamide (HBr salt)

To a solution of COMPOUND 1 (hydrochloride salt) (99 mg, 0.21 mmol) in water (1 mL) was added 1.0 N NaOH (2 mL). The mixture was extracted with $CH_2Cl_2$ (4×10 mL). The combined organic extracts were dried ($Na_2SO_4$) and concentrated and provided 71 mg (99%) of the free base of COMPOUND 1. To a solution of the free base of COMPOUND 1 (99 mg, 0.21 mmol) in $CH_2Cl_2$ (4 mL) was added $Et_3N$ (90 µL, 0.65 mmol) followed by acetic anhydride (40 µL, 0.43 mmol). The resultant solution was stirred at room temperature for 90 minutes. The mixture was diluted with $CH_2Cl_2$ (20 mL), washed with brine (4×5 mL), dried ($Na_2SO_4$), and concentrated. Purification of the crude material by radial chromatography on silica gel (1 mm plate, 25:1:1 $CH_2Cl_2$—$CH_3OH$—$NH_4OH$) provided 72 mg (89%) of the free base of the title compound as a white foam.

Using General Procedure B: Conversion of the foam (72 mg) to the HBr salt, followed by reprecipitation of the intermediate solid from MeOH/ether gave COMPOUND 14 (107 mg, 78%) as a white solid. $^1H$ NMR($D_2O$) δ 1.01-1.22 (m, 4H), 1.45-1.57 (m 2H), 1.65-1.73 (m, 1H), 1.85 (s, 3H), 1.92-1.98 (m, 1H), 1.99-2.28 (m, 4H), 2.60 (s, 6H), 2.86 (t, 2H, J=6.3 Hz), 4.58 (dd, 2H, J=2.4, 11.1 Hz), 7.89 (dd, 2H, J=5.7, 8.1 Hz), 8.43 (d, 2H, J=8.1 Hz), 8.66 (d, 2H, J=5.7 Hz); $^{13}C$ NMR($D_2O$) δ 17.07, 20.23, 22.21, 22.45, 26.37, 32.57, 38.74, 53.05, 58.19, 125.98, 136.88, 139.69, 149.48, 154.92, 174.08; ES-MS m/z 381 ($M^+H$). Anal. Calcd. For $C_{23}H_{32}N_4O$·3.0HBr·1.8$H_2O$·1.2$CH_3CO_2H$: C, 41.92; H, 6.01; N, 7.70; Br, 32.94. Found: C, 42.04; H, 6.12; N, 7.71; Br, 32.86.

EXAMPLE 15

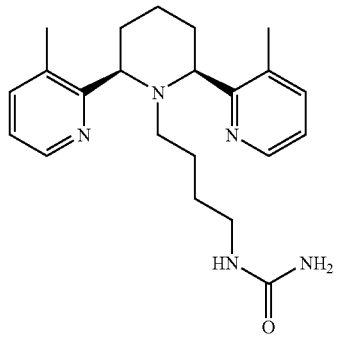

COMPOUND 15: [4-(3,3"-Dimethyl-3',4',5',6'-tetrahydro-2'H-cis-[2,2';6',2]terpyridin-1'-yl)-butyl]-urea (HBr salt)

To a solution of COMPOUND 1 free base (75 mg, 0.22 mmol) in 2-propanol (2 mL) was added trimethylsilyl-isocyanate (30 µL, 0.22 mmol). The resultant solution was stirred at room temperature overnight then concentrated. Purification of the crude material by radial chromatography on silica gel (1 mm plate, 20:1:1 $CH_2Cl_2$—$CH_3OH$—$NH_4OH$) provided 33 mg (40%) of the free base of the title compound as a white foam.

Using General Procedure B: Conversion of the white foam (33 mg) to the HBr salt, followed by reprecipitation of the intermediate solid from MeOH/ether gave COMPOUND 15 (42 mg, 28%) as a white solid. $^1H$ NMR($D_2O$) δ 1.04-1.27 (m, 4H), 1.48-1.60 (m, 2H), 1.67-1.80 (m, 2H), 1.94-2.00 (m, 1H), 2.09-2.27 (m, 4H), 2.62 (s, 6H), 2.80 (t, 2H, J=6.3 Hz), 4.61 (dd, 2H, J=2.7, 11.1 Hz), 7.91 (dd, 2H, J=6.0, 7.8 Hz), 8.44 (d, 2H, J=7.8 Hz), 8.67 (d, 2H, J=6.0 Hz); $^{13}C$ NMR ($D_2O$) δ 17.06, 20.00, 22.44, 26.92, 32.58, 39.03, 53.14, 58.28, 125.95, 136.89, 139.67, 149.45, 154.92; ES-MS m/z 382 ($M^+H$). Anal. Calcd. For $C_{22}H_{31}$ $N_5O$·3.1HBr·2.4$H_2O$·0.4$CH_3CH_2OCH_2CH_3$: C, 40.19; H, 6.13; N, 9.93; Br, 35.12. Found: C, 40.45; H, 6.05; N, 9.92; Br, 34.78.

EXAMPLE 16

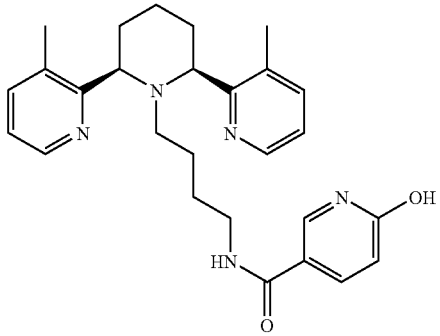

COMPOUND 16: N-[4-(3,3"-Dimethyl-3',4',5',6'-tetrahydro-2'H-cis-[2,2';6',2"]terpridin-1'-yl)-butyl]-6-hydroxy-nicotinamide (HBr salt)

To a solution of COMPOUND 1 free base (149 mg, 0.42 mmol) in dry DMF (4 mL) was added 6-hydroxy-nicotinic acid (80 mg, 0.57 mmol) followed by EDCI (113 mg, 0.59 mmol), HOBT (80 mg, 0.59 mmol), DMAP (10 mg, 0.09 mmol), and DIPEA (0.15 mL, 0.86 mmol). The resultant mixture was stirred at room temperature for 6 hours. The mixture was diluted with EtOAc (20 mL), brine (5 mL), and water (5 mL). The phases were separated and the organic phase was washed with brine (4×5 mL), dried ($MgSO_4$) and concentrated. Purification of the crude material by radial chromatography on silica gel (1 mm plate, 10:1:1 $CH_2Cl_2$—$CH_3OH$—$NH_4OH$) provided 69 mg (35%) of the free base of the title compound as a white foam.

Using General Procedure B: Conversion of the free base (59 mg) to the HBr salt followed by reprecipitation of the intermediate solid from MeOH/ether gave COMPOUND 16 (79 mg, 83%) as a white solid. $^1H$ NMR($D_2O$) δ 1.16-1.22 (m, 4H), 1.45-1.57 (m, 2H), 1.66-1.79 (m, 1H), 1.94-1.98 (m, 1H), 2.0-2.16 (m, 2H), 2.25-2.31 (m, 2H), 2.55 (s, 6H), 3.09-3.13 (m, 2H), 4.59 (dd, 2H, J=11.4, 3.0 Hz), 6.71 (d, 1H, J=9.3 Hz), 7.84-8.01 (m, 4H), 8.34 (d, 2H, J=7.5 Hz), 8.67 (d, 2H, J=5.1 Hz) $^{13}C$ NMR($D_2O$) δ 17.02, 20.19, 22.41, 26.47, 32.55, 38.84, 53.23, 58.29, 115.50, 119.43, 125.91, 136.75, 137.50, 139.72, 140.90, 149.32, 154.94, 165.47, 166.89; ES-MS m/z 460 ($M^+H$). Anal. Calcd. For $C_{27}H_{33}N_5O_2$·3.0HBr·2.5$H_2O$: C, 43.39; H, 5.53; N, 9.37; Br, 32.07. Found: C, 43.33; H, 5.54; N, 9.31; Br, 32.11.

EXAMPLE 17

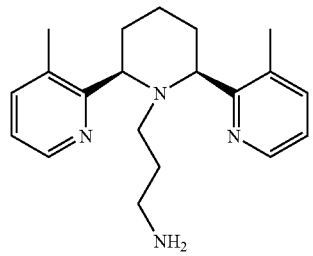

COMPOUND 17: meso-2'β,6'β-[3-(3,3"-dimethyl-3', 4'5',6'-tetrahydro-2'H-cis-[2,2';6',2"]terpyridin-1'-yl-propylamine]

To a solution of dibromopropane (0.61 mL, 6.0 mmol) in DMF (8 mL) was added potassium phthalimide (0.2756 g, 1.5 mmol), and was stirred at 90° C. for 17 hours. The mixture was concentrated, 1N NaOH (10 mL) was added, and extracted with $CH_2Cl_2$ (2×30 mL). The combined organic extracts were washed with water (1×15 mL), dried ($Na_2SO_4$), and concentrated. Purification of the crude material by column chromatography on silica gel (4:1 hexanes-EtOAc) provided 0.1977 g (49%) of 2-(3-bromo-propyl)-isoindole-1,3-dione as a white solid. $^1$H NMR(CDCl$_3$) δ 2.21-2.30 (m, 2H), 3.41 (t, 2H, J=6.0 Hz), 3.83 (t, 2H, J=6.0 Hz), 7.69-7.75 (m, 2H), 7.82-7.86 (m, 2H).

Following General Procedure A: A mixture of meso-2',6'-[3,3"-dimethyl-1',2',3',4',5',6'-hexahydro-cis-[2,2';6'2"]terpyridine] (0.1796 g, 0.67 mmol), 2-(3-bromo-propyl)-isoindole-1,3-dione (0.1977 g, 0.74 mmol), KI (0.0116 g, 0.07 mmol), DIPEA (0.23 mL, 1.34 mmol), and DMF (6.7 mL) were stirred at 60° C. for 18 hours. Purification of the crude material by column chromatography on silica gel (33:1:1 $CH_2Cl_2$—MeOH—$NH_4OH$) provided 0.2823 g (93%) of meso-2',6'-[2-[3-(3,3"-dimethyl-3',4',5',6'-tetrahydro-2'H-[2,2';6'2"]terpyridin-1'-yl)-propyl]-isoindole-1,3-dione] as an orange foam. $^1$H NMR(CDCl$_3$) δ 1.55-1.64 (m, 2H), 1.86-1.95 (m, 2H), 2.28-2.30 (m, 2H), 2.46-2.48 (m, 4H), 2.88-2.95 (m, 2H), 4.00-4.05 (m, 2H), 6.87-6.88 (m, 2H), 7.23-7.25 (m, 2H), 7.67-7.73 (m, 4H), 8.29-8.30 (m, 2H).

To a solution of meso-2',6'-[2-[3-(3,3"-dimethyl-3',4',5',6'-tetrahydro-2'H-cis-[2,2';6'2"]terpyridin-1'-yl)-propyl]-isoindole-1,3-dione](0.2823 g, 0.62 mmol) in EtOH (6.2 mL) was added hydrazine monohydrate (0.30 mL, 6.21 mmol), and stirred at room temperature for 16 hours. The reaction mixture was concentrated, and purification of the crude material by column chromatography on silica gel (25:1:1 then 12:1:1 $CH_2Cl_2$—MeOH—$NH_4OH$) provided 0.1606 g (80%) of COMPOUND 17 as a pale yellow sticky oil. $^1$H NMR (CDCl$_3$) δ 0.69 (s, 1H), 1.53-1.66 (m, 3H), 2.01-2.02 (m, 5H), 2.29-2.30 (m, 2H), 2.52 (s, 6H), 2.52-2.53 (m, 1H), 4.04 (d, 2H, J=9.9 Hz), 7.04-7.08 (m, 2H), 7.41 (d, 2H, J=7.5 Hz), 8.43 (s, 2H). $^{13}$C NMR(CDCl$_3$) δ 19.03, 25.48, 29.67, 40.13, 46.71, 64.73, 71.53, 122.18, 131.97, 138.63, 146.81, 160.45. ES-MS m/z 325.4 (M$^+$H). Anal. Calcd. for $C_{20}H_{28}N_4 \cdot 0.7CH_2Cl_2$: C, 64.76; H, 7.72; N, 14.59. Found: C, 64.51; H, 7.96; N, 14.65.

EXAMPLE 18

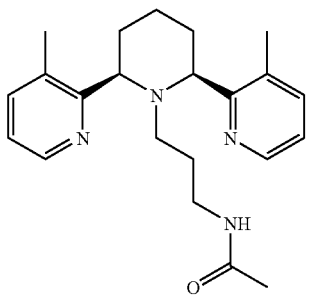

COMPOUND 18: N-[3-(3,3"-Dimethyl-3',4',5',6'-tetrahydro-2'H-cis-[2,2';6',2"]terpyridin-1'-yl)-propyl]-acetamide (HBr salt)

To a solution of COMPOUND 17 (0.118 g, 0.36 mmol) in $CH_2Cl_2$ (7 mL) was added Et$_3$N (0.15 mL, 1.08 mmol) followed by acetic anhydride (0.07 mL, 0.75 mmol). The resultant solution was stirred at room temperature overnight. The mixture was diluted with $CH_2Cl_2$ (30 mL), washed with brine (3×10 mL), dried ($Na_2SO_4$), and concentrated. Purification of the crude material by radial chromatography on silica gel (1 mm plate, 20:1:1 $CH_2Cl_2$—$CH_3OH$—$NH_4OH$) provided 105 mg (79%) of the free base of the title compound as a colorless oil.

Using General Procedure B: Conversion of the oil (27 mg) to the HBr salt gave COMPOUND 18 (172 mg, 93%) as a white solid. $^1$H NMR(D$_2$O) δ 1.23-1.63 (m, 8H), 1.79-1.84 (m, 1H), 1.98-2.08 (m, 4H), 2.45 (s, 6H), 2.60 (t, 2H, J=6.0 Hz), 4.43 (dd, 2H, J=3.0, 11.1 Hz), 7.79 (dd, 2H, J=6.0, 8.1 Hz), 8.31 (d, 2H, J=8.1 Hz), 8.53 (d, 2H, J=6.0 Hz); $^{13}$C NMR(D$_2$O) δ 17.05, 22.03, 22.40, 23.05, 32.49, 37.00, 50.27, 58.04, 126.07, 136.95, 139.92, 149.40, 154.66, 180.52; ES-MS m/z 367 (M$^+$H). Anal. Calcd. For $C_{22}H_{30}N_4O \cdot 3.0HBr \cdot 1.8H_2O$: C, 41.18; H, 5.75; N, 8.73; Br, 37.36. Found: C, 41.22; H, 5.65; N, 8.50; Br, 37.40.

EXAMPLE 19

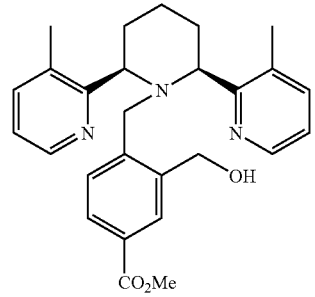

COMPOUND 19: 4-(3,3"-Dimethyl-3',4'5',6'-tetrahydro-2'H-cis-[2,2',6',2"]terpyridin-1'-ylmethyl)-3-hydroxymethyl-benzoic acid methyl ester To a solution of 4-(3,3"-dimethyl-3',4',5',6'-tetrahydro-2'H-cis-[2,2';6',2"]terpyridin-1'-ylmethyl)-3-hydroxymethyl-benzoic acid (0.107 g, 0.25 mmol) in MeOH (10 mL) was added concentrated H2SO$_4$ (0.5 mL) and the mixture was heated to reflux overnight. The mixture was cooled to room temperature and concentrated under reduced pressure. The residue was dissolved in $CH_2Cl_2$ (30 mL) and saturated aqueous $Na_2CO_3$ (10 mL). The phases were separated and the aqueous phase was extracted with $CH_2Cl_2$ (3×10 mL). The combined organic extracts were dried ($Na_2SO_4$) and concentrated. Purification of the crude material by radial chromatography on silica gel (1 mm plate, 50:1:1 $CH_2Cl_2$—$CH_3OH$—$NH_4OH$) gave COMPOUND 19 (86 mg, 75%) as a white solid. $^1$H NMR(CDCl$_3$) δ 1.60-1.77(m, 3H), 2.07-2.11 (m, 1H), 2.34-2.46 (m, 2H), 2.51 (s, 6H), 3.72 (s, 2H), 3.81 (s, 3H), 4.10 (d, 2H, J=12.0 Hz), 4.44 (s, 2H), 4.90 (br s, 1H), 6.82-6.87 (m, 3H), 7.23 (d, 2H, J=7.5 Hz), 7.34 (d, 1H, J=9.0 Hz), 7.59 (s, 1H), 8.21 (d, 2H, J=3.9 Hz); $^{13}$C NMR(CDCl$_3$) δ 19.38, 25.69, 29.11, 52.20, 53.05, 62.82, 67.35, 122.41, 127.86, 128.01, 128.93, 130.27, 131.99, 138.50, 138.92, 144.87, 146.82, 159.60, 167.35; ES-MS m/z 446 (M$^+$H).

Anal. Calcd. For $C_{27}H_{31}N_3O_3 \cdot 0.2CH_2Cl_2$: C, 70.63; H, 6.84; N, 9.08. Found: C, 70.61; H, 6.95; N, 8.91.

EXAMPLE 20

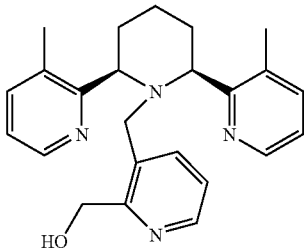

COMPOUND 20: [3-(3,3"-Dimethyl-3',4',5',6'-tetrahydro-2'H-cis-[2,2';6',2"]terpyridin-1'-ylmethyl)-pyridin-2-yl]-methanol To a solution of 3-methylpicolinonitrile (700 mg, 5.93 mmol) in $CCl_4$ (15 mL) was added recrystallized N-bromosuccinimide (1.21 g, 6.82 mmol), followed by glacial HOAc (0.34 mL, 1.0 eq), and AIBN (97 mg, 0.60 mmol). The resultant mixture was heated to 65° C. for 3 hours, 80° C. for 2 hours, and then cooled to room temperature. The mixture was filtered through filter paper, and the filtrate was concentrated. Purification of the crude material by flash chromatography (Hexanes/EtOAc, 90:10 followed by 80:20) provided 3-bromomethyl-pyridine-2-carbonitrile (250 mg, 21%) as a white solid. $^1$H NMR(CDCl$_3$) δ 4.63 (s, 2H), 7.55 (dd, 1H, J=8.0, 4.6 Hz), 7.93 (dd, 1H, J=7.9, 1.2 Hz), 8.64 (dd, 1H, J=4.8, 1.4 Hz).

Using General Procedure A: A solution of 3,3"-dimethyl-1',2',3',4',5',6'-hexahydro-cis-[2,2';6',2"]terpyridine (0.104 g, 0.39 mmol), 3-Bromomethyl-pyridine-2-carbonitrile (0.115 g, 0.58 mmol), KI (23 mg, 0.14 mmol), and DIPEA (0.15 mL, 0.86 mmol) in DMF (4 mL) was heated at 60° C. for 20 hours. Purification of the crude material by column chromatography on silica gel (20:1:1 $CH_2Cl_2$—$CH_3OH$—$NH_4OH$) provided 133 mg (88%) of 3-(3,3 "-Dimethyl-3',4',5',6'-tetrahydro-2'H-cis-[2,2';6',2"]terpyridin-1'-ylmethyl)-pyridine-2-carbonitrile as a tan solid.

To a solution of 3-(3,3"-dimethyl-3',4',5',6'-tetrahydro-2'H-cis-[2,2';6',2"]terpyridin-1'-ylmethyl)-pyridine-2-carbonitrile (0.127 g, 0.33 mmol) in MeOH (3 mL) was added water (3 mL) and solid NaOH (0.120 g, 2.99 mmol). The resultant mixture was heated to reflux overnight then cooled to room temperature. The mixture was adjusted to pH 4 with 3 N HCl (~1 mL) and extracted with $CH_2Cl_2$ (5×10 mL). The combined organic extracts were dried ($Na_2SO_4$) and concentrated and provided 0.14 g of a white solid. The white solid (0.14 g) was dissolved in MeOH (10 mL), treated with concentrated $H_2SO_4$ (0.5 mL) and heated to reflux overnight. The mixture was cooled to room temperature and concentrated under reduced pressure. The residue was dissolved in $CH_2Cl_2$ (20 mL) and saturated aqueous $Na_2CO_3$ (5 mL). The phases were separated and the aqueous phase was extracted with $CH_2Cl_2$ (3×10 mL). The combined organic extracts were dried ($Na_2SO_4$) and concentrated. Purification of the crude material by radial chromatography on silica gel (1 mm plate, 20:1:1 $CH_2Cl_2$—$CH_3OH$—$NH_4OH$) gave 72.0 mg (52%) of 3-(3,3"-dimethyl-3',4',5',6'-tetrahydro-2'H-cis-[2,2';6',2"]terpyridin-1'-ylmethyl)-pyridine-2-carboxylic acid methyl ester as a white solid.

To a cold (0° C.) solution of 3-(3,3"-dimethyl-3',4',5',6'-tetrahydro-2'H-cis-[2,2';6',2"]terpyridin-1'-ylmethyl)-pyridine-2-carboxylic acid methyl ester (72 mg, 0.17 mmol) in THF (2 mL) and MeOH (2 mL) was added LiBH$_4$ (75 mg, 3.45 mmol) and the mixture was allowed to warm to room temperature overnight. The mixture was diluted with 1.0 N NaOH (10 mL) and extracted with $CH_2Cl_2$ (5×10 mL). The combined organic extracts were dried ($Na_2SO_4$) and concentrated. Purification of the crude material by column chromatography on silica gel (25:1:1 $CH_2Cl_2$—$CH_3OH$—$NH_4OH$) gave COMEPOUND 20 (50 mg, 74%) as a white solid. $^1$H NMR(CDCl$_3$) δ 1.65-1.78 (m, 3H), 2.12-2.14 (m, 1H), 2.33-2.48 (m, 8H), 3.49 (s, 2H), 4.21 (d, 2H, J=11.1 Hz), 4.29 (s, 2H), 4.66 (br s, 1H), 6.74 (dd, 1H, J=4.8, 7.5 Hz), 6.86 (dd, 2H, J=4.5, 7.5 Hz), 7.20 (d, 2H, J=7.5 Hz), 7.45 (d, 1H, J=7.5 Hz), 7.96 (d, 1H, J=4.5 Hz), 8.28 (d, 2H, J=4.5 Hz); $^{13}$C NMR(CDCl$_3$) δ19.15, 25.70, 27.29, 46.27, 61.30, 66.87, 121.16, 122.46, 132.32, 133.57, 136.63, 138.18, 144.84, 146.78, 154.48, 159.25; ES-MS m/z 389 (M$^+$H). Anal. Calcd. For $C_{24}H_{28}N_4O \cdot 0.3H_2O$: C, 73.18; H, 7.32; N, 14.22. Found: C 73.17; H, 7.23; N, 14.17.

EXAMPLE 21

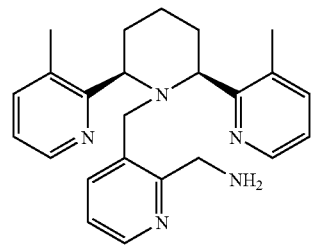

COMPOUND 21: C-[3-(3,3"-Dimethyl-3',4'5',6'-tetrahydro-2'H-cis-[2,2';6',2"]terpyridin-1'-ylmethyl)-pyridin-2-yl]-methylamine (HBr salt)

A solution of 3-(3,3"-dimethyl-3,4,5',6'-tetrahydro-2'H-cis-[2,2';6',2"]terpyridin-1'-ylmethyl)-pyridine-2-carbonitrile (0.161 g, 0.42 mmol) in $NH_3$ saturated MeOH (8 mL) was treated with Raney nickel (80 mg) and placed under 50 psi $H_2$, on a Parr shaker, for 19 h. The mixture was filtered through Celite and the cake was washed with MeOH. The eluant was concentrated under reduced pressure. Purification of the crude material by radial chromatography on silica gel (1 mm plate, 20:1:1 $CH_2Cl_2$—$CH_3OH$—$NH_4OH$) provided 109 mg (67%) of the free base of the title compound as a white solid.

Using General Procedure B: Conversion of the white solid (101 mg) to the HBr salt gave COMPOUND 21 (194 mg, 94%) as a white solid. $^1$H NMR(D$_2$O) δ 1.55-1.86 (m, 3H), 1.99-2.08 (m, 1H), 2.17-2.22 (m, 2H), 2.56 (s, 6H), 3.79 (s, 2H), 4.07 (s, 2H), 4.59 (d, 2H J=9.0 Hz), 7.16 (dd, 1H, J=7.5, 4.5 Hz), 7.60 (d, 1H, J=7.5 Hz), 7.77 (dd, 2H, J=7.8, 5.7 Hz),8.19 (d, 1H, J=4.5 Hz),8.31 (d, 2H, J=7.8 Hz), 8.62 (d, 2H, J=5.7 Hz); $^{13}$C NMR (D$_2$O) δ 17.35, 22.25, 33.09, 40.58, 57.76, 61.98, 124.19, 126.25, 130.22, 136.94, 139.65, 140.10, 149.19, 149.37, 149.67, 154.93; ES-MS m/z 388

EXAMPLE 22

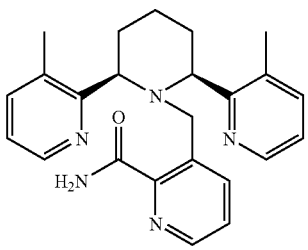

COMPOUND 22: 3-(3,3"-Dimethyl-3',4',5',6'-tetrahydro-2'H-cis-[2,2';6',2"]terpyridin-1'-ylmethyl)-pyridine-2-carboxylic acid amide To a solution of 3 N NaOH (0.76 mL, 2.28 mmol) and 50% $H_2O_2$ (0.06 mL, 1.04 mmol) in MeOH (1 mL) was added a solution of 3-(3,3"-dimethyl-3',4',5',6'-tetrahydro-2'H-cis-[2,2';6',2"]terpyridin-1'-ylmethyl)-pyridine-2-carbonitrile (0.175 g, 0.46 mmol) in MeOH (4 mL). The resultant mixture was heated at 60° C. for 6 hours and cooled to room temperature. The mixture was diluted with brine (10 mL) and extracted with $CH_2Cl_2$ (4×15 mL). The combined organic extracts were dried ($Na_2SO_4$) and concentrated. Purification of the crude material by column chromatography on silica gel (25:1:1 $CH_2Cl_2$—$CH_3OH$—$NH_4OH$) gave COMPOUND 22 (138 mg, 75%) as a white solid. $^1H$ NMR($CDCl_3$) δ 1.61-1.71 (m, 3H), 1.97-2.03 (m, 1H), 2.22-2.34 (m, 2H), 2.43 (s, 6H), 4.05-4.10 (m, 4H), 5.27 (br s, 1H), 6.80 (dd, 2H, J=4.8, 7.5 Hz), 7.09 (dd, 1H, J=4.8, 7.5 Hz), 7.21 (d, 2H, J=7.5 Hz), 7.51 (br s, 1H), 7.95 (d, 1H, J=4.8 Hz), 8.22 (d, 2H, J=3.3 Hz), 8.40 (d, 1H, J=7.8 Hz); $^{13}C$ NMR($CDCl_3$) δ 19.51, 25.33, 31.27, 52.74, 53.85, 67.03, 121.91.124.85, 131.56, 138.21, 139.60, 141.42, 145.07, 147.19, 160.26, 169.19; ES-MS m/z 402 ($M^+H$). Anal. Calcd. For $C_{24}H_{27}N_5O.0.3H_2O$: C, 70.84; H, 6.84; N, 17.21. Found: C, 70.85; H, 6.74; N, 17.16.

EXAMPLE 23

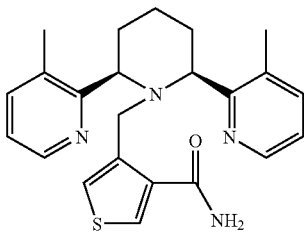

COMPOUND 23: 4-(3,3"-Dimethyl-3',4'5',6'-tetrahydro-2'H-cis-[2,2';6',2"]terpyridin-1'-ylmethyl)-thiophene-3-carboxylic acid amide Using General Procedure A: A solution of 3,3"-dimethyl-1',2',3',4',5',6'-hexahydro-cis-[2,2';6',2"]terpyridine (0.097 g, 0.37 mmol), 4-Bromomethyl-thiophene-3-carbonitrile (0.168 g, 0.83 mmol) (Terpstra, J. W., et al., *J. Org. Chem.* (1986) 51:230-238), KI (21 mg, 0.13 mmol), and DIPEA (0.15 mL, 0.86 mmol) in DMF (3 mL) was heated at 60° C. for 21 hours. Purification of the crude material by column chromatography on silica gel (20:1:1 $CH_2Cl_2$—$CH_3OH$—$NH_4OH$) provided 118 mg (84%) of 4-(3,3"-dimethyl-3',4',5',6'-tetrahydro-2'H-[2,2';6',2"]terpyridin-1'-ylmethyl)-thiophene-3-carbonitrile as a tan solid.

To a solution of 4-(3,3"-dimethyl-3',4',5',6'-tetrahydro-2'H-cis-[2,2';6',2"]terpyridin-1'-ylmethyl)-thiophene-3-carbonitrile (0.118 g, 0.30 mmol) in MeOH (3 mL) was added water (3 mL) and solid NaOH (0.109 g, 2.72 mmol). The resultant mixture was heated to reflux overnight then cooled to room temperature. The mixture was adjusted to pH ~4 with 3 N HCl (~1 mL) and extracted with $CH_2Cl_2$ (5×10 mL). The combined organic extracts were dried ($Na_2SO_4$) and concentrated and provided 0.12 g of a tan solid. The tan solid (0.12 g) was dissolved in MeOH (10 mL), treated with concentrated $H_2SO_4$ (0.5 mL) and heated to reflux overnight. The mixture was cooled to room temperature and concentrated under reduced pressure. The residue was dissolved in $CH_2Cl_2$ (20 mL) and saturated aqueous $Na_2CO_3$ (5 mL). The phases were separated and the aqueous phase was extracted with $CH_2Cl_2$ (3×10 mL). The combined organic extracts were dried ($Na_2SO_4$) and concentrated. Purification of the crude material by radial chromatography on silica gel (1 mm plate, 25:1:1 $CH_2Cl_2$—$CH_3OH$—$NH_4OH$) gave COMPOUND 23 (43 mg, 31%) as a white solid. $^1H$ NMR($CDCl_3$) δ 1.53-1.64 (m, 1H), 1.69-1.74 (m, 2H), 1.91-1.98 (m, 1H), 2.08-2.22 (m, 2H), 2.34 (s, 6H), 3.56 (s, 2H), 3.82 (dd, 2H, J=11.4, 3.0 Hz), 5.55 (br s, 1H), 6.84-6.91 (m, 3H), 7.22 (d, 2H, J=7.5 Hz), 7.47 (d, 1H, J=2.7 Hz), 8.36 (d, 2H, J=3.6 Hz), 9.27 (br s, 1H); $^{13}C$ NMR($CDCl_3$) δ 19.34, 24.65, 33.00, 56.95, 66.39, 122.27, 125.11, 130.22, 132.84, 136.92, 137.16, 138.35, 147.33, 160.54, 164.99; ES-MS m/z 407 ($M^+H$). Anal. Calcd. For $C_{23}H_{26}N_4OS.0.5CH_2Cl_2$: C, 62.86; H, 6.06; N, 12.48; S, 7.14. Found: C, 63.08; H, 6.36; N, 12.31; S, 6.94.

EXAMPLE 24

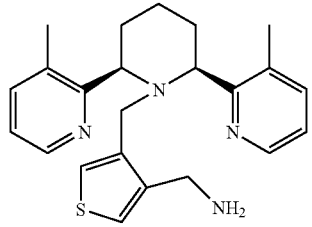

COMPOUND 24: C-[4-(3,3"-Dimethyl-3',4',5',6'-tetrahydro-2'H-cis-[2,2';6',2"]teroyridin-1'-ylmethyl) thiophen-3-yl]-methylamine (HBr salt)

To a cold (0° C.) mixture of $LiAlH_4$ (131 mg, 3.46 mmol) in dry THF (3 mL) was added 4-(3,3"-dimethyl-3',4',5',6'-tetrahydro-2'H-cis-[2,2';6',2"]terpyridin-1'-ylmethyl-thiophene-3-carbonitrile (129 mg, 0.33 mmol) as a solution in THF (6 mL). The resultant mixture was stirred at room temperature for 6 hours then cooled in an ice water bath. The mixture was treated with saturated aqueous sodium-potassium tartrate (2 mL) and diluted with THF (10 mL). The mixture was treated with solid Na$_2$SO$_4$ (2 scoops) and filtered through filter paper. The eluant was concentrated and the thus obtained material was purified by radial chromatography on silica gel (1 mm plate, 20:1:1 CH$_2$Cl$_2$—CH$_3$OH—NH$_4$OH) and provided 47 mg (35%) of the free base of the title compound as a white foam.

Using General Procedure B: Conversion of the white foam (47 mg) to the HBr salt gave COMPOUND 24 (69 mg, 84%) as a white solid. $^1$H NMR(D$_2$O) δ 1.49-1.61 (m, 2H), 1.68-1.78 (m, 1H), 1.95-2.01 (m, 1H), 2.14-2.19 (m, 2H), 2.53 (s, 6H), 3.70 (s, 4H), 4.52 (dd, 2H, J=12.0, 3.0 Hz), 7.11 (d, 1H, J=3.0 Hz), 7.36 (d, 1H, J=3.0 Hz), 7.78 (dd, 2H, J=7.8, 6.0 Hz), 8.32 (d, 2H, J=7.8 Hz), 8.60 (d, 2H, J=6.0 Hz); $^{13}$C NMR(D$_2$O) δ 17.23, 22.24, 32.93, 36.10, 54.38, 61.57, 125.91, 128.31, 128.68, 131.57, 134.97, 136.57, 139.45, 149.23, 155.44; ES-MS m/z 393 (M$^+$H). Anal. Calcd. For C$_{23}$H$_{28}$N$_4$S.3.2HBr.2.4H$_2$O: C, 39.76; H, 5.22; N, 8.06; Br, 36.81; S, 4.61. Found: C, 39.77; H, 5.12; N, 7.78; Br, 36.81; S, 4.48.

EXAMPLE 25

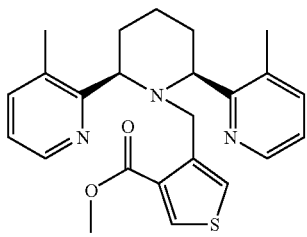

COMPOUND 25: 4-(3,3″-Dimethyl-3′,4′,5′,6′-tetrahydro-2′H-cis-[2,2′;6′,2″]terpyridin-1′-ylmethyl)-thiophene-3-carboxylic acid methyl ester A solution of 4-(3,3″-dimethyl-3′,4′,5′,6′-tetrahydro-2′H-cis-[2,2′;6′,2″]terpyridin-1′-ylmethyl)-thiophene-3-carbonitrile (0.120 g, 0.31 mmol) in MeOH (6 mL), treated with concentrated H$_2$SO$_4$ (0.5 mL) and concentrated HCl (0.5 mL) and the resultant solution was heated to reflux overnight. The mixture was cooled to room temperature and neutralized with 1.0 N NaOH (~10 mL). The mixture was extracted with CH$_2$Cl$_2$ (5×20 mL). The combined organic extracts were dried (Na$_2$SO$_4$) and concentrated. Purification of the crude material by radial chromatography on silica gel (1 mm plate, 50:1:1 CH$_2$Cl$_2$—CH$_3$OH—NH$_4$OH) gave COMPOUND 25 (50 mg, 39%) as a white solid. $^1$H NMR(CDCl$_3$) δ 1.51-1.70 (m, 3H), 1.92-1.99 (m, 1H), 2.12-2.25 (m, 2H), 2.34 (s, 6H), 3.66 (s, 3H), 3.81 (s, 2H), 4.03 (d, 2H, J=9.6 Hz), 6.90 (dd, 2H, J=4.8, 7.2 Hz), 7.24-7.27 (m, 2H), 7.37 (br s, 1H), 7.52 (d, 1H, J=3.3 Hz), 8.34 (d, 2H, J=4.8 Hz); $^{13}$C NMR(CDCl$_3$) δ 19.26, 25.57, 29.46, 47.58, 51.60, 66.60, 122.07, 124.99, 132.06, 132.42, 138.21, 139.75, 142.64, 146.85, 160.17, 163.50; ES-MS m/z 422 (M$^+$H). Anal. Calcd. For C$_{24}$H$_{27}$N$_3$O$_2$S.0.7H$_2$O: C, 66.39; H, 6.59; N, 9.68; S, 7.38. Found: C, 66.75; H, 6.74; N, 9.47; S, 7.11.

EXAMPLE 26

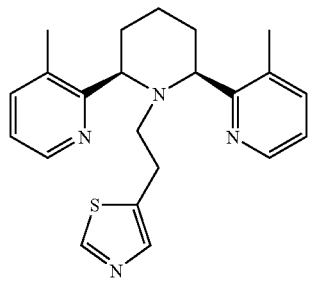

COMPOUND 26: The (2′R,6′S)-3,3″-dimethyl-1′-(2-thiazol-5-yl-ethyl)-1′,2′,3′,4′5′,6′-hexahydro-[2,2′;6′,2″]terpyridine (HBr salt)

A mixture of 5-methyl-thiazole (1.00 g, 10.1 mmol), NBS (2.06 g, 11.6 mmol) and 2,2′-azobisisobutyronitrile (0.164, 1.00 mmol) in CCl$_4$ (60 mL) was stirred and heated at reflux for 3 h. After the solution was cooled to room temperature NaS$_2$O$_3$ (5 g) in water (50 mL) was added, and the organic layer was collected. The aqueous layer was extracted with CH$_2$Cl$_2$ (3×60 mL). The organic layers were combined, washed with water (50 mL), and concentrated to ~150 mL by evaporation under vacuum. DMF (40 mL) and NaCN (1.00 g, 20.4 mmol) in water (20 mL) were then added, and the low boiling solvents (CH$_2$Cl$_2$ and CCl$_4$) were removed by evaporation under vacuum. The residue was then stirred overnight. Water (40 mL) was added, and the mixture was extracted with Et$_2$O (5×100 mL). The extracts were combined, washed with water (50 mL) and dried over Na$_2$SO$_4$. After filtration the solvent was removed by evaporation under vacuum, and the residue was purified by flash chromatography on a silica gel column (3:4 Et$_2$O/CH$_2$Cl$_2$) to afford thiazole-5-carbonitrile as a pale yellow liquid (0.550 g, 44%). $^1$H NMR(CDCl$_3$) δ 3.97 (s, 2H), 7.85 (s, 1H), 8.81 (s, 1H).

A suspension of thiazole-5-carbonitrile (0.550 g, 4.43 mmol) in aqueous NaOH (3 N, 20 mL) was stirred and heated at 50° C. for 2 h, and then cooed to room temperature. Aqueous HCl (4 N) was added to adjust the acidity of the solution to pH=~3, and the solution was extracted with EtOAc (10×50 mL). The extracts were combined and dried over Na$_2$SO$_4$. After filtration the solvent was removed by evaporation under vacuum to provide thiazol-5-yl-acetic acid as a pale yellow solid.

The solid was dissolved in dry THF (10 mL) and the solution was cooled to 0° C. BH$_3$ (1.0 M in THF, 10 mL, 10 mmol) was added slowly. After addition the mixture was stirred at room temperature for 20 h. MeOH (10 mL) was then added, and the mixture was heated at reflux for 2 h. At room temperature the mixture was concentrated by evaporation under vacuum, and the residue was purified by flash chromatography on a silica gel column ((EtOAc) to afford 2-thiazol-5-yl-ethanol as a pale yellow liquid (0.154 g, 27% two steps).

At 0° C., to a solution of 2-thiazol-5-yl-ethanol (0.154 g, 1.19 mmol) in CH$_2$Cl$_2$ (10 mL) was added MsCl (0.150 g, 1.31 mmol) and Et$_3$N (0.180 g, 1.79 mmol). The mixture was stirred at room temperature for 1 h. Water (20 mL) was added, and the mixture was extracted with CH$_2$Cl$_2$ (3×30 mL). The extracts were combined and dried over Na₂SO₄. After filtration the solvent was removed by evaporation under vacuum, and the residue was purified by flash chromatography on a silica gel column (EtOAc), affording methanesulfonic acid 2-thiazol-5-yl-ethyl ester as a pale yellow liquid (0.246 g, 100%). $^1$H NMR(CDCl₃) δ 2.99 (s, 3H), 3.33 (t, 2H, J=6.3 Hz), 4.42 (t, 2H, J=6.3 Hz), 7.73 (s, 1H), 8.74 (s, 1H).

A mixture of (2'R,6'S)-3,3''-dimethyl-1',2',3',4',5',6'-hexahydro-[2,2';6'2'']terpyridin (0.140 g, 0.523 mmol), methanesulfonic acid 2-thiazol-5-yl-ethyl ester (0.105 g, 0.505 mmol) and 2,2,6,6-tetramethylpiperidine (0.107 g, 0.758 mmol) in CH₃CN (2 mL) was stirred and heated at reflux overnight. The solvent was removed, saturated aqueous NaHCO₃ (10 mL) was added, and the mixture was extracted with CH₂Cl₂ (3×20 mL). The extracts were combined and dried over Na₂SO₄. After filtration the solvent was removed by evaporation under vacuum, and the residue was purified by flash chromatography on a silica gel column (500:25:1 CH₂Cl₂/CH₃OH/NH₄OH), affording a colorless oil (0.144 g, 75%).

Following General Procedure B the oil (0.115 g, 0.303 mmol) was treated with HBr/MeOH to afford an HBr salt as a yellow solid (0.210 g, 96%). $^1$H NMR(D₂O) δ 1.52-1.64 (2H), 1.72-1.86 (m, 1H), 1.95-2.00 (m, 1H), 2.17-2.22 (m, 2H), 2.59-2.70 (m, 8H), 3.07-3.13 (m, 2H), 4.70-4.76 (m, 2H), 7.78 (s, 1H), 7.92 (dd, 2H, J=5.4, 8.1 Hz), 8.45 (d, 2H, J=8.1 Hz), 8.70 (d, 2H, J=5.4 Hz), 9.65 (s, 1H); $^{13}$C NMR (D₂O) δ 17.41, 21.03, 22.35, 32.60, 52.84, 57.74, 126.34, 131.83, 137.08, 140.23, 140.77, 149.97, 153.75, 157.08. ES-MS m/z 379 (M⁺H). Anal. Calcd. for C₂₂H₂₆N₄S.3.6HBr.1.8H₂O.0.3C₄H₁₀O: C, 38.46; H, 5.04; N, 7.73; Br, 39.70; S, 4.43. Found: C, 38.46; H, 5.07; N, 7.66; Br, 39.63; S, 4.37.

EXAMPLE 27

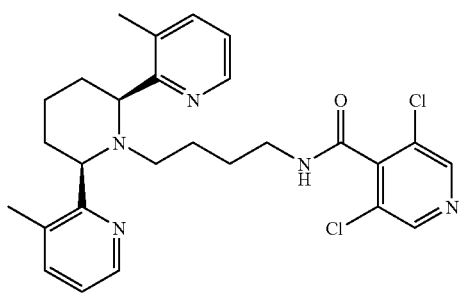

COMPOUND 27: 3,5-Dichloro-N-[4-(3,3''-dimethyl-3',4',5',6'-tetrahydro-2'H-cis-[2,2';6',2'']terpyridin-1'-yl)-butyl]-isonicotinamide COMPOUND 1(103 mg, 0.22 mmol) was neutralized with 1M NaOH (25 mL) and the free base was extracted with CHCl₃ (25 mL×3). The combined organic solution was dried (Na₂SO₄), filtered and concentrated under reduced pressure, giving the free base as a yellow oil (72 mg, 100%).

To a suspension of 3,5-dichloropyridine-4-carboxylic acid (89 mg, 0.46 mmol) and DMF (2 drops) in CH₂Cl₂ (4 mL) was added oxalyl chloride (0.12 mL, 1.4 mmol). The resulting suspension was stirred at room temperature under N₂ for 25 minutes, and then the solvent was evaporated under reduced pressure. The crude acid chloride was dried under reduced pressure, and then a solution of the free base in THF (4 mL), and NEt₃ (0.04 mL, 0.3 mmol) were added. The resulting suspension was stirred at room temperature under N₂ for 50 minutes. The reaction was diluted with saturated aqueous NaHCO₃ (25 mL) and extracted with CH₂Cl₂ (25 mL×3). The combined organic solution was dried (Na₂SO₄), filtered and concentrated under reduced pressure. Purification by flash column chromatography on silica (CH₂Cl₂/MeOH/NH₄OH, 19:1:0.2) gave the amide as a white foam (77.5 mg, 0.15 mmol, 68%). $^1$H NMR(MeOH-d₄) δ 0.82-0.97 (m, 3H), 1.60-1.78 (m, 3H), 1.95-2.18 (m, 3H), 2.22-2.34 (m, 2H), 2.55-2.78 (m, 6H), 2.83-3.01 (m, 3H), 3.91-4.21 (m, 2H), 7.16-7.28 (m, 2H), 7.62 (d, 2H, J=8.4 Hz), 8.24-8.38 (m, 2H), 8.56 (s, 2H). ES-MS m/z 512 (M⁺H), 514 (M⁺2⁺H). Anal. Calcd. for C₂₇H₃₁Cl₂N₅O.0.6CH₄O: C, 62.35; H, 6.33; N, 13.17; Cl, 13.34. Found: C, 62.03; H, 607; N, 13.42; Cl, 13.61.

EXAMPLE 28

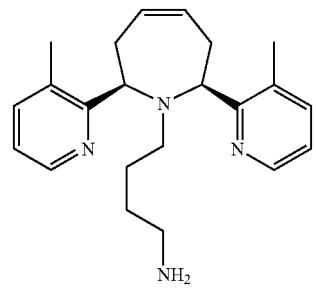

COMPOUND 28: 4-meso-[2,7-Bis-(3-methyl-pyridin-2-yl)-2,3,6,7-tetrahydroazepin-1-yl]butylamine 3-Methyl-2-pyridinecarboxaldehyde (2.42 g, 20 mmol) was dissolved in MeOH (100 mL, anhydrous) at room temperature. NH₄OAc (0.86 g, 11 mmol) was added and the mixture was stirred until all solids had dissolved. Indium powder (99.99%, −100 mesh, 1.84 g) was added in one portion, and then allyl bromide (1.9 mL, 22 mmol) was added drop-wise over 5 min. The mixture was left stirring at room temperature overnight under N₂, and then quenched with saturated NaHCO₃ (100 mL). Celite (5 g) was added and the mixture was filtered. The filter cake was rinsed with MeOH (50 mL) and CH₂Cl₂ (50 mL). The filtrate was concentrated on a rotary evaporator to remove most of the volatiles, and the residue was extracted with CH₂Cl₂. The combined extract was dried over Na₂SO₄, concentrated on a rotary evaporator, and purified by column chromatography using 200 mL silica and a gradient of 1:1 hexane-EtOAc to EtOAc as the eluent to give bis-[1-(3-methyl-pyridin-2-yl)-but-3-enyl]-amine as a light brown oil, 2.06 g (67%). $^1$H NMR δ (CDCl₃): 1.86 (s, 6H), 2.54-2.31 (m, 4H), 2.69 (br, 1H), 3.70 (t, 2H, J=7.5 Hz), 4.97-4.85 (m, 4H), 5.58 (m, 2H), 7.00 (dd, 2H, J=7.5, 4.5 Hz), 7.29 (dd, 2H, J=5, 0.9 Hz), 8.47 (dd, 2H, J=4.5, 0.9 Hz); $^{13}$C NMR δ (CDCl₃): 160.52, 147.07, 137.54, 135.15, 131.45, 121.36, 116.89, 56.31, 40.91, 17.99.

To a solution of bis-[1-(3-methyl-pyridin-2-yl)-but-3-enyl]-amine (1.40 g, 4.55 mmol), DIPEA (0.79 mL, 9.10 mmol) and catalytic DMAP in CH₂Cl₂ (20 mL) at room temperature was added TFAA (0.77 mL, 5.46 mmol). The reaction was complete in 15 minutes. The volatiles were removed in vacuo and the residue was purified by flash column chromatography on silica gel (4:1 hexanes:EtOAc⁺1% NH₄OH) to provide 1.01 g (55%) of 2,2,2-trifluoro-N,N-bis-

[1-(3-methyl-pyridine-2-yl)-but-3-enyl}-acetamide as a cream colored solid. $^1$H NMR(CDCl$_3$) δ 2.05 (br s, 3H), 2.20 (br s, 3H), 2.39 (br s, 1H), 2.52 (br s, 1H), 3.51-3.65 (m, 2H), 4.96-5.25 (m, 6H), 5.55 (br s, 1H), 5.84 (br s, 1H), 6.75 (br s, 2H), 6.86-6.93 (m, 2H), 8.15-8.21 (m, 2H); ES-MS m/z 426 (M$^+$Na$^+$), 404 (M$^+$H$^+$).

A solution of 2,2,2-trifluoro-N,N-bis-[1-(3-methyl-pyridine-2-yl)-but-3-enyl]-acetamide (1.00 g, 2.48 mmol) in toluene (70 mL) was purged with Ar under vigorous stirring. Grubb's catalyst (benzylidene bis(tricyclohexylphosphine) dichlororuthenium) (204 mg, 10 mol %) was added and the reaction mixture was heated to 60° C. for 4 hours. The progress of the reaction was monitored by TLC. Another batch of the catalyst (160 mg) was added and the reaction mixture was stirred for 2 days. The solvent was removed in vacuo and the residue was purified by column chromatography (5:1 hexanes:EtOAc) on silica gel to provide 76.1 mg (8%) of product (containing a small amount of a side-product) and 117.2 mg side-product containing 30% 1-[2,7-bis-(3-methyl-pyridin-2-yl)-2,3,6,7-tetrahydro-azepin-1-yl]-2,2,2-trifluoroethanone as well as 665 mg of recovered starting material. $^1$H NMR(CDCl$_3$) δ 2.31 (6H, s), 3.01-3.07 (m, 2H), 3.38 (dd, 2H, J=16.2, 4.2 Hz), 5.56 (s, 2H), 5.98 (br s, 2H), 7.07 (dd, 2H, J=7.5, 4.2 Hz), 7.40 (d, 2H, J=7.5 Hz), 8.35 (d, 2H, J=4.2 Hz); ES-MS m/z 376 (M$^+$H$^+$).

A solution of 1-[2,7-bis-(3-methyl-pyridin-2-yl)-2,3,6,7-tetrahydro-azepin-1-yl]-2,2,2-trifluoroethanone (73 mg, 0.194 mmol) was dissolved in MeOH (8 mL) and 6N HCl (2 mL) and was heated to 65° C. for 5 hours. The mixture turned black in color. The solvent was removed in vacuo and the residue was basified with 10 N NaOH solution. The mixture was extracted with CH$_2$Cl$_2$ (3×50 mL). The organic extracts were dried (MgSO4), filtered and concentrated. The residue was purified by radial chromatography (1 mm plate, 1:5 EtOAc:hexanes then EtOAc then 10:1 EtOAc/MeOH) to provide 30.2 mg of 2,7-bis-(3-methyl-pyridin-2-yl)-2,3,6,7-tetrahydro-1H-azepine. $^1$H NMR(CDCl$_3$) δ 2.29-2.36 (m 3H), 2.41 (6H, s), 3.04 (dd, 2H, J=16.2, 10.2 Hz), 5.15 (d, 2H, J=15.6 Hz), 5.81-5.90 (m, 2H), 7.04 (dd, 2H, J=7.5, 4.2 Hz), 7.43 (d, 2H, J=7.5 Hz), 8.35 (d, 2H, J=4.2 Hz).

A mixture of 2,7-bis-(3-methyl-pyridin-2-yl)-2,3,6,7-tetrahydro-1H-azepine (30.2 mg, 0.108 mmol), 2-(4-bromo-butyl)-isoindole-1,3-dione (33.5 mg, 0.119 mmol), DMF (3 mL), DIPEA (0.3 mL), and KI (4 mg) were heated to 110° C. for 4 h and overnight at 90° C. The solvent was removed and CH$_2$Cl$_2$ (20 mL) was added to the residue. It was washed with saturated NaHCO$_3$ (10 mL). The aqueous layer was extracted two more times with CH$_2$Cl$_2$. The organic layer was dried (MgSO4), filtered and concentrated. Purification of the crude material by radial chromatography on silica gel (1 mm plate, 2:1 hexanes:EtOAc) provided 13.3 mg of 2-{4-[2,7-bis-(3-methyl-pyridin-2-yl)-2,3,6,7-tetrahydro-azepin-1-yl]-butyl}-isoindole-1,3-dione as a film. $^1$H NMR(CDCl$_3$) δ 0.53-0.59 (m, 1H), 0.65-1.00 (m, 3H), 2.36 (s, 6H), 2.36-2.41 (m, 1H), 2.47-2.50 (m, 2H), 3.02-3.24 (m, 5H), 4.72 (dd, 2H, J=9.6, 1.8 Hz), 5.80-5.83 (m, 2H), 6.90 (dd, 2H, J=7.5, 4.2 Hz), 7.23 (d, 2H, J=7.5 Hz), 7.67-7.73 (m, 2H), 7.76-7.86 (m, 2H), 8.35 (d, 2H, J=4.2 Hz).

To a solution of 2-{4-[2,7-bis-(3-methyl-pyridin-2-yl)-2,3,6,7-tetrahydro-azepin-1-yl]-butyl}-isoindole-1,3-dione (13 mg, 0.027 mmol) in EtOH (2 mL) was added excess (10 eq) of n-butyl amine and the reaction mixture was stirred at reflux for 17 hours. The solvent was removed in vacuo and the residue was purified by radial chromatography (1 mm plate, 100:10:1 CH$_2$Cl$_2$—CH$_3$OH—NH$_4$OH) on silica gel to provide 3.8 mg (40%) of COMPOUND 28 as an oil. $^1$H NMR (CDCl$_3$) δ 0.51-0.59 (m, 1H), 0.65-0.87 (m, 3H), 1.00-1.25 (br, 3H), 2.14 (t, 2H, J=6.9 Hz), 2.37-2.46 (m, 3H), 2.46 (s, 6H), 2.47-2.53 (m, 1H), 3.05 (dt, 1H, J=13.5, 8.1 Hz), 4.77 (d, 2H, J=9.8 Hz), 5.83 (s, 2H), 7.02 (dd, 2H, J=4.8, 7.5 Hz), 7.36 (d, 2H, J=7.5 Hz), 8.40 (d, 2H, J=4.8 Hz); $^{13}$C NMR(CDCl$_3$) δ 19.0, 26.5, 31.3, 31.5, 42.1, 49.4, 62.5, 122.1, 129.7, 132.2, 138.3, 146.3, 161.9; ES-MS m/z 351 (M$^+$H).

EXAMPLE 29

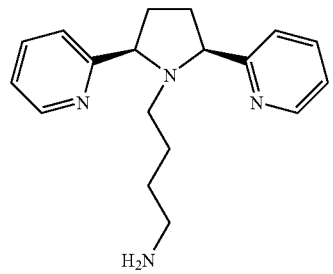

COMPOUND 29: Meso-cis-2',5'-[4-(2,5-di-pyridin-2-yl-pyrrolidin-1-yl)-butylamine]HBr salt To a solution of 2-pyridine carboxaldehyde (4.0 mL, 42.0 mmol) in EtOH (45 mL) purged with Ar, was added sodium acetate (1.1388 g, 8.4 mmol) and 3-benzyl-5-(2-hydroxy-ethyl)-4-methyl-1,3-thiazolium chloride (1.1323 g, 4.2 mmol), and was heated to reflux (80° C.) while stirring. Divinyl sulfone (2.1 mL, 21.0 mmol) was added dropwise over 30 minutes to the reaction (Tetrahedron (1996) 52, 26:8707-8724). The reaction mixture was stirred for 18 hours at 80° C., and then cooled to room temperature and concentrated. It was diluted with CH$_2$Cl$_2$ (300 mL) and water (100 mL), and the phases were separated. The aqueous phase was extracted with CH$_2$Cl$_2$ (3×200 mL), and the combined organic extracts were washed with brine (1×150 mL), dried (Na2SO$_4$), and concentrated. Purification of the crude material by column chromatography on silica gel (4:1 hexanes-EtOAc, and later MeOH) provided 1.18 g (23%) of 1,4-di-pyridin-2-yl-butane-1,4-dione as a beige solid. $^1$H NMR (CDCl$_3$) δ 3.70 (s, 4H), 7.48-7.50 (m, 2H), 7.83-7.84 (m, 2H), 8.03-8.06 (m, 2H), 8.71 (d, 2H, J=3.0 Hz).

Following General Procedure C: To a solution of 1,4-di-pyridin-2-yl-butane-1,4-dione (0.2049 g, 0.85 mmol) and NaBH(OAc)$_3$ (0.4584 g, 2.13 mmol) in CH$_2$Cl$_2$ (10 mL) was added dropwise over 2 hours a solution of (4-amino-butyl)-carbamic acid tert-butyl ester (0.1621 g, 0.85 mmol) in CH$_2$Cl$_2$ (5 mL), and was stirred for 19 hours at room temperature. Purification of the crude material by column chromatography on silica gel (100:1:1 CH$_2$Cl$_2$-MeOH—NH$_4$OH) followed by radial chromatography on silica gel (200: 1:1 CH$_2$Cl$_2$-MeOH—NH$_4$OH) provided 48.6 mg (14%) of meso-cis-2',5'-[4-(2,5-di-pyridin-2-yl-pyrrolidin-1- yl)-butyl]-carbamic acid tert-butyl ester as an orange oil. ¹H NMR(CDCl₃) δ 1.14-1.25 (m, 3H), 1.39 (s, 9H), 1.77 (s, 2H), 1.84-1.88 (m, 2H), 2.34-2.38 (m, 2H), 2.56-2.61 (m, 2H), 2.80 (t, 2H, J=6.0 Hz), 4.00-4.06 (m, 2H), 7.15-7.19 (m, 2H), 7.71-7.78 (m, 4H), 8.53 (d, 2H, J=3.0 Hz).

Following General Procedure B: meso-cis-2',5'-[4-(2,5-dipyridin-2-yl-pyrrolidin-1-yl)-butyl]-carbamic acid tert-butyl ester (0.0486 g, 0.12 mmol) was converted to the HBr salt followed by reprecipitation of the intermediate solid from MeOH/ether gave COMPOUND 29 (72.1 mg, 94%) as a yellow solid. ¹H NMR(D₂O) δ 1.33-1.35 (m, 2H), 1.43-1.46 (m, 2H), 2.04-2.05 (m, 2H), 2.63-2.64 (m, 2H), 2.75-2.85 (m, 4H), 3.33 (s, 1H), 4.68-4.70 (m, 3H), 7.95 (t, 2H, J=6.3 Hz), 8.13 (d, 2H, J=8.1 Hz), 8.50-8.55 (m, 2H), 8.76 (d, 2H, J=5.1 Hz), ¹³C NMR(D₂O) δ 24.26, 25.05, 33.18, 39.37, 53.34, 65.99, 126.67, 141.55, 147.80, 157.15. ES-MS m/z 297 (M⁺H). Anal. Calcd. for C₁₈H₂₄N₄.3.12HBr.2.88H₂O: C, 35.99; H, 5.52; N, 9.33; Br 41.49. Found: C, 36.07; H, 5.64; N, 9.04; Br, 41.50.

EXAMPLE 30

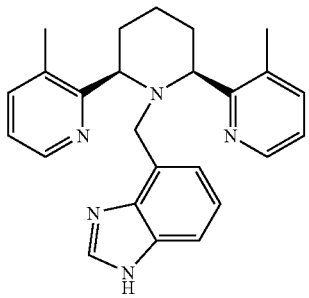

COMPOUND 30: The (2'R,6'S)-1'-(1H-benzoimidazol-4-ylmethyl)-3,3"-dimethyl-1',2',3',4',5',6'-hexahydro-[2,2':6',2"]terpyridine Following General Procedure A using (2'R,6'S)-3,3"-dimethyl-1',2',3',4',5',6'-hexahydro-[2,2':6',2"]terpyridine (0.134 g, 0.501 mmol), 4-bromomethyl-benzoimidazole-1-carboxylic carboxylic acid tert-butyl ester (0.168 g, 0.602 mmol), DIPEA (0.129 g, 1.00 mmol) and KI (0.0083 g, 0.050 mmol) in CH₃CN (5 mL). A white solid was obtained after purification by flash chromatography on a silica gel column (500:20:1 CH₂Cl₂/CH₃OH/NH₄OH).

The resulting white solid was treated with TFA (1 mL) in CH₂Cl₂ (2 mL) to remove the Boc protecting group. A white solid (0.109 g, 53% two steps) was obtained after purification by flash chromatography on a silica gel column (20:1:1 CH₂Cl₂/CH₃OH/NH₄OH). ¹H NMR(CDCl₃) δ 1.62-1.78 (m, 4H), 1.92-2.20 (m, 8H), 3.65 (s, br. 2H), 3.87-3.92 (m, 2H), 6.05 (s, br. 1H), 6.51 (t, 1H, J=8.1 Hz), 6.85 (s, br. 2H), 7.07 (s, br. 2H), 7.29 (d, 1H, J=8.1 Hz), 8.13 (s, 1H), 8.24 (s, br. 2H); ¹³C NMR(CDCl₃) δ 18.78, 25.14, 32.57 (br.), 59.28, 117.21, 120.40, 120.93, 122.21, 124.38, 131.97 (br.), 132.88, 138.51, 140.13, 142.48, 146.01, 160.24. ES-MS m/z 398 (M⁺Na). Anal. Calcd. for C₂₅H₂₇N₅.0.4CH₂Cl₂: C, 70.70; H, 6.49; N, 16.23. Found: C, 70.79; H, 6.61; N, 15.98.

EXAMPLE 31

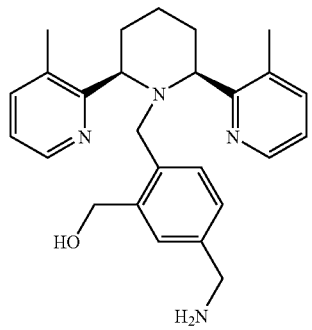

COMPOUND 31: Meso-2',6'-[5-aminomethyl-2-(3,3"-dimethyl-3',4',5',6'-tetrahydro-2'H-cis-[2,2';6',2"]terpyridin-1'-ylmethyl)-phenyl]-methanol Following General Procedure A: To a solution of meso-2',6'-[3,3"-dimethyl-1',2',3',4',5',6'-hexahydro-cis-[2,2';6'2"]terpyridine] (0.4647 g, 1.7 mmol) in DMF (17 mL) was added 2-bromomethyl-5-cyano-benzoic acid methyl ester (0.5035 g, 2.0 mmol), KI (0.0309 g, 0.2 mmol), and DIPEA (0.62 mL, 3.6 mmol). The mixture stirred at 60° C. for 23 hours before it was concentrated. Saturated NaHCO₃ (50 mL) was added and was extracted with CH₂Cl₂ (3×75 mL). The combined organic extracts were washed with brine (1×50 mL), dried (Na₂SO₄), and concentrated. Purification of the crude material by column chromatography on silica gel (33:1:1 CH₂Cl₂-MeOH—NH₄OH) provided 0.6284 g (82%) of meso-2',6'-[5-cyano-2-(3,3"-dimethyl-3',4',5',6'-tetrahydro-2'H-cis-[2,2';6'2"]terpyridin-1'-ylmethyl)-benzoic acid methyl ester] as an orange solid. ¹H NMR(CDCl₃) δ 1.61-1.74 (m, 3H), 2.06-2.10 (m, 1H), 2.26-2.38 (m, 2H), 2.44 (s, 6H), 3.85 (s, 3H), 3.98 (s, 2H), 4.14 (d, 2H, J=9.0 Hz), 6.83-6.88 (m, 2H), 7.19 (d, 2H, J=9.0 Hz), 7.34-7.38 (m, 1H), 7.56 (d, 1H, J=3.0 Hz), 7.90-7.93 (m, 1H), 8.22 (d, 2H, J=6.0 Hz).

To a solution of meso-2',6'-[5-cyano-2-(3,3"-dimethyl-3',4',5',6'-tetrahydro-2'H-cis-[2,2';6'2"]terpyridin-1'-ylmethyl)-benzoic acid methyl ester] (0.6284 g, 1.42 mmol) in MeOH (14 mL) under Ar was added LiBH₄ (0.3505 g, 14.2 mmol), and stirred at room temperature for 1 hour. The reaction mixture was concentrated, CH₂Cl₂ (50 mL) and 1N NaOH (15 mL) were added and separated, and the aqueous phase was extracted with CH₂Cl₂ (2×50 mL). The combined organic extracts were dried (Na₂SO₄), filtered, and concentrated to provided 0.5703 g (97%) of meso-2',6-[4-(3,3"-dimethyl-3',4',5',6'-tetrajudrp-2'H-cis-[2,2';6'2"]terpyridin-1'-ylmethyl)-3-hydroxymethylbenzonitrile] as a beige powder. ¹H NMR (CDCl₃) δ 1.62-1.76 (m, 3H), 2.32-2.43 (m, 3H), 2.50 (s, 6H), 3.70 (s, 2H), 4.12 (d, 2H, J=9.0 Hz), 4.45 (d, 2H, J=6.0 Hz), 6.83-6.96 (m, 4H), 7.17-7.24 (m, 3H), 8.21 (d, 2H, J=3.0 Hz). ¹³C NMR(CDCl₃) δ 19.26, 25.61, 28.03, 51.97, 61.64, 66.92, 109.29, 119.57, 122.28, 129.19, 129.68, 131.03, 132.28, 138.44, 139.92, 144.92, 146.59.

To Raney Nickel, which had been washed with MeOH, was added meso-2',6'-[4-(3,3"-dimethyl-3',4',5',6'-tetrahydro-2'H-cis-[2,2';6'2"]terpyridin-1'-ylmethyl)-3-hydroxymethyl-benzonitrile] (0.5703 g, 1.38 mmol) in MeOH (10 mL). $NH_{3(g)}$ was bubbled through the solution for 10 minutes, then placed on the hydrogenator at 40 psi for 22 hours. The resulting mixture was flushed with Ar and filtered through a plug of celite with $CH_2Cl_2$ and concentrated. Purification of the crude material by column chromatography on silica gel (25:1:1 $CH_2Cl_2$-MeOH—$NH_4OH$) provided 0.2823 g (49%) of COMPOUND 31 as a white solid. $^1H$ NMR($CDCl_3$) δ1.61-1.70 (m, 3H), 2.00-2.01 (m, 1H), 2.29-2.33 (m, 2H), 2.48 (s, 6H), 3.54 (s, 2H), 3.61 (s, 2H), 4.00 (d, 2H, J=12.0 Hz), 4.32 (s, 2H), 6.59 (d, 1H, J=6.0 Hz), 6.73 (d, 1H, J=6.0 Hz), 6.80-6.84 (m, 3H), 7.22 (d, 2H, J=6.0 Hz), 8.22 (d, 2H, J=3.0 Hz). $^{13}C$ NMR ($CDCl_3$) δ 19.32, 25.62, 29.36, 46.27, 52.37, 62.47, 67.08, 122.02, 125.09, 127.30, 129.26, 131.94, 137.32, 138.27, 139.23, 140.84, 146.61, 159.99. ES-MS m/z 417.3 ($M^+H$). Anal. Calcd. for $C_{26}H_{32}N_4O.0.3CH_2Cl_2.0.5H_2O$: C, 70.03; H, 7.51; N, 12.42. Found: C, 69.82; H, 7.55; N, 12.12.

EXAMPLE 32

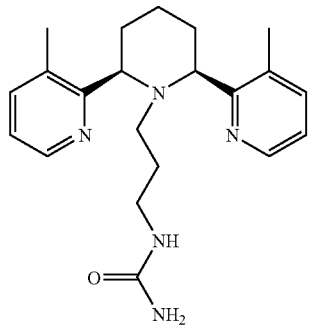

COMPOUND 32: Meso-2',6'-[3-(3,3"-dimethyl-3',4'5',6'-tetrahydro-2'H-cis-[2,2';6',2"]terpyridin-1'-yl)-propyl]-urea To a solution of meso-2',6'-[3-(3,3"-dimethyl-3',4',5',6'-tetrahydro-2'H-cis-[2,2';6',2"]terpyridin-1'-yl)-propylamine] (0.0869 g, 0.27 mmol), in 2-propanol (3 mL) was added trimethyl isocyanate (0.15 mL, 1.11 mmol), and the mixture was stirred at room temperature for 18 hours. The mixture was concentrated, and purification of the crude material by column chromatography on silica gel (25:2:1 then 16:1:1 $CH_2Cl_2$-MeOH—$NH_4OH$) provided 0.0697 g (64%) of COMPOUND 32 as a white solid. $^1H$ NMR($CDCl_3$) δ 1.56-1.68 (m, 3H), 1.97-2.00 (m, 1H), 2.12-2.17 (m, 2H), 2.34-2.47 (m, 4H), 2.49 (s, 6H), 3.65 (s, 1H), 3.95 (d, 2H, J=12.0 Hz), 4.47 (s, 1H), 7.09-7.11 (m, 2H), 7.44 (d, 2H, J=6.0 Hz), 8.44 (s, 2H). $^{13}C$ NMR ($CDCl_3$) δ 19.18, 25.35, 26.91, 30.97, 39.22, 49.73, 64.71, 122.34, 131.68, 138.82, 146.98, 159.44, 160.73. ES-MS m/z 368.2 ($M^+H$). Anal. Calcd. for $C_{21}H_{29}N_5O.0.4CH_2Cl_2$: C, 64.02; H, 7.48; N, 17.44. Found: C, 63.75; H, 7.52; N, 17.16.

EXAMPLE 33

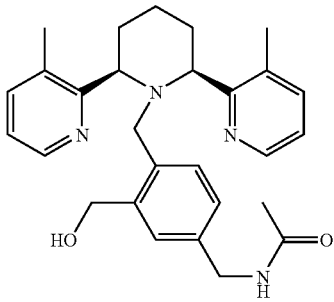

COMPOUND 33: Meso-2',6'-N-[4-(3,3"-dimethyl-3',4',5',6'-tetrahydro-2'H-cis-[2,2';6',2"]terpyridin-1'-ylmethyl)-3-hydroxymethyl-benzyl]-acetamide To a solution of meso-2',6'-[5-aminomethyl-2-(3,3"-dimethyl-3',4',5',6'-tetrahydro-2'H-cis-[2,2';6',2"]terpyridin-1'-ylmethyl)-phenyl]-methanol (0.1089 g, 0.35 mmol) in $CH_3CN$ (4 mL) was added acetic anhydride (0.03 mL, 0.35 mmol), $Et_3N$ (0.07 mL, 0.53 mmol), and KI (0.0059 g, 0.04 mmol), and was stirred at room temperature for 18 hours. Saturated $NaHCO_3$ (10 mL) was added and extracted with $CH_2Cl_2$ (3×30 mL), and the combined organic extracts were dried ($Na_2SO_4$), filtered, and concentrated. Purification of the crude material by radial chromatography on silica gel (20:1:1 $CH_2Cl_2$-MeOH—$NH_4OH$) provided 0.0709 g (37%) of COMPOUND 33 as a white solid. $^1H$ NMR($CDCl_3$) δ1.61-1.69 (m, 3H), 1.96 (s, 3H), 2.04-2.08 (m, 1H), 2.30-2.38 (m, 2H), 2.51 (s, 6H), 3.65 (s, 2H), 4.04 (d, 2H, J=11.4 Hz), 4.12 (d, 2H, J=5.4 Hz), 4.37 (s, 2H), 5.45 (s, 1H), 6.58 (d, 1H, J=7.5 Hz), 6.72 (d, 2H, J=7.5 Hz), 6.81-6.86 (m, 3H), 7.23 (d, 2H, J=7.8 Hz), 8.21 (d, 2H, J=4.5 Hz). $^{13}C$ NMR($CDCl_3$) δ19.42, 23.56, 25.66, 29.73, 43.50, 53.68, 62.79, 67.54, 122.10, 126.19, 128.48, 129.44, 131.88, 136.26, 138.24, 138.42, 139.30, 146.74, 160.00, 170.11. ES-MS m/z 459.3 ($M^+H$). Anal. Calcd. for $C_{28}H_{34}N_4O_2.1.1CH_2Cl_2$: C, 63.32; H, 6.61; N, 10.15. Found: C, 63.65; H, 6.65; N, 10.19.

EXAMPLE 34

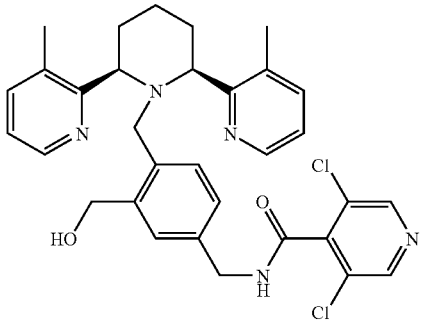

COMPOUND 34: Meso-2',6'-[3,5-dichloro-N-[4-(3,3"-dimethyl-3',4',5',6'-tetrahydro-2'H-cis-[2,2';6',2"]terpyridin-1'-ylmethyl)-3-hydroxymethyl-benzyl]-isonicotinamide]

To a solution of meso-2',6'-[5-aminomethyl-2-(3,3"-dimethyl-3',4',5',6'-tetrahydro-2'H-cis-[2,2';6',2"]terpyridin-1'- ylmethyl)-phenyl]-methanol (0.1765 g, 0.57 mmol) in DMF (6 mL) was added 3,5-dichloro-isonicotinic acid (0.1201 g, 0.63 mmol), EDCI (0.1309 g, 0.68 mmol), HOBT (0.0915 g, 0.68 mmol), and DIPEA (0.2 mL, 1.14 mmol), and was stirred at room temperature for 16 hours. The reaction mixture was concentrated, and brine (10 mL), water (5 mL), and EtOAc (30 mL) were added and stirred for 10 minutes. The phases were separated, and the organic layer was washed with brine (3×20 mL), dried ($Na_2SO_4$), filtered, and concentrated. Purification of the crude material by column chromatography on silica gel (25:1:1 $CH_2Cl_2$-MeOH—$NH_4OH$) provided 0.0403 g (45%) of COMPOUND 34 as a white solid. $^1H$ NMR($CDCl_3$) δ 1.60-1.64 (m, 3H), 2.02-2.06 (m, 1H), 2.29-2.33 (m, 4H), 2.50 (s, 6H), 3.62 (s, 2H), 4.02 (d, 2H, J=10.5 Hz), 4.33 (s, 2H), 4.38 (d, 2H, J=5.7 Hz), 6.02 (s, 1H), 6.67-7.76 (m, 2H), 6.80-6.84 (m, 2H), 6.90 (s, 1H), 7.23 (d, 2H, J=7.5 Hz), 8.19 (d, 2H, J=4.2 Hz), 8.50 (s, 2H). $^{13}C$ NMR($CDCl_3$) δ 18.04, 24.22, 28.52, 42.38, 52.87, 61.33, 66.19, 120.73, 124.83, 127.23, 127.98, 128.22, 130.43, 133.53, 137.09, 138.12, 141.34, 145.36, 146.63, 158.62. ES-MS m/z 591.2 ($M^+H$). Anal. Calcd. for $C_{32}H_{33}N_5Cl_2O_2.1.1CH_2Cl_2.0.6H_2O$: C, 57.22; H, 5.28; N, 10.08; Cl, 21.43. Found: C, 57.18; H, 5.21; N, 9.95; Cl, 21.36.

EXAMPLE 35

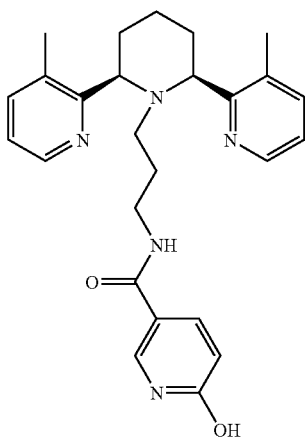

COMPOUND 35: Meso-2',6'-N-[3-(3,3"-dimethyl-3',4'5'6'-tetrahydro-2'H-cis-[2,2';6',2"]terpyridin-1'-yl)-propyl]-6-hydroxy-nicotinamide To a solution of meso-2',6'-[3-(3,3"-dimethyl-3',4',5',6'-tetrahydro-2'H-icis-[2,2';6',2"]terpyridin-1'-yl)-propylamine] (0.2190 g, 0.67 mmol) in $CH_2Cl_2$ (10 mL) was added 6-hydroxynicotinic acid (0.1406 g, 1.01 mmol), EDCI (0.1973 g, 1.01 mmol), HOBT (0.1397 g, 1.01 mmol), and DIPEA (0.2 mL, 1.01 mmol), and was stirred at room temperature for 16 hours. Saturated $NaHCO_3$ (15 mL) was added and extracted with $CH_2Cl_2$ (3×40 mL). The combined organic extracts were dried ($Na_2SO_4$), filtered, and concentrated. Purification of the crude material by column chromatography on silica gel (20:1:1 then 15:1:1 $CH_2Cl_2$-MeOH—$NH_4OH$) provided 0.2624 g (76%) of COMPOUND 35 as a white solid. $^1H$ NMR($CDCl_3$) δ 1.66-1.70 (m, 4H), 1.95-2.06 (m, 3H), 2.32-2.33 (m, 2H), 2.54 (s, 6H), 2.68 (s, 4H), 3.30-3.32 (m, 1H), 3.94-4.07 (m, 2H), 6.50 (d, 1H, J=9.6 Hz), 7.08-7.12 (m, 2H), 7.49 (d, 2H, J=6.9 Hz), 7.67-7.91 (m, 2H), 8.19-8.26 (m, 2H). $^{13}C$ NMR ($CDCl_3$) δ 19.43, 21.96, 26.45, 32.82, 39.28, 65.69, 72.44, 116.02, 120.28, 123.80, 133.80, 138.86, 140.77, 141.44, 147.73, 161.67, 166.03. ES-MS m/z 446.4 ($M^+H$). Anal. Calcd. for $C_{26}H_{31}N_5O_2.07CH_2Cl_2$: C, 63.50; H, 6.47; N, 13.87. Found: C, 63.64; H, 6.70; N, 14.09.

EXAMPLE 36

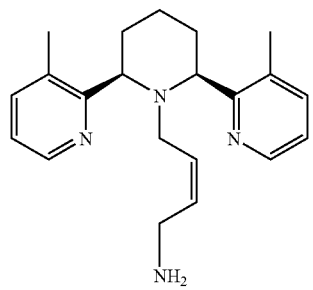

COMPOUND 36: Meso-2',6'-[4-(3,3"-dimethyl-3',4',5 ',6'-tetrahydro-2'H-cis-2,2';6',2"]terpyridin-1'-yl)-but-2-enylamine] (HBr salt)

Following General Procedure A: meso-2',6'-[3,3"-dimethyl-1',2',3',4',5',6'-hexahydro-cis-[2,2';6'2"]terpyridine] (0.1456 g, 0.54 mmol), (4-chloro-but-2-enyl)-carbamic acid tert-butyl ester (Casara, P, et al., *J Am. Chem. Soc.* (1989) 111:9111-9113) (0.1358 g, 0.65 mmol), KI (0.0090 g, 0.05 mmol), DIPEA (0.2 mL, 1.08 mmol), and DMF (6 mL) were stirred at 60° C. for 18 hours. Purification of the crude material by column chromatography on silica gel (33:1:1 $CH_2Cl_2$-MeOH—$NH_4OH$) followed by radial chromatography on silica (50:1:1 $CH_2Cl_2$-MeOH—$NH_4OH$) provided 0.0968 g (41%) of meso-2',6'-[4-(3,3"-dimethyl-3',4',5',6'-tetrahydro-2'H-cis-[2,2';6'2"]terpyridin-1'-yl)-but-2-enyl]-carbamic acid tert-butyl ester as a beige solid. $^1H$ NMR ($CDCl_3$) δ 1.37 (s, 9H), 1.87-1.89 (m, 6H), 2.46 (s, 6H), 2.93-2.95 (m, 2H), 3.12-3.14 (m, 2H), 4.22 (s, 1H), 4.50-4.51 (m, 2H), 5.41-5.43 (m, 1H), 7.10-7.14 (m, 2H), 7.46-7.48 (m, 2H), 8.43-8.44 (m, 2H).

Following General Procedure B: meso-2',6'-[4-(3,3"-dimethyl-3',4',5',6'-tetrahydro-2'H-cis-[2,2';6'2"]terpyridin-1'-yl)-but-2-enyl]-carbamic acid tert-butyl ester (0.0968 g, 0.22 mmol) was converted to the HBr salt followed by reprecipitation of the intermediate solid from MeOH/ether to give COMPOUND 36 (0.0879 g, 65%) as a white solid. $^1H$ NMR ($D_2O$) δ 1.51-1.60 (m, 2H), 1.66-1.74 (m, 1H), 1.93-1.94 (m, 1H), 2.15 (d, 2H, J=13.2 Hz), 2.54 (s, 6H), 3.03-3.04 (s, 4H), 4.59 (d, 2H, J=10.8 Hz), 5.42-5.44 (m, 1H), 5.76-5.78 (m, 1H), 7.85-7.89 (m, 2H), 8.39 (d, 2H, J=7.5 Hz), 8.66 (d, 2H, J=4.2 Hz). $^{13}C$ NMR ($D_2O$) δ 17.12, 22.37, 32.54, 35.84, 50.96, 59.22, 124.55, 126.17, 130.56, 137.00, 139.88, 149.51, 154.58. ES-MS m/z 337.4 ($M^+H$). Anal. Calcd. for $C_{21}H_{28}N_4.3.0HBr.2.0H_2O$: C, 41.00; H, 5.73; N, 9.11; Br, 38.96. Found: C, 41.17; H, 5.70; N, 8.78; Br, 38.88.

EXAMPLE 37

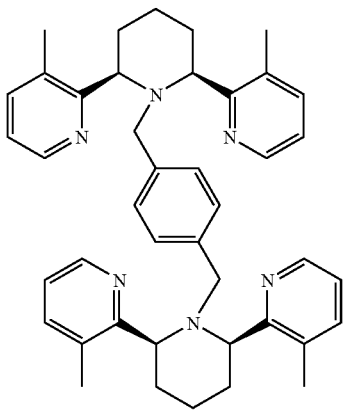

COMPOUND 37: Meso-2',6'-[1,4-bis-N-(3,3"-Dimethyl-1',2',3'4',5',6'-hexahydro-cis-[2,2';6'2"]terpyridine)methyl-benzene]

Following General Procedure A: meso-2',6'-[3,3"-dimethyl-1',2',3',4',5',6'-hexahydro-cis-[2,2';6'2"]terpyridine] (0.2324 g, 0.87 mmol), 1,4-bis-bromomethyl-benzene (0.1148 g, 0.43 mmol), KI (0.0066 g, 0.04 mmol), DIPEA (0.22 mL, 1.29 mmol), and DMF (5 mL) were stirred at 60° C. for 18 hours. Purification of the crude material by column chromatography on silica gel (33:1:1 $CH_2Cl_2$-MeOH—$NH_4OH$) provided 0.1603 g (47%) of COMPOUND 37 as a beige solid. $^1H$ NMR ($CDCl_3$) δ 1.65-1.70 (m, 4H), 1.95-2.03 (m, 6H), 2.33 (s, 12H), 3.42 (s, 4H), 3.91 (s, 4H), 4.98-5.00 (m, 2H), 6.21 (s, 4H), 6.97-7.01 (m, 4H), 7.30 (d, 4H, J=7.5 Hz), 8.44 (d, 4H, J=2.1 Hz). $^{13}C$ NMR ($CDCl_3$) δ 19.18, 25.57, 29.94, 51.43, 64.60, 122.03, 128.19, 132.25, 136.41, 138.60, 146.80, 160.61. ES-MS m/z 637.8 ($M^+H$). Anal. Calcd. for $C_{42}H_{48}N_6 \cdot 1.8CH_2Cl_2$: C, 66.61; H, 6.59; N, 10.64. Found: C, 66.47; H, 6.53; N, 10.73.

EXAMPLE 38

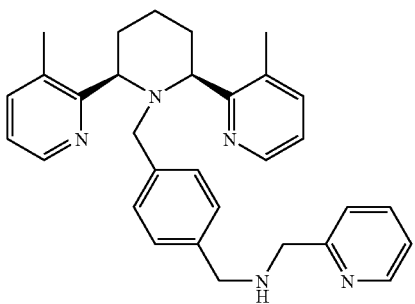

Comound 38: Meso-2',6'-[4-(3,3"-dimethyl-3',4',5',6'-tetrahydro-2'H-cis-[2,2';6',2"]terpyridin-1'-ylmethyl)-benzyl]-pyridin-2-ylmethyl-amine To a stirring solution of N-(4-hydroxymethyl-benzyl)-2-nitro-N-pyridin-2-ylmethyl-benzenesulfonamide (Bridger, et al., U.S. Ser. No. 09/111,895) (0.2096 g, 0.51 mmol) in $CH_2Cl_2$ (5 mL) at 0° C. under Ar, was added $Et_3N$ (0.14 mL, 1.02 mmol) and MsCl (0.05 mL, 0.66 mmol). The mixture was stirred at 0° C. for 2 hours, then stirred at room temperature for 3 hours. Additional $Et_3N$ (0.30 mL, 2.16 mmol) and MsCl (0.10 mL, 1.32 mmol) were added, and stirred for 18 hours. Saturated $NaHCO_3$ (10 mL) was added and extracted with $CH_2Cl_2$ (3×30 mL). The combined organic extracts were dried ($Na_2SO_4$), filtered, and concentrated to provide 0.2383 g (95%) of methanesulfonic acid 4-{[(2-nitro-benzenesulfonyl)-pyridin-2-ylmethyl-amino]-methyl}-benzyl ester as a yellow oil. $^1H$ NMR ($CDCl_3$) δ 3.14 (s, 3H), 4.51 (s, 2H), 4.60 (s, 4H), 7.02-7.24 (m, 6H), 7.54-7.57 (m, 2H), 7.66 (d, 2H, J=3.0 Hz), 7.94 (d, 1H, J=9.0 Hz), 8.41-8.43 (m, 1H).

To a solution of meso-2',6'-[3,3"-dimethyl-1',2',3',4',5',6'-hexahydro-cis-[2,2';6'2"]terpyridine] (0.0997 g, 0.37mmol) and methanesulfonic acid 4-{[(2-nitro-benzenesulfonyl)-pyridin-2-ylmethyl-amino]-methyl}-benzyl ester (0.2383 g, 0.48 mmol) in DMF (4 mL), were added KI (0.0066 g, 0.04 mmol) and DIPEA (0.13 mL, 0.74 mmol). The mixture was stirred at room temperature for 66 hours then concentrated. Saturated $NaHCO_3$ (10 mL) was added and extracted with $CH_2Cl_2$ (3×30 mL). The combined organic extracts were washed with brine (2×20 mL), dried ($Na_2SO_4$), filtered, and concentrated. Purification of the crude material by column chromatography on silica gel (50:1:1 $CH_2Cl_2$-MeOH—$NH_4OH$) provided 0.2005 g (82%) of meso-2',6'-N-[4-(3,3"-dimethyl-3',4',5',6'-tetrahydro-2'H-cis-[2,2';6',2"]terpyridin-1'-ylmethyl)-benzyl]-2-nitro-N-pyridin-2-ylmethyl-benzenesulfonamide as a beige solid. $^1H$ NMR ($CDCl_3$) δ 1.57-1.70 (m, 2H), 1.99-2.03 (m, 1H), 2.12-2.25 (m, 2H), 2.36 (s, 6H), 3.43-3.48 (m, 3H), 4.05 (d, 2H, J=9.0 Hz), 4.43 (d, 4H, J=9.0 Hz), 6.42 (d, 2H, J=6.0 Hz), 6.71 (d, 2H, J=6.0 Hz), 6.97-7.00 (m, 2H), 7.09-7.12 (m, 2H), 7.27-7.28 (m, 2H), 7.49-7.51 (m, 2H), 7.61-7.63 (m, 2H), 7.92 (d, 1H, J=6.0 Hz), 8.40-8.41 (m, 3H).

To a solution of meso-2',6'-N-[4-3,3"-dimethyl-3',4',5',6'-tetrahydro-2'H-cis[2,2';6',2"]terpyridin-1'-ylmethyl)-benzyl]-2-nitro-N-pyridin-2-ylmethyl-benzenesulfonamide (0.2005 g, 0.30 mmol) in $CH_3CN$ (3 mL) was added $K_2CO_3$ (0.2625 g, 1.80 mmol) and thiophenol (0.16 mL, 1.51 mmol). After stirring for 16 hours at room temperature, the mixture was concentrated, and $CH_2Cl_2$ (50 mL) was added and washed with brine (3×30 mL), dried ($Na_2SO_4$), filtered, and concentrated. Purification of the crude material by column chromatography on silica gel (25:1:1 $CH_2Cl_2$—MeOH—$NH_4OH$) provided 0.0763 g (49%) of COMPOUND 38 as a pale yellow oil. $^1H$ NMR ($CDCl_3$) δ 1.50-1.70 (m, 4H), 1.96-2.00 (m, 1H), 2.08-2.20 (m, 2H), 2.37 (s, 6H), 3.52 (s, 2H), 3.66 (s, 2H), 3.82 (s, 2H), 4.05 (d, 2H, J=10.8 Hz), 6.68 (d, 2H, J=7.2 Hz), 6.91 (d, 2H, J=7.5 Hz), 6.95-6.99 (m, 2H) 7.13-7.17 (m, 1H), 7.27-7.28 (m, 2H), 7.62-7.63 (m, 1H), 8.43 (d, 2H, J=3.3 Hz), 8.54 (d, 1H, J=4.5 Hz). $^{13}C$ NMR ($CDCl_3$) δ 19.17, 25.65, 29.56, 52.11, 53.51, 54.64, 65.13, 122.13, 122.26, 122.63, 127.42, 129.03, 130.38, 132.37, 136.74, 137.73, 138.46, 146.85, 149.69, 160.21, 160.53. ES-MS m/z 478.3 ($M^+H$). Anal. Calcd. for $C_{31}H_{35}N_5 \cdot 0.5CH_2Cl_2$: C, 72.74; H, 6.98; N, 13.46. Found: C, 72.56; H, 6.94; N, 13.35.

EXAMPLE 39

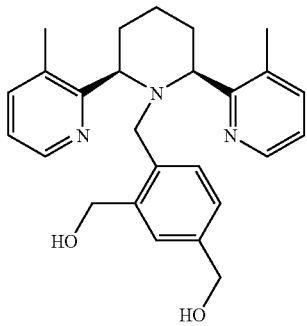

COMPOUND 39: Meso-2',6'-[4-(3,3''-dimethyl-3',4', 5',6'-tetrahydro-2'H-cis-[2,2';6',2'']terpyridin-1'-ylmethyl)-3-hydroxymethyl-phenyl]-methanol Following General Procedure A: To a solution of meso-2', 6'-[3,3''-dimethyl-1',2',3',4',5',6'-hexahydro-cis-[2,2';6'2''] terpyridine] (0.1339 g, 0.50 mmol) in DMF (5 mL) was added 4-bromomethyl-isophthalic acid dimethyl ester (0.1438 g, 0.50 mmol), KI (0.0083 g, 0.05 mmol), and DIPEA (0.17 mL, 1.00 mmol). The mixture stirred at 60° C. for 16 hours before it was concentrated. Purification of the crude material by column chromatography on silica gel (50:1:1 $CH_2Cl_2$—MeOH—$NH_4OH$) provided 0.2473 g (100%) of meso-2'β, 6'β-[4-(3,3''-dimethyl-3',4',5',6'-tetrahydro-2'H-[2,2';6'2''] terpyridin-1'-ylmethyl)-isophthalic acid dimethyl ester] as a yellow solid. $^1$H NMR ($CDCl_3$) δ 1.64-1.69 (m, 2H), 2.31-2.41 (m, 2H), 2.44 (s, 6H), 2.75 (s, 2H), 3.83 (s, 6H), 3.99 (s, 2H), 4.15 (d, 2H, J=12.0 Hz), 6.80-6.84 (m, 2H), 7.14-7.17 (m, 2H), 7.74 (s, 2H), 7.92 (s, 1H), 8.23 (d, 2H, J=3.0 Hz).

To a solution of meso-2',6'-[4-(3,3''-dimethyl-3',4',5',6'-tetrahydro-2'H-cis-[2,2';6'2'']terpyridin-1'-ylmethyl)-isophthalic acid dimethyl ester] (0.2273 g, 0.48 mmol) in THF (5 mL) at 0° C. under Ar was added $LiAlH_4$ (0.3100 g, 4.80 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with $CH_2Cl_2$ and concentrated. Purification of the crude material by column chromatography on silica gel (25:1:1 $CH_2Cl_2$—MeOH—$NH_4OH$) provided 0.1282 g (59%) of COMPOUND 39 as a white solid. $^1$H NMR ($CDCl_3$) δ 1.61-1.65 (m, 3H), 2.01-2.02 (m, 1H), 2.30-2.34 (m, 2H), 2.49 (s, 6H), 3.63 (s, 2H), 4.02 (d, 2H, J=11.1 Hz), 4.33 (s, 2H), 4.38 (s, 2H), 6.65-6.68 (m, 1H), 6.74-6.77 (m, 1H), 6.80-6.85 (m, 2H), 6.90 (s, 1H), 7.22 (d, 2H, J=7.5 Hz), 8.20 (d, 2H, J=3.9 Hz). $^{13}$C NMR ($CDCl_3$) δ 19.44, 25.67, 29.69, 53.70, 62.82, 64.86, 67.61, 122.15, 125.24, 127.71, 129.23, 131.93, 138.00, 138.45, 138.90, 139.44, 146.72, 159.97. ES-MS m/z 418.5 ($M^+H$). Anal. Calcd. for $C_{26}H_{31}N_3O_2$·0.4$CH_2Cl_2$: C, 70.15; H, 7.09; N, 9.29. Found: C, 70.17; H, 7.05; N, 9.19.

EXAMPLE 40

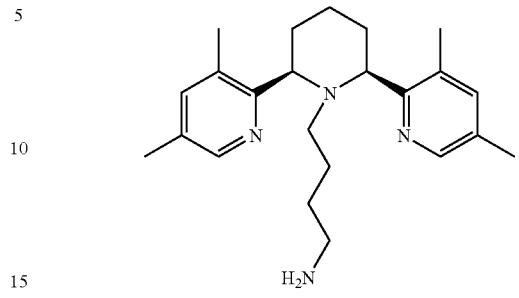

COMPOUND 40: Meso-2',6'-[4-(3,5,3'',5''-tetramethyl-3',4',5',6'-tetrahydro-2'H-cis-[2,2';6',2'']terpyridin-1'-yl)-butylamine] (HBr salt)

To a solution of (3,5-dimethyl-pyridin-2-yl)-methanol (2.12 g, 15.45 mmol) (Weidmann, K., et al., *J. Med. Chem.* (1992) 35:438-450) in $CH_2Cl_2$ (50 mL) was added $MnO_2$ (9.41 g, 108.18 mmol) and the reaction mixture was refluxed overnight. Then it was cooled and the mixture was filtered through a layer of celite. The filtrate was concentrated to afford a brown/yellow oil. Purification by flash column chromatography on silica gel using 30% EtOAc/hexane afforded 3,5-dimethyl-pyridine-2-carbaldehyde as a yellow oil (960 mg, 31% over 3 steps). $^1$H NMR ($CDCl_3$) δ 2.39 (s, 3H), 2.62 (s, 3H), 7.41 (s, 1H), 8.47 (s, 1H), 10.15 (s, 1H).

Following General Procedure D: To a solution of 3,5-dimethyl-pyridine-2-carbaldehyde (0.6551 g, 4.9 mmol) in MeOH (24 mL) was added $NH_4OAc$ (0.2172 g, 2.6 mmol) and 1,3-acetonedicarboxylic acid (0.3533 g, 2.4 mmol), and stirred at room temperature for 4 hours. Purification of the crude material by column chromatography on silica gel (200:1:1 $CH_2Cl_2$—MeOH—$NH_4OH$) provided 0.4526 g (61%) of meso-2',6'-[3,5,3'',5''-tetramethyl-2',3',5',6'-tetrahydro-1'H-cis-[2,2';6'2'']terpyridin-4'-one] as a yellow solid. $^1$H NMR ($CDCl_3$) δ 2.27 (s, 6H), 2.32 (s, 6H), 2.46-2.55 (m, 2H), 2.78-2.86 (m, 2H), 3.24 (t, 1H, J=12.0 Hz), 4.40-4.47 (m, 2H), 7.25 (s, 2H), 8.28 (s, 2H).

Following General Procedure E: meso-2',6'-[3,5,3'',5''-tetramethyl-2',3',5',6'-tetrahydro-1'H-cis-[2,2';6'2'']terpyridin-4'-one] (0.4526 g, 1.5 mmol), KOH (1.64 g, 29.3 mmol), hydrazine monohydrate (2.84 mL, 58.5 mmol), and diethylene glycol (10 mL) were used. Purification of the crude material by column chromatography on silica gel (50:1:1 $CH_2Cl_2$—MeOH—$NH_4OH$) provided 0.3521 g (79%) of meso-2'β,6'β-[3,5,3'',5''-tetramethyl-1',2',3',4',5',6'-hexahydro-[2,2';6'2'']terpyridine] as a dark orange oil. $^1$H NMR ($CDCl_3$) δ 1.55-1.63 (m, 2H), 1.79-1.84 (m, 3H), 2.09-2.13 (m, 1H), 2.24 (s, 6H), 2.33 (s, 6H), 4.16-4.19 (m, 2H), 7.20 (s, 2H), 8.27 (s, 2H).

Following General Procedure A: meso-2',6'-[3,5,3'',5''-tetramethyl-1',2',3',4',5',6'-hexahydro-cis-[2,2';6'2'']terpyridine] (0.0939 g, 0.32 mmol), 2-(4-bromo-butyl)-isoindole-1,3-dione (0.0913 g, 0.32 mmol), KI (0.0053 g, 0.03 mmol), DIPEA (0.11 mL, 0.64 mmol), and DMF (3.2 mL) were stirred at 60° C. for 17 hours. Purification of the crude material by column chromatography on silica gel (50:1:1

CH₂Cl₂—MeOH—NH₄OH) provided 0.0951 g (60%) of meso-2',6'-[2-[4-(3,5,3",5"-tetramethyl-3',4',5',6'-tetrahydro-2'H-cis-[2,2';6'2"]terpyridin-1'-yl)-butyl]-isoindole-1,3-dione] as a white solid. $^1$H NMR (CDCl$_3$) δ 0.92-0.94 (m, 2H), 1.63-1.64 (m, 2H), 1.94-2.04 (m, 2H), 2.22 (s, 6H), 2.23-2.26 (m, 2H), 2.40 (s, 6H), 2.49-2.58 (m, 2H), 2.95-3.03 (m, 2H), 3.20-3.25 (m, 2H), 3.99-4.00 (m, 2H), 7.13 (s, 2H), 7.68-7.71 (m, 2H), 7.77-7.82 (m, 2H), 8.23 (s, 2H).

To a solution of meso-2',6'-[2-[4-(3,5,3",5"-tetramethyl-3',4',5',6'-tetrahydro-2'H-cis-[2,2';6'2"]terpyridin-1'-yl)-butyl]-isoindole-1,3-dione] (0.0951 g, 0.19 mmol) in EtOH (2 mL) was added hydrazine monohydrate (0.1 mL, 1.90 mmol), and stirred at room temperature for 17 hours. The reaction mixture was concentrated, and purification of the crude material by column chromatography on silica gel (25:1:1 then 12:1:1 CH₂Cl₂—MeOH—NH₄OH) provided 0.0474 g (68%) of meso-2',6'-[4-(3,5,3",5"-tetramethyl-3',4',5',6'-tetrahydro-2'H-cis-[2,2';6',2"]terpyridin-1'-yl)-butylamine] as a colorless oil. $^1$H NMR (CDCl$_3$) δ 0.76-0.91 (m, 2H), 1.58-1.62 (m, 4H), 1.91-2.04 (m, 3H), 2.18-2.23 (m, 4H), 2.26 (s, 6H), 2.45 (s, 6H), 2.58-2.59 (m, 1H), 3.98 (d, 2H, J=12.0 Hz), 7.22 (s, 2H), 8.26 (s, 2H).

Following General Procedure B: meso-2',6'-[4-(3,5,3",5"-tetramethyl-3',4',5',6'-tetrahydro-2'H-cis-[2,2';6',2"]terpyridin-1'-yl)-butylamine] was converted to the HBr salt followed by reprecipitation of the intermediate solid from MeOH/ether to give COMPOUND 40 (0.0621 g, 68%) as a white solid. $^1$H NMR (D$_2$O) δ 1.14-1.15 (m, 2H), 1.28-1.29 (m, 2H), 1.39-1.50 (m, 2H), 1.59-1.67 (m, 1H), 1.87-1.91 (m, 1H), 2.03-2.10 (m, 2H), 2.17-2.20 (m, 2H), 2.45 (s, 6H), 2.51 (s, 6H), 2.69-2.70 (m, 2H), 4.51 (d, 2H, J=10.2 Hz), 8.22 (s, 2H), 8.46 (s, 2H). $^{13}$C NMR (D$_2$O) δ 16.92, 17.53, 19.99, 22.41, 25.16, 32.63, 39.31, 52.07, 57.49, 135.99, 137.37, 139.18, 150.04, 151.71. EMS m/z 367.4 (M⁺H). Anal. Calcd. for C₂₃H₃₄N₄·3.3HBr·2.1CH₄O: C, 43.02; H, 6.57; N, 7.99; Br, 37.62. Found: C, 42.96; H, 6.44; N, 8.23; Br, 37.49.

EXAMPLE 41

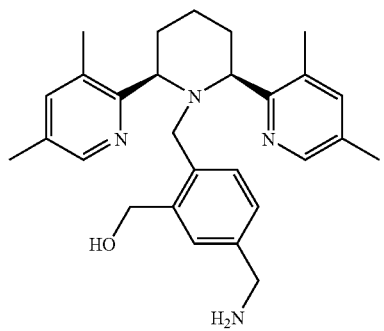

COMPOUND 41: Meso-2',6'-[5-aminomethyl-2-(3,5,3",5"-tetramethyl-3',4',5',6'-tetrahydro-2'H-cis-[2,2';6',2"]terpyridin-1'-ylmethyl)-phenyl]-methanol Following General Procedure D: To a solution of 3,5-dimethyl-pyridine-2-carbaldehyde (0.6551 g, 4.9 mmol) in MeOH (24 mL) was added NH₄OAc (0.2172 g, 2.6 mmol) and 1,3-acetonedicarboxylic acid (0.3533 g, 2.4 mmol), and stirred at room temperature for 4 hours. Purification of the crude material by column chromatography on silica gel (200:1:1 CH₂Cl₂—MeOH—NH₄OH) provided 0.4526 g (61%) of meso-2',6'-[3,5,3",5"-tetramethyl-2',3',5',6'-tetrahydro-1'H-cis-[2,2';6'2"]terpyridin-4'-one] as a yellow solid. $^1$H NMR (CDCl$_3$) δ 2.27 (s, 6H), 2.32 (s, 6H), 2.46-2.55 (m, 2H), 2.78-2.86 (m, 2H), 3.24 (t, 1H, J=12.0 Hz), 4.40-4.47 (m, 2H), 7.25 (s, 2H), 8.28 (s, 2H).

Following General Procedure E: meso-2',6'-[3,5,3",5"-tetramethyl-2',3',5',6'-tetrahydro-1'H-cis-[2,2';6'2"]terpyridin-4'-one] (0.4526 g, 1.5 mmol), KOH (1.64 g, 29.3 mmol), hydrazine monohydrate (2.84 mL, 58.5 mmol), and diethylene glycol (10 mL) were used. Purification of the crude material by column chromatography on silica gel (50:1:1 CH₂Cl₂—MeOH—NH₄OH) provided 0.3521 g (79%) of meso-2'β,6'β-[3,5,3",5"-tetramethyl-1',2',3',4',5',6'-hexahydro-[2,2';6'2"]terpyridine] as a dark orange oil. $^1$H NMR (CDCl$_3$) δ 1.55-1.63 (m, 2H), 1.79-1.84 (m, 3H), 2.09-2.13 (m, 1H), 2.24 (s, 6H), 2.33 (s, 6H), 4.16-4.19 (m, 2H), 7.20 (s, 2H), 8.27 (s, 2H).

Following General Procedure A: meso-2',6'-[3,5,3",5"-tetramethyl-1',2',3',4',5',6'-hexahydro-cis-[2,2';6'2"]terpyridine] (0.1903 g, 0.64 mmol), 2-bromomethyl-5-cyano-benzoic acid methyl ester (0.1630 g, 0.64 mmol), KI (0.0100 g, 0.06 mmol), DIPEA (0.22 mL, 1.29 mmol), and DMF (6.4 mL) were stirred at 60° C. for 17 hours. Purification of the crude material by column chromatography on silica gel (50:1:1 CH₂Cl₂—MeOH—NH₄OH) provided 0.2682 g (89%) of meso-2',6'-[5-cyano-2-(3,5,3",5"-tetramethyl-3',4',5',6'-tetrahydro-cis-[2,2';6'2"]terpyridin-1'-ylmethyl)-benzoic acid methyl ester] as a brown oil. $^1$H NMR (CDCl$_3$) δ 1.63-1.67 (m, 3H), 2.00-2.05 (m, 1H), 2.12 (s, 6H), 2.21-2.31 (m, 2H), 2.36 (s, 6H), 3.84 (s, 3H), 3.90-3.94 (m, 2H), 4.0-4.08 (m, 2H), 6.96 (s, 2H), 7.37 (d, 1H, J=9.0 Hz), 7.56 (d, 1H, J=3.0 Hz), 7.90 (s, 1H), 8.02 (s, 2H).

To a solution of meso-2',6'-[5-cyano-2-(3,5,3",5"-tetramethyl-3',4',5',6'-tetrahydro-cis-[2,2'; 6'2"]terpyridin-1'-ylmethyl)-benzoic acid methyl ester] (0.2682 g, 0.57 mmol) in THF (6 mL) at 0° C. under Ar was added dropwise 1.0 M LiAlH₄ in THF (5.7 mL, 5.72 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with CH₂Cl₂ and concentrated. Purification of the crude material by column chromatography on silica gel (25:1:1 CH₂Cl₂—MeOH—NH₄OH) provided 0.1435 g (54%) of COMPOUND 41 as a white solid. $^1$H NMR (CDCl$_3$) δ 1.58-1.62 (m, 4H), 2.01-2.07 (m, 2H), 2.10 (s, 6H), 2.31-2.35 (m, 2H), 2.45 (s, 6H), 3.58 (d, 4H, J=10.8 Hz), 4.36 (s, 2H), 6.57-6.67 (m, 2H), 6.85 (s, 1H), 7.02 (s, 2H), 8.01 (s, 2H). $^{13}$C NMR (CDCl$_3$) δ 18.08, 19.26, 25.84, 29.08, 46.30, 52.52, 62.98, 67.18, 125.22, 125.72, 127.84, 129.13, 131.23, 131.41, 138.04, 138.94, 140.91, 146.94, 157.02. ES-MS m/z 445.5 (M⁺H). Anal. Calcd. for C₂₈H₃₆N₄O·0.2CH₂Cl₂·0.3H₂O: C, 72.53; H, 7.99; N, 12.00. Found: C, 72.91; H, 8.07; N, 11.91.

EXAMPLE 42

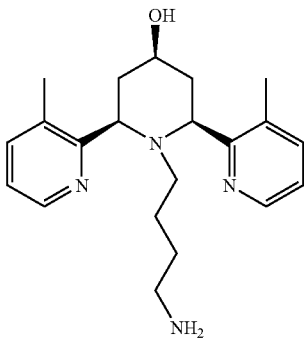

COMPOUND 42: Meso-2'β,4'α,6'β-[1'-(4-amino-butyl)-3,3"-dimethyl-1',2',3',4',5',6'-hexahydro-[2,2'; 6',2"]terpyridin-4'-ol]

To a solution of meso-2',6'-[3,3"-dimethyl-2',3',5',6'-tetrahydro-1'H-cis-[2,2';6'2"]terpyridin-4'-one] (0.1666 g, 0.59 mmol) in MeOH (6 mL) under Ar was added NaBH$_4$ (0.0552 g, 1.48 mmol), and stirred at room temperature for 1 hour. The mixture was then concentrated, and saturated NaHCO$_3$ (10 mL) was added and extracted with CH$_2$Cl$_2$ (3×40 mL). The combined organic extracts were dried (Na$_2$SO$_4$), filtered, and concentrated. Purification of the crude material by column chromatography on silica gel (25:1:1 CH$_2$Cl$_2$—MeOH—NH$_4$OH) provided 0.1462 g (82%) of meso-2'β,4'β,6'β-[3,3"-dimethyl-1',2',3',4',5',6'-hexahydro-[2,2';6'2"]terpyridin-4'-ol] as a yellow solid. $^1$H NMR (CDCl$_3$) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H), J=6.0 Hz).

Following General Procedure A: To a solution of meso-2'β, 4'α,6'β-[3,3"-dimethyl-1',2',3',4',5',6'-hexahydro-[2,2';6'2"]terpyridin-4'-ol] (0.1462 g, 0.49 mmol) in DMF (5 mL) was added 2-(4-bromo-butyl)-isoindole-1,3-dione (0.1466 g, 0.49 mmol), KI (0.0081 g, 0.05 mmol), and DIPEA (0.17 mL, 0.97 mmol). The mixture stirred at 60° C. for 17 hours before it was concentrated. Purification of the crude material by column chromatography on silica gel (33:1:1 CH$_2$Cl$_2$—MeOH—NH$_4$OH) provided 0.1144 g (47%) of meso-2'β,4'β, 6'β-[2-[4-(4'-hydroxy-3,3"-dimethyl-3',4',5',6'-tetrahydro-2'H-[2,2';6'2"]terpyridin-1'-yl)-butyl]-isoindole-1,3-dione] as a beige solid. $^1$H NMR (CDCl$_3$) δ 0.78-0.83 (m, 2H), 1.50-1.58 (m, 1H), 1.98-2.04 (m, 2H), 2.14-2.23 (m, 4H), 2.30-2.46 (m, 2H), 2.46 (s, 6H), 3.11-3.15 (m, 2H), 3.92 (s, 1H), 4.08-4.18 (m, 2H), 6.92-6.96 (m, 2H), 7.23-7.25 (m, 2H), 7.73-7.80 (m, 4H), 8.38 (d, 2H, J=3.0 Hz).

To a solution of meso-2'β,4'α,6'β-[2-[4-(4'-hydroxy-3,3"-dimethyl-3',4',5',6'-tetrahydro-2'H-[2,2';6'2"]terpyridin-1'-yl)-butyl]-isoindole-1,3-dione] (0.1144 g, 0.23 mmol) in EtOH (3 mL) was added hydrazine monohydrate (0.11 mL, 2.28 mmol), and stirred at room temperature for 18 hours. The reaction mixture was concentrated, and purification of the crude material by column chromatography on silica gel (13:1:1 CH$_2$Cl$_2$—MeOH—NH$_4$OH) provided 0.0537 g (62%) of COMPOUND 42 as a white solid. $^1$H NMR (CDCl$_3$) δ 0.52-0.55 (m, 1H), 0.72 (t, 2H, J=6.9 Hz), 2.02-2.24 (m, 10H), 2.48 (s, 6H), 2.65 (s, 2H), 3.84-3.89 (m, 1H), 4.13 (d, 2H, J=9.9 Hz), 7.06-7.10 (m, 2H), 7.44 (d, 2H, J=7.5 Hz), 8.42 (d, 2H, J=3.0 Hz). $^{13}$C NMR (CDCl$_3$) δ 19.06, 23.81, 30.78, 38.81, 41.42, 47.56, 62.01, 69.75, 122.46, 132.04, 138.76, 146.92, 159.38. ES-MS m/z 355.4 (M$^+$H). Anal. Calcd. for C$_{21}$H$_{30}$N$_4$O.0.1CH$_2$Cl$_2$.0.5CH$_4$O: C, 68.45; H, 8.56; N, 14.78. Found: C, 68.11; H, 8.48; N, 14.61.

EXAMPLE 43

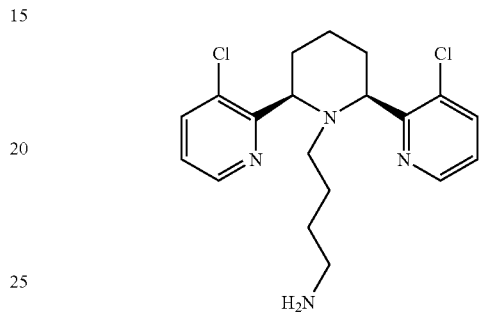

COMPOUND 43: Meso-2',6'-[4-(3,3"-dichloro-3',4', 5',6'-tetrahydro-2'H-cis-[2,2';6',2"]terpyridin-1'-yl)-butylamine]

Following General Procedure D: To a solution of 3-chloro-pyridine-2-carbaldehyde (0.6151 g, 4.35 mmol) in MeOH (22 mL) was added NH$_4$OAc (0.1841 g, 2.39 mmol) and 1,3-acetonedicarboxylic acid (0.3211 g, 2.17 mmol), and stirred at room temperature for 2.5 hours. Purification of the crude material by column chromatography on silica gel (3:2 then 1:1 hexanes-EtOAc) provided 0.2018 g (29%) of meso-2',6'-[3,3"-dichloro-3',4',5',6'-tetrahydro-1'H-cis-[2,2';6',2"]terpyridin-4'-one] as a white solid. $^1$H NMR (CDCl$_3$) δ 2.55-2.63 (m, 2H), 2.70-2.76 (m, 2H), 3.42-3.43 (m, 1H), 4.84 (t, 2H, J=9.0 Hz), 7.16-7.20 (m, 2H), 7.66-7.69 (m, 2H), 8.54-8.56 (m, 2H).

Following General Procedure E: meso-2',6'-[3,3"-dichloro-3',4',5',6'-tetrahydro-1'H-cis-[2,2';6',2"]terpyridin-4'-one] (0.3667 g, 1.14 mmol), KOH (1.2943 g, 22.76 mmol), hydrazine monohydrate (2.21 mL, 45.52 mmol), and diethylene glycol (6 mL) were used to provide 0.4004 g (100%) of meso-2',6'-[3,3"-dichloro-1',2',3',4',5',6'-hexahydro-cis-[2, 2';6',2"]terpyridine] as a yellow oil. $^1$H NMR (CDCl$_3$) δ 1.70 (s, 2H), 1.89-1.98 (m, 4H), 3.12-3.21 (m, 1H), 3.61-3.66 (m, 1H), 3.75-3.78 (m, 1H), 4.50-4.53 (m, 2H), 7.09-7.14 (m, 2H), 7.62-7.68 (m, 2H), 8.52-8.54 (m, 2H).

Following General Procedure A: meso-2',6'-[3,3"-dichloro-1',2',3',4',5',6'-hexahydro-cis-[2,2';6',2"]terpyridine] (0.4004 g, 1.3 mmol), 2-(4-bromo-butyl)-isoindole-1, 3-dione (0.4815 g, 1.7 mmol), KI (0.0216 g, 0.1 mmol), DIPEA (0.45 mL, 2.6 mmol), and DMF (13 mL) were stirred at 60° C. for 22 hours. Purification of the crude material by column chromatography on silica gel (100:1:1 CH$_2$Cl$_2$—MeOH—NH$_4$OH) provided 0.4142 g (63%) of meso-2',6'-[2-[4-(3,3"-dichloro-3',4',5',6'-tetrahydro-2'H-cis-[2,2';6',2"] terpyridin-1'-yl)-butyl]-isoindole-1,3-dione] as an orange oil. $^1$H NMR (CDCl$_3$) δ 1.06-1.08 (m, 4H), 1.56-1.62 (m, 2H), 1.89-2.03 (m, 3H), 2.12-2.17 (m, 2H), 3.32-3.36 (m, 2H), 4.37 (d, 2H, J=9.0 Hz), 7.06-7.10 (m, 2H), 7.55-7.58 (m, 2H), 7.68-7.70 (m, 2H), 7.77-7.78 (m, 2H), 8.52-8.54 (m, 2H).

To a solution of meso-2',6'-[2-[4-(3,3'-dichloro-3',4',5',6'-tetrahydro-2'H-cis-[2,2';6',2"]terpyridin-1'-yl)-butyl]-isoindole-1,3-dione] (0.4142 g, 0.81 mmol) in EtOH (8 mL) was added hydrazine monohydrate (0.4 mL, 8.13 mmol), and stirred at room temperature for 16 hours. The reaction mixture was concentrated, and purification of the crude material by column chromatography on silica gel (100:1:1, then 50:1:1, then 20:1:1 $CH_2Cl_2$—MeOH—$NH_4OH$) provided 0.1399 g (44%) of COMPOUND 43 as a white solid. $^1$H NMR ($CDCl_3$) δ 0.78-0.88 (m, 2H), 1.05-1.15 (m, 2H), 1.53-1.62 (m, 1H), 1.72 (d, 2H, J=11.4 Hz), 1.92-1.99 (m, 3H), 2.14 (t, 2H, J=8.1 Hz), 2.30 (t, 2H, J=6.9 Hz), 4.39 (d, 2H, J=10.5 Hz), 7.09-7.13 (m, 2H), 7.64 (d, 2H, J=8.1 Hz), 8.57 (d, 2H, J=3.6 Hz). $^{13}$C NMR ($CDCl_3$) δ 20.83, 24.83, 31.46, 31.78, 41.69, 50.27, 61.97, 122.82, 130.62, 137.29, 147.80, 159.07. EMS m/z 379.3 ($M^+H$). Anal. Calcd. for $C_{19}H_{24}N_4Cl_2$.0.7$H_2O$: C, 58.23; H, 6.53; N, 14.29; Cl, 18.09. Found: C, 58.30; H, 6.33; N, 14.07; Cl, 18.23.

EXAMPLE 44

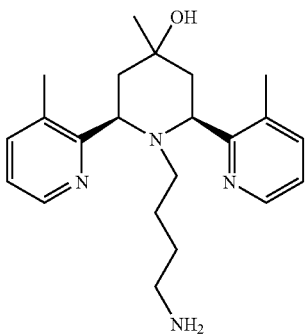

COMPOUND 44: A 1:1 mixture of meso-2'β,4'α,6'β-[1'-(4-amino-butyl)-3,4',3"-trimethyl-1',2',3',4',5',6'-hexahydro-[2,2';6',2"]terpyridin-4'-ol] and meso-2'β,4'β,6'β-[1'-(4-amino-butyl)-3,4',3"-trimethyl-1',2',3',4',5',6'-hexahydro-[2,2';6',2"]terpyridin-4'-ol]

To a solution of meso-2',6'-[3,3"-dimethyl-2',3',5',6'-tetrahydro-1'H-[2,2';6'2"]terpyridin-4'-one] (2.0601 g, 7.32 mmol) in THF (50 mL) were added $Et_3N$ (2.04 mL, 14.64 mmol) and $Boc_2O$ (1.6083 g, 7.32 mmol) in THF (20 mL). The mixture was stirred at 70° C. for 18 hours, then concentrated. Saturated $NaHCO_3$ (30 mL) was added and extracted with $CH_2Cl_2$ (2×50 mL). The combined organic extracts were washed with brine (2×30 mL), dried ($Na_2SO_4$), filtered, and concentrated. Purification of the crude material by column chromatography on silica gel (1:1 hexanes-EtOAc) provided 1.9598 g (70%) of meso-2',6'-[3,3"-dimethyl-4'-oxo-3',4',5',6'-tetrahydro-2'H-[2,2';6'2"]terpyridine-1'-carboxylic acid tert-butyl ester] as an orange solid. $^1$H NMR ($CDCl_3$) δ 1.27 (s, 9H), 2.37 (s, 6H), 2.50-2.58 (m, 2H), 3.16-3.24 (m, 2H), 5.78 (t, 2H, J=6.0 Hz), 6.93-6.98 (m, 2H), 7.35 (d, 2H, J=9.0 Hz), 8.07 (d, 2H, J=6.0 Hz).

To a solution of meso-2',6'-[3,3"-dimethyl-4'-oxo-3',4',5',6'-tetrahydro-2'H-[2,2';6'2"]terpyridine-1'-carboxylic acid tert-butyl ester] (1.1179 g, 2.9 mmol) in THF (30 mL) at 0° C. under Ar was added dropwise 3.0 M MeMgBr in $Et_2O$ (4.88 mL, 14.7 mmol). The mixture was stirred at 70° C. for 20 hours, then cooled to 0° C. and distilled water (30 mL) was slowly added, and stirred for 15 minutes. Next, it was concentrated to remove the THF and extracted with EtOAc (3×100 mL). The combined organic extracts were dried ($Na_2SO_4$), filtered, and concentrated. Purification of the crude material by column chromatography on silica gel (25:1:1 $CH_2Cl_2$—MeOH—$NH_4OH$) followed by another column (1:1 hexanes-EtOAc) provided 0.1256 g (11%) of meso-2'β,6'β-[4'*-hydroxy-3,4',3"-trimethyl-3',4',5',6'-tetrahydro-2'H-[2,2';6'2"]terpyridine-1'-carboxylic acid tert-butyl ester] as a colorless oil and 0.1606 g (19%) of meso-2'β,6'β-[3,4',3"-trimethyl-1',2',3',4',5',6'-hexahydro-[2,2';6',2"]terpyridin-4'*-ol as a beige solid. $^1$H NMR ($CDCl_3$) δ 1.19 (s, 9H), 1.22-1.40 (m, 2H), 1.47 (s, 3H), 1.86-1.92 (m, 2H), 2.35-2.38 (m, 2H), 2.42 (s, 6H), 5.37-5.39 (m, 2H), 6.97-7.01 (m, 2H), 7.38(d, 2H, J=6.0 Hz), 8.13 (d, 2H, J=3.0 Hz) and $^1$H NMR ($CDCl_3$) δ 1.51 (s, 3H), 1.56-1.64 (m, 2H), 1.82-1.94 (m, 3H), 2.36 (s, 6H), 3.09-3.11 (m, 1H), 4.15-4.21 (m, 2H), 7.00-7.06 (m, 2H), 7.40 (d, 2H, J=6.0 Hz), 8.45 (d, 2H, J=3.0 Hz) respectively.

To a solution of meso-2'β,6'β-[3,4',3"-trimethyl-1',2',3',4',5',6'-hexahydro-[2,2';6',2"]terpyridin-4'*-ol (0.2499 g, 0.84 mmol) in DMF (9 mL) was added 2-(4-bromo-butyl)-isoindole-1,3-dione (0.2605 g, 0.92 mmol), KI (0.0142 g, 0.08mmol), and DIPEA (0.29 mL, 1.68 mmol), and stirred at 60° C. for 24 hours. The mixture was concentrated, and saturated $NaHCO_3$ (30 mL) was added and extracted with $CH_2Cl_2$ (3×35 mL). The combined organic extracts were washed with brine (2×20 mL), dried ($Na_2SO_4$), filtered, and concentrated. Purification of the crude material by column chromatography on silica gel (50:1:1 $CH_2Cl_2$—MeOH—$NH_4OH$) provided 0.3144 g (75%) of meso-2'β,6'β-[2-[4-(4'*-hydroxy-3,4',3"-trimethyl-3',4',5',6'-tetrahydro-2'H-[2,2';6',2"]terpyridin-1'yl)-butyl]-isoindole-1,3-dione as a white solid. $^1$H NMR ($CDCl_3$) δ 0.48 (s, 1H), 0.86 (s, 2H), 1.42 (s, 3H), 1.68-1.72 (m, 2H), 2.18-2.38 (m, 6H), 2.45 (s, 6H), 3.15 (t, 2H, J=6.0 Hz), 4.13 (d, 2H, J=12.0 Hz), 6.94-7.03 (m, 2H), 7.25-7.34 (m, 2H), 7.67-7.70 (m, 2H), 7.75-7.78 (m, 2H), 8.32-8.34 (m, 2H).

To a solution of meso-2'β,6'β-[2-[4-(4'*-hydroxy-3,4',3"-trimethyl-3',4',5',6'-tetrahydro-2'H-[2,2';6',2"]terpyridin-1"yl)-butyl]-isoindole-1,3-dione] (0.3144 g, 0.63 mmol) in EtOH (6 mL) was added hydrazine monohydrate (0.31 mL, 6.31 mmol), and stirred for 19 hours, then concentrated. Purification of the crude material by column chromatography on silica gel (20:1:1 $CH_2Cl_2$—MeOH—$NH_4OH$) provided 0.1324 g (52%) of COMPOUND 44 as a white solid. $^1$H NMR ($CDCl_3$) δ 0.72-0.76 (m, 4H), 1.42 (s, 3H), 1.42 (d, 2H, J=12.0 Hz), 2.19-2.73 (m, 6H), 2.45 (s, 6H), 2.46-4.48 (m, 1H), 4.12 (d, 2H, J=11.4 Hz), 7.03-7.07 (m, 2H), 7.41 (d, 2H, J=7.2 Hz), 8.37-8.38 (m, 2H). $^{13}$C NMR ($CDCl_3$) δ 18.98, 22.71, 25.31, 31.15, 41.47, 44.21, 48.20, 61.01, 69.41, 122.29, 131.23, 138.75, 146.95, 159.68. ES-MS m/z 369.4 ($M^+H$). Anal. Calcd. for $C_{22}H_{32}N_4O$.0.2$CH_2Cl_2$.0.7$CH_4O$: C, 67.43; H, 8.70; N, 13.73. Found: C, 67.25; H, 8.57; N, 13.66.

EXAMPLE 45

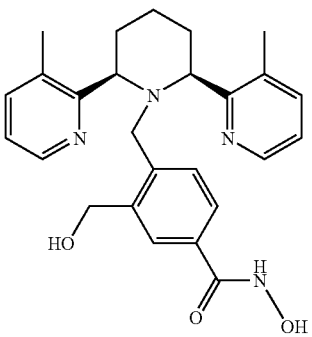

COMPOUND 45: 4-(3,3''-Dimethyl-3',4',5',6'-tetrahydro-2'H-[2,2';6',2'']terpyridin-1'-ylmethyl)-N-hydroxy-3-hydroxymethyl-benzamide Following General Procedure A: 3,3''-dimethyl-1',2',3',4',5',6'-hexahydro-[2,2';6',2'']terpyridine (1.6 g, 6.0 mmol) was reacted with 2-bromomethyl-5-cyano-benzoic acid methyl ester (1.5 g, 6.0 mmol) to give 5-cyano-2-(3,3''-dimethyl-3',4',5',6'-tetrahydro-2'H-[2,2';6',2'']terpyridin-1'-ylmethyl)-benzoic acid methyl ester (2.05 g, 78%), as a pale-yellow solid.

To a stirred, room temperature solution of the ester from above (2.05 g, 4.6 mmol) in MeOH (50 mL) was added LiBH$_4$ (1.0 g, 50 mmol) in three portions. Effervescence was observed, and the mixture was stirred for 3.5 hours. The mixture was concentrated and 1 N NaOH (50 mL) was added to the resultant residue. The aqueous mixture was extracted with CH$_2$Cl$_2$ (3×50 mL). The organic extracts were combined, dried (Na$_2$SO$_4$), and concentrated. Purification of the crude material by column chromatography on silica gel (40 g, eluted with 5% NH$_4$OH/5% MeOH/CH$_2$Cl$_2$) provided 4-3,3''-dimethyl-3',4',5',6'-tetrahydro-2'H-[2,2';6',2'']terpyridin-1'-ylmethyl)-3-hydroxymethyl-benzonitrile (1.63 g, 86%) as a pale yellow solid.

The nitrile from above (1.13 g, 2.7 mmol) was stirred in refluxing 50% H$_2$SO$_4$ (50 mL) for 16 hours. The solution was cooled to room temperature and concentrated to remove water. The residue was taken up in MeOH (50 mL) and concentrated three times. MeOH was added to the resultant residue and the solution was refluxed for 2 hours. The solution was concentrated to remove MeOH. The residue was basified with 10 N NaOH (final pH=10) and extracted with CH$_2$Cl$_2$ (3×100 mL). The combined organic extracts were dried (Na$_2$SO$_4$) and concentrated. Purification of the crude material by silica gel column chromatography (30 g, eluted with 5% NH$_4$OH/5% MeOH/CH$_2$Cl$_2$) gave two products: 4-(3,3''-dimethyl-3',4',5',6'-tetrahydro-2'H-[2,2';6',2'']terpyridin-1'-ylmethyl)-3-hydroxymethyl-benzoic acid methyl ester (700 mg, 58%), and 4-(3,3''-dimethyl-3',4',5',6'-tetrahydro-2'H-[2,2';6',2'']terpyridin-1'-ylmethyl)-3-methoxymethyl-benzoic acid methyl ester (210 mg, 17%).

To a stirred solution of sodium (320 mg, 14 mmol) in anhydrous MeOH (15 mL) was added NH$_2$OH.H$_2$O (550 mg, 7.9 mmol) followed by a solution of 4-(3,3''-dimethyl-3',4',5',6'-tetrahydro-2'H-[2,2';6',2'']terpyridin-1'-ylmethyl)-3-hydroxymethyl-benzoic acid methyl ester (700 mg, 1.6 mmol) in anhydrous MeOH (7 mL). The mixture was stirred for 2 h, at which time TLC indicated that the reaction had stalled. A solution of sodium (320 mg, 14 mmol) and NH$_2$OH.H$_2$O (550 mg, 7.9 mmol) in anhydrous MeOH (8 mL) was added to the reaction mixture and stirring was continued for 2 hours. The reaction mixture was diluted with CHCl$_3$ (100 mL) and poured into a saturated NaHCO$_3$ solution (100 mL). The aqueous layer was extracted with CHCl$_3$ (5×100 mL). The combined organic portions were concentrated to 100 mL, washed once with saturated NaHCO$_3$ solution (20 mL), dried over Na$_2$SO$_4$, concentrated, and dried under high vacuum to give COMPOUND 45 (647 mg, 92%) as an off-white solid. $^1$H NMR (DMSO-d$_6$) δ 1.46 (d, 2H, J=12.0 Hz), 1.69-1.84 (m, 1H), 2.01-2.11 (m, 1H), 2.48 (s, 6H), 3.59 (s, 2H), 4.13 (d, 2H, J=3.8 Hz), 4.40 (d, 2H, J=10.8 Hz), 4.79-4.85 (m, 1H), 5.74 (s, 1H), 6.84-6.91 (m, 3H), 7.06 (d, 1H, J=7.5 Hz), 7.18-7.28 (m, 3H), 8.14 (d, 2H, J=3.3 Hz), 8.75 (s br, 1H), 10.82 (s br, 1H); $^{13}$C NMR (D$_2$O) δ 18.38(2), 24.40, 25.32(2), 55.27, 60.85(2), 64.75, 122.31(2), 123.64, 124.88, 126.82, 132.62, 137.64(2), 138.08, 143.18, 145.86(2), 158.58, 164.49; ES-MS m/z 447 (M$^+$H). Anal. Calcd. For C$_{26}$H$_{30}$N$_4$O$_3$.1.1H$_2$O: C, 66.96; H, 6.96; N, 12.01. Found: C, 66.95; H, 6.71; N, 11.66.

EXAMPLE 46

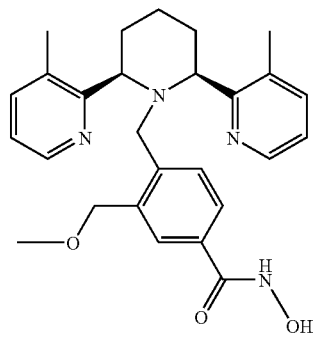

COMPOUND 46: 4-(3,3''-Dimethyl-3',4',5',6'-tetrahydro-2'H-[2,2';6',2'']terpyridin-1'-ylmethyl)-N-hydroxy-3-methoxymethyl-benzamide To a stirred solution of sodium (100 mg, 4.2 mmol) in anhydrous MeOH (4 mL) was added NH$_2$OH.H$_2$O (260 mg, 3.7 mmol) followed by a solution of 4-(3,3''-dimethyl-3',4',5',6'-tetrahydro-2'H-[2,2';6',2'']terpyridin-1'-ylmethyl)-3-methoxymethyl-benzoic acid methyl ester (170 mg, 0.37 mmol) in anhydrous MeOH (4 mL). The mixture was stirred for 16 hours, diluted with CHCl$_3$ (50 mL) and poured into a saturated NaHCO$_3$ solution (50 mL). The aqueous layer was extracted with CHCl$_3$ (5×25 mL). The combined organic portions were dried over Na$_2$SO$_4$ and concentrated. The resultant crude material was purified on a silica gel column (10 g, eluted with 5% NH$_4$OH/10% MeOH/CH$_2$Cl$_2$) and dried under high vacuum to give COMPOUND 46 (60 mg, 35%) as a white solid. $^1$H NMR (CDCl$_3$) δ 1.57-1.71 (m, 2H), 1.80-2.14 (m, 2H), 2.31-2.40 (m, 2H), 2.44 (s, 6H), 3.25 (s, 3H), 3.61 (s, 2H), 4.12 (s, 4H), 6.61-6.71 (m, 1H), 6.74-6.84 (m, 2H), 6.88-6.97 (m, 1H), 7.20 (s, 3H), 8.22 (s, 2H), 9.85 (s br, 1H); ES-MS m/z 461 (M$^+$H).

EXAMPLE 47

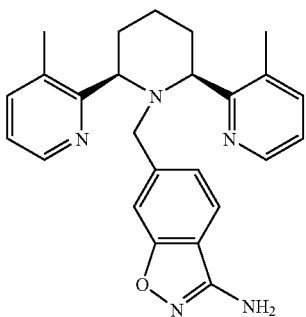

COMPOUND 47: The 6-((2'S,6'R)-3,3"-dimethyl-3', 4',5',6'-tetrahydro-2'H-2,2';6',2"-terpyridin-1'-ylmethyl)-1,2-benzisoxazol-3-ylamine (HBr salt)

Under $N_2$, to a suspension of 1-bromo-2-fluoro-4-methylbenzene (2.59 g, 13.7 mmol) and $Zn(CN)_2$ (1.60 g, 13.7 mmol) in dry DMF (50 mL) was added 1,1'-bis(diphenylphosphino)ferrocene (DPPF) (0.0753 g, 0.136 mmol) and $Pd_2(dba)_3$ (dba=di(benzylidene)acetone) (0.0623 g, 0.0681 mmol). After the mixture was heated at 130° C. for 2 days, the solvent was removed by evaporation under vacuum, and saturated aqueous $NaHCO_3$ (40 mL) was added. The aqueous suspension was extracted with $CH_2Cl_2$ (3×40 mL), and the extract was dried over $Na_2SO_4$. After filtration the solvent was removed by evaporation under vacuum, and the residual solid was purified by flash chromatography on silica gel (1:20 EtOAc/hexanes), affording 2-fluoro-4-methyl-benzonitrile as a pale yellow solid (1.21 g, 65%). $^1$H NMR ($CDCl_3$) δ 2.43 (s, 3H), 7.01-7.07 (m, 2H), 7.48-7.52 (m, 1H).

To a solution of 2-fluoro-4-methyl-benzonitrile (1.45 g, 10.7 mmol) in $CCl_4$ (100 mL) was added 1,1'-azobis(cyclohexanecarbonitrile) (0.240 g, 0.982 mmol) and NBS (2.19 g, 12.3 mmol). The mixture was stirred and heated at reflux overnight, and then cooled to room temperature. A solution of $Na_2S_2O_3$ (5 g) in $H_2O$ (100 mL) was added, and the organic layer was collected. The aqueous layer was extracted with $CH_2Cl_2$ (3×50 mL), and the extracts were combined and dried over $Na_2SO_4$. After filtration the solvent was removed by evaporation under vacuum, and the residue was purified on silica gel column (1:10 EtOAc/hexanes), affording 4-bromomethyl-2-fluoro-benzonitrile as a pale yellow oil (1.49 g, 65%). $^1$H NMR ($CDCl_3$) δ 4.45 (s, 2H), 7.24-7.30 (m, 2H), 7.60 (dd, 1H, J=6.3, 8.1 Hz).

A mixture of (2'R,6'S)-3,3"-dimethyl-1',2',3',4',5',6'-hexahydro-[2,2';6',2"]terpyridine (0.267 g, 1.00 mmol), 4-bromomethyl-2-fluoro-benzonitrile (0.321 g, 0.150 mmol), DIPEA (0.259 g, 2.00 mmol) and KI (0.017 g, 0.10 mmol) in dry $CH_3CN$ (10 mL) was stirred at 60° C. for 16 h. After that period of time the $CH_3CN$ was removed by evaporation under vacuum, and saturated aqueous $NaHCO_3$ (20 mL) was added. The aqueous mixture was extracted with $CH_2Cl_2$ (3×30 mL, and the extract was dried over $Na_2SO_4$. After filtration the solvent was removed by evaporation under vacuum, and the residue was purified on a silica gel column (1000:30:1, $CH_2Cl_2/CH_3OH/NH_4OH$), affording 4-((2'R,6'S)-3,3"-dimethyl-3',4',5',6'-tetrahydro-2'H-[2,2';6',2"]terpyridin-1'-ylmethyl)-2-fluoro-benzonitrile as a white foam (0.400 g, 100%). $^1$H NMR ($CDCl_3$) δ 1.65-1.80 (m, 3H), 2.09-2.14 (m, 1H), 2.20-2.38 (m, 2H), 2.44 (s, 6H), 3.58 (s, 2H), 4.16 (s, 1H), 4.20 (s, 1H), 6.37-6.43 (m, 2H), 6.93-7.03 (m, 3H), 7.23 (d, 2H, J=7.5 Hz), 8.35 (dd, 2H, J=0.9, 4.5 Hz).

To a solution of potassium tert-butoxide (0.140 g, 1.25 mmol) in dry DMF (5 mL) was added acetone oxime (0.0877 g, 1.20 mmol), and the mixture was stirred for 30 min. A solution of 4-((2'R,6'S)-3,3"-dimethyl-3',4',5',6'-tetrahydro-2'H-[2,2';6',2"]terpyridin-1'-ylmethyl)-2-fluoro-benzonitrile (0.400 g, 1.00 mmol) in dry DMF (5 mL) was then added, and the mixture was stirred overnight. The solvent was then removed by evaporation under vacuum, and saturated aqueous $NaHCO_3$ (10 mL) was added. The mixture was extracted with EtOAc (3×30 mL), and the extract was dried over $Na_2SO_4$. After filtration the solvent was removed by evaporation under vacuum, and the residue was purified on silica gel column (1000:25:1 $CH_2Cl_2/CH_3OH/NH_4OH$), affording 4-((2'R,6'S)-3,3"-dimethyl-3',4',5',6'-tetrahydro-2'H-[2,2';6',2"]terpyridin-1'-ylmethyl)-2-isopropylideneaminooxy-benzonitrile as a pale yellow solid (0.311 g, 69%). $^1$H NMR ($CDCl_3$) δ 1.65-1.75 (m, 3H), 2.06 (s, 3H), 2.07 (s, 3H), 2.09-2.14 (m, 1H), 2.20-2.40 (m, 2H), 2.45 (s, 6H), 3.58 (s, 2H), 4.19 (s, 1H), 4.23 (s, 1H), 6.14 (d, 1H, J=7.8 Hz), 6.68 (s, 1H), 6.91-6.96 (m, 3H), 7.22 (d, 2H, J=7.2 Hz), 8.35 (d, 2H, J=3.9 Hz).

To a solution of 4-((2'R,6'S)-3,3"-dimethyl-3',4',5',6'-tetrahydro-2'H-[2,2';6',2"]terpyridin-1'-ylmethyl)-2-isopropylideneaminooxy-benzonitrile (0.145 g, 0.320 mmol) in EtOH (4 mL) was added aqueous HCl (3 N, 4 mL), and the mixture was stirred and heated at reflux overnight. The mixture was then cooled to room temperature, EtOH was removed, and saturated aqueous $NaHCO_3$ (20 mL) was added. The aqueous mixture was extracted with $CH_2Cl_2$ (4×40 mL), and the combined extract was dried over $Na_2SO_4$. After filtration the solvent was removed by evaporation under vacuum, and the residue was purified on silica gel column (100:5:2 $CH_2Cl_2/CH_3OH/NH_4OH$), affording 6-((2'S,6'R)-3,3"-dimethyl-3', 4', 5', 6'-tetrahydro-2H-2,2';6',2"-terpyridin-1'-ylmethyl)-1,2-benzisoxazol-3-ylamine as a white solid (0.082 g, 62%).

Following General Procedure B the white solid (0.060 g, 0.15 mmol) was treated with HBr/MeOH to afford an HBr salt as a yellow solid (0.099 g, 96%). $^1$H NMR ($CD_3OD$) δ 1.83-1.94 (m, 3H), 2.03-2.16 (m, 3H), 2.63 (s, 6H), 3.77 (s, 2H), 4.57-4.60 (m, 2H), 6.99 (d, 1H, J=8.1 Hz), 7.03 (s, 1H), 7.43 (d, 1H, J=8.1 Hz), 7.76 (dd, 2H, J=5.7, 7.8 Hz), 8.29 (d, 2H, J=7.8 Hz), 8.69 (d, 2H, J=5.7 Hz). $^{13}$C NMR ($CD_3OD/D_2O$) δ 16.98, 22.07, 38.37, 61.33, 61.83, 110.25, 114.90, 122.14, 124.69, 125.39, 136.38, 138.93, 139.65, 148.66, 154.78, 157.50, 161.07. ES-MS m/z 414 (M$^+$H). Anal. Calcd. for $C_{25}H_{27}N_5O.3.4HBr.1H_2O$: C, 42.39; H, 4.64; N, 9.89; Br, 38.35. Found: C, 42.22; H, 4.55; N, 9.60; Br, 38.54.

EXAMPLE 48

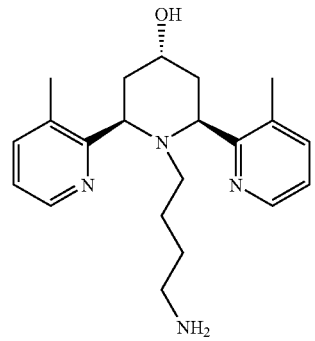

COMPOUND 48: Meso-2'β,4'α,6'β-[1'-(4-aminobutyl)-3,3"-dimethyl-1',2',3',4',5',6'-hexahydro-[2,2'; 6',2"]terpyridin-4'-ol]

To a solution of meso-2'β,6'β-[3,3"-dimethyl-2',3',5',6'-tetrahydro-1'H-[2,2';6'2"]terpyridin-4'-one] (3.5417 g, 12.6 mmol) in THF (90 mL) under Ar at −78° C. was slowly added L-selectride (13.8 mL, 13.8 mmol), and was stirred for 30 minutes (*Tetrahedron: Asymmetry* (1999) 10:2225-2235).

MeOH (35 mL) was added, and at room temperature distilled water (70 mL) was added and extracted with CH$_2$Cl$_2$ (3×150 mL). The combined organic extracts were dried (Na$_2$SO$_4$), filtered, and concentrated to provide 5.37 g (100%) of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] as a sticky orange oil. $^1$H NMR (CDCl$_3$) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44-8.45 (m, 2H).

To a solution of a 1:1 mixture of meso-2'β,4'α,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] in THF (90 mL) was added DIPEA (4.36 mL, 25.2 mmol) and Boc$_2$O (3.3407 g, 15.1 mmol) and stirred at 50° C. for 16 hours. The mixture was concentrated, and saturated NaHCO$_3$ (75 mL) was added and extracted with CH$_2$Cl$_2$ (3×100 mL). The combined organic extracts were washed with brine (2×75 mL), dried (Na$_2$SO$_4$), filtered, and concentrated. Purification of the crude material by column chromatography on silica gel (1:1 hexanes-EtOAc) provided 1.2984 g (27%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester as a yellow solid and 0.8605 g (18%) of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester a pale yellow solid. $^1$H NMR (CDCl$_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz) and $^1$H NMR (CDCl$_3$) δ 1.50 (s, 9H), 1.67-1.76 (m, 2H), 2.21 (s, 6H), 2.69-2.76 (m, 2H), 5.62-5.67 (m, 1H), 5.80-5.83 (m, 2H), 6.68-6.72 (m, 2H), 6.97-7.05 (m, 2H), 7.99 (d, 2H, J=3 Hz), respectively.

To a solution of meso-2'β,4'α,6'β-[4'-(4'-hydroxy-3,3"-dimethyl-3',4',5',6'-tetrahydro-2'H-[2,2';6'2"]terpyridine]-1'-carboxylic acid tert-butyl ester (0.2508 g, 0.66 mmol) in CH$_{Cl2}$ (5 mL) was added TFA (5 mL), and stirred at room temperature for 3.5 hours. The mixture was concentrated, and distilled water (2 mL) and 10 N NaOH (2 mL) were added and extracted with CH$_2$Cl$_2$ (3×50 mL). The combined organic extracts were dried (Na$_2$SO$_4$), filtered, and concentrated to provide 0.2182 g (100%) of meso-2'β,4'α,6'β-[3,3"-dimethyl-1',2',3',4',5',6'-hexahydro-[2,2';6'2"]terpyridin-4'-ol] as a beige solid. $^1$H NMR (CDCl$_3$) δ 1.82-1.97 (m, 4H), 2.39 (s, 6H), 4.46-4.48 (m, 1H), 4.90-4.93 (m, 2H), 7.04-7.08 (m, 2H), 7.40-7.43 (m, 2H), 8.44 (d, 2H, J=3.0 Hz).

Following General Procedure A: To a solution of meso-2'β,4'α,6'β-[3,3"-dimethyl-1',2',3',4',5',6'-hexahydro-[2,2';6'2"]terpyridin-4'-ol] (0.2182 g, 0.77 mmol) in DMF (5 mL) was added 2-(4-bromo-butyl)-isoindole-1,3-dione (0.2389 g, 0.85 mmol), KI (0.0128 g, 0.08 mmol), and DIPEA (0.27 mL, 1.54 mmol). The mixture stirred at 60° C. for 21 hours before it was concentrated. Purification of the crude material by column chromatography on silica gel (25:1:1 CH$_2$Cl$_2$—MeOH—NH$_4$OH) provided 0.2356 g (61%) of meso-2'β,4'α,6'β-2-[4-(4'-hydroxy-3,3"-dimethyl-3',4',5',6'-tetrahydro-2H-[2,2';6'2"]terpyridin-1'-yl)-butyl]-isoindole-1,3-dione. $^1$H NMR (CDCl$_3$) δ 0.46-0.47 (m, 2H), 0.85-0.89 (m, 2H), 1.72 (d, 2H, J=12.0 Hz), 2.34-2.40 (m, 2H), 2.48 (s, 6H), 2.49-2.50 (m, 2H), 3.16 (t, 2H, J=6.0 Hz), 4.44-4.45 (m, 1H), 4.71 (d, 2H, J=6.0 Hz), 6.94-6.98 (m, 2H), 7.27-7.29 (m, 2H), 7.69-7.72 (m, 2H), 7.78-7.81 (m, 2H), 8.38 (d, 2H, J=6.0 Hz).

To a solution of meso-2'β,4'α,6'β-2-[4-(4'-hydroxy-3,3"-dimethyl-3',4',5',6'-tetrahydro-2'H-[2,2';6',2"]terpyridin-1'-yl)-butyl]-isoindole-1,3-dione (0.2356 g, 0.47 mmol) in EtOH (5 mL) was added hydrazine monohydrate (0.23 mL, 4.70 mmol), and stirred at room temperature for 17 hours. The reaction mixture was concentrated, and purification of the crude material by column chromatography on silica gel (15:1:1 CH$_2$Cl$_2$—MeOH—NH$_4$OH) provided 0.1297 g (72%) of COMPOUND 48 as a white solid. $^1$H NMR (CDCl$_3$) δ 0.40-0.42 (m, 2H), 0.66-0.71 (m, 2H), 1.72 (d, 2H, J=15.0 Hz), 2.13-2.14 (m, 2H), 2.27-2.32 (m, 2H), 2.49-2.54 (m, 2H), 2.55 (s, 6H), 4.44 (s, 1H), 4.70 (d, 2H, J=9.0 Hz), 7.06-7.10 (m, 2H), 7.43 (d, 2H, J=9.0 Hz), 8.43 (d, 2H, J=3.0 Hz). $^{13}$C NMR (CDCL$_3$) δ 19.02, 24.67, 28.82, 35.26, 41.38, 46.36, 57.34, 64.78, 122.19, 132.69, 138.41, 146.53, 160.21. ES-MS m/z 355.3 (M$^+$H). Anal. Calcd. for C$_{21}$H$_{30}$N$_4$O.0.2CH$_2$Cl$_2$.0.8H$_2$O: C, 65.99; H, 8.36; N, 14.52. Found: C, 66.22; H, 8.28; N, 14.88.

EXAMPLE 49

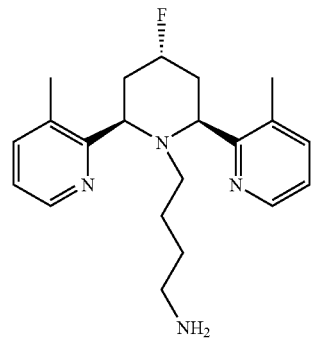

COMPOUND 49: Meso-2'β,4'α,6'β-[4-(4'-fluoro-3,3"-dimethyl-3',4',5',6'tetrahydro-2'H-[2,2';6',2"]terpyridin-1'-yl)-butylamine]

To a solution of meso-2'β,4'β,6'β-[4'-hydroxy-3,3"-dimethyl-3',4',5',6'-tetrahydro-2H-[2,2';6'2"]terpyridine]-1'-carboxylic acid tert-butyl ester (0.5022 g, 1.31 mmol) in CH$_2$Cl$_2$ (13 mL) at 0° C. under Ar was added dropwise (diethylamino) sulfur trifluoride (0.19 mL, 1.44 mmol) and stirred for 20 minutes, then stirred at room temperature for 40 minutes. Saturated NaHCO$_3$ (20 mL) was added and extracted with CH$_2$Cl$_2$ (3×30 mL). The combined organic extracts were washed with brine (1×20 mL), dried (Na$_2$SO$_4$), filtered, and concentrated. Purification of the crude material by column chromatography on silica gel (1:1 hexanes-EtOAc, then EtOAc) provided 0.1524 g (30%) of meso-2'β,4'α,6'β-[4'-fluoro-3,3"-dimethyl-3',4',5',6'-tetrahydro-2'H-[2,2';6'2"]terpyridine]-1'-carboxylic acid tert-butyl ester as an amber oil. $^1$H NMR (CDCl$_3$) δ 1.43 (s, 9H), 1.44-1.45 (m, 1H), 1.88-2.01 (m, 2H), 2.25 (s, 6H), 2.78-2.88 (m, 2H), 5.78 (t, 2H, J=5.1 Hz), 6.75-6.79 (m, 2H), 7.11 (d, 2H 2H, J=4.8 Hz).

To a solution of meso-2β,4'α,6'β-[4'-fluoro-3,3"-dimethyl-3',4',5',6'-tetrahydro-2'H-[2,2';6'2"]terpyridine]-1'-carboxylic acid tert-butyl ester in CH$_2$Cl$_2$ (5 mL) was added TFA (5 mL), and stirred at room temperature for 18 hours. The mixture was concentrated, and distilled water (2 mL) and 10 N NaOH (2 mL) were added and extracted with CH$_2$Cl$_2$ (3×40 mL). The combined organic extracts were dried (Na$_2$SO$_4$), filtered, and concentrated to provide 0.0834 g (73%) of meso-2'β,4'α,6'β-[4'-fluoro-3,3"-dimethyl-1',2',3',4',5',6'-hexahydro-[2,2';6'2"]terpyridine] as an amber oil. $^1$H NMR (CDCl$_3$) δ 1.81-1.90 (m, 1H), 1.96-2.18 (m, 4H), 2.40 (s, 6H), 2.71-

3.00 (m, 1H), 4.68 (d, 2H, J=10.2 Hz), 7.03-7.07 (m, 2H), 7.41 (d, 2H, J=7.7 Hz), 8.43 (d, 2H, J=4.5).

Following General Procedure A: To a solution of meso-2'β,4'α,6'β-[4'-fluoro-3,3"-dimethyl-1',2',3',4',5',6'-hexahydro-[2,2';6'2"]terpyridine] (0.0834 g, 0.29 mmol) in DMF (5 mL) was added 2-(4-bromo-butyl)-isoindole-1,3-dione (0.0946 g, 0.32 mmol), KI (0.0048 g, 0.03 mmol), and DIPEA (0.10 mL, 0.58 mmol). The mixture stirred at 60° C. for 21 hours before it was concentrated. Purification of the crude material by column chromatography on silica gel (100:1:1 $CH_2Cl_2$—MeOH-$NH_4OH$) provided 0.0839 g (63%) of meso-2β,4'α,6'β-[4-(4'-fluoro-3,3"-dimethyl-3',4',5',6'-tetrahydro-2'H-[2,2';6'2"]terpyridin-1'-yl)-butylamine]. $^1H$ NMR (CDCl$_3$) δ 0.74-0.84 (m, 2H), 1.87 (s, 6H), 2.34-2.44 (m, 3H), 2.48 (s, 6H), 3.12 (t, 2H, J=7.0 Hz), 4.67 (d, 2H, J=11.4 Hz), 6.92-6.96 (m, 2H), 7.23-7.25 (m, 2H), 7.71-7.73 (m, 2H), 7.78-7.82 (m, 2H), 8.36 (d, 2H, J=6.0 Hz).

To a solution of meso-2'β,4'α,6'β-[4-(4'-fluoro-3,3"-dimethyl-3',4',5',6'-tetrahydro-2'H-[2,2';6'2"]terpyridin-1'-yl)-butylamine] (0.0839 g, 0.018 mmol) in EtOH (2 mL) was added hydrazine monohydrate (0.10 mL, 1.83 mmol), and stirred at room temperature for 20 hours. The reaction mixture was concentrated, and purification of the crude material by column chromatography on silica gel (75:1:1 then 25:1:1 $CH_2Cl_2$—MeOH—$NH_4OH$) provided 0.0482 g (73%) of COMPOUND 49 as a white solid. $^1H$ NMR (CDCl$_3$) δ 0.36-0.38 (m, 2H), 0.61-0.71 (m, 3H), 1.97 (t, 2H, J=12.0 Hz), 2.10 (t, 2H, J=6.3 Hz), 2.30 (t, 2H, J=7.8 Hz), 2.41-2.61 (m, 4H), 2.53 (s, 6H), 4.66 (d, 2H, J=11.7 Hz), 7.07-7.12 (m, 2H), 7.44 (d, 2H, J=7.5 Hz), 8.43 (d, 2H, J=4.2 Hz). $^{13}C$ NMR (CDCl$_3$) δ 18.94, 25.73, 31.18, 31.64, 31.90, 41.76, 44.59, 57.59, 122.87, 133.03, 138.37, 146.68, 159.05. ES-MS m/z 357.3 (M$^+$H). Anal. Calcd. for $C_{21}H_{29}N_4F$.0.1$CH_2Cl_2$: C, 69.44; H, 8.06; N, 15.35; F, 5.21. Found C, 69.57; H, 8.12; N, 15.04; F, 5.06.

EXAMPLE 50

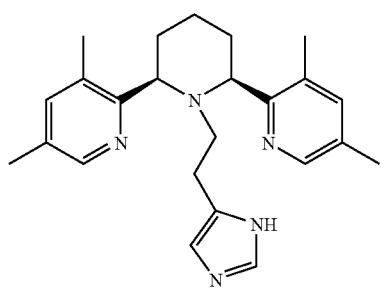

COMPOUND 50: Meso-2'β,6'β-[2-(3, 5,3",5"-tetramethyl-3',4',5',6'-tetrahydro-2'H-[2,2';6',2"]terpyridin-1'-ylmethyl)-benzonitrile]

To a solution of meso-2'β,6=β-[3,5,3",5"-tetramethyl-1',2',3',4',5',6'-hexahydro-[2,2';6',2"]terpyridine (0.2860 g, 0.97 mmol) in DMF (10 mL) was added 5-(2-chloro-ethyl)-1H-imidazole (0.1896 g, 1.45 mmol), KI (0.0161 g, 0.10 mmol), and DIPEA (0.34 mL, 1.94 mmol). The reaction was stirred at 80° C. for 18 hours, then concentrated. Saturated NaHCO$_3$ (25 mL) was added and extracted with CH$_2$Cl$_2$ (3×50 mL). The combined organic extracts were washed with brine (3×30 mL), dried (Na$_2$SO$_4$), filtered, and concentrated. Purification of the crude material by column chromatography on silica gel (100:1:1 then 50:1:1 CH$_2$Cl$_2$—MeOH—NH$_4$OH) provided 76.7 mg (19%) of COMPOUND 50 as a beige solid. $^1H$ NMR (CDCl$_3$) δ 1.53-1.67 (m, 4H), 1.84-2.06 (m, 4H), 2.21 (s, 6H), 2.34 (s, 6H), 2.46-2.57 (m, 2H), 3.86 (d, 2H, J=6.0 Hz), 6.14 (s, 1H), 7.18 (s, 2H), 7.39 (s, 1H), 8.17 (s, 2H). $^{13}C$ NMR (CDCl$_3$) 17.44, 18.22, 22.51, 24.67, 31.07, 50.85, 64.51, 119.07, 130.19, 130.81, 133.62, 138.86, 140.08, 146.54, 157.06. ES-MS m/z 390.3 (M$^+$H). Anal. Calcd. for $C_{24}H_{31}N_5$.0.4CH$_2$Cl$_2$: C, 69.20; H, 7.57; N, 16.54. Found: C, 69.05; H, 7.75; N, 16.46.

EXAMPLE 51

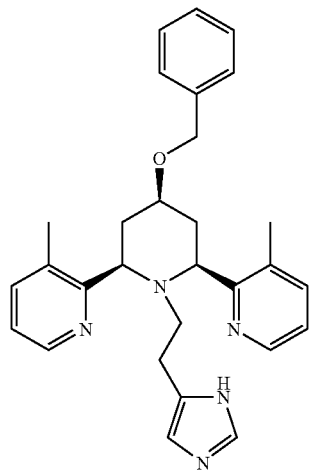

COMPOUND 51: Meso-2'β,4'β,6'β-[4'-benzyloxy-1'-[2-(3H-imidazol-4-yl)-ethyl]-3,3"-dimethyl-1',2',3',4',5',6'-hexahydro-[2,2',6',2"]terpyridine To a solution of meso-2'β,4'β,6'β-[4'-hydroxy-3,3'-dimethyl-3',4',5',6'-tetrahydro-2'H-[2,2';6'2"]terpyridine-1'-carboxylic acid tert-butyl ester] (0.7035 g, 1.8 mmol) in DMF (18 mL) was added NaH, 60% dispersion in mineral oil (0.1440 g, 3.6 mmol), and stirred at room temperature for 1 hour. Benzyl bromide (1.07 mL, 9.0 mmol) and KI (0.0664 g, 0.4 mmol) were added, and stirred at 80° C. for 20 hours. The mixture was concentrated, and saturated NaHCO$_3$ (30 mL) was added and extracted with CH$_2$Cl$_2$ (3×50 mL). The combined organic extracts were washed with brine (3×50 mL), dried (Na$_2$SO$_4$), filtered, and concentrated. Purification of the crude material by column chromatography on silica gel (100:1:1 CH$_2$Cl$_2$—MeOH—NH$_4$OH) provided a 1:1 mixture of recovered starting material meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester] and product meso-2'β,4'β,6'β-[4'-benzyloxy-3,3"-dimethyl-3',4',5',6'-tetrahydro-2'H-[2,2';6'2"]terpyridine-1'-carboxylic acid tert-butyl ester] as a dark red oil.

To a solution of the above in CH$_2$Cl$_2$ (10 mL) was added TFA (10 mL) and stirred at room temperature for 1 hour. The reaction was concentrated, and water (5 mL) and CH$_2$Cl$_2$ (40 mL) were added. 10N NaOH was slowly added (10 mL) until basic, and the phases were separated. The aqueous phase was extracted with CH$_2$Cl$_2$ (2×40 mL), and the combined organic extracts were dried (Na$_2$SO$_4$), filtered, and concentrated. Purification of the crude material by column chromatography on silica gel (50:1:1 CH$_2$Cl$_2$—MeOH—NH$_4$OH) followed by another column (100:1:1 CH$_2$Cl$_2$—MeOH—NH$_4$OH) provided 0.1282 g (19%, 2 steps) of meso-2'β,4'β,6'β-[4'-benzyloxy-3,3"-dimethyl-1',2',3',4',5',6'-hexahydro-[2,2';6'2"]terpyridine as a yellow oil. $^1$H NMR (CDCl$_3$) δ 2.19-2.31 (m, 2H), 2.37 (s,3H), 2.42 (s, 3H), 3.84-3.89 (m, 1H), 4.20 (d, 2H, J=9.0 Hz), 4.63 (s, 2H), 5.39 (t, 1H, J=7.5 Hz), 7.01-7.07 (m, 4H), 7.29-7.42 (m, 5H), 8.45 (d, 2H, J=3.0 Hz).

To a solution of meso-2'β,4'β,6'β-[4'-benzyloxy-3,3"-dimethyl-1',2',3',4',5',6'-hexahydro-[2,2';6'2"]terpyridine (0.1282 g,0.34 mmol) in DMF (4 mL) were added 2-(2-chloro-ethyl)-1H-imidazole (0.0672 g, 0.51 mmol), DIPEA (0.12 mL, 0.68 mmol), and KI (0.0056 g, 0.03 mmol). The reaction was stirred at 80° C. for 65 hours, then concentrated. Saturated NaHCO$_3$ (15 mL) was added and extracted with CH$_2$Cl$_2$ (3×20 mL). The combined organic extracts were washed with brine (2×30 mL), dried (Na$_2$SO$_4$), filtered, and concentrated. Purification of the crude material by column chromatography on silica gel (50:1:1, 25:1:1, then 10:1:1 CH$_2$Cl$_2$—MeOH—NH$_4$OH) followed by radial chromatography on silica (20:1:1 CH$_2$Cl$_2$—MeOH—NH$_4$OH) provided 24.4 mg (13%) of COMPOUND 51 as a white solid. $^1$H NMR (CDCl$_3$) δ 2.09-2.28 (m, 4H), 2.40 (s, 6H), 2.53-2.65 (m, 2H),2.95-3.04 (m, 1H), 3.71-3.77, 4.02 (d, 2H J=11.7 Hz), 4.20 (t, 1H, J=6.9 Hz), 4.59 (s, 2H), 6.15 (s, 1H), 7.05-7.09 (m, 2H), 7.28-7.33 (m, 5H), 7.36-7.42 (m, 3H), 8.38-8.39 (m, 2H). $^{13}$C NMR (CDCl$_3$) 19.10, 24.07, 30.27, 32.30, 36.52, 44.46, 47.36, 50.02, 166.68, 122.72, 127.85, 128.76, 131.88, 134.38, 135.70, 137.17, 139.09, 140.39, 146.59, 147.05, 159.32. ES-MS m/z 468.5 (M$^+$H). Anal. Calcd. for C$_{29}$H$_{33}$O.0.6CH$_2$Cl$_2$.0.6H$_5$NO: C, 65.89; H, 6.95; N, 14.54. Found: C, 66.08; H, 6.79; N, 14.75.

EXAMPLE 52

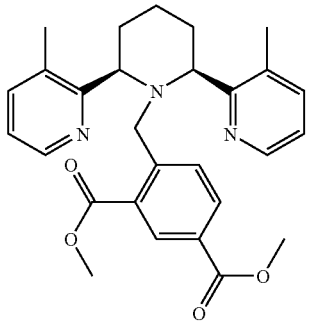

COMPOUND 52: 4-(3,3"-Dimethyl-3',4',5',6'-tetrahydro-2'H-[2,2':6',2"]terpyridin-1'-ylmethyl)-isophthalic acid dimethyl ester 5-Cyano-2-methyl-benzoic acid methyl ester (1.09 g, 6.22 mmol) was suspended in a mixture of water (25 mL) and concentrated sulfuric acid (10 mL). The yellow solution was stirred at 150° C. for 4 hours to give a pale yellow slurry. The reaction mixture was cooled to room temperature and the precipitate was isolated via suction filtration, washed with water (2×10 mL) and dried in vacuo to yield 4-methyl-isophthalic acid as a tan solid. The diacid was then suspended in MeOH (25 mL) and concentrated sulfuric acid (10 mL) and the resulting mixture was stirred at 90° C. for 14 hours to give a bright yellow solution. The MeOH was removed under reduced pressure and the remaining aqueous solution was diluted with brine (60 mL) and EtOAc (50 mL) and then neutralized with 3M NaOH until pH of aqueous layer was approximately 10. The mixture was extracted with EtOAc (3×100 mL), dried (Na$_2$SO$_4$), filtered, and concentrated in vacuo to give pure 4-methyl-isophthalic acid dimethyl ester as a pale orange solid (1.06 g, 82%, 2-steps). $^1$H NMR (CDCl$_3$) δ 2.66 (s, 3H), 3.92 (s, 3H), 3.93 (s, 3H), 7.33 (d, 1H, J=9.0 Hz), 8.05 (dd, 1H, J=9.0, 3.0 Hz), 8.57 (d, 1H, J=3.0 Hz).

4-Methyl-isophthalic acid dimethyl ester (1.06 g, 5.10 mmol), N-bromosuccinimide (1.00 g, 5.61 mmol) and 1,1'-azobis(cyclohexanecarbonitrile)(0.31 g, 1.27 mmol) were suspended in carbon tetrachloride (22 mL) and the resulting mixture was refluxed for 16 hours under N$_2$. The orange solution was concentrated under reduced pressure and the resulting orange residue was purified via column chromatography on silica gel (hexanes;EtOAc, 7:1, v/v). 4-Bromomethyl-isophthalic acid dimethyl ester was isolated as a yellow crystalline solid (1.05 g, 72%). $^1$H NMR (CDCl$_3$) δ 3.95 (s, 3H), 3.97 (s, 3H), 4.96 (s, 2H), 7.57 (d, 1H, J=9.0 Hz), 8.13 (dd, 1H, J=9.0, 3.0 Hz), 8.62 (d, 1H, J=3.0 Hz).

Using General Procedure A: A solution of 3,3"-Dimethyl-1',2',3',4',5',6'-hexahydro-[2,2';6',2"]terpyridine (0.402 g, 1.50 mmol), 4-bromomethyl-isophthalic acid dimethyl ester (0.603 g, 2.10 mmol), KI (63 mg, 0.38 mmol), and DIPEA (0.60 mL, 3.44 mmol) in DMF (7.5 mL) was heated at 60 °C. for 24 hours. Purification of the crude material by column chromatography on silica gel (20:1:1 CH$_2$Cl$_2$—CH$_3$OH—NH$_4$OH) provided 710 mg (99%) of COMPOUND 52 as a white solid. $^1$H NMR (CDCl$_3$) δ 1.63-1.77 (m, 3H), 2.09 (br s, 1H), 2.34-2.52 (m, 8H), 3.84 (s, 6H), 4.02 (s, 2H), 4.18 (d, 2H, J=11.1 Hz), 6.82 (dd, 2H, J=4.8, 7.5 Hz), 7.14 (d, 2H, J=7.5 Hz), 7.72 (s, 2H), 7.92 (s, 1H), 8.22 (d, 2H, J=4.8 Hz); $^{13}$C NMR (CDCl$_3$) δ 19.32, 25.66, 28.30, 50.13, 52.23, 52.36, 67.14, 122.20, 126.83, 128.07, 130.49, 131.08, 131.33, 132.14, 138.08, 146.90, 149.71, 159.50, 166.88, 167.23; ES-MS m/z 474 (M$^+$H). Anal. Calcd. For C$_{28}$H$_{31}$N$_3$O$_4$.0.3H$_2$O: C, 70.21; H, 6.65; N, 8.77. Found: C, 70.17; H, 6.60; N, 8.72.

EXAMPLE 53

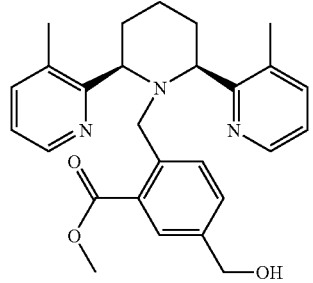

COMPOUND 53: 2-(3,3"-Dimethyl-3',4',5',6'-tetrahydro-2'H-[2,2';6',2"]terpyridin-1'-ylmethyl)-5-hydroxymethyl-benzoic acid methyl ester To a cold (0° C.) solution of 4-(3,3"-Dimethyl-3',4',5',6'-tetrahydro-2'H-[2,2';6',2"]terpyridin-1'-ylmethyl)-isophthalic acid dimethyl ester (0.710 g, 1.50 mmol) in THF (15 mL) and MeOH (15 mL) was added LiBH$_4$ (720 mg, 33.1 mmol) and the mixture was allowed to warm to room temperature overnight. The mixture was diluted with 1.0 N NaOH (15 mL) and extracted with CH$_2$Cl$_2$ (5×40 mL). The combined organic extracts were dried ($Na_2SO_4$) and concentrated. Purification of the crude material by column chromatography on silica gel (20:1:1 $CH_2Cl_2$—$CH_3OH$—$NH_4OH$) provided 31 mg (4%) of 4-(3,3''-dimethyl-3',4',5',6'-tetrahydro-2'H-[2,2';6',2'']terpyridin-1'-ylmethyl)-isophthalic acid dimethyl ester as a white foam, 155 mg (23%) of 4-3,3''-dimethyl-3',4',5',6'-tetrahydro-2'H-[2,2';6',2'']terpyridin-1'-ylmethyl)-3-hydroxymethyl-benzoic acid methyl ester as a white foam, and 375 mg (56%) of COMPOUND 53 as a white foam. Characterization data for COMPOUND 53: $^1$H NMR ($CDCl_3$) δ 1.52-1.74 (m, 3H), 2.05-2.10 (m, 1H), 2.31-2.45 (m, 8H), 2.62 (br s, 1H, OH), 3.80 (s, 3H), 3.96 (s, 2H), 4.14 (d, 2H, J=11.1 Hz), 4.46 (d, 2H, J=3 Hz), 6.82-6.87 (dd, 2H, J=4.8, 7.5 Hz), 7.10-7.17 (m, 3H), 7.25 (s, 1H), 7.62 (d, 1H, J=7.5 Hz), 8.24 (d, 2H, J=4.8 Hz); $^{13}$C NMR ($CDCl_3$) δ 19.38, 25.62, 28.97, 50.63, 52.01, 64.91, 67.26, 122.05, 127.58, 128.07, 129.26, 131.61, 132.08, 137.64, 138.09, 143.24, 146.85, 159.86, 167.97; ES-MS m/z 446 ($M^+H$). Anal. Calcd. For $C_{27}H_{31}N_3O_3 \cdot 1.3H_2O$: C, 69.15; H, 7.22; N, 8.96. Found: C, 69.22; H, 6.90; N, 8.87.

EXAMPLE 54

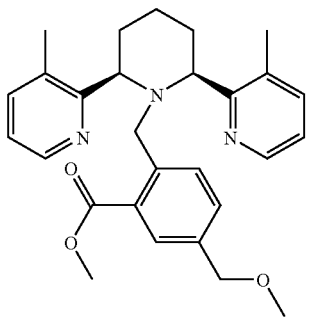

COMPOUND 54 2-(3,3''-Dimethyl-3',4',5',6'-tetrahydro-2'H-[2,2';6',2'']terpyridin-1'-ylmethyl)-5-methoxymethyl-benzoic acid methyl ester To a cold (0° C.) solution of 2-(3,3''-Dimethyl-3',4',5',6'-tetrahydro-2'H-[2,2';6',2'']terpyridin-1'-ylmethyl)-5-hydroxymethyl-benzoic acid methyl ester (0.290 g, 0.65 mmol) in THF (3 mL) was added a slurry of NaH (95% dry, 0.105 g, 4.38 mmol) in THF (10 mL) followed by neat MeI (0.40 mL, 6.43 mmol). The resultant mixture was stirred for 3 hours and treated with saturated aqueous $NaHCO_3$ (15 mL) and $CH_2Cl_2$ (50 mL). The phases were separated and the aqueous phase was extracted with $CH_2Cl_2$ (3×15 mL). The combined organic extracts were dried ($Na_2SO_4$) and concentrated. Purification of the crude material by column chromatography on silica gel (20:1:1 $CH_2Cl_2$—$CH_3OH$—$NH_4OH$) gave COMPOUND 54 (239 mg, 80%) as a white solid. $^1$H NMR ($CDCl_3$) δ 1.63-1.69 (m, 3H), 2.04-2.08 (m, 1H), 2.30-2.48 (m, 8H), 3.24 (s, 3H), 3.80 (s, 3H), 3.95 (s, 2H), 4.13 (d, 2H, J=11.7 Hz), 4.23 (s, 2H), 6.82 (dd, 2H, J=4.5, 7.5 Hz), 7.06-7.22 (m, 4H), 7.61 (d, 1H, J=7.8 Hz), 8.25 (d, 2H, J=4.5 Hz); $^{13}$C NMR ($CDCl_3$) δ 19.31, 25.55, 28.99, 50.64, 51.97, 58.01, 66.99, 74.20, 122.01, 127.92, 128.41, 130.02, 131.46, 131.98, 134.84, 138.05, 143.31, 146.84, 159.84, 167.91; ES-MS m/z 460 ($M^+H$). Anal. Calcd. For $C_{28}H_{33}N_3O_3$: C, 73.18; H, 7.24; N, 9.14. Found: C, 73.07; H, 7.15; N, 9.16.

EXAMPLE 55

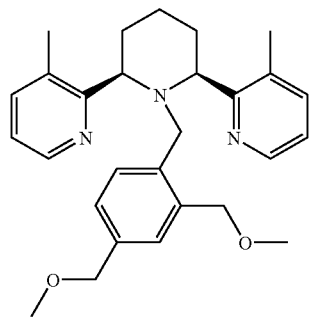

COMPOUND 55: 1'-(2,4-Bis-methoxymethyl-benzyl)-3,3''-dimethyl-1',2',3',4',5',6'-hexahydro-[2,2';6',2'']terpyridine To a solution of 2-(3,3''-dimethyl-3',4',5',6'-tetrahydro-2'H-[2,2';6',2'']terpyridin-1'-ylmethyl)-5-methoxymethyl-benzoic acid methyl ester (0.191 g, 0.42 mmol) in THF (8 mL) was added $LiBH_4$ (89 mg, 4.07 mmol) and the mixture was heated to reflux for 3 hours then cooled to room temperature. The mixture was diluted with 1.0 N NaOH (5 mL) and extracted with $CH_2Cl_2$ (5×15 mL). The combined organic extracts were dried ($Na_2SO_4$) and concentrated. Purification of the crude material by radial chromatography on silica gel (1 mm plate, 20:1:1 $CH_2Cl_2$—$CH_3OH$—$NH_4OH$) gave 153 mg (83%) of [2-(3,3''-dimethyl-3',4',5',6'-tetrahydro-2'H-[2,2';6',2'']terpyridin-1'-ylmethyl)-5-methoxymethyl-phenyl]-methanol as a white solid. $^1$H NMR ($CDCl_3$) δ 1.61-1.73 (m, 3H), 2.02-2.14 (m, 1H), 2.29-2.42 (m, 2H), 2.50 (s, 6H), 3.19 (s, 3H), 3.65 (s, 2H), 4.03 (d, 2H, J=10.8 Hz), 4.17 (s, 2H), 4.35 (s, 2H), 5.09 (br s, 1H), 6.63 (d, 1H, J=7.5 Hz), 6.74 (d, 1H, J=7.5 Hz), 6.82-6.86 (m, 3H), 7.23 (d, 2H, J=7.2 Hz), 8.22 (d, 2H, J=3.6 Hz); $^{13}$C NMR ($CDCl_3$) δ 19.44, 25.66, 30.06, 54.39, 57.89, 62.89, 67.47, 74.45, 122.08, 126.07, 128.95, 129.20, 131.76, 136.26, 138.42, 139.05, 146.82, 160.11; ES-MS m/z 432 ($M^+H$). Anal. Calcd. For $C_{27}H_{33}N_3O_2 \cdot 0.6H_2O$: C, 73.31; H, 7.79; N, 9.50. Found: C, 73.20; H, 7.60; N, 9.36.

To a cold (0° C.) solution of [2-(3,3''-Dimethyl-3',4',5',6'-tetrahydro-2'H-[2,2';6',2'']terpyridin-1'-ylmethyl)-5-methoxymethyl-phenyl]-methanol (0.085 g, 0.20 mmol) in THF (2 mL) was added a slurry of NaH (95% dry, 0.100 g, 4.17 mmol) in THF (2 mL) followed by neat MeI (0.25 mL, 4.02 mmol). The resultant mixture was stirred for 2.5 hours and treated with brine (5 mL) and $CH_2Cl_2$ (10 mL). The phases were separated and the aqueous phase was extracted with $CH_2Cl_2$ (4×10 mL). The combined organic extracts were dried ($Na_2SO_4$) and concentrated. Purification of the crude material by radial chromatography on silica gel (1 mm plate, 50:1:1 $CH_2Cl_2$—$CH_3OH$—$NH_4OH$) gave COMPOUND 55 (60 mg, 64%) as a colorless oil. $^1$H NMR ($CDCl_3$) δ 1.65-1.73 (m, 3H), 2.00-2.07 (m, 1H), 2.20-2.41 (m, 8H), 3.21 (s, 6H), 3.56 (s, 2H), 3.97 (m, 2H), 4.18 (s, 2H), 4.22 (s, 2H), 6.77 (s,1H), 6.83-6.89 (m, 3H), 7.14-7.20 (m, 3H), 8.31 (d, 2H, J=3.6 Hz); $^{13}$C NMR (CDCl$_3$) δ 19.22, 25.72, 28.37, 48.62, 57.85, 58.50, 66.60, 72.27, 74.68, 122.14, 125.94, 126.81, 129.51, 132.43, 135.29, 135.36, 138.11, 138.62, 146.56, 160.00; ES-MS m/z 446 (M$^+$H). Anal. Calcd. For C$_{28}$H$_{35}$N$_3$O$_2$.0.3CH$_2$Cl$_2$: C, 72.16; H, 7.62; N, 8.92. Found: C, 71.88; H, 7.61; N, 8.95.

EXAMPLE 56

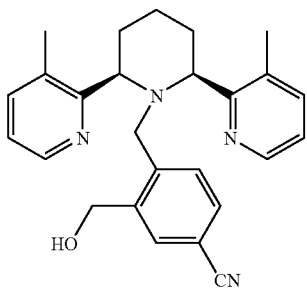

COMPOUND 56: 4-(3,3"-Dimethyl-3',4',5',6'-tetrahydro-2'H-[2,2';6',2"]terpyridin-1'-ylmethyl)-3-hydroxymethyl-benzonitrile Using General Procedure A: A solution of 3,3"-dimethyl-1',2',3',4',5',6'-hexahydro-[2,2';6',2"]terpyridine (0.260 g, 0.98 mmol), 2-bromomethyl-5-cyano-benzoic acid methyl ester (0.360 g, 1.42 mmol), KI (37 mg, 0.22 mmol), and DIPEA (0.35 mL, 2.01 mmol) in DMF (5 mL) was heated at 60° C. for 17 hours. Purification of the crude material by column chromatography on silica gel (20:1:1 CH$_2$Cl$_2$—CH$_3$OH—NH$_4$OH) provided 415 mg (96%) of 5-cyano-2-(3, 3"-dimethyl-3',4',5',6'-tetrahydro-2'H-[2,2';6',2"]terpyridin-1'-ylmethyl)-benzoic acid methyl ester as a tan solid. To a cold (0° C.) solution of 5-Cyano-2-(3,3"-dimethyl-3',4',5',6'-tetrahydro-2'H-[2,2';6',2"]terpyridin-1'-ylmethyl)-benzoic acid methyl ester (0.409 g, 0.937 mmol) in THF (4.5 mL) and MeOH (9 mL) was added LiBH$_4$ (229 mg, 10.52 mmol) and the mixture was allowed to warm to room temperature overnight. The mixture was diluted with 1.0 N NaOH (10 mL) and extracted with CH$_2$Cl$_2$ (5×25 mL). The combined organic extracts were dried (Na$_2$SO$_4$) and concentrated. Purification of the crude material by column chromatography on silica gel (20:1:1 CH$_2$Cl$_2$—CH$_3$OH—NH$_4$OH) provided 0.332 g (87%) of COMPOUND 56 as a white foam. $^1$H NMR (CDCl$_3$) δ 1.61-1.77 (m, 3H), 2.05-2.14 (m, 1H), 2.30-2.44 (m, 2H), 2.51 (s, 6H), 3.71 (s, 2H), 4.11 (d, 2H, J=10.8 Hz), 4.46 (s, 2H), 4.94 (br s, 1H), 6.87-6.96 (m, 4H), 7.22-7.27 (m, 3H), 8.21 (d, 2H, J=4.2 Hz). $^{13}$C NMR (CDCl$_3$) δ 19.35, 25.70, 28.19, 51.31, 62.24, 67.36, 109.58, 119.48, 122.56, 129.25, 130.02, 132.00, 132.24, 138.53, 139.79, 145.29, 146.76, 159.25; ES-MS m/z 413 (M$^+$H). Anal. Calcd. For C$_{26}$H$_{28}$N$_4$O.1.0H$_2$O$_2$: C, 72.53; H, 7.02; N, 13.01. Found: C, 72.46; H, 6.73; N, 12.91.

EXAMPLE 57

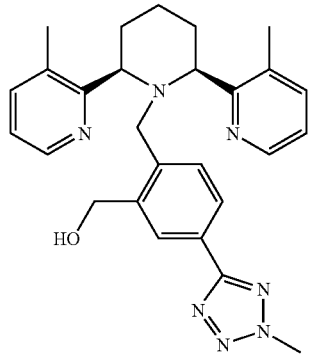

COMPOUND 57: [2-(3,3"-Dimethyl-3',4',5',6'-tetrahydro-2'H-[2,2';6',2"]terpyridin-1'-ylmethyl)-5-(2-methyl-2H-tetrazol-5-yl)-phenyl]-methanol To a solution of 5-cyano-2-methylbenzoic acid methyl ester (1.069 g, 6.10 mmol) in 2-methoxyethanol (6 mL) was added NaN$_3$ (0.400 g, 6.16 mmol) followed by LiCl (0.421 g, 9.94 mmol). The resultant mixture was heated to reflux for 6 hours then cooled to room temperature. The mixture was poured onto ice (~25 g) and treated with 37% HCl (2 mL). The mixture was extracted with CH$_2$Cl$_2$ (4×25 mL). The combined organic extracts were dried (Na$_2$SO$_4$) and concentrated and provided 1.43 g of an orange solid. To a cold (0° C.) solution of the orange solid (1.43 g) in DMF (6 mL) and 1,4-dioxane (6 mL) was added K$_2$CO$_3$ (2.52 g, 18.23 mmol) followed by MeI (1.0 mL, 16.06 mmol). The mixture was warmed to room temperature. After 4 hours, the mixture was diluted with water (10 mL) and EtOAc (60 mL). The phases were separated and the orgnaic phase was washed with brine (3×10 mL), dried (Na$_2$SO$_4$) and concentrated. Purification of the crude material by column chromatography on silica gel (8:1 hexanes-EtOAc) provided 0.50 g (30%) of 5-(2-methyl-2H-tetrazol-5-yl)-2-methylbenzoic acid 2-methoxyethyl ester as a white solid. $^1$H NMR (CDCl$_3$) δ 2.66 (s, 3H), 3.44 (s, 3H), 3.75 (t, 2H, J=6.6 Hz), 4.41 (s, 3H), 4.49 (t, 2H, J=6.6 Hz), 7.37 (d, 1H, J=7.5 Hz), 8.15 (dd, 1H, J=7.5, 2.4 Hz).

To a solution of 5-(2-methyl-2H-tetrazol-5-yl)-2-methylbenzoic acid 2-methoxyethyl ester in CCl$_4$ (6 mL) was added N-bromosuccinimide (0.366 g, 2.06 mmol) followed by 1,1'-azobis(cyclohexanecarbonitrile) (74 mg, 0.30 mmol). The resultant mixture was refluxed for 6 hours then cooled to room temperature, filtered through filter paper, and concentrated. Purification of the crude material by column chromatography on silica gel (4:1 :hexanes-EtOAc) provided 0.35 g of a white solid. Using General Procedure A: A solution of 3,3"-dimethyl-1',2',3',4',5',6'-hexahydro-[2,2';6',2"]terpyridine (0.140 g, 0.52 mmol), the white solid (0.35 g), KI (16 mg, 0.10 mmol), and DIPEA (0.18 mL, 1.03 mmol) in DMF (5 mL) was heated at 60° C. for 23 hours. Purification of the crude material by column chromatography on silica gel (40:1:1 CH$_2$Cl$_2$—CH$_3$OH—NH$_4$OH) provided 0.28 g (99%) of 5-(2-methyl-2H-tetrazol-5-yl)  2-(3,3"-dimethyl-3',4',5',6'-tetrahydro-2'H-[2,2';6',2"]terpyridin-1'-ylmethyl)-benzoic acid 2-methyoxyethyl ester as a tan solid. To a cold solution of the ester (0.280 g, 0.52 mmol) in THF (10 mL) was added LiBH$_4$ (168 mg, 7.72 mmol) and the mixture was refluxed overnight. The mixture was cooled to room temperature, diluted with 1.0 N NaOH (5 mL) and extracted with CH$_2$Cl$_2$ (4×20 mL). The combined organic extracts were dried (Na$_2$SO$_4$) and concentrated. Purification of the crude material by column chromatography on silica gel (20:1:1 CH$_2$Cl$_2$—CH$_3$OH—NH$_4$OH) provided 0.215 g (85%) of COMPOUND 57 as a white solid. $^1$H NMR (CDCl$_3$) δ 1.63-1.77 (m, 3H), 2.06-2.13 (m, 1H), 2.38-2.47 (m, 2H), 2.54 (s, 6H), 3.75 (s, 2H), 4.12 (d, 2H, J=12.0 Hz), 4.34 (s, 3H), 4.48 (s, 2H), 4.98 (br s, 1H), 6.82 (dd, 2H, J=7.5, 4.8 Hz), 6.90 (d, 1H, J=7.5 Hz), 7.23 (d, 2H, J=7.5 Hz), 7.44 (dd, 1H, J=7.5, 1.5 Hz), 7.66 (d, 1H, J=1.5 Hz), 8.22 (d, 2H, J=4.8 Hz). $^{13}$C NMR (CDCl$_3$) δ 19.42, 25.72, 28.99, 39.75, 52.92, 63.08, 67.58, 122.31, 124.98, 125.19, 127.58, 129.53, 132.08, 138.49, 139.38, 141.98, 146.80, 159.69, 165.44; ES-MS m/z 470 (M$^+$H). Anal. Calcd. For C$_{27}$H$_{31}$N$_7$O.0.8H$_2$O: C, 67.00; H, 6.79; N, 20.26. Found: C, 66.68; H, 6.39; N, 19.93.

EXAMPLE 58

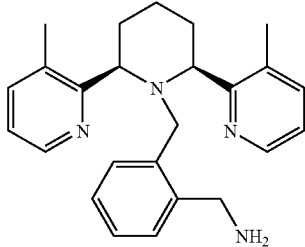

COMPOUND 58: 2-(3,3"-Dimethyl-3',4',5',6'-tetrahydro-2'H-[2,2';6',2"]terpyridin-1'-ylmethyl)-benzylamine (HBr salt)

Using General Procedure A: A solution of 3,3"-dimethyl-1',2',3',4',5',6'-hexahydro-[2,2';6',2"]terpyridine (0.602 g, 2.25 mmol), α-bromo-o-tolunitrile (0.668 g, 3.41 mmol), KI (100 mg, 0.60 mmol), and DIPEA (0.80 mL, 4.59 mmol) in DMF (11 mL) was heated at 60° C. for 23 hours. Purification of the crude material by column chromatography on silica gel (40:1:1 CH$_2$Cl$_2$—CH$_3$OH—NH$_4$OH) provided 0.78 g (91%) of 2-(3,3"-dimethyl-3',4',5',6'-tetrahydro-2'H-[2,2';6',2"]terpyridin-1'-ylmethyl)-benzonitrile as a tan solid. $^1$H NMR (CDCl$_3$) δ 1.63-1.73 (m, 3H), 2.02-2.07 (m, 1H), 2.26-2.38 (m, 2H), 2.48 (s, 6H), 3.69 (s, 2H), 4.12 (d, 2H, J=10.8 Hz), 6.83-6.89 (m, 3H), 6.99 (d, 1H, J=7.2 Hz), 7.19-7.26 (m, 3H), 7.64 (d, 1H, J=7.8 Hz), 8.27 (d, 2H, J=3.9 Hz). $^{13}$C NMR (CDCl$_3$) δ 19.44, 25.53, 29.42, 52.72, 67.05, 109.86, 118.06, 122.19, 125.90, 130.68, 131.41, 131.54, 132.02, 138.18, 145.77, 147.23, 159.61; ES-MS m/z 383 (M$^+$H). Anal. Calcd. For C$_{25}$H$_{26}$N$_4$ C, 78.50; H, 6.852; N, 14.65. Found: C, 78.28; H, 6.93; N, 14.57.

A solution of 2-(3,3"-dimethyl-3',4',5',6'-tetrahydro-2'H-[2,2';6',2"]terpyridin-1'-ylmethyl)-benzonitrile (0.129 g, 0.34 mmol) in NH$_3$ saturated MeOH (5 mL) was treated with Raney nickel (60 mg) and placed under 50 psi H$_2$, on a Parr shaker, for 3.5 hours. The mixture was filtered through Celite and the cake was washed with MeOH. The eluant was concentrated under reduced pressure. Purification of the crude material by column chromatography on silica gel (10:1:1 CH$_2$Cl$_2$—CH$_3$OH—NH$_4$OH) provided 96 mg (73%) of the free base of the title compound as a white solid. Using General Procedure B: Conversion of the white solid (92 mg) to the HBr salt gave COMPOUND 58 (152 mg, 96%) as a white solid. $^1$H NMR (D$_2$O) δ 1.49-1.61 (m, 2H), 1.71-1.84 (m, 1H), 1.96-2.03 (m, 1H), 2.14-2.20 (m, 2H), 2.54 (s, 6H), 3.82 (s, 2H), 3.96 (s, 2H), 4.57 (dd, 2H J=11.4, 3.0 Hz), 6.96 (d, 1H, J=7.8 Hz), 7.08-7.13 (m, 1H), 7.18-7.26 (m, 2H), 7.73 (dd, 2H, J=7.8, 5.7 Hz), 8.26 (d, 2H, J=7.8 Hz), 8.53 (d, 2H, J=5.7 Hz); $^{13}$C NMR (D$_2$O) δ 17.25, 22.25, 33.11, 39.91, 58.88, 61.96, 125.96, 129.91, 130.13, 130.57, 131.21, 132.11, 134.86, 136.53, 139.49, 149.14, 155.32; ES-MS m/z 387 (M$^+$H). Anal. Calcd. For C$_{25}$H$_{30}$N$_4$.3.0HBr.2.0H$_2$O: C, 45.13; H, 5.61; N, 8.42; Br, 36.03. Found C, 45.07; H, 5.71; N, 8.23; Br, 36.20.

EXAMPLE 59

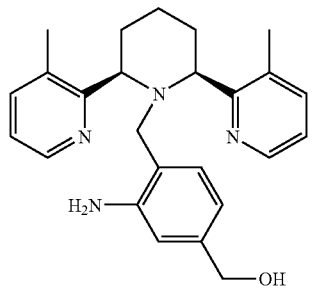

COMPOUND 59: [3-Amino-4-(3,3"-dimethyl-3',4',5',6'-tetrahydro-2'H-[2,2';6',2"]terpyridin-1'-ylmethyl)-phenyl]-methanol To a solution of 4-methyl-3-nitrobenzoic acid (5.52 g, 30.5 mmol) in MeOH (100 mL) was added 98% sulfuric acid (2 mL) and the resultant mixture was refluxed overnight, then cooled to room temperature. The mixture was concentrated and the residue was dissolved in CH$_2$Cl$_2$ (50 mL) and water (20 mL). Solid Na$_2$CO$_3$ was added until the aqueous phase was basic to litmus paper. The phases were separated and the aqueous phase was extracted with CH$_2$Cl$_2$ (5×20 mL). The combined organic extracts were dried (Na$_2$SO$_4$) and concentrated and provided 5.79 g (97%) of 4-methyl-3-nitrobenzoic acid methyl ester as a white solid. To a solution of 4-methyl-3-nitrobenzoic acid methyl ester (5.01 g, 25.7 mmol) in CCl$_4$ (65 mL) was added N-bromosuccinimide (5.04 g, 28.3 mmol) followed by 1,1'-azobis(cyclohexanecarbonitrile) (1.21 g, 4.96 mmol). The resultant mixture was refluxed for 24 hours then cooled to room temperature, filtered through filter paper, and concentrated. Purification of the crude material by column chromatography on silica gel (9:1 :hexanes-EtOAc) provided 4.30 g (61%) of 4-bromomethyl-3-nitrobenzoic acid methyl ester as a yellow oil. $^1$H NMR (CDCl$_3$) δ 3.98 (s, 3H), 4.85 (s, 2H), 7.67 (d, 1H, J=7.8 Hz), 8.25 (d, 1H, J=7.8, 1.5 Hz), 8.66 (d, 1H, J=1.5 Hz).

Using General Procedure A: A solution of 3,3"-dimethyl-1',2',3',4',5',6'-hexahydro-[2,2';6',2"]terpyridine (0.829 g, 3.10 mmol), 4-bromomethyl-3-nitrobenzoic acid methyl ester (1.26 g, 4.61 mmol), KI (115 mg, 0.69 mmol), and DIPEA (1.20 mL, 6.89 mmol) in DMF (16 mL) was heated at 60° C. for 18 hours. Purification of the crude material by column chromatography on silica gel (40:1:1 CH$_2$Cl$_2$—CH$_3$OH—NH$_4$OH) provided 1.40 g (98%) of 4-3,3"-dimethyl-3',4',5',6'-tetrahydro-2'H-[2,2';6',2"]terpyridin-1'-ylmethyl)-3-nitro-benzoic acid methyl ester as a tan solid. To a solution of 4-(3,3"-dimethyl-3',4',5',6'-tetrahydro-2'H-[2,2';6',2"]terpyridin-1'-ylmethyl)-3-nitro-benzoic acid methyl ester (1.40 g, 3.03 mmol) in MeOH (15 mL) and EtOAc (15 mL) was added palladium (50% wet with water), 10 wt. % on activated carbon (0.30 g). The resultant mixture was hydrogenated at 30 psi on a Parr shaker for 3 hours. The mixture was vacuum filtered through celite and the cake was washed with MeOH and EtOAc. The solvent was removed from the filtrate under reduced pressure and the thus obtained oil was purified by column chromatography on silica gel (40:1:1 $CH_2Cl_2$—$CH_3OH$—$NH_4OH$) and provided 0.90 g (69%) of 3-amino-4-(3,3"-dimethyl-3',4',5',6'-tetrahydro-2'H-[2,2';6',2"]terpyridin-1'-ylmethyl)-benzoic acid methyl ester.

To a solution of 3-amino-4-(3,3"-dimethyl-3',4',5',6'-tetrahydro-2'H-[2,2';6',2"]terpyridin-1'-ylmethyl)-benzoic acid methyl ester (0.61 g, 1.42 mmol) in THF (14 mL) was added $LiBH_4$ (430 mg, 19.74 mmol) and the mixture was heated to reflux overnight. The mixture was cooled to room temperature, diluted with 1.0 N NaOH (20 mL) and extracted with $CH_2Cl_2$ (5×30 mL). The combined organic extracts were dried ($Na_2SO_4$) and concentrated. Purification of the crude material by radial chromatography on silica gel (2 mm plate, 20:1:1 $CH_2Cl_2$—$CH_3OH$—$NH_4OH$) provided 0.220 g (37%) of COMPOUND 59 as a white solid. $^1$H NMR ($CDCl_3$) δ 1.23 (br s, 1H), 1.47-1.72 (m, 3H), 1.88-1.95 (m, 1H), 2.04-2.18 (m, 2H), 2.35 (s, 6H), 3.32 (s, 2H), 3.73 (dd, 2H, J=11.7, 3.0 Hz), 4.26 (d, 2H, J=3.3 Hz), 4.53 (br s, 2H), 6.03 (s, 1H), 6.07 (d, 1H, J=7.8 Hz), 6.48 (d, 1H, J=7.2 Hz), 6.86 (dd, 2H, J=7.8, 4.8 Hz), 7.15 (d, 2H, J=7.5 Hz), 8.33 (d, 2H, J=3.9 Hz). $^{13}$C NMR ($CDCl_3$) δ 19.44, 25.02, 32.92, 60.69, 65.60, 68.25, 112.98, 115.09, 122.09, 122.80, 129.96, 131.38, 138.18, 140.42, 146.89, 147.51, 161.18; ES-MS m/z 403 (M$^+$H). Anal. Calcd. For $C_{25}H_{30}N_4O.1.0H_2O$: C, 71.40; H, 7.67; N, 13.32. Found: C, 71.31; H, 7.55; N, 13.22.

EXAMPLE 60

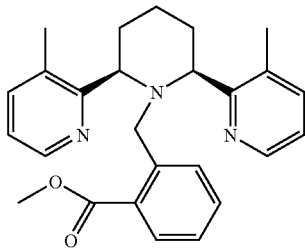

COMPOUND 60: 2-(3,3"-Dimethyl-3',4',5',6'-tetrahydro-2'H-[2,2';6',2"]terpyridin-1'-ylmethyl)-benzoic acid methyl ester To a solution of 2-methyl-benzoic acid methyl ester (4.58 g, 30.5 mmol) in $CCl_4$ (75 mL) was added N-bromosuccinimide (5.79 g, 32.5 mmol) followed by 1,1'-azobis(cyclohexanecarbonitrile) (1.42 g, 5.80 mmol). The resultant mixture was refluxed for 6 hours then cooled to room temperature, filtered through filter paper, and concentrated. Purification of the crude material by column chromatography on silica gel (20:1 :hexanes-EtOAc) provided 5.44 g (78%) of 2-bromomethyl-benzoic acid methyl ester as a colorless oil. $^1$H NMR ($CDCl_3$) δ 3.95 (s, 3H), 4.96 (s, 2H), 7.36-7.50 (m, 3H), 7.97 (d, 1H, J=7.8 Hz).

Using General Procedure A: A solution of 3,3"-dimethyl-1',2',3',4',5',6'-hexahydro-[2,2';6',2"]terpyridine (0.901 g, 3.37 mmol), 2-bromomethyl-benzoic acid methyl ester (1.17 g, 5.13 mmol), KI (121 mg, 0.73 mmol), and DIPEA (1.50 mL, 8.61 mmol) in DMF (17 mL) was heated at 60° C. for 23 hours. Purification of the crude material by column chromatography on silica gel (40:1:1 $CH_2Cl_2$—$CH_3OH$—$NH_4OH$) provided 1.19 g (85%) of COMPOUND 60 as a tan solid. $^1$H NMR ($CDCl_3$) δ 1.58-1.72 (m, 3H), 2.02-2.06 (m, 1H), 2.31-2.42 (m, 8H), 3.80 (s, 3H), 3.94 (s, 2H), 4.11 (d, 2H, J=10.5 Hz), 6.79-6.91 (m, 3H), 7.09-7.26 (m, 4H), 7.63 (d, 1H, J=7.5 Hz), 8.26 (d, 2H, J=3.6 Hz). $^{13}$C NMR ($CDCl_3$) δ 19.39, 25.69, 28.76, 50.43, 51.98, 67.31, 122.06, 124.90, 128.02, 129.03, 130.54, 131.20, 132.11, 138.04, 143.92, 146.89, 159.83, 168.12; ES-MS m/z 416 (M$^+$H). Anal. Calcd. For $C_{26}H_{29}N_3O_2.0.2H_2O$: C, 74.51; H, 7.07; N, 10.03. Found: C, 74.56; H, 7.08; N, 9.99.

EXAMPLE 61

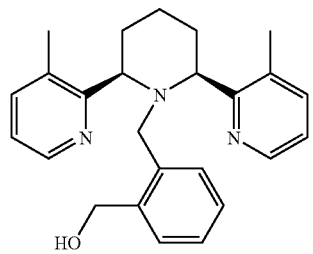

COMPOUND 61: [2-3,3"-dimethyl-3',4',5',6'-tetrahydro-2'H-[2,2':6',2"]terpyridin-1'-ylmethyl)-phenyl]-methanol To a solution of 2-(3,3"-dimethyl-3',4',5',6'-tetrahydro-2'H-[2,2';6',2"]terpyridin-1'-ylmethyl)-benzoic acid methyl ester (0.204 g, 0.49 mmol) in THF (5 mL) was added $LiBH_4$ (133 mg, 6.13 mmol) and the mixture was heated to reflux overnight. The mixture was cooled to room temperature, diluted with 1.0 N NaOH (5 mL) and extracted with $CH_2Cl_2$ (4×10 mL). The combined organic extracts were dried ($Na_2SO_4$) and concentrated. Purification of the crude material by column chromatography on silica gel (20:1:1 $CH_2Cl_2$—$CH_3OH$—$NH_4OH$) provided 0.139 g (70%) of COMPOUND 61 as a white solid. $^1$H NMR ($CDCl_3$) δ 1.60-1.73 (m, 3H), 2.02-2.40 (m, 3H), 2.50 (s, 6H), 3.66 (s, 2H), 4.04 (d, 2H, J=9.0 Hz), 4.36 (s, 2H), 5.14 (br s, 1H), 6.63-6.93 (m, 6H), 7.24 (d, 2H, J=8.1 Hz), 8.22 (d, 2H, J=3.9 Hz). $^{13}$C NMR ($CDCl_3$) δ 19.46, 25.67, 29.68, 54.30, 63.19, 67.73, 122.24, 126.60, 126.81, 128.99, 129.61, 131.87, 138.43, 138.85, 139.13, 146.85, 159.92; ES-MS m/z 388 (M$^+$H). Anal. Calcd. For $C_{25}H_{29}N_3O.0.9H_2O$: C, 74.37; H, 7.69; N, 10.41. Found: C, 74.43; H, 7.44; N, 10.34.

EXAMPLE 62

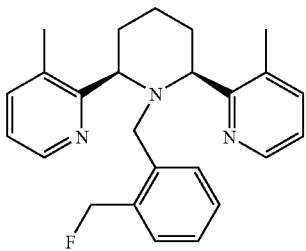

COMPOUND 62: 1'-(2-Fluoromethyl-benzyl)-3,3"-dimethyl-1',2',3',4',5',6'-hexahydro-[2,2';6',2"]terpyridine To a cold (0° C.) solution of [2-(3,3"-dimethyl-3',4',5',6'-tetrahydro-2'H-[2,2';6',2"]terpyridin-1'-ylmethyl)-phenyl]-methanol (0.107 g, 0.28 mmol) in CH$_2$Cl$_2$ (3 mL) was added (diethylamino)sulfur trifluoride (80 μL, 0.61 mmol). After 15 minutes, the cooling bath was removed and the reaction mixture was warmed to room temperature. After an additional 3 hours, the reaction mixture was treated with saturated aqueous NaHCO$_3$ (5 mL) and extracted with CH$_2$Cl$_2$ (4×10 mL). The combined organic extracts were dried (Na$_2$SO$_4$) and concentrated. Purification of the crude material by radial chromatography on silica gel (1 mm plate, 100:1:1 CH$_2$Cl$_2$—CH$_3$OH—NH$_4$OH) provided 0.032 g (29%) of COMPOUND 62 as a white solid. $^1$H NMR (CDCl$_3$) δ 1.60-1.74 (m, 3H), 2.02-2.10 (m, 1H), 2.26-2.41 (m, 8H), 3.56 (s, 2H), 4.13 (d, 2H, J=11.1 Hz), 5.06 (d, 2H, J$_{C-F}$=48 Hz), 6.81-6.88 (m, 5H), 7.14-7.16 (m, 3H), 8.31 (d, 2H, J=3.6 Hz). $^{13}$C NMR (CDCl$_3$) δ 19.24, 25.64, 28.65, 50.09, 67.20, 82.93 (d, J$_{C-F}$=648 Hz), 122.29, 125.94, 127.47, 127.62, 129.79, 132.36, 133.66 (d, J$_{C-F}$=62 Hz), 138.14, 139.34, 146.63, 159.99; ES-MS m/z 390 (M$^+$H). Anal. Calcd. For C$_{25}$H$_{28}$N$_3$F.0.1H$_2$O: C, 76.73; H, 7.26; N, 10.74. Found: C, 76.66; H, 7.23; N, 10.70.

EXAMPLE 63

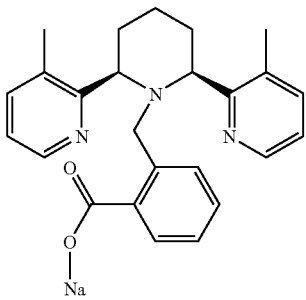

COMPOUND 63: 2-(3,3"-Dimethyl-3',4',5',6'-tetrahydro-2'H-[2,2';6',2"]terpyridin-1'-ylmethyl)-benzoic acid sodium salt To a solution of 2-(3,3"-Dimethyl-3',4',5',6'-tetrahydro-2'H-[2,2';6',2"]terpyridin-1'-ylmethyl)-benzoic acid methyl ester (0.723 g, 1.74 mmol) in MeOH (5 mL) was added water (5 mL) and solid NaOH (0.757 g, 18.93 mmol). The resultant mixture was heated to reflux overnight then cooled to room temperature. The mixture was extracted with CH$_2$Cl$_2$ (5×20 mL). The combined organic extracts were dried (Na$_2$SO$_4$) and concentrated and provided 0.80 g (97%) of COMPOUND 63 as a while solid. $^1$H NMR (D$_2$O) δ 1.58-1.73 (m, 3H), 1.88-2.04 (m, 3H), 2.36 (s, 6H), 3.66 (s, 2H), 4.12 (d, 2H, J=10.2 Hz), 6.82 (t, 1H, J=7.2 Hz), 6.92-7.03 (m, 4H), 7.40-7.47 (m, 3H), 8.13 (d, 2H, J=3.9 Hz). $^{13}$C NMR (D$_2$O) δ 16.66, 24.13, 32.40, 56.97, 65.27, 122.76, 125.65, 127.27, 128.10, 130.45, 132.60, 136.88, 139.70, 146.15, 159.77, 177.12; ES-MS m/z 402 (M$^+$H), 424 (M$^+$Na). Anal. Calcd. For C$_{25}$H$_{26}$N$_3$O$_2$Na.2.7H$_2$O: C, 63.60; H, 6.70; N, 8.90. Found: C, 63.60; H, 6.78; N, 8.55.

EXAMPLE 64

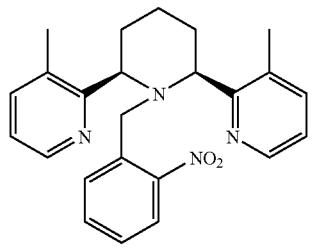

COMPOUND 64: 3,3"-Dimethyl-1'-(2-nitro-benzyl)-1',2',3',4',5',6'-hexahydro-[2,2';6',2"]terpyridine Using General Procedure A: A solution of 3,3"-dimethyl-1',2',3',4',5',6'-hexahydro-[2,2';6',2"]terpyridine (0.431 g, 1.61 mmol), 2-nitrobenzyl bromide (0.509 g, 2.75 mmol), KI (60 mg, 0.36 mmol), and DIPEA (0.6 mL, 3.44 mmol) in DMF (8 mL) was heated at 60° C. for 24 hours. Purification of the crude material by column chromatography on silica gel (40:1:1 CH$_2$Cl$_2$—CH$_3$OH—NH$_4$OH) provided 0.58 g (90%) of COMPOUND 64 as a yellow solid. $^1$H NMR (CDCl$_3$) δ 1.63-1.70 (m, 3H), 2.04-2.08 (m, 1H), 2.31-2.43 (m, 8H), 3.85 (s, 2H), 4.12 (d, 2H, J=11.1 Hz), 6.83-6.91 (m, 3H), 7.18-7.29 (m, 4H), 7.78 (d, 1H, J=7.5 Hz), 8.24 (d, 2H, J=3.9 Hz); ES-MS m/z 403 (M$^+$H).

EXAMPLE 65

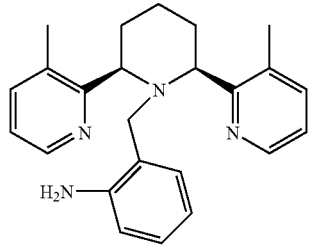

COMPOUND 65: 2-(3,3"-Dimethyl-3',4',5',6'-tetrahydro-2'H-[2,2';6',2"]terpyridin-1'-ylmethyl)-phenylamine To a solution of 3,3"-dimethyl-1'-(2-nitro-benzyl)-1',2',3', 4',5',6'-hexahydro-[2,2';6',2"]terpyridine (0.55 g, 1.37 mmol)

in MeOH (20 mL) was added palladium (50% wet with water), 10 wt.% on activated carbon (0.113 g). The resultant mixture was hydrogenated at 30 psi on a Parr shaker for 3 hours. The mixture was vacuum filtered through celite and the cake was washed with MeOH. The solvent was removed from the filtrate under reduced pressure and the thus obtained oil was purified by radial chromatography on silica gel (2 mm plate, 100:1:1 $CH_2Cl_2$—$CH_3OH$—$NH_4OH$) and provided 80 mg (16%) of COMPOUND 65 as a white solid. $^1$H NMR ($CDCl_3$) δ 1.49-1.72 (m, 3H), 1.88-1.95 (m, 1H), 2.06-2.20 (m, 2H), 2.36 (s, 6H), 3.33 (s, 2H), 3.75 (dd, 2H, J=11.7, 3.0 Hz), 4.47 (br s, 2H), 6.07 (dd, 2H, J=7.5, 6.0 Hz), 6.42-6.45 (m, 1H), 6.54 (td, 1H, J=7.5, 1.2 Hz), 6.87 (dd, 2H, J=7.5, 4.8 Hz), 7.15 (d, 2H, J=7.5 Hz), 8.33 (d, 2H, J=3.9 Hz); ES-MS m/z 373 (M$^+$H).

EXAMPLE 66

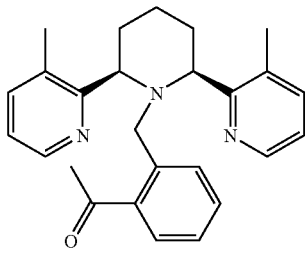

COMPOUND 66: 1-[2-3,3''-Dimethyl-3',4',5',6'-tetrahydro-2'H-[2,2';6',2'']terpyridin-1'-ylmethyl)-phenyl]-ethanone To a solution of 2'-methyl-acetophenone (2.68 g, 20.0 mmol) in benzene (100 mL) was added ethylene glycol (2.0 mL, 35.9 mmol) followed by p-toluenesulfonic acid monohydrate (0.39 g, 2.10 mmol). The reaction flask was topped with a Dean-Stark trap, and the mixture was heated to reflux overnight. The mixture was cooled to room temperature, diluted with $Et_2O$ (100 mL), washed with saturated aqueous $NaHCO_3$ (5×20 mL) and brine (3×25 mL), dried ($MgSO_4$), and concentrated. The resultant colorless oil (3.6 g) was dissolved in $CCl_4$ (50 mL) and to this solution was added N-bromosuccinimide (3.76 g, 21.1 mmol) followed by 1,1'-azobis (cyclo-hexanecarbonitrile) (0.98 g, 3.99 mmol). The resultant mixture was refluxed for 5 hours then cooled to room temperature, filtered through filter paper, and concentrated. Purification of the crude material by column chromatography on silica gel (20:1:hexanes-EtOAc) provided 4.09 g (80%) of 2-(2-bromomethyl-phenyl)-2-methyl-[1,3]dioxolane as a colorless oil. $^1$H NMR ($CDCl_3$) δ 1.74 (s, 3H), 3.75-3.81 (m, 2H), 4.04-4.08 (m, 2H), 4.89 (s, 2H), 7.24-7.31 (m, 2H), 7.44-7.57 (m, 2H).

Using General Procedure A: A solution of 3,3''-dimethyl-1',2',3',4',5',6'-hexahydro-[2,2';6',2'']terpyridine (0.547 g, 2.04 mmol), 2-(2-bromomethyl-phenyl)-2-methyl-[1,3]dioxolane (1.03 g, 3.99 mmol), KI (73 mg, 0.42 mmol), and DIPEA (0.70 mL, 4.02 mmol) in DMF (10 mL) was heated at 60° C. for 24 hours. Purification of the crude material by column chromatography on silica gel (40:1:1 $CH_2Cl_2$—$CH_3OH$—$NH_4OH$) provided 0.81 g (90%) of 3,3''-dimethyl-1'-[2-(2-methyl-[1,3]dioxolan-2-yl)-benzyl]-1',2',3',4',5',6'-hexahydro-[2,2';6',2'']terpyridine as a white solid. $^1$H NMR ($CDCl_3$) δ 1.46 (s, 3H), 1.60-1.83 (m, 3H), 2.15-2.20 (m, 1H), 2.47-2.57 (m, 8H), 3.26-3.31 (m, 2H), 3.82-3.87 (m, 2H), 4.01 (s, 2H), 4.44 (d, 2H, J=10.8 Hz), 6.72-6.82 (m, 4H), 7.05 (dd, 1H, J=7.2, 1.5 Hz), 7.21 (d, 2H, J=7.2 Hz), 7.46 (d, 1H, J=6.9 Hz), 8.19 (d, 2H, J=4.8 Hz); ES-MS m/z 444 (M$^+$H).

To a solution of 3,3''-dimethyl-1'-[2-(2-methyl-[1,3]dioxolan-2-yl)-benzyl]-1',2',3',4',5',6'-hexahydro-[2,2';6',2''] terpyridine (0.78 g, 1.76 mmol) in THF (8 mL) was added 1.0 N HCl (18 mL, 18.0 mmol) and the mixture was stirred at room temperature overnight. The mixture was diluted with 10 N NaOH (2 mL) and extracted with $CH_2Cl_2$ (4×50 mL). The combined organic extracts were dried ($Na_2SO_4$) and concentrated. Purification of the crude material by column chromatography on silica gel (30:1:1 $CH_2Cl_2$—$CH_3OH$—$NH_4OH$) provided 0.64 g (91%) of COMPOUND 66 as a white solid. $^1$H NMR ($CDCl_3$) δ 1.58-1.71 (m, 3H), 2.02-2.12 (m, 1H), 2.30-2.37 (m, 5H), 2.44 (s, 6H), 3.82 (s, 2H), 4.09 (d, 2H, J=11.1 Hz), 6.81-6.85 (m, 3H), 7.04-7.18 (m, 4H), 7.76 (d, 1H, J=7.8 Hz), 8.26 (d, 2H, J=3.6 Hz); ES-MS m/z 400 (M$^+$H).

EXAMPLE 67

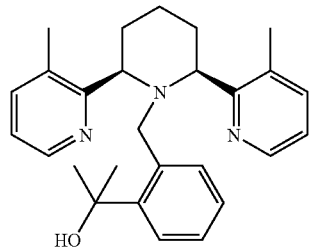

COMPOUND 67: 2-[2-(3,3''-Dimethyl-3', 4',5', 6'-tetrahydro-2'H-[2,2';6'2'']terpyridin-1'-ylmethyl)-phenyl]-propan-2-ol To a cold (−78° C.) solution of 1-[2-3,3''-dimethyl-3',4',5',6'-tetrahydro-2'H-[2,2';6',2'']terpyridin-1'-ylmethyl)-phenyl]-ethanone (0.283 g, 0.71 mmol) in THF (14 mL) was added MeLi (1.32 M in $Et_2O$, 1.10 mL, 1.45 mmol). After 15 minutes, the cooling bath was removed and the reaction mixture was warmed to room temperature. After an additional 5 hours, the reaction mixture was diluted with brine (15 mL) and EtOAc (30 mL). The phases were separated and the organic phase was washed with brine (2×10 mL), dried ($Na_2SO_4$) and concentrated. Purification of the crude material by radial chromatography on silica gel (1 mm plate, 50:1:1 $CH_2Cl_2$—$CH_3OH$—$NH_4OH$) provided 0.111 g (38%) of COMPOUND 67 as a pale yellow solid. $^1$H NMR ($CDCl_3$) δ 1.46 (s, 6H), 1.57-1.78 (m, 3H), 2.14-2.20 (m, 1H), 2.52-2.62 (m, 8H), 4.14-4.40 (m, 5H), 6.59-6.84 (m, 6H), 7.10-7.27 (m, 2H), 8.14-8.21 (m, 2H); ES-MS m/z 416 (M$^+$H).

EXAMPLE 68

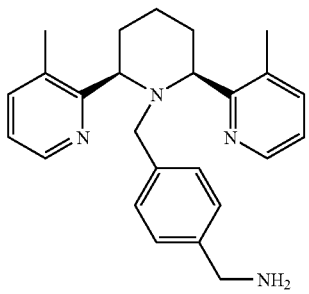

COMPOUND 68: 4-(3,3''-Dimethyl-3',4',5',6'-tetrahydro-2'H-[2,2';6',2'']terpyridin-1'-ylmethyl)-benzylamine Using General Procedure A: A solution of 3,3''-dimethyl-1',2',3',4',5',6'-hexahydro-[2,2'; 6',2'']terpyridine (0.502 g, 1.83 mmol), α-bromo-p-tolunitrile (0.538 g, 2.75 mmol), KI (65 mg, 0.40 mmol), and DIPEA (0.72 mL, 4.13 mmol) in DMF (9 mL) was heated at 60° C. for 16 hours. Purification of the crude material by column chromatography on silica gel (40:1:1 $CH_2Cl_2$—$CH_3OH$—$NH_4OH$) provided 0.66 g (94%) of 4-(3,3''-dimethyl-3',4',5',6'-tetrahydro-2'H-[2,2';6',2''] terpyridin-1'-ylmethyl)-benzonitrile as a white solid. $^1$H NMR ($CDCl_3$) δ 1.60-1.73 (m, 3H), 2.02-2.12 (m, 1H), 2.18-2.34 (m, 2H), 2.41 (s, 6H), 3.56 (s, 2H), 4.14 (d, 2H, J=10.5 Hz), 6.64 (d, 2H, J=8.1 Hz), 6.95 (dd, 2H, J=7.5, 4.8 Hz), 7.10 (d, 2H, J=7.8 Hz), 7.22 (d, 2H, J=7.2 Hz), 8.37 (d, 2H, J=3.9 Hz); ES-MS m/z 383 (M$^+$H).

A solution of 4-(3,3''-Dimethyl-3',4',5',6'-tetrahydro-2'H-[2,2';6',2'']terpyridin-1'-ylmethyl)-benzonitrile (0.122 g, 0.32 mmol) in $NH_3$ saturated MeOH (3 mL) was treated with Raney nickel (100 mg) and placed under 50 psi $H_2$, on a Parr shaker, for 4 hours. The mixture was filtered through Celite and the cake was washed with MeOH. The eluant was concentrated under reduced pressure. Purification of the crude material by column chromatography on silica gel (20:1:1 $CH_2Cl_2$—$CH_3OH$—$NH_4OH$) provided 93 mg (76%) of COMPOUND 68 as a white solid. $^1$H NMR ($CDCl_3$) δ 1.44-1.57 (m, 1H), 1.66-1.72 (m, 2H), 1.90-2.11 (m, 3H), 2.34 (s, 6H), 3.51 (s, 2H), 3.71 (s, 2H), 3.98 (d, 2H J=10.5 Hz), 6.54 (d, 2H, J=7.8 Hz), 6.93 (d, 2H, J=7.8 Hz), 7.01 (dd, 2H, J=7.5, 4.8 Hz), 7.34 (d, 2H, J=7.5 Hz), 8.47 (d, 2H, J=3.9 Hz); ES-MS m/z 387 (M$^+$H).

EXAMPLE 69

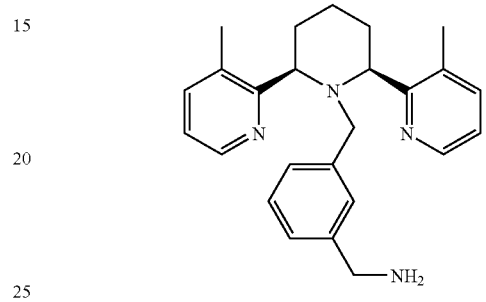

COMPOUND 69: 3-(3,3''-Dimethyl-3',4',5',6'-tetrahydro-2'H-[2,2';6',2'']terpyridin-1'-ylmethyl)-benzylamine Using General Procedure A: A solution of 3,3''-dimethyl-1',2',3',4',5',6'-hexahydro-[2,2';6',2'']terpyridine (0.414 g, 1.55 mmol), α-bromo-m-tolunitrile (0.466 g, 2.38 mmol), KI (53 mg, 0.32 mmol), and DIPEA (0.55 mL, 3.16 mmol) in DMF (8 mL) was heated at 60° C. for 18 hours. Purification of the crude material by column chromatography on silica gel (40:1:1 $CH_2Cl_2$—$CH_3OH$—$NH_4OH$) provided 0.447 g (75%) of 3-(3,3''-dimethyl-3',4',5 ,6'-tetrahydro-2'H-[2,2';6', 2'']terpyridin-1'-ylmethyl)-benzonitrile as a beige solid. $^1$H NMR ($CDCl_3$) δ 1.56-1.72 (m, 3H), 2.05-2.10 (m, 1H), 2.18-2.34 (m, 2H), 2.41 (s, 6H), 3.53 (s, 2H), 4.10 (d, 2H, J=11.1 Hz), 6.71 (s, 1H), 6.83 (d, 1H, J=7.8 Hz), 6.93-7.00 (m, 3H), 7.13 (d, 1H, J=7.5 Hz), 7.25-7.27 (m, 2H), 8.39 (dd, 2H, J=4.8, 1.2 Hz); ES-MS m/z 383 (M$^+$H).

A solution of 3-3,3''-dimethyl-3',4',5',6'-tetrahydro-2'H-[2, 2';6',2'']terpyridin-1'-ylmethyl)-benzonitrile (0.107 g, 0.28 mmol) in $NH_3$ saturated MeOH (5 mL) was treated with Raney nickel (100 mg) and placed under 50 psi $H_2$, on a Parr shaker, for 4 hours. The mixture was filtered through Celite and the cake was washed with MeOH. The eluant was concentrated under reduced pressure. Purification of the crude material by column chromatography on silica gel (10:1:1 $CH_2Cl_2$—$CH_3OH$—$NH_4OH$) provided 62 mg (58%) of COMPOUND 69 as a white solid. $^1$H NMR ($CDCl_3$) δ 1.49-1.71 (m, 3H), 1.95-2.23 (m, 3H), 2.36 (s, 6H), 3.52 (s, 2H), 3.61 (s, 2H), 4.01 (d, 2H J=10.2 Hz), 6.42-6.48 (m, 2H), 6.91-7.02 (m, 4H), 7.24-7.31 (m, 2H), 8.45 (d, 2H, J=3.9 Hz); ES-MS m/z 387 (M$^+$H).

EXAMPLE 70

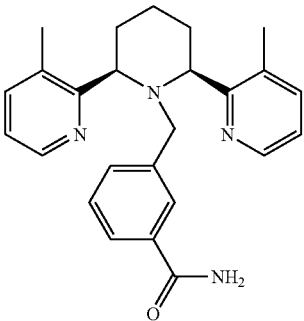

COMPOUND 70: 3-(3,3"-Dimethyl-3',4',5=,6'-tetrahydro-2'H-[2,2';6',2"]terpyridin-1'-ylmethyl)-benzamide To a solution of 3-(3,3"-dimethyl-3',4',5',6'-tetrahydro-2'H-[2,2';6',2"]terpyridin-1'-ylmethyl)-benzonitrile (0.178 g, 0.47 mmol) in MeOH (5.0 mL) was added water (2.0 mL) followed by sodium perborate tetrahydrate (0.218 g, 1.42 mmol). The resultant mixture was heated at 50° C. for 5 hours then cooled to room temperature. The mixture was diluted with water (10 mL) and extracted with CH$_2$Cl$_2$ (5×10 mL). The combined organic extracts were dried (Na$_2$SO$_4$) and concentrated. Purification of the crude material by radial chromatography on silica gel (1 mm plate, 25:1:1 CH$_2$Cl$_2$—CH$_3$OH—NH$_4$OH) provided 52 mg (28%) of COMPOUND 70 as a white solid. $^1$H NMR (CDCl$_3$) δ 1.55-1.75 (m, 3H), 1.93-2.01 (m, 1H), 2.06-2.19 (m, 2H), 2.40 (s, 6H), 3.37 (s, 2H), 3.96 (dd, 2H, J=11.4, 2.7 Hz), 5.52 (br s, 1H), 6.46 (d, 1H, J=7.5 Hz), 6.74 (dd, 1H, J=7.5, 7.5 Hz), 6.85 (dd, 2H, J=4.8, 7.5 Hz), 7.25-7.28 (m, 2H), 7.40 (d, 1H, J=7.8 Hz), 7.85 (s, 1H), 8.24 (d, 2H, J=3.6 Hz), 8.57 (br s, 1H); ES-MS m/z 401 (M$^+$H).

EXAMPLE 71

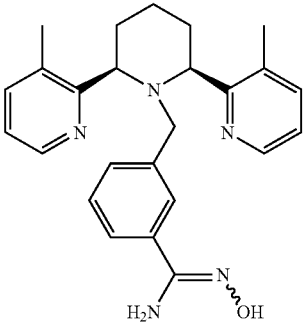

COMPOUND 71: 3-(3,3"-Dimethyl-3',4',5',6'-tetrahydro-2'H-[2,2';6',2"]terpyridin-1'-ylmethyl)-N-hydroxy-benzamidine To a solution of 3-(3,3"-dimethyl-3',4',5',6'-tetrahydro-2'H-[2,2';6',2"]terpyridin-1'-ylmethyl)-benzonitrile (0.117 g, 0.31 mmol) in MeOH (3.0 mL) was added Et$_3$N (0.14 mL, 1.00 mmol) followed by NH$_2$OH.H$_2$O (0.070 g, 1.01 mmol). The resultant mixture was stirred at room temperature overnight. The mixture was diluted with water (5 mL) and extracted with CH$_2$Cl$_2$ (5×10 mL). The combined organic extracts were dried (Na$_2$SO$_4$) and concentrated. Purification of the crude material by column chromatography on silica gel (10:1:1 CH$_2$Cl$_2$—CH$_3$OH—NH$_4$OH) provided 113 mg (88%) of COMPOUND 71 as a white solid. $^1$H NMR (CDCl$_3$) δ 1.50-1.72 (m, 3H), 1.94-2.19 (m, 3H), 2.40 (s, 6H), 3.40 (s, 2H), 3.97 (d, 2H, J=9.3 Hz), 5.75 (br s, 2H), 6.37 (d, 1H, J=7.5 Hz), 6.71 (dd, 1H, J=7.5, 7.5 Hz), 6.89 (dd, 2H, J=7.5, 4.8 Hz), 7.19 (d, 1H, J=8.1 Hz), 7.26-7.29 (m, 2H), 7.42 (s, 1H), 8.30 (d, 2H, J=3.9 Hz); ES-MS m/z 416 (M$^+$H).

EXAMPLE 72

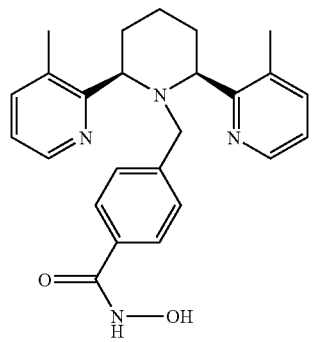

COMPOUND 72: 4-(3,3"-Dimethyl-3',4',5',6'-tetrahydro-2'H-[2,2';6',2"]terpyridin-1'-ylmethyl)-N-hydroxy-benzamide Using General Procedure A: A solution of 3,3"-dimethyl-1',2',3',4',5',6'-hexahydro-[2,2';6',2"]terpyridine (0.485 g, 1.81 mmol), 4-bromomethyl-benzoic acid methyl ester (0.642 g, 2.80 mmol), KI (64 mg, 0.38 mmol), and DIPEA (0.65 mL, 3.73 mmol) in DMF (9 mL) was heated at 60° C. for 23 hours. Purification of the crude material by column chromatography on silica gel (40:1:1 CH$_2$Cl$_2$—CH$_3$OH—NH$_4$OH) provided 0.67 g (89%) of 4-3,3"-dimethyl-3',4',5',6'-tetrahydro-2'H-[2,2';6',2"]terpyridin-1'-ylmethyl)-benzoic acid methyl ester as a white solid. $^1$H NMR (CDCl$_3$) δ 1.54-1.72 (m, 3H), 2.02-2.08 (m, 1H), 2.20-2.34 (m, 2H), 2.40 (s, 6H), 3.58 (s, 2H), 3.83 (s, 3H), 4.12 (d, 2H, J=11.4 Hz), 6.57 (d, 2H, J=7.8 Hz), 6.96 (dd, 2H, J=7.5, 4.5 Hz), 7.23 (d, 2H, J=7.5 Hz), 7.53 (d, 2H, J=7.8 Hz), 8.26 (d, 2H, J=4.5 Hz); ES-MS m/z 416 (M$^+$H).

To a solution of 4-(3,3"-dimethyl-3',4',5',6'-tetrahydro-2'H-[2,2';6',2"]terpyridin-1'-ylmethyl)-benzoic acid methyl ester (0.420 g, 1.01 mmol) in MeOH (5 mL) was added water (5 mL) and solid NaOH (0.448 g, 11.21 mmol). The resultant mixture was heated to reflux overnight then cooled to room temperature. The mixture was adjusted to pH ~5 with 6 N HCl (~2 mL) and extracted with CH$_2$Cl$_2$ (5×20 mL). The combined organic extracts were dried (Na$_2$SO$_4$) and concentrated and provided 0.440 g (quantitative yield) of 4-(3,3"-dimethyl-3',4',5',6'-tetrahydro-2'H-[2,2';6',2"]terpyridin-1'-ylmethyl)-benzoic acid as a white solid. $^1$H NMR (CDCl$_3$) δ 1.80-2.05 (m, 6H), 2.42 (s, 6H), 3.83 (br s, 2H), 4.55 (br s, 2H) 6.79 (d, 2H, J=8.1 Hz), 7.02 (dd, 2H, J=7.5, 5.1 Hz), 7.34 (d, 2H, J=7.5 Hz), 7.65 (d, 2H, J=7.8 Hz), 8.42 (d, 2H, J=3.9 Hz); ES-MS m/z 402 (M$^+$H).

To a cold (0° C.) solution of 4-(3,3"-Dimethyl-3',4',5',6'-tetrahydro-2'H-[2,2';6',2"]terpyridin-1'-ylmethyl)-benzoic acid (0.124 g, 0.31 mmol) in CH$_2$Cl$_2$ (3 mL) and DMF (5 drops) was added oxalyl chloride (0.11 mL, 1.26 mmol). After 15 minutes, the mixture was concentrated and provided a beige solid. The solid was dissolved in DMF (3 mL) and treated with DIPEA (0.50 mL, 2.87 mmol) followed by NH$_2$OH.H$_2$O (72 mg, 1.04 mmol). The resultant mixture was stirred at room temperature overnight. The mixture was diluted with saturated aqueous NH$_4$Cl (5 mL) and extracted with CH$_2$Cl$_2$ (5×10 mL). The combined organic extracts were dried (Na$_2$SO$_4$) and concentrated. Purification of the crude material by radial chromatography on silica gel (1 mm plate, 5:1:1 CH$_2$ClN—CH$_3$OH—NH$_4$OH) provided 21 mg (16%) of COMPOUND 72 as a white solid. $^1$H NMR (CDCl$_3$) δ 1.48-1.67 (m, 3H), 1.88-2.13 (m, 3H), 2.31 (s, 6H), 3.46 (s, 2H), 3.94 (d, 2H, J=10.5 Hz), 6.54 (d, 2H, J=6.9 Hz), 6.93 (dd, 2H, J=7.5, 4.5 Hz), 7.26-7.39 (m, 4H), 8.28 (d, 2H, J=3.3 Hz); ES-MS m/z 417 (M$^+$H).

EXAMPLE 73

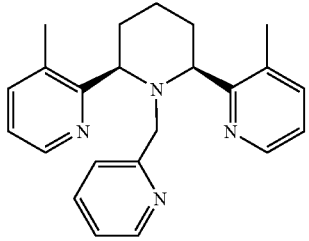

COMPOUND 73: (2'R,6'S)-3,3''-Dimethyl-1'-pyridin-2-ylmethyl-1',2',3',4',5',6'-hexahydro-[2,2';6',2'']terpyridine A solution of (2'R,6'S)-3,3''-dimethyl-1',2',3',4',5',6'-hexahydro-[2,2';6',2'']terpyridine (166 mg, 0.621 mmol), 2-(bromomethyl)pyridine hyrdobromide (189 mg, 0.745 mmol), DIPEA (265 µL, 1.52 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 73 (127 mg, 57%) as an orange solid. $^1$H NMR (CDCl$_3$) δ 1.75-1.85 (m, 3H), 1.93-2.02 (m, 1H), 2.09-2.21 (m, 2H), 2.42 (s, 6H), 3.80 (bs, 2H), 6.81-6.85 (m, 2H), 6.96 (dd, 2H, J=7.7, 3.9 Hz), 7.23-7.30 (m, 3H), 8.18 (d, 1H, J=4.8 Hz), 8.40 (d, 2H, J=4.4 Hz); ES-MS m/z 359 (M$^+$H).

EXAMPLE 74

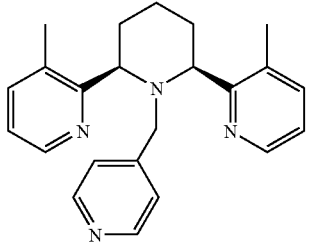

COMPOUND 74: (2'R,6'S)-3,3''-Dimethyl-1'-pyridin-4-ylmethyl-1',2',3',4',5',6'-hexahydro-[2,2';6',2'']terpyridine A solution of (2'R,6'S)-3,3''-dimethyl-1',2',3',4',5',6'-hexahydro-[2,2';6',2'']terpyridine (163 mg, 0.609 mmol), 4-(bromomethyl)pyridine hyrdobromide (185 mg, 0.730 mmol), DIPEA (256 µL, 1.52 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 74 (110 mg, 37%) as an orange oily solid. $^1$H NMR (CDCl$_3$) δ 1.63-1.73 (m, 3H), 2.08-2.20 (m, 2H), 2.28-2.42 (m, 2H), 2.46 (s, 6H), 3.56 (s, 2H), 4.22 (d, 2H, J=11.8 Hz), 6.14 (d, 2H, J=5.3 Hz), 6.96 (dd, 2H, J=7.5, 4.8 Hz), 7.22 (d, 2H, J=7.9 Hz), 8.00 (d, 2H, J=4.4 Hz), 8.37 (d, 2H, J=4.4 Hz); ES-MS m/z 359 (M$^+$H).

EXAMPLE 75

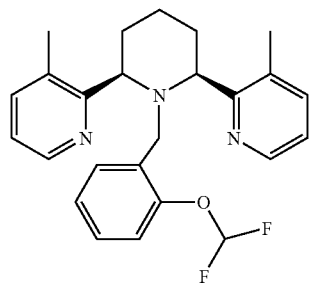

COMPOUND 75: (2'R, 6'S)-1'-(2-Difluoromethoxy-benzyl)-3,3''-dimethyl-1',2',3',4',5',6'-hexahydro-[2,2';6',2'']terpyridine A solution of (2'R,6'S)-3,3''-dimethyl-1',2',3',4',5',6'-hexahydro-[2,2';6',2'']terpyridine (169 mg, 0.624 mmol), 2-(difluoromethoxy)benzyl bromide (114 µL, 0.745 mmol), DIPEA (160 µL, 0.936 mmol) and KI (10 mg, 0.060 mmol) in CH$_3$CN (6 mL) was warmed to 50° C. and stirred for 15.5 h according to General Procedure A. Purification by flash chromatography on silica gel using CH$_2$Cl$_2$/MeOH/NH$_4$OH (94:5:1) afforded COMPOUND 75 (238 mg, 90%) as an white solid. $^1$H NMR (CDCl$_3$) δ 1.65-1.70 (m, 3H), 2.05-2.07 (m, 2H), 2.30-2.45 (m, 3H), 3.63 (s, 2H), 4.16 (d, 2H, J=10.2 Hz), 6.50 (s, 1H), 6.78-6.83 (m, 4H), 7.20-7.30 (m, 3H), 8.30 (d, 2H, J=3.1 Hz); ES-MS m/z 424 (M$^+$H).

EXAMPLE 76

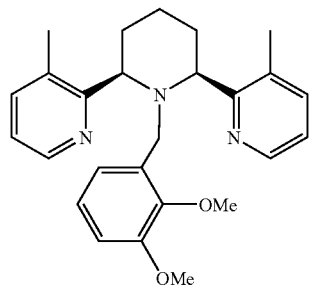

COMPOUND 76: (2'R,6'S)-1'-(2,3-Dimethoxy-benzyl)-3,3''-dimethyl-1',2',3',4',5',6'-hexahydro-[2,2',6',2'']terpyridine A solution of (2'R,6'S)-3,3''-dimethyl-1',2',3',4',5',6'-hexahydro-[2,2';6'2'']terpyridine (164 mg, 0.613 mmol), 2,3- dmethoxybenzy chloride (136 mg, 0.731 mmol), DIPEA (160 µL, 0.936 mmol) and KI (10 mg, 0.060 mmol) in CH₃CN (6 mL) was warmed to 50° C. and stirred for 15.5 h according to General Procedure A. Purification by flash chromatography on silica gel using CH2Cl₂/MeOH/NH₄OH (94:5:1) afforded COMPOUND 76 (61 mg, 24%) as an white solid. $^1$H NMR (CDCl₃) δ 1.61-1.76 (m, 3H), 2.16-2.23 (m, 3H), 2.45 (s, 6H), 3.68 (s, 6H), 4.16 (d, 2H, J=9.1 Hz), 6.45-6.48 (m, 1H), 6.62-6.65 (m, 2H), 6.89-6.73 (m, 2H), 7.26-7.29 (m, 2H), 8.38 (d, 2H, J=3.1 Hz); ES-MS m/z 418 (M⁺H).

EXAMPLE 77

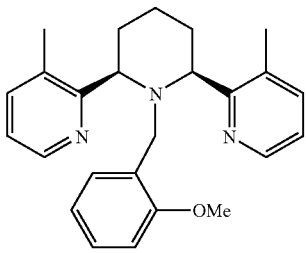

COMPOUND 77: (2'R,6'S)-1'-(2-Methoxy-benzyl)-3,3''-dimethyl-1',2',3',4',5',6'-hexahydro-[2,2';6',2''] terpyridine A solution of (2'R,6'S)-3,3''-dimethyl-1',2',3',4',5',6'-hexahydro-[2,2';6',2'']terpyridine (197.6 mg, 0.739 mmol), 2-methoxybenzy chloride (125 µL, 0.898 mmol), DIPEA (195 µL, 1.12 mmol) and KI (10 mg, 0.060 mmol) in CH₃CN (6 mL) was warmed to 50° C. and stirred for 26 h according to General Procedure A. Purification by flash chromatography on silica gel using CH₂Cl₂/MeOH/NH₄OH (94:5:1) afforded COMPOUND 77 (78 mg, 31%) as an white solid. $^1$H NMR (CDCl₃) δ 1.20-1.30 (m, 3H), 1.65-1.72 (m, 1H), 2.15-2.25 (m, 2H), 2.40 (s, 6H), 3.59 (s, 3H), 4.05-4.15 (m, 2H), 6.32 (bs, 1H), 6.55-6.60 (m, 1H), 6.81-6.91 (m, 4H), 7.23-7.25 (m, 2H), 8.36 (bs, 2H); ES-MS m/z 388 (M⁺H).

EXAMPLE 78

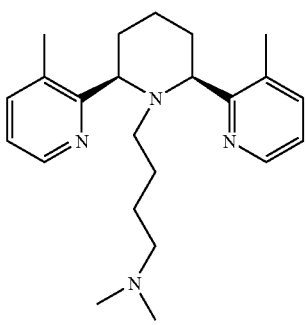

COMPOUND 78: [4-((2'R,6'S)-3,3''-Dimethyl-3',4',5',6'-tetrahydro-2'H-[2,2';6',2'']terpyridin-1'-yl)-butyl]-dimethyl-amine HBr salt A solution of 4-(3,3''-dimethyl-3',4',5',6'-tetrahydro-2'H-cis-[2,2';6',2'']terpyridin-1'-yl)-butylamine (221 mg, 0.476 mmol) dissolved in water (10 mL) was basified to pH13 with 1N NaOH (3 mL), which was extracted with CH₂Cl₂ (3×40 mL). The combined organic layers were dried over Na₂SO₄ and concentrated in vacuo to afford the freebase (177 mg) as a yellow oil.

To a solution of the freebase (177 mg, 0.511 mmol) in CH₂Cl₂ (5 mL) was added paraformaldehyde (133 mg, 4.43 mmol). The mixture was stirred for 10 min. then NaBH(OAc)₃ (1.30 g, 6.14 mmol) was added and the mixture was stirred for 16 h at ambient temperature. The reaction was quenched with a saturated solution of NaHCO₃ (10 mL), diluted with CH₂Cl₂ (30 mL) and separated. The aqueous layer was extracted with CH₂Cl₂ (3×30 mL). The combined organic layers were dried over Na₂SO₄ and concentrated in vacuo. Purification by flash chromatography on silica gel using CH₂Cl₂/MeOH/NH₄OH (94.5:5:0.5) afforded the title compound (188 mg, 100%) as a yellow oil. $^1$H NMR (CDCl₃) δ 0.75-0.80 (m, 3H), 1.64-1.77 (m, 5H), 1.95-2.05 (m, 9H), 2.17-2.23 (m, 2H), 2.45-2.75 (m, 9H), 4.07 (d, 2H, J=10.5 Hz), 7.07 (dd, 2H, J=7.5, 4.8 Hz), 7.42 (d, 2H, J=7.5 Hz), 8.46 (bs, 2H).

To a solution of [4-((2'R,6'S)-3,3''-dimethyl-3',4',5',6'-tetrahydro-2'H-[2,2';6',2'']terpyridin-1'-yl)-butyl]-dimethyl-amine (188 mg, 0.511 mmol) in MeOH (1 mL) was added a saturated solution of HBr in MeOH (1 mL) according to General Procedure B. COMPOUND 78 was collected as a white solid (199 mg, 38%). $^1$H NMR (D₂O) δ 1.25-1.34 (m, 4H), 1.45-1.55 (m, 2H), 1.67-1.78 (m, 1H), 1.92-2.00 (m, 1H), 2.15 (d, 2H, J=13.6 Hz), 2.25-2.31 (m, 2H), 2.60 (s, 6H), 2.71 (s, 6H), 2.99-2.93 (m, 2H), 4.60 (dd, 2H, J=11.3, 2.9 Hz), 7.90 (dd, 2H, J=8.0, 5.9 Hz), 8.44 (d, 2H, J=7.7 Hz), 8.68 (d, 2H, J=5.5 Hz); $^{13}$C NMR (D₂O) δ 19.44, 22.19, 24.71, 34.83, 45.26, 54.39, 56.69, 60.03, 128.34, 139.34, 142.13, 151.92; ES-MS m/z 367 (M⁺H). Anal Calcd. For C₂₃H₃₄N₄.4.0(HBr). 1.0(H₂O).0.5(C₄H₁₀O): C, 40.29; H, 6.09; N, 7.52; Br, 42.89. Found: C, 40.31; H, 6.36; N, 7.57; Br, 42.81.

EXAMPLE 79

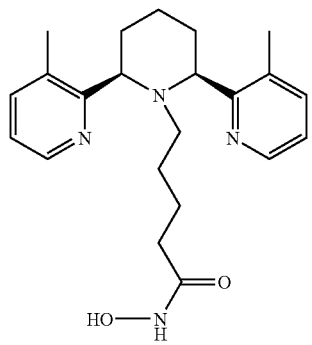

COMPOUND 79: 5-((2'R,6'S)-3,3''-Dimethyl-3',4',5',6'-tetrahydro-2'H-[2,2';6',2'']terpyridin-1'-yl)-pentanoic acid hydroxyamide A solution of (2'R,6'S)-3,3''-dimethyl-1',2',3',4',5',6'-hexahydro-[2,2';6',2'']terpyridine (306 mg, 1.12 mmol), 5-bromo-pentanoic acid ethyl ester (263 mg, 1.12 mmol), DIPEA (260 µL, 1.49 mmol) and KI (10 mg, 0.060 mmol) in CH₃CN (12 mL) was warmed to 60° C. and stirred for 23 h according to General Procedure A. Purification by flash chromatography on silica gel using CH₂Cl₂/MeOH/NH₄OH (94:

5:1) afforded 5-((2'R,6'S)-3,3"-dimethyl-3',4',5',6'-tetrahydro-2'H-[2,2';6',2"]terpyridin-1'-yl)-pentanoic acid ethyl ester (417 mg, 90%) as a yellow oil. $^1$H NMR (CDCl$_3$) δ 0.75-0.94 (m, 3H), 1.17 (t, 3H, J=7.1 Hz), 1.55-2.01 (m 8H), 2.20-2.35 (m, 6H), 2.47 (s, 6H), 3.99 (q, 2H, J=7.2 Hz), 7.05-7.09 (m, 2H), 7.43 (d, 2H, J=7.6 Hz), 8.46 (bs, 2H).

A warmed (50° C.) solution of KOH (1.36 g, 28.9 mmol) in MeOH (6.0 mL) was added to a warmed (50° C.) solution of NH$_2$OH.H$_2$O (1.00 g, 14.3 mmol) in MeOH (10.2 mL). Stirred for 5 min. during which time a white precipitate formed immediately. Cooled in an ice bath and decanted clear hydroxylamine freebase solution.

The freshly prepared solution of hydroxylamine in MeOH (5.3 mL) was added to a 5-((2'R,6'S)-3,3"-dimethyl-3',4',5',6'-tetrahydro-2'H-[2,2';6',2"]terpyridin-1'-yl)-pentanoic acid ethyl ester (228 mg, 0.575 mmol) and stirred for 23 h at ambient temperature. The mixture was concentrated to remove volatiles. Taken up in CH$_2$Cl$_2$ (50 mL) was washed with a saturated solution of NaHCO$_3$ (30 mL) to pH8. Separated and the aqueous layer was extracted with CH$_2$Cl$_2$ (2×50 mL). Combine organic layers were dried over Na$_2$SO$_4$ and concentrated in vacuo. Purification by flash chromatography on silica gel using CH$_2$Cl$_2$/MeOH/NH$_4$OH (89:10:1) afforded COMPOUND 79(121.3, 55%) as a white solid. $^1$H NMR (CDCl$_3$) δ 0.85-0.95 (m, 4H), 1.55-2.00 (m, 14H), 2.40 (s, 6H), 3.85-3.93 (bs, 2H), 7.03-7.06 (m, 2H), 7.47 (d, 2H, J=Hz), 8.31 (bs, 2H); $^{13}$C NMR (CDCl$_3$) δ 18.86, 22.73, 23.59, 32.31, 32.76, 53.44, 62.23, 122.17, 130.73, 139.26, 146.78, 169.62; ES-MS m/z 383 (M$^+$H). Anal Calcd. For C$_{22}$H$_{30}$N$_4$O$_2$.0.5(CH$_2$Cl$_2$): C, 63.59; H, 7.35; N, 13.18. Found: C, 63.69; H, 7.51; N, 13.36.

EXAMPLE 80

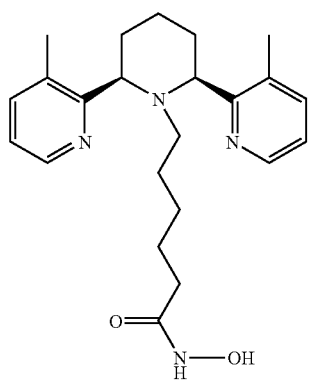

COMPOUND 80: 6-((2'R,6'S)-3,3"-Dimethyl-3',4',5',6'-tetrahydro-2'H-[2,2';6',2"]terpyridin-1'-yl)-hexanoic acid hydroxyamide A solution of (2'R,6'S)-3,3"-dimethyl-1',2',3',4',5',6'-hexahydro-[2,2';6',2"]terpyridine (308 mg, 1.15 mmol), 6-bromo-hexanoic acid ethyl ester (283 mg, 1.27 mmol), DIPEA (260 μL, 1.49 mmol) and KI (10 mg, 0.060 mmol) in CH$_3$CN (12 mL) was warmed to 60° C. and stirred for 23 h according to General Procedure A. Purification by flash chromatography on silica gel using CH$_2$Cl$_2$/MeOH/NH$_4$OH (94:5:1) afforded 6-((2'R,6'S)-3,3"-dimethyl-3',4',5',6'-terahydro-2'H-[2,2';6',2"]terpyridin-1'-yl)-hexanoic acid ethyl ester (425 mg, 90%) as a yellow oil. $^1$H NMR (CDCl$_3$) δ 0.60-0.68 (m, 2H), 0.79-0.85 (m, 1H), 1.13-1.25 (m, 5H), 1.58-1.70 (m, 3H), 1.94-1.98 (m, 4H), 2.08-2.25 (m, 7H), 2.48 (bs, 6H), 1.50-2.63 (m, 2H), 4.03 (q, 2H, J=7.1 Hz), 7.05-7.08 (m, 2H), 7.43 (d, 2H, J=7.3 Hz), 8.47 (bs, 2H).

A warmed (50° C.) solution of KOH (1.36 g, 28.9 mmol) in MeOH (6.0 mL) was added to a warmed (50° C.) solution of NH$_2$OH.H$_2$O (1.00 g, 14.3 mmol) in MeOH (10.2 mL). Stirred for 5 min. during which time a white precipitate formed immediately. Cooled in an ice bath and decanted clear hydroxylamine freebase solution.

The freshly prepared solution of hydroxylamine in MeOH (5.8 mL) was added to a 5-((2'R,6'S)-3,3'-dimethyl-3',4',5',6'-tetrahydro-2'H-[2,2';6',2"]terpyridin-1'-yl)-pentanoic acid ethyl ester (262 mg, 0.638 mmol) and stirred for 23 h at ambient temperature. The mixture was concentrated to remove volatiles. Taken up in CH$_2$Cl$_2$ (50 mL) was washed with a saturated solution of NaHCO$_3$ (30 mL) to pH8. Separated and the aqueous layer was extracted with CH$_2$Cl$_2$ (2×50 mL). Combine organic layers were dried over Na$_2$SO$_4$ and concentrated in vacuo. Purification by flash chromatography on silica gel using CH$_2$Cl$_2$/MeOH/NH$_4$OH (89:10:1) afforded COMPOUND 80 (152, 60%) as a white solid. $^1$H NMR (CDCl$_3$) δ 0.20-0.30 (m, 2H), 0.70-0.78 (m , 2H), 1.14-1.19 (m, 2H), 1.50-1.63 (m, 2H), 1.85-1.95 (m, 6H), 2.39 (s, 6H), 3.86 (bs, 2H), 7.02-7.06 (m, 2h), 7.46 (d, 2H, J=6.7 Hz), 8.48 (d, 2H, J=3.0 Hz); $^{13}$C NMR (CDCl$_3$) δ 19.03, 23.29, 24.69, 25.93, 32.47, 33.05, 53.44, 62.82, 121.91, 130.74, 139.15, 146.71, 160.24, 169.87; ES-MS m/z 383 (M$^+$H). Anal Calcd. For C$_{23}$H$_{32}$N$_4$O$_2$.0.4(CH$_2$Cl$_2$): C, 65.29; H, 7.68; N, 13.01. Found: C, 65.59; H, 7.78; N, 13.21.

EXAMPLE 81

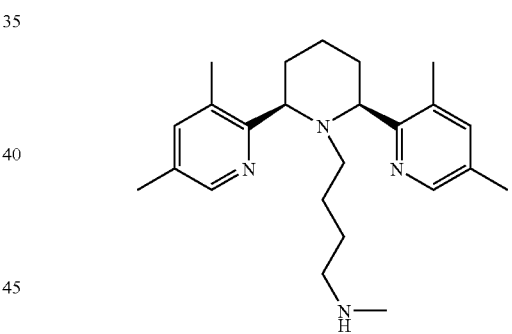

COMPOUND 81: Methyl-[4-(3,5,3",5"-tetramethyl-3',4',5',6'-tetrahydro-2'H-[2,2';6',2"]terpyridin-1'-yl)-butyl]-amine HBr salt To a solution cooled (0° C.) solution of (4-hydroxy-butyl)-methyl-carbamic acid tert-butyl ester (497 mg, 2.44 mmol) and Et$_3$N (850 μL, 6.10 mmol) in CH$_2$Cl$_2$ (12 mL) was added MsCl (416 μL, 0.537 mmol). The mixture was warmed to ambient temperature and stirred for 1 h. Water (20 mL) was added and the mixture was extracted with CH$_2$Cl$_2$ (33 50 mL). The combined organic layers were dried over Na$_2$SO$_4$ and concentrated in vacuo to afford the mesylate (815 mg) as a yellow oil.

To a solution of the mesylate (815 mg) and 2,2,6,6-tetramethylpiperidine (240 μL, 1.42 mmol) in CH$_3$CN (10 mL) was a 3,5,3",5"-tetramethyl-1',2',3',4',5',6'-hexahydro-[2,2';6',2"]terpyridine (328 mg, 1.11 mmol). The mixture was warmed to 60° C. and stirred for 16 h according to General Procedure A.

Purification by flash chromatography on silica gel using CH₂Cl₂/MeOH/NH₄OH (94.3:5:0.7) afforded the product containing fractions that were concentrated. The mixture of product was dissolved in CH₂Cl₂ (12 mL) to which was added TFA (3 mL) and stirred for 16 h. The reaction was basified with 10 N NaOH (7 mL), diluted with water (15 mL) and extracted with CH₂Cl₂ (50 mL). The aqueous layer was extracted with CH₂Cl₂ (2×40 mL). The combined organic layers were dried over Na₂SO₄ and concentrated in vacuo. Purification by flash chromatography on silica gel using CH₂Cl₂/MeOH/NH₄OH (90:5:5) afforded the free base (168 mg, 40%). $^1$H NMR (CDCl₃) δ 0.79-0.93 (m, 3H), 1.41-1.64 (m, 3H), 1.86-2.25 (m, 16H), 2.42 (s, 6H), 2.45-2.60 (m, 1H), 3.97 (d, 2H, J=Hz), 7.22 (s, 2H), 8.18-8.29 (m, 2H).

To a solution of methyl-[4-(3,5,3″,5″-tetramethyl-3′,4′,5′,6′-tetrahydro-2′H-[2,2′;6′,2″]terpyridin-1′-yl)-butyl]-amine (168 mg, 0.440 mmol) in MeOH (1 mL) was added a saturated solution of HBr in MeOH (1 mL) according to General Procedure B. COMPOUND 81 was collected as a white solid (240 mg, 82%). $^1$H NMR (D₂O) δ 1.19-1.31 (m, 4H), 1.46-1.56 (m, 2H), 1.65-1.70 (m, 1H), 1.90-1.95 (m, 1H), 2.11 (d, 2H, J=13.0 Hz), 2.22-2.27 (m, 2H), 2.50 (s, 6H), 2.55 (s, 6H), 2.57 (s, 3H), 2.75-2.81 (m, 2H), 4.53 (d, 2H, J=9.1 Hz), 8.26 (s, 2H), 8.51 (s, 2H); $^{13}$C NMR (D₂O) δ 16.96, 17.56, 20.05, 22.43, 23.84, 32.65, 32.99, 48.80, 52.14, 57.55, 136.00, 137.42, 139.20, 150.10, 151.69; ES-MS nm/z 381 (M⁺H). Anal Calcd. For C₂₄H₃₆N₄·3.0(HBr)·2.1(H₂O): C, 43.60; H, 6.59; N, 8.47; Br, 36.26. Found: C, 43.62; H, 6.38; N, 8.15; Br, 36.26.

EXAMPLE 82

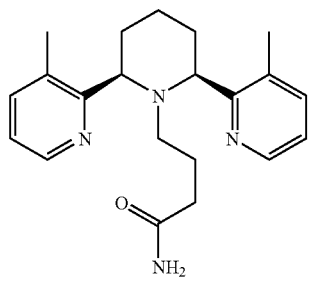

COMPOUND 82: 4-(3,3″-Dimethyl-3′,4′,5′,6′-tetrahydro-2′H-cis-[2,2′;6′,2″]terpyridin-1′-yl)-butyramide (HBr salt)

To a solution of 4-(3,3″-dimethyl-3′,4′,5′,6′-tetrahydro-2′H-cis-[2,2′;6′,2″]terpyridin-1′-yl)-butyronitrile (121 mg, 0.363 mmol) in TFA (2.5 mL) was added conc. H₂SO₄ (5-6 drops) and the solution stirred at reflux overnight. The reaction was cooled to room temperature, diluted with H₂O (10 mL), basified with 4 N NaOH until pH>10 and extracted with CH₂Cl₂ (3×15 mL). The combined organic extracts were dried (Na₂SO₄), concentrated and purified by radial chromatography on silica gel (1 mm plate, CH₂Cl₂/MeOH/NH₄OH, 25:1:1) to afford the primary amide (94 mg, 74%) as a white solid.

Using General Procedure B: Conversion of the free base from above (94 mg, 0.27 mmol) to a HBr salt followed by re-precipitation of the crude material from MeOH/ether gave COMPOUND 82 as a white solid (136 mg, 79%). $^1$H NMR (D₂O) δ 1.46-1.59 (m, 4H), 1.66-1.78 (m, 1H), 1.85 (t, 2H, J=6.9 Hz), 1.93-1.98 (m, 1H), 2.11-2.24 (m, 4H), 2.60 (s, 6H), 4.60 (dd, 2H, J=11.4, 2.7 Hz), 7.89 (dd, 2H, J=8.1, 6 Hz), 8.42 (d, 2H, J=8.1 Hz), 8.67 (d, 2H, J=5.7 Hz); $^{13}$C NMR (D₂O) δ 17.16, 19.26, 22.45, 32.33, 32.57, 52.08, 58.07, 126.04, 137.09, 139.72, 149.56, 154.59, 178.48; ES-MS m/z 353 (M⁺H). Anal. Calcd. for C₂₁H₂₈N₄O·2.7 HBr·2.8 H₂O·0.3 C₄H₁₀O: C, 41.43; H, 6.15; N, 8.70; Br, 33.52. Found: C, 41.30; H, 5.86; N, 8.56; Br, 33.77.

EXAMPLE 83

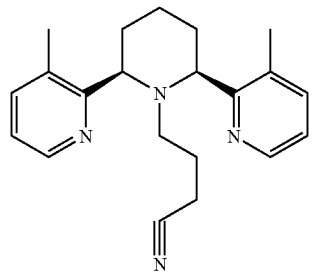

COMPOUND 83: 4-(3,3″-Dimethyl-3′,4′,5′,6′-tetrahydro-2′H-cis-[2,2′;6′,2″]terpyridin-1′-yl)-butyronitrile (HBr salt)

Following General Procedure A: A solution of 3,3″-dimethyl-1′,2′,3′,4′,5′,6′-hexahydro-cis-[2,2′;6′,2″]terpyridine (0.293 g, 1.10 mmol), 4-bromobutyronitrile (0.15 mL, 1.51 mmol), KI (10 mg), and DIPEA (0.30 mL, 1.73 mmol) in DMF (3 mL) was heated at 65° C. for 17 hours. Purification of the crude material by column chromatography on silica gel (CH₂Cl₂—CH₃OH, 96:4) provided 290 mg (79%) of 4-(3,3″-dimethyl-3′,4′,5′,6′-tetrahydro-2′H-cis-[2,2′;6′,2″]terpyridin-1′-yl)-butyronitrile as a colorless oil.

Using General Procedure B: Conversion of the free base from above (60 mg, 0.18 mmol) to a HBr salt followed by re-precipitation of the crude material from MeOH/ether gave COMPOUND 83 as a yellow solid (86 mg, 90%). $^1$H NMR (D₂O) δ 1.50-1.80 (m, 5H), 1.95-2.00 (m, 1H), 2.12-2.18 (m, 4H), 2.30-2.40 (m, 2H), 2.61 (s, 6H), 4.63 (dd, 2H, J=11.4, 3.0 Hz), 7.91 (dd, 2H, J=8.1, 6 Hz), 8.44 (d, 2H, J=8.1 Hz), 8.69 (d, 2H, J=5.7 Hz); $^{13}$C NMR (D₂O) δ 14.88, 17.19, 19.02, 22.39, 32.55, 51.34, 57.89, 120.71, 126.16, 137.16, 139.92, 149.716, 154.27; ES-MS m/z 335 (M⁺H). Anal. Calcd. for C₂₁H₂₆N₄·2.1HBr·1.4H₂O: C, 47.63; H, 5.88; N, 10.58; Br, 31.68. Found: C, 47.64; H, 5.85; N, 10.60; Br, 31.61.

EXAMPLE 84

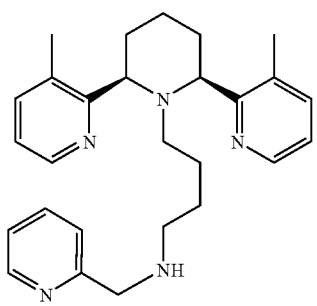

COMPOUND 84: [4-(3,3″-Dimethyl-3′,4′,5′,6′-tetrahydro-2′H-cis-[2,2′;6′,2″]terpyridin-1′-yl)-butyl]-pyridin-2-ylmethyl-amine (HBr salt)

Following General Procedure C: To a solution of 4-(3,3″-dimethyl-3′,4′,5′,6′-tetrahydro-2′H-cis-[2,2′;6′,2″]terpyridin-1′-yl)-butylamine (84 mg, 0.249 mmol) in CH₂Cl₂ (5 mL) was added 2-pyridinecarboxaldehyde (0.019 mL, 0.20 mmol)

followed by NaBH(OAc)$_3$ (73 mg, 0.34 mmol) and the reaction stirred at room temperature for 3 h. Purification of the crude material by radial chromatography on silica gel (1 mm plate, 25:1:1 CH$_2$Cl$_2$—MeOH—NH$_4$OH) provided 30 mg (35%) of [4-(3,3''-Dimethyl-3',4',5',6'-tetrahydro-2'H-cis-[2,2';6',2'']terpyridin-1'-yl)-butyl]-pyridin-2-ylmethyl-amine as a colorless oil Using General Procedure B: Conversion of the free base from above (30 mg, 0.070 mmol) to a HBr salt followed by re-precipitation of the crude material from MeOH/ether gave COMPOUND 84 as an orange solid (26 mg, 46%). $^1$H NMR (D$_2$O) δ 1.35-1.57 (m, 6H), 1.64-1.76 (m, 1H), 1.92-1.97 (m, 1H), 2.12-2.16 (m, 2H), 2.25-2.30 (m, 2H), 2.60 (s, 6H), 2.99-3.04 (m, 2H), 4.50 (s, 2H), 4.61 (d, 2H, J=9.3 Hz), 7.82-7.99 (m, 4H), 8.42 (d, 2H, J=7.8 Hz), 8.44-8.49 (m, 1H), 8.68 (d, 2H, J=5.7 Hz), 8.77 (d, 1H, J=5 Hz); $^{13}$C NMR (D$_2$O) δ 17.28, 19.99, 22.44, 23.98, 32.55, 48.07, 48.43, 52.11, 57.74, 126.05, 127.67, 127.78, 136.97, 139.85, 145.04, 146.11, 149.67, 154.51; ES-MS m/z 430 (M$^+$H). Anal. Calcd. for C$_{27}$H$_{35}$N$_5$.3.9 HBr.3.3 H$_2$O: C, 40.30; H, 5.70; N, 8.70; Br, 38.73. Found: C, 40.53; H, 5.53; N, 8.32; Br, 38.81.

EXAMPLE 85

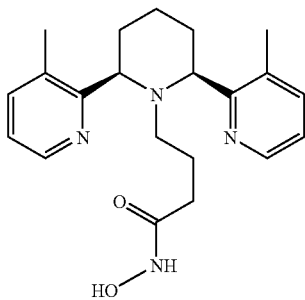

COMPOUND 85: 4-(3,3''-Dimethyl-3',4',5',6'-tetrahydro-2'H-cis-[2,2';6',2'']terpyridin-1'-yl)-N-hydroxy-butyramide To a solution of 4-(3,3''-dimethyl-3',4',5',6'-tetrahydro-2'H-cis-[2,2';6',2'']terpyridin-1'-yl)-butyronitrile (348 mg, 1.04 mmol) in EtOH/H$_2$O (1:1, 10 mL) was added NaOH (455 mg, 11.4 mmol) and the reaction refluxed overnight. The mixture was then cooled, acidified with 6 N HCl to pH 3-4 and extracted with CH$_2$Cl$_2$ (3×15 mL). The combined organic extracts were dried (Na$_2$SO$_4$) and concentrated to afford the desired carboxylic acid as a brown foam (270 mg).

To a solution of the crude acid from above (270 mg) in CH$_2$Cl$_2$ (5 mL) at 0° C. was added DMF (3 drops) followed by oxalyl chloride (0.10 mL, 1.15 mmol). The reaction was warmed to room temperature, stirred 1 h 45 min. then concentrated in vacuo. To a solution of the resultant crude residue in CH$_2$Cl$_2$ (5 mL) was added DIPEA (0.35 mL, 2.01 mmol), NH$_2$OH.H$_2$O (82 mg, 1.18 mmol), EDC (157 mg, 0.82 mmol) and HOBt (110 mg, 0.81 mmol) and the mixture stirred overnight. The reaction was diluted with CH$_2$Cl$_2$ (25 mL) and saturated aqueous NaHCO$_3$ (25 mL) and the aqueous layer extracted with CH$_2$Cl$_2$ (2×10 mL). The combined organic extracts were dried (Na$_2$SO$_4$), concentrated and purified by radial chromatography on silica gel (1 mm plate, CH$_2$Cl$_2$—MeOH—NH$_4$OH, 25:1:1) to afford COMPOUND 85 (52 mg, 18% 2 steps) as a colorless oil. $^1$H NMR (CDCl$_3$) δ 1.22-1.30 (br m, 2H), 1.46-1.56 (m, 3H), 1.67-1.71 (m, 2H), 1.80-1.87 (m, 5H), 2.05 (br s, 2H), 2.46 (s, 6H), 3.92 (d, 2H, J=9 Hz), 7.01 (dd, 2H, J=7.5, 4.8 Hz), 7.50 (d, 2H, J=7.5 Hz), 8.10 (d, 2H, J=4.8 Hz); $^{13}$C NMR (CDCl$_3$) δ 18.62, 19.48, 25.76, 31.22, 33.55, 51.21, 62.85, 122.21, 131.26, 139.48, 146.87, 160.16, 169.24; ES-MS m/z 369 (M$^+$H). Anal. Calcd. for C$_{21}$H$_{28}$N$_4$O$_2$.0.7 H$_2$O: C, 66.19; H, 7.78; N, 14.70. Found: C, 66.22; H, 7.64; N, 14.40.

EXAMPLE 86

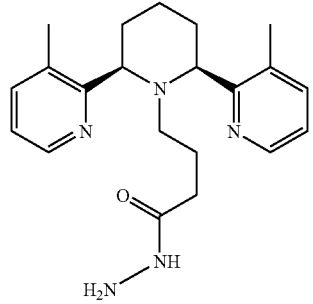

COMPOUND 86: 4-(3,3''-Dimethyl-3',4',5',6'-tetrahydro-2'H-cis-[2,2';6',2'']terpyridin-1'-yl)-butyric acid hydrazide To a solution of 4-(3,3''-dimethyl-3',4',5',6'-tetrahydro-2'H-cis-[2,2';6',2'']terpyridin-1'-yl)-butyric acid ethyl ester (163 mg, 0.445 mmol) in EtOH (5 mL) was added hydrazine monohydrate (0.65 mL, 13.4 mmol) and the reaction heated to 80° C. for 2.5 d. The mixture was then concentrated and purified by radial chromatography on silica gel (1 mm plate, CH$_2$Cl$_2$/CH$_3$OH/NH$_4$OH, 50:1:1 then 25:1:1) to afford COMPOUND 86 as a white solid (145 mg, 89%). $^1$H NMR (CDCl$_3$) δ 0.77-0.81 (br m, 2H), 1.49-1.66 (m, 5H), 1.92-2.11 (m, 3H), 2.22-2.29 (m, 2H), 2.47 (s, 6H), 3.66 (br s, 2H), 3.98 (dd, 2H, J=11.4, 2.4 Hz), 4.34 (br s, 1H), 7.07 (dd, 2H, J=7.5, 4.8 Hz), 7.42 (d, 2H, J=7.5 Hz), 8.43 (br m, 2H); $^{13}$C NMR (CDCl$_3$) δ 19.25, 22.19, 25.18, 32.19, 32.46, 52.60, 63.79, 122.22, 131.13, 138.91, 147.09, 161.00, 173.75; ES-MS m/z 368 (M$^+$H). Anal. Calcd. for C$_{21}$H$_{29}$N$_5$O.1.2 H$_2$O: C, 64.82; H, 8.13; N, 18.00. Found: C, 64.99; H, 7.97; N, 17.69.

EXAMPLE 87

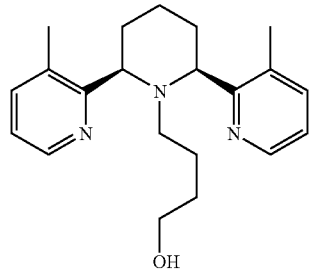

COMPOUND 87: 4-(3,3''-Dimethyl-3',4',5',6'-tetrahydro-2'H-cis-[2,2';6',2'']terpyridin-1'-yl)-butan-1-ol To a solution of 4-3,3''-dimethyl-3',4',5',6'-tetrahydro-2H-cis-[2,2';6',2'']terpyridin-1-yl)-butyric acid ethyl ester (332 mg, 0.87 mmol) in THF (5 mL) at 0° C. was added LiAlH$_4$ (1.0 M in THF, 1.4 mL, 1.4 mmol) and the reaction stirred from 0° C. to room temperature over 2 h. The mixture was quenched with H$_2$O (0.050 mL), 15% aqueous NaOH (0.050 mL) and then water again (0.15 mL) and stirred for 15 min.

The mixture was dried (Na₂SO₄) and filtered, washing with CH₂Cl₂. The filtrate was concentrated and purified by column chromatography on silica gel (CH₂Cl₂/CH₃OH/NH₄OH, 96:4:0 then 88:10:2) to afford COMPOUND 87 as a colorless oil (266 mg, 90%). ¹H NMR (CDCl₃) δ 0.88-0.92 (m, 4H), 1.57-1.63 (m, 3H), 1.92-2.06 (m, 3H), 2.22-2.29 (m, 2H), 2.46 (s, 6H), 2.63 (m, 1H), 3.13-3.15 (m, 2H), 4.15-4.21 (m, 2H), 7.08 (dd, 2H, J=7.5, 4.8 Hz), 7.43 (d, 2H, J=7.5 Hz), 8.44 (br m, 2H); ¹³C NMR (CDCl₃) δ 19.04, 21.57, 25.11, 30.51, 49.73, 62.15, 63.65, 71.12, 122.37, 131.86, 138.87, 147.02, 160.10; ES-MS m/z 340 (M⁺H). Anal. Calcd. for C₂₁H₂₉N₃O.1.4 H₂O: C, 69.16; H, 8.79; N, 11.52. Found: C, 69.21; H, 8.56; N, 11.50.

EXAMPLE 88

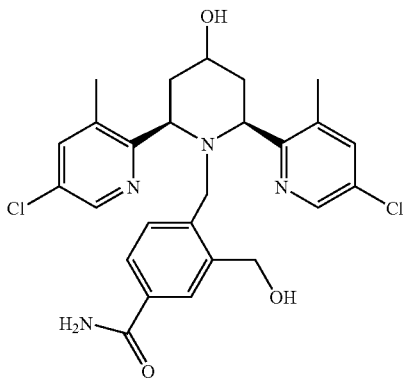

COMPOUND 88: 4-(5,5"-Dichloro-4'-hydroxy-3,3"-dimethyl-3',4',5',6'-tetrahydro-2'H-cis-[2,2';6',2"]terpyridin-1'-ylmethyl)-3-hydroxymethyl-benzamide To a solution of 5-chloro-3-methyl-pyridine-2-carbaldehyde (1.99 g, 12.81 mmol) in MeOH (30 mL) was added NH₄OAc (530 mg, 6.88 mmol) and 1,3-acetonedicarboxylic acid (913 mg, 6.25 mmol), and the mixture was stirred at room temperature for 29 h. The mixture was concentrated in vacuo and saturated NaHCO₃ (50 mL) followed by CH₂Cl₂ (75 mL) were added. The layers were separated and the aqueous layer was extracted with CH₂Cl₂ (2×30 mL). The organic extracts were dried (Na₂SO₄), filtered and concentrated. Purification of the crude material by flash column chromatography on silica gel (EtOAc:hexanes, 1:3 then 1:1) provided 5,5"-Dichloro-3,3"-dimethyl-1',2',3',4',5',6'-hexahydro-cis-[2,2';6',2"]terpyridin-4'-one as yellow foam.

To a solution of the ketone from above (1.12 g) in MeOH (20 mL) at 0° C. was added NaBH₄ (260 mg, 6.87 mmol) and the reaction stirred at 0° C. for 30 min. then warmed to room temperature and stirred 5 h. The mixture was concentrated in vacuo then diluted with CH₂Cl₂ (40 mL) and saturated, aqueous NaHCO₃ (30 mL). The aqueous layer was extracted with CH₂Cl₂ (2×10 mL) and the combined organic extracts dried (Na₂SO₄) and concentrated. Purification of the crude orange oil (369 mg) by column chromatography on silica gel (CH₂Cl₂/MeOH, 96:4 then 92:8) afforded 5,5"-dichloro-3,3"-dimethyl-1',2',3',4',5',6'-hexahydro-cis-[2,2';6',2"]terpyridin-4'-ol (590 mg, 27% 2 steps). ¹H NMR (CDCl₃) δ 1.30 (q, 2H, J=11.7 Hz), 1.98 (d, 2H, J=12 Hz), 2.31 (s, 6H), 2.72-2.82 (m, 2H), 3.84-3.89 (m, 1H), 4.05 (t, 2H, J=11.1 Hz), 7.40 (s, 2H), 8.35 (s, 2H).

Using General Procedure A: A solution of 5,5"-dichloro-3,3"-dimethyl-1',2',3',4',5',6'-hexahydro-cis-[2,2';6',2"]terpyridin-4'-ol (590 mg, 1.68 mmol), 2-bromomethyl-5-cyano-benzoic acid methyl ester (39144-20059.00 US patent application) (512 mg, 2.02 mmol), KI (15 mg), and DIPEA (0.45 mL, 2.59 mmol) in DMF (4 mL) was heated at 70° C. for 17 hours. Purification of the crude material by column chromatography on silica gel (CH₂Cl₂—CH₃OH, 99:1 then 96:4) provided 779 mg (88%) of the desired alkylated material as a brown foam.

To a cold (0° C.) solution of the methyl ester form above (152 mg, 0.29 mmol) in THF (5 mL) was added LiBH₄ (51 mg, 2.34 mmol) and the mixture was allowed to warm to room temperature before being heated to 65° C. for 4 h 15 min. The mixture was diluted with 1 N NaOH (10 mL) and extracted with CH₂Cl₂ (3×15 mL). The combined organic extracts were dried (Na₂SO₄) and concentrated and the resultant alcohol was used without further purification in the next reaction.

To a solution of the nitrile from above in MeOH/H₂O (2:1, 6 mL) was added NaBO₃·4H₂O (121 mg, 0.79 mmol) and the reaction heated to 55° C. for 2.5 d. The mixture was concentrated and purified by radial chromatography on silica gel (1 mm plate, CH₂Cl₂—CH₃OH—NH₄OH, 100:1:1 then 50:1:1) to afford COMPOUND 88 as a white solid (25 mg, 17% 2 steps). ¹H NMR (DMSO-d₆) δ 1.70-1.75 (m, 2H), 2.22 (q, 2H, J=12 Hz), 2.50 (s, 6H), 3.48 (s, 2H), 3.84-3.90 (m, 1H), 4.18 (d, 2H, J=4.8 Hz), 4.41 (br d, 2H, J=11.7 Hz), 4.82 (d, 2H, J=4.5 Hz), 6.79 (d, 1H, J=7.8 Hz), 7.02 (s, 1H), 7.25 (d, 1H, J=7.8 Hz), 7.37 (s, 1H), 7.43 (s, 2H), 7.59 (s, 1H), 8.18 (s, 2H); ¹³C NMR (DMSO-d₆) δ 17.96, 33.68, 41.65, 61.10 61.73, 68.61, 124.71, 125.84, 126.51, 129.64, 130.88, 135.14, 137.00, 138.04, 142.85, 144.15, 156.53, 168.02; ES-MS m/z 537 (M⁺Na). Anal. Calcd. for C₂₆H₂₈N₄O₃Cl₂.1.8 H₂O: C, 57.00; H, 5.81; N, 10.23; Cl, 12.94. Found: C, 56.98; H, 5.79; N, 9.88; Cl, 12.95.

EXAMPLE 89

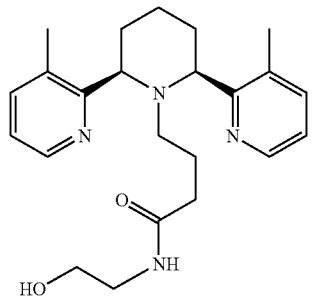

COMPOUND 89: 4-(3,3"-Dimethyl-3',4',5',6'-tetrahydro-2'H-cis-[2,2';6',2"]terpyridin-1'-yl)-N-(2-hydroxy-ethyl)-butyramide To a solution of 4-(3,3"-dimethyl-3',4',5',6'-tetrahydro-2'H-cis-[2,2';6',2"]terpyridin-1'-yl)-butyronitrile (430 mg, 1.29 mmol) in EtOH/H₂O (1:1, 4 mL) was added NaOH (590 mg, 14.75 mmol) and the reaction stirred at reflux overnight. The reaction was cooled to room temperature, adjusted to pH 3 with 6 N HCl and extracted with CH₂Cl₂ (3×15 mL). The combined organic extracts were dried (Na₂SO₄) and concentrated to afford the desired acid as a beige foam (0.42 g).

To a solution of the crude acid from above (107 mg) in CH$_2$Cl$_2$ (5 mL) was added DIPEA (0.12 mL, 0.69 mmol) followed by HOBt (59 mg, 0.44 mmol), ethanolamine (0.040 mL, 0.66 mmol) and EDC (76 mg, 0.40 mmol) and the mixture stirred overnight. The reaction was diluted with CH$_2$Cl$_2$ (15 mL) and saturated aqueous NaHCO$_3$ (25 mL) and the aqueous layer extracted with CH$_2$Cl$_2$ (2×10 mL). The combined organic extracts were dried (Na$_2$SO$_4$), concentrated and purified by radial chromatography on silica gel (1 mm plate, CH$_2$Cl$_2$—MeOH—NH$_4$OH, 100:1:1 then 25:1:1) to afford COMPOUND 89 as a colorless oil (83 mg, 70% 2 steps). $^1$H NMR (CDCl$_3$) δ 0.69-0.73 (m, 2H), 1.42 (t, 2H, J=6.3 Hz), 1.50-1.68 (m, 3H), 1.91-1.97 (m, 1H), 2.04-2.17 (m, 2H), 2.23 (t, 2H, J=6.3 Hz), 2.42 (s, 6H), 3.93-3.43 (m, 2H), 3.57-3.70 (m, 1H), 3.77-3.81 (m, 2H), 3.85 (d, 2H, J=12 Hz), 7.07 (dd, 2H, J=7.5, 4.8 Hz), 7.44 (dd, 2H, J=7.5, 0.9 Hz), 8.12 (br s, 1H), 8.41 (d, 2H, J=3.9 Hz); $^{13}$C NMR (CDCl$_3$) δ 19.54, 22.99, 25.78, 32.67, 36.18, 43.08, 55.05, 62.34, 65.59, 122.52, 131.29, 138.99, 147.16, 160.56, 174.15; ES-MS m/z 397 (M$^+$H). Anal. Calcd. for C$_{23}$H$_{32}$N$_4$O$_2$.2.2 H$_2$O: C, 63.34; H, 8.41;N, 12.85. Found: C, 63.31; H, 8.21;N, 12.55.

EXAMPLE 90

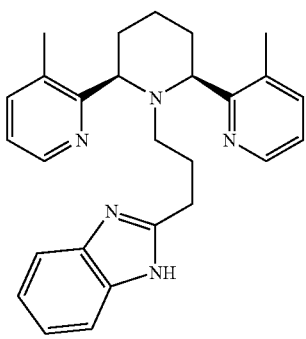

COMPOUND 90: (2'S,6'R)-1'-[3-(1H-Benzoimidazol-2-yl)-propyl]-3,3''-dimethyl-1',2',3',4',5',6'-hexahydro-cis-[2,2';6',2'']terpyridine To a solution of 4-(3,3''-dimethyl-3',4',5',6'-tetrahydro-2'H-cis-[2,2';6',2'']terpyridin-1'-yl)-butyric acid (113 mg, 0.32 mmol) in 3 M HCl (3 mL) was added 1,2-phenylene diamine (40 mg, 0.37 mmol) and the reaction refluxed overnight. The mixture was cooled to room temperature, neutralized with solid Na$_2$CO$_3$ and extracted with CH$_2$Cl$_2$ (3×15 mL). The combined organic extracts were dried (Na$_2$SO$_4$), concentrated and purified by radial chromatography on silica gel (1 mm plate, CH$_2$Cl$_2$—MeOH—NH$_4$OH, 50:1:1 then 25:1:1) to afford COMPOUND 90 as a pale yellow oil (31 mg, 23%). $^1$H NMR (CDCl$_3$) δ 1.16-1.26 (m, 2H), 1.50-1.66 (m, 3H), 1.88-2.07 (m, 3H), 2.21-2.30 (m, 3H), 2.35 (s, 6H), 2.46-2.57 (m, 1H), 3.97 (d, 2H, J=12 Hz), 5.62 (br s, 1H), 6.87 (dd, 2H, J=7.2, 4.8 Hz), 7.13-7.20 (m, 4H), 7.28-7.35 (br m, 1H), 7.53-7.59 (br m, 1H), 8.20-8.26 (m, 2H); $^{13}$C NMR (CDCl$_3$) δ 19.22, 24.78, 25.14, 27.09, 32.66, 52.74, 63.85, 111.25, 118.84, 121.76, 122.17, 131.17, 138.85, 146.79, 155.44, 160.86; ES-MS m/z 426 (M$^+$H). Anal. Calcd. for C$_{27}$H$_{31}$N$_5$. 3.0 H$_2$O: C, 67.62; H, 7.78; N, 14.60. Found: C, 67.36; H, 7.68; N, 14.97.

EXAMPLE 91

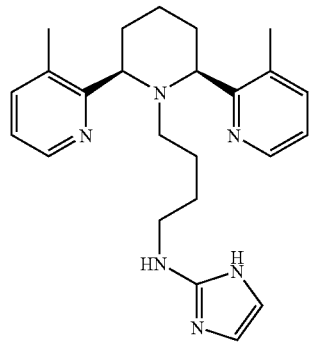

COMPOUND 91: [4-(3,3''-Dimethyl-3,',4',5',6'-tetrahydro-2'H-cis-[2,2';6',2'']terpyridin-1'-yl)-butyl]-(1H-imidazol-2-yl)-amine To a stirred solution of oxalyl chloride (0.2 mL, 2.29 mmol) in CH$_2$Cl$_2$ (5 mL) at −78° C. was added DMSO (0.40 mL, 5.64 mmol). After 15 min., a solution of 4-(3,3''-dimethyl-3',4',5',6'-tetrahydro-2'H-cis-[2,2';6',2'']terpyridin-1'-yl)-butan-1-ol (227 mg, 0.67 mmol) in CH$_2$Cl$_2$ (5 mL) was added at −78° C. followed by Et$_3$N (1.0 mL, 7.18 mmol) and the reaction warmed to room temperature and stirred 2 h. The reaction was diluted with CH$_2$Cl$_2$ (20 mL) and saturated aqueous NaHCO$_3$ (25 mL) and the aqueous phase was extracted with CH$_2$Cl$_2$ (3×10 mL). The combined organic phase was dried (Na$_2$SO$_4$), filtered and concentrated under reduced pressure to give the desired aldehyde (250 mg) as a brown oil.

A suspension of 2-aminoimidazole sulfate (354 mg, 2.68 mmol) and NaOH (120 mg, 3.0 mmol) in MeOH (3 mL) was stirred overnight then diluted with CH$_2$Cl$_2$ (20 mL) and filtered through Celite, washing with 10:1 CH$_2$Cl$_2$/MeOH. The filtrate was concentrated to afford the free 2-aminoimidazole (167 mg) as a brown oil. A solution of the free aminoimidazole and aldehyde from above (0.67 mmol) in MeOH (5 mL) was stirred at 40° C. for 3 d. NaBH$_4$ (110 mg, 2.91 mmol) was then added and the reaction stirred 1 h, concentrated, diluted with CH$_2$Cl$_2$ (25 mL) and saturated aqueous NaHCO$_3$ (25 mL). The aqueous phase was extracted with CH$_2$Cl$_2$ (2×10 mL) and the combined organic phase was dried (Na$_2$SO$_4$), concentrated under reduced pressure and purified by radial chromatography on silica gel (1 mm plate, CH$_2$Cl$_2$—MeOH—NH$_4$OH, 50:1:1 then 25:1:1) to afford COMPOUND 91 as a beige foam (78 mg, 29% over 2 steps). $^1$H NMR (CDCl$_3$) δ 0.70-0.75 (m, 3H), 1.50-1.65 (m, 3H), 1.89-2.08 (m, 6H), 2.39 (s, 6H), 2.69-2.73 (m, 3H), 3.95 (dd, 2H, J=9.6, 1.2 Hz), 4.17 (br s, 1H), 6.56 (s, 2H), 6.96-7.01 (m, 2H), 7.36 (d, 2H, J=7.5 Hz), 8.29 (d, 2H, J=3 Hz); $^{13}$C NMR (CDCl$_3$) δ 19.16, 22.60, 25.35, 28.06, 31.72, 43.81, 50.61, 63.37, 117.98, 122.22, 131.45, 138.90, 146.93, 151.64, 160.86; ES-MS m/z 405 (M$^+$H). Anal. Calcd. for C$_{24}$H$_{32}$N$_6$.1.4 H$_2$O: C, 67.07; H, 8.16; N, 19.55. Found: C, 67.23; H, 7.83; N, 19.17.

EXAMPLE 92

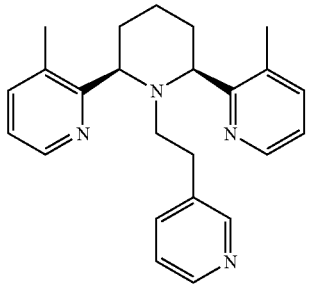

COMPOUND 92: (3,3"-Dimethyl-1'-(2-pyridin-3-yl-ethyl)-1',2',3',4',5',6'-hexahydro-cis-[2,2':6',2"]terpyridine To a solution of ethyl 3-pyridylacetate (983 mg, 5.95 mmol) in THF (10 mL) at 0° C. was added a solution of LiAlH$_4$ (1.0 M in THF, 9.0 mL, 9.0 mmol) and the reaction stirred for 15 min. before quenching at 0° C. with H$_2$O (0.35 mL) then 15% aqueous NaOH (0.35 mL) then H$_2$O (1.0 mL). The mixture was stirred 10 min. then filtered, washing with Et$_2$O and EtOAc. The filtrate was concentrated and purified by column chromatography on silica gel (CH$_2$Cl$_2$/MeOH, 96:4) to afford the desired alcohol (0.47 g, 64%) as a colorless oil.

To a solution of the alcohol from above (366 mg, 2.98 mmol) in CH$_2$Cl$_2$ (10 mL) at −78° C. was added Et$_3$N (0.85 mL, 6.11 mmol) and mesyl chloride (0.35 mL, 4.52 mmol) and the reaction stirred at −78° C. for 25 min. The mixture was diluted with CH$_2$Cl$_2$ (25 mL) and saturated aqueous NaHCO$_3$ (25 mL) and the aqueous phase was extracted with CH$_2$Cl$_2$ (2×10 mL). The combined organic phase was dried (Na$_2$SO$_4$) and concentrated to afford methanesulfonic acid 2-pyridin-3-yl-ethyl ester, used without further purification in the next reaction.

Using General Procedure A: A solution of 3,3"-Dimethyl-1',2',3',4',5',6'-hexahydro-cis-[2,2';6',2"]terpyridine (0.219 g, 0.82 mmol), methanesulfonic acid 2-pyridin-3-yl-ethyl ester (approx. 3 mmol), KI (15 mg), and DIPEA (0.25 mL, 1.44 mmol) in DMF (3 mL was heated at 80° C. for 17 hours. Purification of the crude material by column chromatography on silica gel (CH$_2$Cl$_2$—CH$_3$OH—NH$_4$OH, 94:4:2) followed by radial chromatography on silica gel (1 mm plate, CH$_2$Cl$_2$—CH$_3$OH—NH$_4$OH, 50:1:1) provided 193 mg (63%) of COMPOUND 92 as a colorless oil. $^1$H NMR (CDCl$_3$) δ 1.61-1.70 (m, 4H), 2.00-2.22 (m, 4H), 2.51 (s, 6H), 2.51-2.55 (m, 2H), 4.14-4.18 (m, 2H), 6.55-6.60 (m, 1H), 6.85 (dd, 1H, J=7.5, 4.8 Hz), 7.09-7.12 (m, 2H), 7.42 (d, 2H, J=6.9 Hz), 7.54-7.60 (m, 1H), 8.18 (dd, $^1$H, J=4.8, 1.5 Hz), 8.42-8.46 (m, 2H); $^{13}$C NMR (CDCl$_3$) δ 17.59, 22.43, 24.32, 26.23, 28.85, 30.67, 47.26, 51.85, 63.52, 70.06, 121.05, 121.87, 131.24, 134.51, 137.16, 138.57, 145.34, 145.73, 148.78, 158.55; ES-MS m/z 373 (M+H). Anal. Calcd. for C$_{24}$H$_{28}$N$_4$.0.3 H$_2$O: C, 76.28; H, 7.63; N, 14.83. Found: C, 76.14; H, 7.78; N, 14.82.

EXAMPLE 93

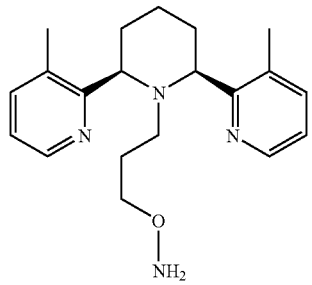

COMPOUND 93: O-[3-(3,3"-Dimethyl-3',4',5',6'-tetrahydro-2'H-cis-[2,2';6',2"]terpyridin-1'-yl)-propyl]-hydroxylamine Using General Procedure A: A solution of 3,3"-dimethyl-1',2',3',4',5',6'-hexahydro-cis-[2,2';6',2"]terpyridine (253 mg, 0.95 mmol), 2-(3-bromo-propoxy)-isoindole-1,3-dione (Canne, L. E, et al., *J. Am. Chem. Soc.* (1996) 118:5891-5896) (334 mg, 1.18 mmol), KI (15 mg), and DIPEA (0.35 mL, 2.01 mmol) in DMF (3 mL) was heated at 70° C. for 17 hours. Purification of the crude material by column chromatography on silica gel (CH$_2$Cl$_2$—CH$_3$OH—NH$_4$OH, 96:4:0 then 94:4:2) afforded the alkylated material (260 mg, 58%) as a brown foam.

To a solution of the phthalimide from about (181 mg. 0.385 mmol) in MeOH (5 mL) was added hydrazine monohydrate (0.10 mL, 2.06 mmol) and the reaction stirred overnight at room temperature. The mixture was filtered, concentrated and purified by radial chromatography on silica gel (1 mm plate, CH$_2$Cl$_2$—CH$_3$OH—NH$_4$OH, 50:1:1 then 25:1:1) to afford COMPOUND 93 as a colorless oil (88 mg, 67%). $^1$H NMR (CDCl$_3$) δ 0.91-0.97 (m, 1H), 1.55-1.66 (m, 3H), 1.94-2.08 (m, 3H), 2.29 (t, 2H, J=6 Hz), 2.50 (s, 6H), 2.95-3.04 (m, 2H), 4.04 (br d, 2H, J=12 Hz), 4.83 (br s, 3H), 7.05 (dd, 1H, J=7.5, 4.8 Hz), 7.40 (d, 2H, J=7.5 Hz), 8.41-8.43 (m, 2H); $^{13}$C NMR (CDCl$_3$) δ 21.06, 26.85, 27.52, 31.84, 47.27, 49.48, 66.12, 73.32, 76.51, 124.11, 140.54, 141.82, 148.93, 162.55; ES-MS m/z 341 (M$^+$H). Anal. Calcd. for C$_{20}$H$_{28}$N$_4$O.0.7 H$_2$O: C, 68.04; H, 8.39; N, 15.87. Found: C, 68.04; H, 8.34; N, 15.62.

EXAMPLE 94

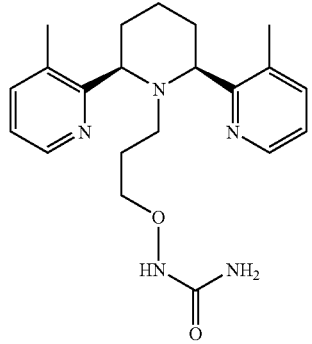

COMPOUND 94: O-[3-(3,3"-Dimethyl-3',4',5',6'-tetrahydro-2'H-cis-[2,2';6',2"]terpyridin-1'-yl)-propyl]-hydroxylurea To a solution of O-[3-(3,3"-dimethyl-3',4',5',6'-tetrahydro-2'H-cis-[2,2';6',2"]terpyridin-1'-yl)-propyl]-hydroxylamine (100 mg, 0.29 mmol) in CH$_2$Cl$_2$ (4.5 mL) was added trimethylsilyl isocyanate (0.075 mL, 0.55 mmol) and the reaction stirred for 2.5 d. The mixture was concentrated and purified by radial chromatography on silica gel (1 mm plate, CH$_2$Cl$_2$—CH$_3$OH—NH$_4$OH, 25:1:1) to afford COMPOUND 94 as a white solid (43 mg, 39%). $^1$H NMR (CD$_3$OD) δ 1.09-1.16 (m, 1H), 1.61-1.70 (m, 4H), 1.98-2.16 (m, 3H), 2.29-2.34 (m, 2H), 2.61-2.71 (m, 6H), 3.09-3.18 (m, 2H), 3.97-4.10 (m, 2H), 7.19-7.23 (m, 2H), 7.61 (d, 2H, J=7.5 Hz), 8.30-8.35 (m, 2H); $^{13}$C NMR (CD$_3$OD) δ 19.38, 20.10, 25.06, 26.55, 29.07, 31.53, 39.72, 47.17, 66.39, 72.15, 75.95, 76.55, 124.05, 134.47, 141.02, 142.25, 147.16, 147.58, 161.33, 164.28; ES-MS m/z 384 (M$^+$H). Anal. Calcd. for C$_{21}$H$_{29}$N$_5$O$_2$.0.3 H$_2$O: C, 64.86; H, 7.67; N, 18.01. Found: C, 64.97; H, 7.63; N, 17.83.

EXAMPLE 95

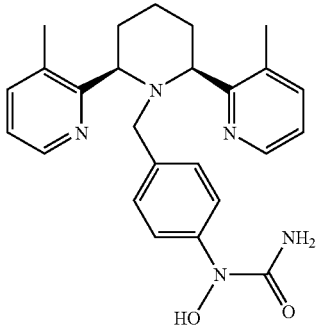

COMPOUND 95: [4-(3,3"-Dimethyl-3',4',5',6'-tetrahydro-2'H-cis-[2,2';6',2"]terpyridin-1'-ylmethyl)-phenyl]-N-hydroxyurea Using General Procedure A: A solution of 3,3"-dimethyl-1',2',3',4',5',6'-hexahydro-cis-[2,2';6',2"]terpyridine (558 mg, 2.09 mmol), 4-nitrobenzyl bromide (547 mg, 2.53 mmol), KI (15 mg), and DIPEA (0.60 mL, 3.45 mmol) in CH$_3$CN (10 mL) was heated at 65° C. for 17 hours. Purification of the crude material by column chromatography on silica gel (CH$_2$Cl$_2$—CH$_3$OH, 96:4 then 92:8) afforded the N-alkylated material (0.73 g, 87%) as a yellow foam.

To a solution of 3,3"-dimethyl-1'-(4-nitro-benzyl)-1',2',3',4',5',6'-hexahydro-cis-[2,2';6',2"]terpyridine (245 mg, 0.61 mmol) in THF (3 mL) was added rhodium (5% on carbon, 15 mg) followed by hydrazine hydrate (0.30 mL, 6.15 mmol) and the reaction stirred 6.5 h. The mixture was filtered through Celite, washing with MeOH and CH$_2$Cl$_2$ and the filtrate concentrated. To a solution of the resultant residue in CH$_2$Cl$_2$ (6 mL) was added trimethylsilyl isocyanate (0.13 mL, 0.96 mmol) and the reaction stirred overnight. The mixture was concentrated and purified by radial chromatography on silica gel (1 mm plate, CH$_2$Cl$_2$—CH$_3$OH—NH$_4$OH, 50:1:1 to 10:1:1) to afford COMPOUND 95 as a yellow foam (37 mg, 14%). $^1$H NMR (CDCl$_3$/CD$_3$OD) δ 1.34-1.42 (m, 1H), 1.59-1.81 (m, 5H), 2.24 (s, 6H), 3.15 (s, 2H), 3.24-3.46 (m, 3H), 3.82 (br d, 2H, J=9 Hz), 6.28 (d, 2H, J=7.5 Hz), 7.00 (dd, 2H, J=7.2, 4.8 Hz), 7.16 (d, 2H, J=8.1 Hz), 7.34 (d, 2H, J=7.2 Hz), 8.29 (d, 2H, J=3 Hz); $^{13}$C NMR (CDCl$_3$/CD$_3$OD) δ 18.79, 24.68, 32.36, 53.94, 62.16, 119.82, 122.59, 129.65, 130.42, 131.67, 138.70, 141.42, 146.67, 158.98, 159.94; ES-MS m/z 432 (M$^+$H). Anal. Calcd. for C$_{25}$H$_{29}$N$_5$O$_2$.1.9 H$_2$O: C, 64.47; H, 7.10; N, 15.04. Found: C, 64.43; H, 6.77; N, 15.05.

EXAMPLE 96

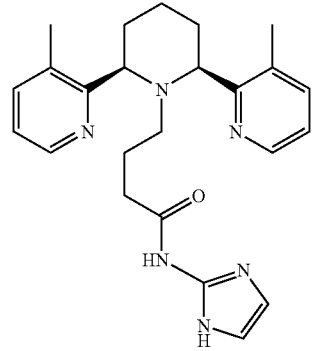

COMPOUND 96: 4-(3,3"-Dimethyl-3',4',5',6'-tetrahydro-2'H-cis-[2,2';6',2"]terpyridin-1'-yl)-N-(1H-imidazol-2-yl)-butyramide To a solution of 4-(3,3"-dimethyl-3',4',5',6'-tetrahydro-2'H-cis-[2,2';6',2"]terpyridin-1'-yl)-butyric acid (192 mg, 0.544 mmol) in DMF (3 mL) was added 2-aminoimidazole sulfate (99 mg, 0.75 mmol), DIPEA (0.30 mL, 1.73 mmol), HOBt (99 mg, 0.73 mmol) and EDC (160 mg, 0.83 mmol) and the mixture stirred overnight. The reaction was diluted with CH$_2$Cl$_2$ (30 mL) and saturated aqueous NaHCO$_3$ (25 mL) and the aqueous layer extracted with CH$_2$Cl$_2$ (2×15 mL). The combined organic extracts were dried (Na$_2$SO$_4$), concentrated and purified by radial chromatography on silica gel (1 mm plate, CH$_2$Cl$_2$—MeOH—NH$_4$OH, 25:1:1) to afford COMPOUND 96 as a white solid (132 mg, 58%). $^1$H NMR (CDCl$_3$) δ 0.97-1.03 (m, 1H), 1.58-1.81 (m, 6H), 1.95-2.15 (m, 3H), 2.32-2.45 (m, 3H), 2.46 (s, 6H), 3.85-3.96 (m, 1H), 4.04-4.08 (m, 2H), 6.41 (br s, 1H), 6.68 (br s, 1H), 6.96 (dd, 2H, J=7.5, 4.8 Hz), 7.32 (d, 2H, J=7.5 Hz), 8.35-8.39 (m, 2H), 10.66 (br s, 1H); $^{13}$C NMR (CDCl$_3$) δ 19.14, 22.20, 25.50, 30.58, 34.48, 49.14, 63.77, 111.36, 122.10, 123.75, 131.56, 138.65, 143.42, 147.09, 160.49, 172.87; ES-MS m/z 419 (M$^+$H). Anal. Cacld. for C$_{24}$H$_{30}$N$_6$O.1.0 H$_2$O: C, 66.03; H, 7.39; N, 19.25. Found: C, 65.96; H, 7.33; N, 19.09.

EXAMPLE 97

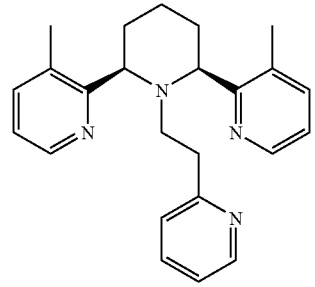

COMPOUND 97: Preparatio of (3,3"-Dimethyl-1'-(2-pyrdin-2-yl-ethyl)-1',2',3',4',5',6'-hexahydro-cis-[2,2';6',2"]terpyridine To a solution of 2-(2-hydroxyethyl)pyridine (602 mg, 4.89 mmol) in CH$_2$Cl$_2$ (10 mL) at −78° C. was added Et$_3$N (1.0 mL, 7.20 mmol) and mesyl chloride (0.45 mL, 5.8 mmol) and the reaction warmed to room temperature and stirred for 15 min. The mixture was diluted with $CH_2Cl_2$ (25 mL) and saturated aqueous $NaHCO_3$ (25 mL) and the aqueous phase was extracted with $CH_2Cl_2$ (2×10 mL). The combined organic phase was dried ($Na_2SO_4$) and concentrated to afford the desired mesylate (1.01 g), used without further purification in the next reaction.

Using General Procedure A: A suspension of 3,3''-dimethyl-1',2',3',4',5',6'-hexahydro-cis-[2,2';6',2'']terpyridine (252 mg, 0.94 mmol), methanesulfonic acid 2-pyridin-2-yl-ethyl ester (approx. 4.9 mmol) and $K_2CO_3$ (1.30 g, 9.42 mmol) in DMF (5 mL) was heated at 85° C. for 2.5 d. Purification of the crude material by column chromatography on silica gel ($CH_2Cl_2$—$CH_3OH$—$NH_4OH$, 96:4:0 then 94:4:2) followed by radial chromatography on silica gel (1 mm plate, $CH_2Cl_2$—$CH_3OH$—$NH_4OH$, 25:1:1) provided 152 mg (43%) of COMPOUND 97 as a pale yellow oil. $^1H$ NMR ($CDCl_3$) δ 1.60-1.72 (m, 3H), 1.96-2.23 (m, 5H), 2.51 (s, 6H), 2.61-2.66 (m, 2H), 4.15 (d, 2H, J=12 Hz), 6.33-6.38 (m, 1H), 6.85 (dd, 1H, J=7.2, 5.1 Hz), 7.07 (dd, 2H, J=7.5, 4.8 Hz), 7.27 (dt, 1H, J=7.5, 1.5 Hz), 7.40 (d, 2H, J=7.5 Hz), 8.19 (d, 1H, J=4.8 hz), 8.42-8.47 (m, 2H); $^{13}C$ NMR ($CDCl_3$) δ 19.18, 25.52, 30.76, 34.77, 49.87, 63.61, 120.80, 122.22, 122.76, 131.72, 136.15, 138.83, 147.10, 149.18, 160.47, 161.42; ES-MS m/z 373 (M+H). Anal. Calcd. for $C_{24}H_{28}N_4.1.6 H_2O$: C, 71.83; H, 7.84; N, 13.96. Found: C, 71.84; H, 7.53; N, 13.65.

EXAMPLE 98

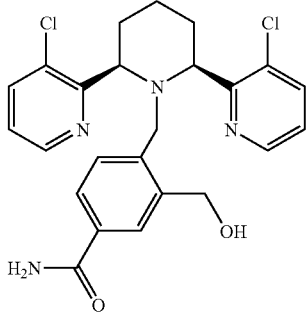

COMPOUND 98: 4-(3,3''-Dichloro-3',4',5',6'-tetrahydro-2'H-[2,2';6',2'']terpyridin-1'-ylmethyl)-3-hydroxymethyl-benzamide Using General Procedure A: 3,3''-dichloro-1',2',3',4',5',6'-hexahydro-[2,2';6',2'']terpyridine (304 mg, 0.987 mmol), 2-Bromomethyl-5-cyano-benzoic acid methyl ester (351 mg, 1.38 mmol), KI (32.7 mg, 0.197 mmol), DIPEA (0.34 mL, 1.97 mmol), and DMF (5 mL) were stirred at 60° C. for 3 h. Purification of the crude material by flash chromatography on silica gel ($CH_2Cl_2$/MeOH, 98:2) afforded 5-Cyano-2-3,3''-dichloro-3',4',5',6'-tetrahydro-2'H-[2,2';6',2'']terpyridin-1'-ylmethyl)-benzoic acid methyl ester (391 mg,82%) as a yellow oil. $^1H$ NMR ($CDCl_3$) δ 1.63-1.78 (m, 3H), 2.01-2.14 (m, 1H), 2.18-2.38 (m, 2H), 3.87 (s, 3H), 3.95 (s, 2H), 4.52 (dd, 2H, J=11.4, 1.6 Hz), 6.89 (dd, 2H, J=8.4, 4.9 Hz), 7.38-7.48 (m, 3H), 7.57 (d, 1H, J=1.7 Hz), 8.22-8.32 (m, 3H).

To a cold (0° C) solution of 5-Cyano-2-3,3''-dichloro-3',4', 5',6'-tetrahydo-2'H-[2,2';6',2'']terpyridin-1'-ylmethyl)-benzoic acid methyl ester (391 mg, 0.813 mmol) in THF (4 mL) and MeOH (4 mL) was added $LiBH_4$ (88 mg, 4.1 mmol), and the mixture was warmed to room temperature and stirred for 3.5 h. The mixture was diluted with 1.0 N NaOH (20 mL) and extracted with $CH_2Cl_2$ (4×10 mL). The combined organic extracts were dried ($Na_2SO_4$), filtered, and concentrated in vacuo to provide 4-(3,3''-Dichloro-3',4',5',6'-tetrahydro-2'H-[2,2';6',2'']terpyridin-1'-ylmethyl)-3-hydroxymethyl-benzonitrile (367 mg) without any further purification. To a solution of the crude material (160 mg) in MeOH (4.5 mL) was added $H_2O$ (2.5 mL) and $NaBO_3$ . 4 $H_2O$ (108 mg, 0.707 mmol). The resultant mixture was heated to 50° C. for 5 h and stirred at room temperature overnight. The reaction mixture was concentrated and the residue was purified by flash chromatography on silica gel ($CH_2Cl_2$/MeOH/$NH_4OH$, 90:5:5 then 85:10:5) to afford COMPOUND 98 (54 mg, 32% over 2 steps) as a white solid. $^1H$ NMR ($CDCl_3$) δ 1.63-1.79 (m, 3H), 1.93-2.06 (m, 1H), 2.11-2.30 (m, 2H), 2.33-2.47 (m, 2H), 3.63 (s, 2H), 4.59 (d, 2H, J=9.92 Hz), 4.41 (s, 2H), 4.99 (br s, 1H), 5.67 (br s, 1H), 6.15 (br s, 1H), 6.85-6.96 (m, 2H), 7.04 (d, 1H, J=7.8 Hz), 7.24 (d, 1H, J=1.8 Hz), 7.38 (d, 1H, J=1.5 Hz), 7.48 (dd, 2H, J=7.8, 1.5 Hz), 8.30 (dd, 2H, J=4.5, 1.2 Hz); $^{13}C$ NMR ($CDCl_3$) δ 24.98, 31.59, 57.28, 62.72, 66.56, 123.45, 126.39, 128.11, 129.90, 131.55, 131.70, 137.47, 140.08, 142.64, 147.77, 158.55, 169.17; ES-MS m/z 473 (M+1+H). Anal. Calcd. for $C_{24}H_{24}N_4Cl_2O_2$. 0.5 $H_2O$: C, 60.01; H, 5.25; N, 11.66. Found: C, 60.00; H, 5.15; N, 11.49.

EXAMPLE 99

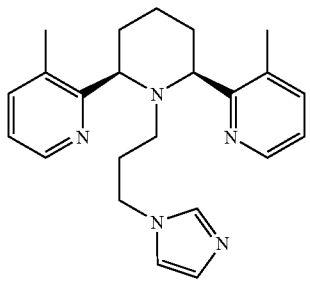

COMPOUND 99: 1'-(3-Imidazol-1-yl-propyl)-3,3''-dimethyl-1',2',3',4',5',6'-hexahydro-[2,2';6',2'']terpyridine (HBr salt)

To a stirred solution of imidazole (500 mg, 7.35 mmol) and 1,3-dibromopropane (2.2 mL, 22.0) in THF (35 mL) was added 60% NaH (356 mg, 8.82 mmol), and the resultant mixture was refluxed for 1H and stirred at room temperature overnight. The mixture was quenched with $H_2O$ (25 mL) and diluted with $CH_2Cl_2$ (40 mL). The aqueous phase was separated and extracted with $CH_2Cl_2$ (3×15 mL). The combined organic extracts were dried ($Na_2SO_4$), filtered, and concentrated to dryness. Purification by flash chromatography on silica gel ($CH_2Cl_2$/MeOH, 97:3) provided 1-(3-Bromo-propyl)-1H-imidazole (410 mg, 30%) as a colorless oil. $^1H$ NMR ($CDCl_3$) δ 2.20-2.34 (m, 2H), 3.31 (t, 2H, J=6.3 Hz), 4.16 (t, 2H, J=6.2 Hz), 6.93 (s, 1H), 7.08 (s, 1H), 7.51 (s, 1H).

Using General Procedure A: 3,3''-dimethyl-1',2',3',4',5',6'-hexahydro-[2,2';6',2'']terpyridine (91.3 mg, 0.341 mmol), 1-(3-Bromo-propyl)-1H-imidazole (129 mg, 0.680 mmol), KI (5.6 mg, 0.034 mmol), DIPEA (0.18 mL, 1.02 mmol), and DMF (3.4 mL) were stirred at 60° C. overnight. Purification of the crude material by flash chromatography on silica gel (CH₂Cl₂/MeOH/NH₄OH, 90:5:5) followed by radial chromatography on a 1 mm TLC grade silica gel plate (CH₂Cl₂/MeOH/NH₄OH, 96:2:2) afforded the free base of the title compound (48 mg, 38%) as a colorless oil.

Using General Procedure B: Conversion of the free base from above (48 mg, 0.13 mmol) to a HBr salt followed by re-precipitation of the crude material from MeOH/ether gave COMPOUND 99 as an off-white solid (84 mg, 94%). ¹H NMR (D₂O) δ 1.42-1.61 (m, 2H), 1.63-2.00 (m, 4H), 2.07-2.25 (m, 4H), 2.55 (s, 6H), 3.93 (t, 2H, J=6.3 Hz), 4.57 (d, 2H, J=11.1 Hz), 7.32 (d, 1H, J=15.9 Hz), 7.91 (dd, 2H, J=7.8, 6.0 Hz), 8.42 (d, 2H, J=8.1 Hz), 8.53 (s, 1H), 8.69 (d, 2H, J=5.4 Hz); ¹³C NMR (D₂O) δ 17.30, 22.39, 24.10, 32.50, 47.16, 49.25, 57.97, 120.62, 121.91, 126.23, 134.97, 136.96, 140.10, 149.71, 153.99; ES-MS m/z 376 (M⁺H). Anal. Calcd. for C₂₃H₂₉N₅. 3.3 HBr.2.8 H₂O: C, 39.87; H, 5.51; N, 10.11; Br, 38.05. Found: C, 39.82; H, 5.45; N, 9.97; Br, 38.30.

EXAMPLE 100

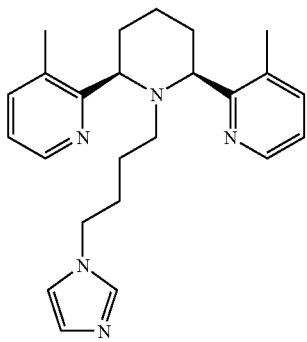

COMPOUND 100: 1'-(4-Imidazol-1-yl-butyl)-3,3"-dimethyl-1',2',3',4',5',6'-hexahydro-[2,2';6',2"]terpyridine (HBr salt)

To a stirred solution of imidazole (500 mg, 7.35 mmol) and 1,4-dibromobutane (2.6 mL, 22.0) in THF (50 mL) was added 60% NaH (356 mg, 8.81 mmol), and the resultant mixture was refluxed for 2 h and stirred at room temperature overnight. The mixture was quenched with H₂O (50 mL) and diluted with CH₂Cl₂ (75 mL). The aqueous phase was separated and extracted with CH₂Cl₂ (3×15 mL). The combined organic extracts were dried (Na₂SO₄), filtered, and concentrated to dryness. Purification by flash chromatography on silica gel (CH₂Cl₂/MeOH, 97:3) resulted in partial decomposition of 1-(4-Bromo-butyl)-1H-imidazole. This material was used without any further purification. Using General Procedure A: 3,3"-Dimethyl-1',2',3',4',5',6'-hexahydro-[2,2';6',2"]terpyridine (94.4 mg, 0.353 mmol), impure 1-(4-Bromo-butyl)-1H-imidazole (145 mg), KI (6.0 mg, 0.035 mmol), DIPEA (0.18 mL, 1.02 mmol), and DMF (3.5 mL) were stirred for 48 h at 60° C. Purification of the crude material by radial chromatography on a 1 mm TLC grade silica gel plate (CH₂Cl₂/MeOH/NH₄OH, 96:2:2) afforded the free base of the title compound (47 mg, 34% over 2 steps) as a colorless oil.

Using General Procedure B: Conversion of the free base from above (48 mg, 0.13 mmol) to a HBr salt followed by re-precipitation of the crude material from MeOH/ether gave COMPOUND 100 as an off-white solid (85 mg, 92%). ¹H NMR (D₂O) δ 1.01-1.19 (m, 2H), 1.35-1.56 (m, 4H), 1.58-1.80 (m, 1H), 1.82-1.95 (m, 1H), 1.96-2.15 (m, 2H), 2.16-2.32 (m, 2H), 2.51 (s, 6H), 4.02 (t, 2H, J=6.9 Hz), 4.52 (d, 2H, J=11.1 Hz), 7.31 (s, 1H), 7.41 (s, 1H), 7.87 (dd, 2H, J=7.8, 6.0 Hz), 8.39 (d, 2H, J=7.8 Hz), 8.58 (s, 1H), 8.65 (d, 2H, J=5.7 Hz); ³C NMR (D₂O) δ 17.21, 20.16, 20.89, 22.43, 27.26, 32.59, 49.06, 52.95, 58.22, 120.30, 122.01, 126.05, 134.75, 136.82, 139.80, 149.59, 154.67; ES-MS m/z 390 (M⁺H). Anal. Calcd. for C₂₄H₃₁N₅.3.9 HBr.2.9 H₂O: C, 38.06; H, 5.42; N, 9.25; Br, 41.15. Found: C, 37.99; H, 5.14; N, 9.30; Br, 41.29.

EXAMPLE 101

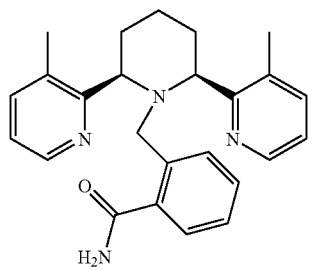

COMPOUND 101: 2-meso-(3,3"-Dimethyl-3',4',5',6'-tetrahydro-2'H-[2,2';6',2"]terpyridin-1'-ylmethyl)-benzamide A solution of meso-3,3"-dimethyl-1',2',3',4',5',6'-hexahydro-[2,2';6',2"]terpyridine (107 mg, 0.40 mmol), 2-bromomethyl-benzonitrile (102 mg, 0.52 mmol), and KI (13 mg, 0.08 mmol) in anhydrous DMF (2.0 mL) was treated with DIPEA (0.14 mL, 0.80 mmol) and stirred at 60° C. for 16 hours. EtOAc (10 mL) was added and the organic solution was washed with brine (5×5 mL), dried (MgSO₄), and concentrated under reduced pressure. This afforded, after purification by column chromatography with silica gel (50:1:0.1 CH₂Cl₂/MeOH/NH₄OH), 2-meso-(3,3"-dimethyl-3',4',5',6'-tetrahydro-2'H-[2,2';6',2"]terpyridin-1'-ylmethyl)-benzonitrile as a light beige-colored solid (143 mg, 93%).

The above nitrile (143 mg, 0.37 mmol) in MeOH (3.0 mL) was added to a solution of 50% H₂O₂ (0.11 mL, 1.9 mmol) and 3N NaOH (0.6 mL, 1.9 mmol). The reaction was heated to 80° C. for 16 hours and cooled to ambient temperature. Water (2 mL) was added and the media extracted with CH₂Cl₂ (3×15 mL). The combined organics were then dried (Na₂SO₄) and concentrated under reduced pressure to afford, after radial chromatographic purification on a silica gel plate (33:1:0.1 CH₂Cl₂/MeOH/NH₄OH), COMPOUND 101 as a white solid (61 mg, 40%). ¹H NMR (CDCl₃) δ 1.64 (m, 3H), 2.02 (m, 1H), 2.28 (q, 2H, J=13.8 Hz), 2.46 (s, 6H), 3.72 (s, 2H), 4.07 (d, 2H, J=11.1 Hz), 5.72 (br, 1H (NH)), 6.79-6.90 (m, 4H), 7.06 (d, 1H, J=7.8 Hz), 7.19 (d, 3H, J=7.5 Hz), 8.24 (d, 2H, J=3.9 Hz), 9.44 (br, 1H (NH)). ¹³C NMR (CDCl₃) δ 18.86 (2C), 24.81, 29.62 (2C), 55.81, 65.95 (2C), 121.92 (2C), 126.60, 128.55, 128.78 (2C), 129.83, 130.88, 135.19, 136.33, 137.94 (2C), 146.45 (2C), 159.77 (2C), 170.68. ES-MS m/z 401 (M⁺H). Anal. Calcd. for $C_{25}H_{28}N_4O\cdot 0.3CH_2Cl_2\cdot 0.1H_2O$: C, 71.03; H, 6.79; N, 13.10. Found: C, 70.75; H, 6.81; N, 12.95.

EXAMPLE 102

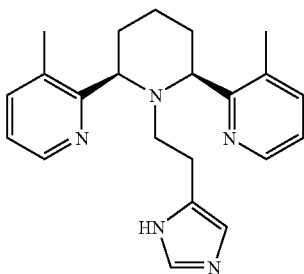

COMPOUND 102: 1'-[2-(3H-imidazol-4-yl)-ethyl]-3,3''-dimethyl-1',2',3',4',5',6'-hexahydro-[2,2';6',2'']terpyridine (HBr salt)

To a solution of 4-imidazoleacetic acid hydrochloride (499 mg, 3.07 mmol) in MeOH (10 mL) was added concentrated sulfuric acid (1 mL) and the mixture was heated to 80° C. overnight. Then the mixture was cooled and concentrated. The residue was dissolved in $CH_2Cl_2$ (30 mL) and washed with saturated $NaHCO_3$ (30 mL). The aqueous layer was saturated with NaCl (s) and extracted with EtOAc (3×30 mL). The combined organic layers were dried ($MgSO_4$), filtered, and concentrated to afford (1H-imidazol-4-yl)-acetic acid mnethyl ester as a yellow oil (330 mg, 66%). $^1$H NMR ($CDCl_3$) δ 3.70 (s, 2H), 3.72 (s, 3H), 6.97 (s, 1H), 7.59 (s, 1H).

To a solution of the ester (330 mg, 2.35 mmol) in DMF (5 mL) was added DIPEA (1.2 mL, 7.05 mmol) and Sem-chloride (0.49 mL, 2.83 mmol) and the reaction mixture was stirred overnight. The mixture was concentrated in cacuo and the residue was dissolved in EtOAc (30 mL) and washed with $H_2O$ (25 mL) and brine (2×25 mL). The combined aqueous layers were extracted with $CH_2Cl_2$ (2×30 mL). The combined organic layers were dried ($MgSO_4$), filtered, and concentrated to afford a yellow oil. Purification by flash column chromatography on silica gel using 2% $CH_3OH/CH_2Cl_2$ afforded [1-(2-trimethylsilanyl-ethoxymethyl)-1H-imieazol-4-yl]-acetic acid methyl ester as a yellow oil (240 mg, 73%). $^1$H NMR ($CDCl_3$) δ −0.03 and −0.02 (s, total 9H), 0.85-0.93 (m, 2H), 3.40-3.50 (m, 2H), 3.71 and 3.72 (s, total 3H), 5.22 and 5.29 (s, total 2H), 6.98 and 7.00 (s, total 2H), 7.52 (s, 1H).

To a solution of the above ester (240 mg, 0.89 mmol) in THF (3 mL) at 0° C. was added $LiAlH_4$ (1.2 mL, 1.15 mmol) and the reaction mixture was stirred for 1 h. The mixture was quenched with $H_2O$ (0.2 mL), 15% NaOH (0.2 mL), and $H_2O$ (0.6 mL), and extracted with $CH_2Cl_2$ (4×20 mL). The combined organic layers were dried ($MgSO_4$), filtered, and concentrated to afford a pale yellow oil. Purification by flash column chromatography on silica gel using 2% $CH_3OH/CH_2Cl_2$ afforded 2-[1-(2-trimethylsilanyl-ethoxymethyl)-1H-imidazol-4-yl]-ethanol as a pale yellow oil (154 mg, 71%). $^1$H NMR ($CDCl_3$) δ 0.88 (td, 2H, J=7.5, 3.0 Hz), 2.78 and 2.87 (t, total 2H, J=6.0 Hz), 3.45 (td, 2H, J=7.5, 3.0 Hz), 3.80-3.88 (m, 2H), 5.19 and 5.24 (s, total 2H), 6.82 and 6.84 (s, 1H), 7.46 and 7.47 (s, 1H).

To a solution of the above alcohol (152 mg, 0.63 mmol) in $CH_2Cl_2$ (5 mL) at −78° C. was added $Et_3N$ (0.18 mL, 1.26 mmol) and MsCI (0.07 mL, 0.94 mmol) according to General Procedure F. No further purification was attempted before proceeding onto the next step.

A solution of the above mesylate (190 mg, 0.59 mmol), meso-4-(3,3'-dimethyl-3',4',5',6'-tetrahydro-2'H-[2,2';6',2'']terpyridin-1'-yl)-butylamine (132 mg, 0.49 mmol), N,N-diisoproylethylamine (0.13 mL, 0.74 mmol), and KI (9 mg. 0.05 mmol) in DMF (5 mL) according to General Procedure A. Purification by radial chromatography on silica gel (2 mm plate; using $CH_2Cl_2/CH_3OH/NH_4OH$; 50:1:1→25:1:1) afforded the product as a yellow oil (50 mg, 20%).

A solution of the above amine (58 mg, 0.12 mmol) in 6N HCl (4 mL) was stirred at 60° C. After 3 h, the reaction mixture was cooled and quenched with $K_2CO_3$ (s) to pH=9. The mixture was extracted with $CH_2Cl_2$ (4×20 mL). The combined organic layers were dried ($MgSO_4$), filtered, and concentrated to afford a pale yellow oil. Purification by radial chroma-tography on silica gel (1 mm plate; using $CH_2Cl_2/CH_3OH/NH_4OH$; 50:1:1→25:1:1→10:1:1) afforded the product as a pale yellow oil (38 mg, 88%). $^1$H NMR ($CDCl_3$) δ 1.60-1.67 (m, 2H), 1.93-1.97 (m, 2H), 2.06-2.14 (m, 2H), 2.40 (s, 6H), 2.50 9t, 2H, J=6.0 Hz), 2.86 (br s, 2H), 3.92 (d, 2H, J=6.0 Hz), 6.13 (s, 1H), 7.02 (t, 2H, J=6.0 Hz), 7.37-7.40 (m, 3H), 8.37 (d, 2H, J=6.0 Hz).

To a solution of the above amine (38 mg, 0.11 mmol) in HOAc (2 mL) was added HBr saturated HOAc (2 mL) according to General Procedure B. After drying in vacuo overnight, COMPOUND 102 was isolated as a yellow solid (49 mg). $^1$H NMR ($D_2O$) δ 1.54-1.58 (m, 2H), 1.70-1.83 (m, 1H), 1.93-1.96 (m, 1H), 2.19 (d, 2H, J=13.5 Hz), 2.60 (s, 6H), 2.63-2.65 (m, 2H), 2.77-2.82 (m, 2H), 4.73-4.74 (m, 2H), 6.92 (s, 1H), 7.91 (dd, 2H, J=8.0, 6.0 Hz), 8.43 (d, 2H, J=3.3 Hz), 8.46 (s, 1H), 8.69 (d, 2H, 147=5.7 Hz). $^{13}$C NMR ($D_2O$) δ 17.13, 18.51, 22.32, 32.57, 50.80, 57.70, 115.85, 126.22, 130.71, 133.69, 137.13, 140.04, 149.78, 154.01. ES-MS m/z 362 [M$^+$H]$^+$. Anal. Calcd. for $C_{22}H_{27}N_5\cdot 3.3HBr\cdot 2.6H_2O\cdot 0.3C_4H_{10}O$: C, 39.95; H, 5.56; N, 10.04; Br, 37.80. Found: C, 39.95; H, 5.46; N, 9.96; Br, 37.85.

EXAMPLE 103

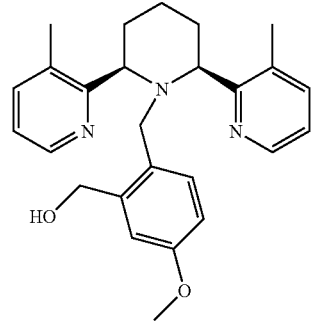

COMPOUND 103: [2-meso-(3,3''-Dimethyl-3',4',5',6'-tetrahydro-2'H-[2,2';6',2'']teryridin-1'-ylmethyl)-5-methoxy-phenyl]-methanol A solution of 4-methyl-3-nitrophenol (1.92 g, 12.5 mmol) in acetone (60 mL) was treated with dimethyl sulfate (1.42 mL, 15.0 mmol) and $K_2CO_3$ (2.59 g, 18.8 mmol) for 18 hours. The solvent was removed under reduced pressure and the solids dissolved in $H_2O$ (50 mL). The aqueous was then extracted with $CH_2Cl_2$ (3×50 mL) and the combined organics were dried (Na$_2$SO$_4$) and concentrated under reduced pressure. This gave, after column chromatographic purification with silica gel (20:1 hexanes/EtOAc) 4-methoxy-1-methyl-2-nitrobenzene as a light yellow liquid (1.91 g, 91%).

The above compound (1.91 g, 11.4 mmol) was dissolved in MeOH (15 mL) and 10% Pd/C (50% wet, 400 mg) was added. The reagents were then agitated under an atmosphere of hydrogen (30 psi) for 1.5 hours. The reaction mixture was filtered through celite and the solvent removed under reduced pressure. This afforded 5-methoxy-2-methyl-phenylamine as a brown liquid (1.57 g, 100%). $^1$H NMR (CDCl$_3$) δ 2.11 (s, 3H), 3.61 (br, 2H (NH2)), 3.75 (s, 3H), 6.27 (s, 1H), 6.29 (d, 1H, J=7.8 Hz), 6.94 (d, 1H, J=7.8 Hz).

The amine from above (1.57 g, 11.4 mmol) was suspended in H$_2$O (3 mL) and concentrated HCl (3 mL). An additional 8 mL of H$_2$O was then added, and the temperature chilled to 0° C. A solution of NaNO$_2$ (0.87 g, 12.6 mmol) in H$_2$O (2 mL) was slowly added and the mixture stirred for 0.5 hour. The acid was then neutralized with K$_2$CO$_3$ (1.9 g, 3.8 mmol) and the mixture poured into a solution of sodium cyanate (1.35 g, 27.5 mmol) and copper (I) cyanide (1.23 g, 13.7 mmol) in H$_2$O (7.5 mL) stirring at 60° C. The temperature was increased to 110° C. and the reaction stirred for 1 hour. CH$_2$Cl$_2$ (50 mL) and brine (50 mL) were then added, and the organic phase separated. The aqueous phase was then extracted with CH$_2$Cl$_2$ (2×50 mL), and the combined organic phases were dried (Na$_2$SO$_4$) and concentrated under reduced pressure to give, after purification by column chromatography with silica gel (10:1 hexanes/EtOAc), 5-methoxy-2-methyl-benzonitrile as a brown liquid (0.93 g, 55%).

The compound above (0.93 g, 6.3 mmol) was dissolved in H$_2$O (12 mL) and concentrated H$_2$SO$_4$ (18 mL) at 160° C. After 4 hours, the solution was cooled and filtered through a medium glass-fritted funnel, washing the residue with Et$_2$O. The filtrate was then extracted with Et$_2$O (3×50 mL), dried (MgSO$_4$) and concentrated under reduced pressure to afford a black solid (0.47 g). This material was dissolved in anhydrous MeOH (10 mL) and c. H$_2$SO$_4$ (0.5 mL), heating to reflux and stirring for 16 hours. The solution was cooled to room temperature and partitioned between Et$_2$O (15 mL) and brine (10 mL). After separating, the organic phase was washed with brine (3×10 mL). The organic was then dried (MgSO$_4$), filtered, and concentrated under reduced pressure to afford, after column chromatography with silica gel (5:1 hexanes/EtOAc), 5-hydroxy-2-methyl-benzoic acid methyl ester as a pale brown solid (0.28 g, 27%). Note the methoxyl group had been lost. $^1$H NMR (CDCl$_3$) δ 2.51 (s, 3H), 3.89 (s, 3H), 4.94 (s, 1H (OH)), 6.91 (dd, 1H, J=1.5, 7.5 Hz), 7.12 (d, 1H, J=7.8 Hz), 7.41 (d, 1H, J=1.5 Hz).

A solution of the above ester (0.28 g, 1.7 mmol) in acetone (9 mL) was treated with dimethyl sulfate (0.19 mL, 2.0 mmmol) and K$_2$CO$_3$ (0.35 g, 2.5 mmol) for 18 hours. The solvent was removed under reduced pressure and the solids dissolved in H$_2$O (5 mL). The aqueous was then extracted with CH$_2$Cl$_2$ (3×10 mL) and the combined organics were dried (Na$_2$SO$_4$) and concentrated under reduced pressure. This gave, after column chromatographic purification with silica gel (20:1 hexanes/EtOAc) 5-methoxy-2-methyl-benzoic acid methyl ester as a light yellow liquid (0.24 g, 80%).

To a solution of the above ester (0.24 g, 1.3 mmol) in CCl$_4$ (5 mL) was added N-bromosuccinimide (0.26 g, 1.5 mmol), and 1,1'-azobis(cyclohexanecarbonitrile) (64 mg, 0.26 mmol). The solution was stirred at reflux for 16 hours and then cooled to room temperature, filtered through a medium glass fritted funnel, and concentrated under reduced pressure. This gave, after column chromatography with silica gel (100:1 hexanes/EtOAc), 2-bromomethyl-5-methoxy-benzoic acid methyl ester as a colorless liquid. (0.24 g, 70%). $^1$H NMR (CDCl$_3$) δ 3.85 (s, 3H), 3.95 (s, 3H), 4.93 (s, 2H), 7.01 (dd, 1H, J=1.5, 7.5 Hz), 7.37 (d, 1H, J=7.5 Hz), 7.48 (d, 1H, J=1.5 Hz).

A solution of meso-3,3"-dimethyl-1',2',3',4',5',6'-hexahydro-[2,2';6',2"]terpyridine (185 mg, 0.69 mmol), 2-bromomethyl-5-methoxy-benzoic acid methyl ester (235 mg, 0.90 mmol), and KI (23 mg, 0.14 mmol) in anhydrous DMF (3.5 mL) was treated with DIPEA (0.24 mL, 1.4 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (2:0.5:97.5 MeOH/NH$_4$OH/CH$_2$Cl$_2$), meso-2-(3,3"-dimethyl-3',4',5',6'-tetrahydro-2'H-[2,2';6',2"]terpyridin-1'-ylmethyl)-5-methoxy-benzoic acid methyl ester as a light beige-colored solid (0.29 g, 93%).

The alkylated product from above (0.29 g, 0.65 mmol) was dissolved in THF (6 mL) and MeOH (6 mL), cooled to 0° C., and treated with solid LiBH$_4$ (0.16 g, 7.8 mmol). After vigorous bubbling subsided, the mixture was let warm to room temperature over 1 hour while stirring. The excess LiBH$_4$ was quenched with 1N NaOH solution (5 mL) plus brine (15 mL). The aqueous phase was then extracted with CH$_2$Cl$_2$ (3×20 mL), dried (Na$_2$SO$_4$), and concentrated under reduced pressure to give, after radial chromatographic purification on a silica get plate (50:1:0.1 CH$_2$Cl$_2$/MeOH/NH$_4$OH), COMPOUND 103 as a fluffy white solid (77 mg, 29%). $^1$H NMR (CDCl$_3$) δ 1.64 (br d, 3H, J=10.8 Hz), 2.00 (br, 1H), 2.30 (m, 2H), 2.49 (s, 6H), 3.56 (s, 2H), 3.60 (s, 3H), 3.95 (br d, 2H, J=11.4 Hz), 4.30 (s, 2H), 6.18 (d, 1H, J=8.1 Hz), 6.50 (s, 1H), 6.62 (d, 1H, J=8.4 Hz), 6.86 (m, 2H), 7.25 (d, 2H, J=8.4 Hz), 8.25 (d, 2H, J=3.9 Hz). $^{13}$C NMR (CDCl$_3$) 19.14 (2C), 25.27, 30.23 (2C), 55.20 (2C), 62.76, 67.78 (2C), 112.24 (2C), 114.22, 121.67 (2C), 130.02, 130.72, 131.23, 138.07 (2C), 140.20, 146.54 (2C), 157.82, 160.00 (2C). ES-MS m/z418 (M$^+$H). Anal. Calcd. for C$_{26}$H$_{31}$N$_3$O$_2$.0.1NH$_4$OH.1.0H$_2$O: C, 71.12; H, 7.69; N, 9.89. Found: C, 71.25; H, 7.41; N, 10.23.

EXAMPLE 104

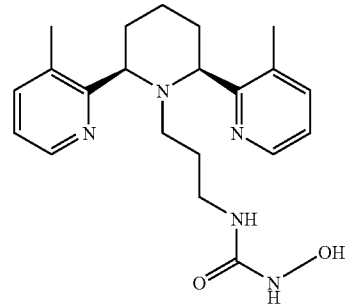

COMPOUND 104: N-[3-meso-(3,3"-Dimethyl-3',4', 5',6'-tetrahydro-2'H-[2,2';6',2"]terpyridin-1'-yl)-propyl]-N'-hydroxyurea A solution of meso-3,3"-dimethyl-1',2',3',4',5',6'-hexahydro-[2,2';6',2"]terpyridine (235 mg, 0.88 mmol) 2-(3-bromopropyl)-isoindole-1,3-dione (306 mg, 1.14 mmol), and KI (29 mg, 0.18 mmol) in anhydrous DMF (4.0 mL) was treated with DIPEA (0.31 mL, 1.8 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (20:1:0.2 CH$_2$Cl$_2$/MeOH/NH$_4$OH), 2-[3-meso-3, 3"-dimethyl-3',4',5',6'-tetrahydro-2'H-[2,2';6',2"]terpyridin-1'-yl)-propyl]-isoindole-1,3-dione as a pale yellow solid (0.40 g, 100%). $^1$H NMR (CDCl$_3$) δ 0.95 (br, 2H), 1.58 (m, 2H), 1.86 (m, 1H), 2.07 (m, 1H), 2.32 (br, 2H), 2.50 (s, 8H), 2.90 (br, 2H), 4.06 (d, 2H), 6.89 (m, 2H), 7.26 (br, 2H), 7.70 (m, 4H), 8.27 (br, 2H).

A solution of the above compound (400 mg, 0.88 mmol) in EtOH (9 mL) was treated with hydrazine monohydrate (0.48 mL, 8.8 mmol) and stirred at room temperature for 16 hours. CH$_2$Cl$_2$ (10 mL) was added and the white mixture filtered to remove the solids. The filtrate was then concentrated under reduced pressure and dried in vacuo. This afforded, after radial chromatography with silica gel (10:1:0.1 CH$_2$Cl$_2$/CH$_3$OH/NH$_4$OH), 3-meso-(3,3"-dimethyl-3',4',5',6'-tetrahydro-2'H-[2,2';6',2"]terpyridin-1'-yl)-propylamine as a pale yellow solid (233 mg, 82%).

A solution of the above compound (233 mg, 0.71 mmol) and 1,1-carbonyldiimidazole (115 mg, 0.71 mmol) in THF (7 mL) was stirred for 30 minutes at room temperature. The solvent was then removed under reduced pressure and the residue dissolved in DMF (3.5 mL). The solution was then treated with NH$_2$OH.H$_2$O (200 mg, 2.8 mmol) and DIPEA (0.62 mL, 3.5 mmol) and stirred at room temperature for 18 hours. The reaction was then partitioned between CH$_2$Cl$_2$ (15 mL) and brine (10 mL) and separated. The organic phase was then washed several times with brine (4×10 mL) and the organic phase dried (Na$_2$SO$_4$) and concentrated under reduced pressure to afford, after column chromatography with silica gel (50:1:0.1 CH$_2$Cl$_2$/MeOH/NH$_4$OH), COMPOUND 104 as a white solid (81 mg, 30%). $^1$H NMR (CDCl$_3$) δ 1.55 (m, 1H), 1.67 (d, 2H, J=11.7 Hz), 1.94 (m, 1H), 2.06 (q, 2H, J=10.5 Hz), 2.35 (br, 2H), 2.44 (s, 6H), 2.60 (br d, 2H, J=12.0 Hz), 6.94 (br, 1H), 7.10 (m, 2H), 7.44 (d, 2H, J=7.8 Hz), 7.70 (br, 1H), 8.48 (br, 2H), 10.14 (br, 1H). $^{13}$C NMR (CDCl$_3$) δ 19.01 (2C), 25.03, 26.34, 32.12 (2C), 38.23, 51.04, 64.37 (2C), 122.09 (2C), 130.95 (2C), 138.84 (2C), 146.89 (2C), 160.05 (2C), 161.86. ES-MS m/z 384 (M$^+$H). Anal. Calcd. for C$_{21}$H$_{29}$N$_5$O$_2$.0.4CH$_2$Cl$_2$: C, 61.57; H, 7.19; N, 16.78. Found: C, 61.23; H, 7.35; N, 16.43.

succinimide (0.27 g, 1.5 mmol), and 1,1'-azobis(cyclohexanecarbonitrile) (68 mg, 0.28 mmol). The solution was stirred at reflux for 16 hours and then cooled to room temperature and concentrated under reduced pressure. This gave, after column chromatography with silica gel (60:1 hexanes/EtOAc), 4-bromomethyl-3-methoxy-benzoic acid methyl ester plus a minor impurity (~15%) as a colorless liquid. (0.39 g, excess). $^1$H NMR (CDCl$_3$) δ 3.92 (s, 3H), 3.95 (s, 3H), 4.55 (s, 2H), 7.39 (d, 1H, J=7.5 Hz), 7.55 (s, 1H), 7.61 (d, 1H, J=7.5 Hz).

A solution of meso-3,3"-dimethyl-1',2',3',4',5',6'-hexahydro-[2,2';6',2"]terpyridine (0.25 g, 0.93 mmol), the above methyl ester (0.36 g, 1.4 mmol), and KI (31 mg, 0.20 mmol) in anhydrous DMF (4.7 mL) was treated with DIPEA (0.32 mL, 1.9 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (saturated NH$_3$/Et$_2$O), 4-meso-(3,3"-dimethyl-3',4',5',6'-tetrahydro-2H-[2,2';6',2"]terpyridin-1'-ylmethyl)-3-methoxy-benzoic acid methyl ester as a colorless solid (0.26 g, 63%).

The alkylated product from above (0.25 g, 0.56 mmol) was dissolved in THF (6 mL) and treated with solid LiBH$_4$ (0.20 g, 7.8 mmol). The mixture was then heated to 75° C. for 16 hours. The excess LiBH$_4$ was quenched with 1N NaOH solution (4 mL) plus brine (15 mL). The aqueous phase was then extracted with CH$_2$Cl$_2$ (3×20 mL), dried (Na$_2$SO$_4$), and concentrated under reduced pressure to give, after column chromatographic purification on a silica gel plate (20:1:0.1 CH$_2$Cl$_2$/MeOH/NH$_4$OH), COMPOUND 105 white solid (200 mg, 87%). $^1$H NMR (CDCl$_3$) δ 1.49 (m, 1H), 1.66 (m, 3H), 1.98 (m, 1H), 2.17 (m, 2H), 2.39 (s, 6H), 3.46 (s, 3H), 3.57 (s, 2H), 4.08 (br d, 2H, J=11.4 Hz), 4.46 (s, 2H), 6.39 (s, 1H), 6.54 (d, 1H, J=7.2 Hz), 6.89 (m, 2H), 6.99 (d, 1H, J=7.2 Hz), 7.22 (d, 2H, J=7.5 Hz), 8.34 (d, 2H, J=3.9 Hz). $^{13}$C NMR (CDCl$_3$) δ 18.84 (2C), 25.12, 30.09 (2C), 46.91 (2C), 54.53, 65.18 (2C), 107.56, 117.77, 121.41 (2C), 127.30, 131.05, 131.59 (2C), 137.66 (2C), 139.80, 146.17 (2C), 156.52, 160.44 (2C). ES-MS m/z 418 (M$^+$H). Anal. Calcd. for C$_{26}$H$_{31}$N$_3$O$_2$.0.4CH$_2$Cl$_2$: C, 70.23; H, 7.10; N, 9.31. Found: C, 70.46; H, 7.33; N, 9.34.

EXAMPLE 105

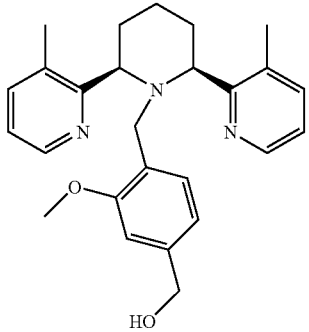

COMPOUND 105: [4-meso-(3,3"-Dimethyl-3',4',5', 6'-tetrahydro-2'H-[2,2';6',2"]terpyridin-1'-ylmethyl)-3-methoxy-phenyl]-methanol To a solution of 3-methoxy-4-methyl-benzoic acid methyl ester (0.25 g, 1.4 mmol) in CCl$_4$ (5 mL) was added N-bromo-

EXAMPLE 106

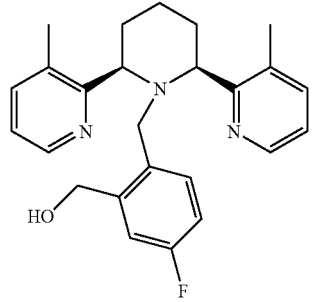

COMPOUND 106: [2-meso-(3,3"-Dimethyl-3',4',5', 6'-tetrahydro-2'H-[2,2';6',2"]terpyridin-1'-ylmethyl)-5-fluoro-phenyl]-methanol 5-Fluoro-2-methyl-benzoic acid (0.29 g, 1.9 mmol) was dissolved in anhydrous MeOH (7 mL) and c. H$_2$SO$_4$ (0.12 mL, 2.3 mmol) was added, heating to reflux for 16 hours. The solution was cooled to room temperature and partitioned between EtOAc (15 mL) and brine (10 mL). After separating, the aqueous phase was extracted with EtOAc (2×10 mL), dried (MgSO$_4$), filtered, and concentrated under reduced pressure to afford 5-fluoro-2-methyl-benzoic acid methyl ester as a pale brown liquid (0.25 g, 78%).

To a solution of the above ester (0.25 g, 1.5 mmol) in CCl$_4$ (5 mL) was added N-bromosuccinimide (0.29 g, 1.6 mmol), and 1,1'-azobis(cyclohexanecarbonitrile) (73 mg, 0.30 mmol). The solution was stirred at reflux for 16 hours and then cooled to room temperature and concentrated under reduced pressure. This gave, after column chromatographic purification with silica gel (50:1 hexanes/EtOAc), 2-bromomethyl-5-fluoro-benzoic acid methyl ester as a pale yellow liquid. (0.23 g, 62%). $^1$H NMR (CDCl$_3$) δ 3.94 (s, 3H), 4.93 (s, 2H), 7.20 (dt, 1H, J=7.5, 1.5 Hz), 7.45 (m, 1H), 7.67 (dd, 1H, J=7.5, 1.5 Hz).

A solution of meso-3,3''-Dimethyl-1',2',3',4',5',6'-hexahydro-[2,2';6',2'']terpyridine (190 mg, 0.72 mmol), the above bromide (235 mg, 0.90 mmol), and KI (23 mg, 0.14 mmol) in anhydrous DMF (3.5 mL) was treated with DIPEA (0.24 mL, 1.4 mmol) and stirred at 60° C. for 16 hours. The mixture was then concentrated under reduced pressure and the residue dissolved in EtOAc (15 mL). The organic solution was washed with brine (5×10 mL), dried (MgSO$_4$), and concentrated under reduced pressure. This afforded, after purification by column chromatography with silica gel (50:1:0.1 CH$_2$Cl$_2$/MeOH/NH$_4$OH), 2-meso-(3,3''-dimethyl-3',4',5',6'-tetrahydro-2'H-[2,2';6',2'']terpyridin-1'-ylmethyl)-5-fluorobenzoic acid methyl ester as a white solid (0.28 g, 90%).

The alkylated product from above (0.28 g, 0.65 mmol) was dissolved in THF (6 mL) and treated with solid LiBH$_4$ (0.17 g, 7.7 mmol). The mixture was then heated to 75° C. for 16 hours. The excess LiBH$_4$ was quenched with 1N NaOH solution (4 mL) plus brine (15 mL). The aqueous phase was then extracted with CH$_2$Cl$_2$ (3×20 mL), dried (Na$_2$SO$_4$), and concentrated under reduced pressure to give COMPOUND 106 as a white solid (239 mg, 92%). $^1$H NMR (CDCl$_3$) δ 1.66 (m, 3H), 2.05 (m, 1H), 2.31 (m, 2H), 2.50 (s, 6H), 3.59 (s, 2H), 4.00 (br d, 2H, J=10.8 Hz), 4.34 (s, 2H), 5.10 (br, 1H (OH)), 6.32 (dt, 1H, J=8.4, 2.4 Hz), 6.63 (dd, 1H, J=9.6, 2.7 Hz), 6.69 (t, 1H, J=7.2 Hz), 6.88 (m, 2H), 7.25 (d, 2H, J=6.0 Hz), 8.25 (d, 2H, J=3.9 Hz). $^{13}$C NMR (CDCl$_3$) δ 19.06 (2C), 25.22, 29.76 (2C), 54.06, 62.13, 67.44 (2C), 112.57 (d, 1C, J=83 Hz), 115.25 (d, 1C, J=84 Hz), 121.84 (2C), 130.24, 131.31 (2C), 134.00, 138.11 (2C), 141.13, 146.51 (2C), 159.71 (2C), 161.08 (d, IC, J=971 Hz). ES-MS m/z 406 (M$^+$H). Anal. Calcd. for C$_{25}$H$_{28}$N$_3$OF.0.2CH$_2$Cl$_2$: C, 71.64; H, 6.77; N, 9.95. Found: C, 71.45; H, 6.85; N, 9.95.

EXAMPLE 107

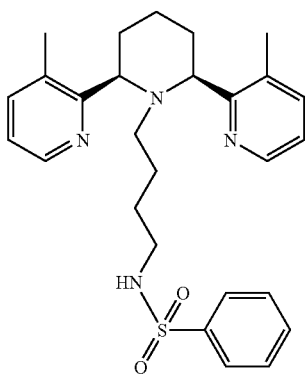

COMPOUND 107: N-[4-meso-(3,3''-Dimethyl-3',4',5',6'-tetrahydro-2'H-[2,2';6',2'']terpyridin-1'-yl)-butyl]-benzenesulfonamide (HBr salt)

A solution of 4-meso-(3,3''-dimethyl-3',4',5',6'-tetrahydro-2'H-[2,2';6',2'']terpyridin-1'-yl)-butylamine (90 mg, 0.27 mmol) in CH$_2$Cl$_2$ (2 mL) was treated with benzenesulfonyl chloride (44 μL, 0.34 mmol) and Et$_3$N (63 μL, 0.45 mmol) for 1 hour. Brine (1 mL) was added and the phases were separated. The aqueous phase was extracted with CH$_2$Cl$_2$ (2×2 mL) and the combined organics dried (Na$_2$SO$_4$) and concentrated under reduced pressure to afford, after column chromatography with silica gel (50:1:0.1 CH$_2$Cl$_2$/MeOH/NH$_4$OH), N-[4-meso-(3,3''-dimethyl-3',4',5',6'-tetrahydro-2'H-[2,2';6',2'']terpyridin-1'-yl)-butyl]-benzenesulfonamide as a white solid (102 mg, 79%).

Using General Procedure B: The above material (100 mg, 0.21 mmol) was converted to the HBr salt to provide COMPOUND 107 (115 mg) as a white solid. $^1$H NMR (D$_2$O) δ 1.04 (qt, 2H, J=6.6 Hz), 1.25 (qt, 2H, J=7.8 Hz), 1.50 (m, 2H), 1.70 (q, 1H, J=12.9 Hz), 1.95 (d, 1H, J=13.2 Hz), 2.16 (m, 4H), 2.55 (m, 2H), 2.59 (s, 6H), 4.55 (d, 2H, J=9.3 Hz), 7.59 (m, 2H), 7.70 (m, 3H), 7.88 (t, 2H, J=6.8 Hz), 8.40 (d, 2H, J=8.1 Hz), 8.65 (d, 2H, J=5.4 Hz). $^{13}$C NMR (D$_2$O) δ 17.16 (2C), 19.32, 22.49, 26.10, 32.57 (2C), 41.97, 52.22, 57.97 (2C), 125.97 (2C), 126.92 (2C), 129.98 (2C), 133.96, 136.90 (2C), 138.43, 139.71 (2C), 149.59 (2C), 154.76 (2C). ES-MS m/z 479 (M$^+$H). Anal. Calcd. for C$_{27}$H$_{34}$N$_4$O$_2$S.2.5HBr.1.8H$_2$O.0.4C$_4$H$_{10}$O: C, 46.23; H, 5.98; N, 7.54; Br, 26.89; S, 4.31. Found: C, 46.37; H, 6.06; N, 7.57; Br, 26.67; S, 4.28.

EXAMPLE 108

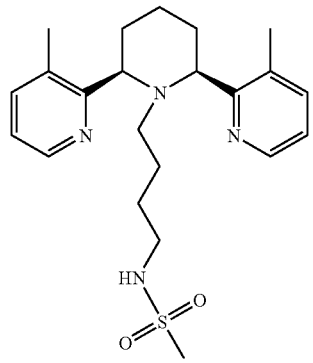

COMPOUND 108: N-[4-meso-(3,3''-Dimethyl-3',4',5',6'-tetrahydro-2'H-[2,2';6',2'']terpyridin-1'-yl)-butyl]-methanesulfonamide (HBr salt)

A solution of 4-meso-(3,3''-dimethyl-3',4',5',6'-tetrahydro-2'H-[2,2';6',2'']terpyridin-1'-yl)-butylamine (97 mg, 0.29 mmol) in CH$_2$Cl$_2$ (2 mL) was treated with MsCl (29 μL, 0.37 mmol) and Et$_3$N (68 μL, 0.49 mmol) for 1 hour. Brine (1 mL) was added and the phases were separated. The aqueous phase was extracted with CH$_2$Cl$_2$ (2×2 mL) and the combined organics dried (Na$_2$SO$_4$) and concentrated under reduced pressure to afford, after column chromatography with silica gel (50:1:0.1 CH$_2$Cl$_2$/MeOH/NH$_4$OH), N-[4-meso-(3,3''-dimethyl-3',4',5',6'-tetrahydro-2'H-[2,2';6',2'']terpyridin-1'-yl)-butyl]-methanesulfonamide as a light brown solid (100 mg, 84%).

Using General Procedure B: The above material (95 mg, 0.24 mmol) was converted to the HBr salt to provide COMPOUND 108 (121 mg) as a white solid. $^1$H NMR (D$_2$O) δ 1.12 (qt, 2H, J=6.6 Hz), 1.31 (qt, 2H, J=7.8 Hz), 1.50 (m, 2H), 1.70 (q, 1H, J=12.9 Hz), 1.95 (d, 1H, J=13.2 Hz), 2.12 (br, 2H), 2.24 (br, 2H), 2.60 (s, 6H), 2.77 (br, 2H), 2.90 (s, 3H), 4.60 (d, 2H, J=9.3 Hz), 7.88 (t, 2H, J=6.8 Hz), 8.40 (d, 2H, J=8.1 Hz), 8.64 (d, 2H, J=5.4 Hz). $^{13}$C NMR (D$_2$O) δ 17.13 (2C), 19.47, 22.46, 26.67, 32.60 (2C), 38.74, 41.95, 52.61, 58.11 (2C), 125.95 (2C), 136.90 (2C), 139.66 (2C), 149.59 (2C), 154.86 (2C). ES-MS m/z 417 (M⁺H). Anal. Calcd. for C₂₂H₃₂N₄O₂S.2.6HBr.1.8H₂O: C, 40.07; H, 5.84; N, 8.50; Br, 31.51; S, 4.86. Found: C, 40.39; H, 6.20; N, 8.14; Br, 31.28; S, 4.60.

EXAMPLE 109

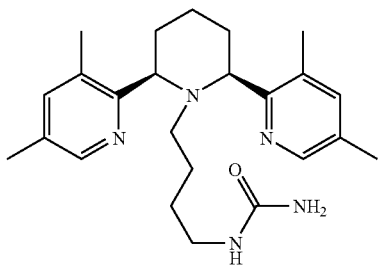

COMPOUND 109: [4-meso-(3,5,3",5"-Tetramethyl-3',4',5',6'-tetrahydro-2'H-[2,2';6',2"]terpyridin-1'-yl)-butyl]-urea (HBr salt)

Using General Procedure A, a solution of the above compound (356 mg, 1.2 mmol) in DMF (6 mL) was added 2-(4-bromo-butyl)-isoindole-1,3-dione (442 mg, 1.6 mmol), KI (40 mg, 0.24 mmol), and DIPEA (0.42 mL, 2.4 mmol) and the mixture stirred at 60° C. overnight. This gave, after work-up and column chromatography with silica gel (20:1:0.2 CH₂Cl₂/MeOH/NH₄OH), 2-[4-meso-(3,5,3",5"-tetramethyl-3',4',5',6'-tetrahydro-2'H-[2,2';6',2"]terpyridine-1'-yl)-butyl]-isoindole-1,3-dione (515 mg, 86%).

A solution of the above compound (515 mg, 1.04 mmol) in EtOH (10 mL) was treated with hydrazine monohydrate (0.50 mL, 10.4 mmol) and stirred at room temperature for 16 hours. CH₂Cl₂ (10 mL) was added and the white mixture filtered to remove the solids. The filtrate was then concentrated under reduced pressure and dried in vacuo. This afforded, after column chromatography with silica gel (20:1:0.1 CH₂Cl₂/CH₃OH/NH₄OH), 4-meso-(3,5,3",5"-tetramethyl-3',4',5',6'-tetrahydro-2'H-[2,2';6',2"]terpyridine-1'-yl)-butylamine as a sticky white solid (0.25 g, 66%). ¹H NMR (CDCl₃) δ 0.80 (br, 3H), 1.54 (m, 1H), 1.62 (d, 2H, J=12.0 Hz), 1.97 (m, 3H), 2.16 (t, 2H, J=7.5 Hz), 2.27 (s, 6H), 2.40 (br, 1H), 2.47 (s, 6H), 2.60 (br, 2H), 3.93 (br, 2H, J=9.0 Hz), 7.24 (s, 2H), 8.31 (s, 2H).

The amine from above was dissolved in isopropanol (2.3 mL) and treated with trimethylsilylisocyanate (64 µL, 0.47 mmol) at room temperature for 16 hours. The solution was then concentrated under reduced pressure and the crude material purified by column chromatography with silica gel (40:1 THF-Et₂O/NH₄OH) to afford [4-meso-(3,5,3",5"-tetramethyl-3',4',5',6'-tetrahydro-2'H-[2,2';6',2"]terpyridin-1'-yl)-butyl]-urea as a colorless oil (46 mg, 33%).

Using General Procedure B: The above material (45 mg, 0.11 mmol) was converted to the HBr salt to provide COMPOUND 109 (44 mg) as a white solid. ¹H NMR (D₂O) δ 1.02 (qt, 2H, J=6.9 Hz), 1.13 (qt, 2H, J=6.6 Hz), 1.46 (m, 2H), 1.65 (m, 1H), 1.90 (m, 1H), 2.07 (d, 2H, J=12.6 Hz), 2.16 (br, 2H), 2.46 (s, 6H), 2.52 (s, 6H), 2.74 (m, 2H), 4.47 (d, 2H, J=9.9 Hz), 8.23 (s, 2H), 8.46 (s, 2H). ¹³C NMR (D₂O) δ 16.91 (2C), 17.57 (2C), 20.26, 22.48, 26.85, 32.71 (2C), 39.11, 53.26, 58.16 (2C), 136.00 (2C), 137.38 (2C), 138.98 (2C), 150.01 (2C), 152.09 (2C), 162.21. ES-MS m/z 410 (M⁺H). Anal. Calcd. for C₂₄H₃₅N₅O.3.1HBr.5.0H₂O: C, 38.41; H, 6.46; N, 9.33; Br, 33.01. Found: C, 38.29; H, 6.30; N, 9.10; Br, 33.17.

EXAMPLE 110

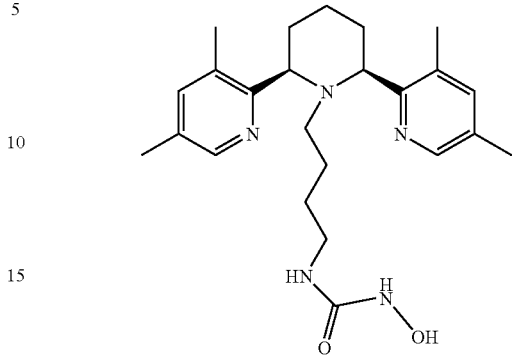

COMPOUND 110: N-[4-meso-(3,5,3",5"-tetramethyl-3',4',5',6'-tetrahydro-2'H-[2,2';6',2"]terpyridine-1'-yl)-butyl]-N'-hydroxyurea A solution of 4-meso-(3,5,3",5"-tetramethyl-3',4',5',6'-tetrahydro-2'H-[2,2';6',2"]terpyridine-1'-yl)-butylamine (127 mg, 0.35 mmol) and 1,1-carbonyldiimidazole (56 mg, 0.35 mmol) in THF (3.5 mL) was stirred for 30 minutes at room temperature. The solvent was then removed under reduced pressure and the residue dissolved in DMF (2 mL). The solution was then treated with NH₂OH.H₂O (97 mg, 1.4 mmol) and DIPEA (0.30 mL, 1.7 mmol) and stirred at room temperature for 18 hours. The reaction was partitioned between CH₂Cl₂ (15 mL) and brine (10 mL) and separated. The organic phase was then washed several times with brine (4×10 mL) and the organic phase dried (Na₂SO₄) and concentrated under reduced pressure to afford, after column chromatography with silica gel (20:1:0.1 CH₂Cl₂/MeOH/NH₄OH), COMPOUND 110 as a white solid (92 mg, 62%). ¹H NMR (CDCl₃) δ 0.79 (br, 3H), 1.60 (br, 3H), 1.95 (br, 3H), 2.26 (s, 6H), 2.39 (s, 6H), 2.72 (m, 5H), 3.87 (br, 2H), 5.65 (br, 1H), 7.25 (s, 2H), 8.20 (br, 1H), 8.29 (s, 2H). ¹³C NMR (CDCl₃) δ 18.25 (2C), 19.12 (2C), 22.24, 25.53, 28.15, 32.81 (2C), 39.28, 51.39, 62.82 (2C), 130.36 (2C), 131.63 (2C), 139.83 (2C), 147.49 (2C), 157.64 (2C), 162.22. ES-MS m/z 426 (M⁺H). Anal. Calcd. for C₂₄H₃₅N₅O₂.1.1H₂O: C, 64.72; H, 8.42; N, 15.72. Found: C, 64.80; H, 8.55; N, 15.72.

EXAMPLE 111

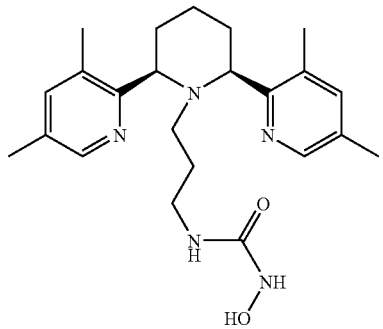

COMPOUND 111: N-[3-meso-(3,5,3",5"-tetramethyl-3',4',5',6'-tetrahydro-2'H-[2,2';6',2"]terpyridine-1'-yl)-propyl]-N'-hydroxyurea Using General Procedure A, a solution of meso-3,5,3",5"-tetramethyl-3',4',5',6'-tetrahydro-2'H-[2,2';6',2"]terpyridine (172 mg, 0.58 mmol) in DMF (3 mL) was added 2-(3-bromopropyl)-isoindole-1,3-dione (203 mg, 0.76 mmol), KI (19 mg, 0.12 mmol), and DIPEA (0.20 mL, 1.2 mmol) and the mixture stirred at 60° C. overnight. This gave, after work-up and column chromatography with silica gel (20:1:0.2 $CH_2Cl_2$/MeOH/$NH_4OH$), 2-[3-meso-(3,5,3",5"-tetramethyl-3',4',5',6'-tetrahydro-2'H-[2,2';6',2"]terpyridine-1'-yl)-propyl]-isoindole-1,3-dione (259 mg, 92%). $^1$H NMR (CDCl$_3$) δ 1.16 (br, 1H), 1.60 (br, 3H), 2.00 (m, 3H), 2.15 (s, 6H), 2.24 (m, 2H), 2.38 (s, 6H), 2.57 (br, 1H), 3.03 (br, 2H), 3.96 (br, 2H), 7.02 (s, 2H), 7.70 (m, 4H), 8.18 (s, 2H).

A solution of the above compound (259 mg, 0.54 mmol) in EtOH (5.4 mL) was treated with hydrazine monohydrate (0.26 mL, 5.4 mmol) and stirred at room temperature for 16 hours. $CH_2Cl_2$ (10 mL) was added and the white mixture filtered to remove the solids. The filtrate was then concentrated under reduced pressure and dried in vacuo. This afforded, after column chromatography with silica gel (20:1:0.1 $CH_2Cl_2$/$CH_3OH$/$NH_4OH$), 3-meso-(3,5,3",5"-tetramethyl-3',4',5',6'-tetrahydro-2'H-[2,2';6',2"]terpyridine-1'-yl)-propylamine as a sticky white solid (0.15 g, 78%).

A solution of the above amine (146 mg, 0.41 mmol) and 1,1-carbonyldiimidazole (67 mg, 0.41 mmol) in THF (4.0 mL) was stirred for 45 minutes at room temperature. The solvent was then removed under reduced pressure and the residue dissolved in DMF (2 mL). The solution was then treated with $NH_2OH.H_2O$ (115 mg, 1.6 mmol) and DIPEA (0.36 mL, 2.1 mmol) and stirred at room temperature for 18 hours. The reaction was partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (20:1:0.1 $CH_2Cl_2$:MeOH/$NH_4OH$), COMPOUND 111 as a white solid (84 mg, 49%). $^1$H NMR (CDCl$_3$) δ 0.44 (br, 2H), 1.60 (br, 3H), 1.95 (br, 3H), 2.27 (s, 6H), 2.39 (s, 6H), 2.50 (br, 2H), 2.60 (br, 2H), 3.72 (br, 2H), 6.86 (br, 1H), 7.26 (s, 2H), 7.77 (br, 1H), 8.30 (s, 2H), 10.41 (br, 1H). $^{13}$C NMR (CDCl$_3$) δ 18.31 (2C), 19.31 (2C), 25.37, 26.80, 32.96 (2C), 38.86, 52.34, 64.61 (2C), 130.57 (2C), 131.90 (2C), 139.85 (2C), 147.68 (2C), 157.58 (2C), 162.29. ES-MS m/z 412 (M$^+$H). Anal. Calcd. for $C_{23}H_{33}N_5O_2$.0.3$H_2O$: C, 66.26; H, 8.12; N, 16.80. Found: C, 66.30; H, 7.96; N, 16.90.

EXAMPLE 112

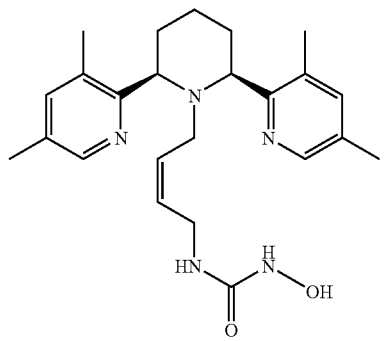

COMPOUND 112: N-[4-meso-(3,5,3",5"-Tetramethyl-3',4',5',6'-tetrahydro-2'H-[2,2';6',2"]terpyridine-1'-yl)-cis-but-2-enyl]-N'-hydroxyurea Following General Procedure A, a solution of meso-3,5,3",5"-tetramethyl-3',4',5',6'-tetrahydro-2'H-[2,2';6',2"]terpyridine (150 mg, 0.51 mmol) in $CH_3CN$ (2.5 mL) was added cis-(4-chloro-but-2-enyl)-carbamic acid tert-butyl ester (115 mg, 0.56 mmol), KI (8 mg, 0.05 mmol), and DIPEA (0.13 mL, 0.76 mmol) and the mixture stirred at 60° C. overnight. This gave, after work-up and column chromatography with silica gel (50:1:0.1 $CH_2Cl_2$/MeOH/$NH_4OH$), [4-meso-(3,5,3",5"-tetramethyl-3',4',5',6'-tetrahydro-2'H-[2,2';6',2"]terpyridin-1'-yl)-cis-but-2-enyl]-carbamic acid tert-butyl ester (213 mg, 90%).

A solution of the above compound (0.213 g, 0.46 mmol) in $CH_2Cl_2$ (1.5 mL) was treated with TFA (1.0 mL) for 1 hour. 15% aqueous NaOH solution (~3 mL) was then added slowly until the acid content was neutralized and the solution became basic (pH=8 to 12). The phases were then separated and the aqueous extracted with $CH_2Cl_2$ (2×10 mL). The combined organics were then dried ($Na_2SO_4$) and concentrated under reduced pressure to give 4-meso-(3,5,3",5"-tetramethyl-3',4',5',6'-tetrahydro-2'H-[2,2';6',2"]terpyridine-1'-yl)-cis-but-2-enylamine (184 mg, excess) which was used immediately in the next reaction.

A solution of the above amine and 1,1-carbonyldiimidazole (80 mg, 0.501 mmol) in THF (5.0 mL) was stirred for 45 minutes at room temperature. The solvent was then removed under reduced pressure and the residue dissolved in DMF (2 mL). The solution was then treated with $NH_2OH.H_2O$ (137 mg, 2.0 mmol) and DIPEA (0.43 mL, 2.5 mmol) and stirred at room temperature for 18 hours. The reaction was partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (20:1:0.1 $CH_2Cl_2$:MeOH/$NH_4OH$), COMPOUND 112 as a white solid (51 mg, 24%). $^1$H NMR (CDCl$_3$) δ 1.54 (br, 1H), 1.64 (br, 2H), 1.92 (br, 3H), 2.23 (s, 6H), 2.37 (s, 6H), 2.96 (br, 2H), 3.03 (br, 2H), 5.30 (br, 2H), 5.73 (br, 1H), 7.26 (s, 2H), 8.27 (br, 2H), 10.44 (br, 1H). $^{13}$C NMR (CDCl$_3$) δ 17.85 (2C), 18.70 (2C), 25.15, 32.90 (2C), 35.83, 46.73, 61.43 (2C), 126.95, 128.48, 130.04, 130.35 (2C), 139.49 (3C), 147.18 (2C), 157.10 (2C), 161.56. ES-MS m/z424 (M$^+$H). Anal. Calcd. for $C_{24}H_{33}N_5O_2$.0.5$CH_2Cl_2$: C, 63.14; H, 7.35; N, 15.03. Found: C, 63.42; H, 7.56; N, 15.01.

EXAMPLE 113

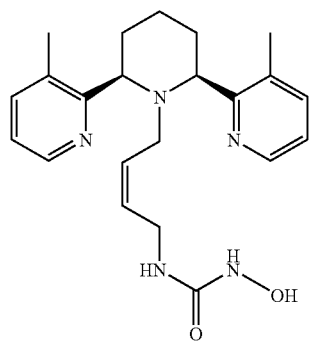

COMPOUND 113: N-[4-meso-(3,3"-Dimethyl-3',4',5',6'-tetrahydro-2'H-[2,2';6',2"]terpyridine-1'-yl)-cis-but-2-enyl]-N'-hydroxyurea Following General Procedure A, a solution of meso-3,3"-dimethyl-3',4',5',6'-tetrahydro-2'H-[2,2';6',2"]terpyridine (133 mg, 0.50 mmol) in $CH_3CN$ (5 mL) was added cis-(4- chloro-but-2-enyl)-carbamic acid tert-butyl ester (113 mg, 0.55 mmol), KI (8 mg, 0.05 mmol), and DIPEA (0.13 mL, 0.76 mmol) and the mixture stirred at 60° C. overnight. This gave, after work-up and column chromatography with silica gel (20:1:0.1 $CH_2Cl_2$/MeOH/$NH_4OH$), [4-meso-(3,3"-dimethyl-3',4',5',6'-tetrahydro-2'H-[2,2';6',2"]terpyridin-1'-yl)-cis-but-2-enyl]-carbamic acid tert-butyl ester (202 mg, 93%). $^1$H NMR ($CDCl_3$) δ 1.39 (s, 9H), 1.60 (m, 1H), 1.73 (br, 2H), 2.00 (br, 3H), 2.45 (br, 5H), 2.57 (s, 3H), 2.68 (br, 1H), 2.89 (br, 2H), 4.02 (br, 2H), 5.17 (br, 1H), 5.42 (br, 1H), 7.08 (m, 2H), 7.41 (m, 2H), 8.47 (br, 2H).

A solution of the above compound (0.20 g, 0.46 mmol) in $CH_2Cl_2$ (1.5 mL) was treated with TFA (1.0 mL) for 1 hour. 15% aqueous NaOH solution (~3 mL) was then added slowly until the acid content was neutralized and the solution became basic (pH=8 to 12). The phases were then separated and the aqueous extracted with $CH_2Cl_2$ (2×10 mL). The combined organics were then dried ($Na_2SO_4$) and concentrated under reduced pressure to give 4-meso-(3,3"-dimethyl-3',4',5',6'-tetrahydro-2'H-[2,2';6',2"]terpyridin-1'-yl)-cis-but-2-enylamine (151 mg, 98%) which was used immediately in the next reaction.

A solution of the above amine and 1,1-carbonyldiimidazole (148 mg, 0.44 mmol) in THF (4.5 mL) was stirred for 45 minutes at room temperature. The solvent was then removed under reduced pressure and the residue dissolved in DMF (2 mL). The solution was then treated with $NH_2OH \cdot H_2O$ (122 mg, 1.8 mmol) and DIPEA (0.38 mL, 2.2 mmol) and stirred at room temperature for 18 hours. The reaction was partitioned between $CH_2Cl_2$ (15 mL) and brine (10 mL) and separated. The organic phase was then washed several times with brine (4×10 mL) and the organic phase dried ($Na_2SO_4$) and concentrated under reduced pressure to afford, after column chromatography with silica gel (20:1:0.1 $CH_2Cl_2$:MeOH/$NH_4OH$), COMPOUND 113 as a white solid (117 mg, 67%). $^1$H NMR ($CDCl_3$) δ 1.53 (m, 1H), 1.67 (m, 2H), 1.92 (m, 3H), 2.40 (s, 6H), 2.88 (br, 2H), 2.98 (br, 2H), 4.02 (br, 2H), 5.28 (br, 1H), 5.40 (m, 1H), 5.62 (br, 1H), 7.05 (m, 2H), 7.46 (d, 2H, J=7.0 Hz), 8.44 (d, 2H, J=3.5 Hz). $^{13}$C NMR ($CDCl_3$) δ 19.24 (2C), 25.46, 33.15 (2C), 36.03, 47.26, 62.35 (2C), 122.41 (2C), 127.25, 129.05, 131.21 (2C), 139.36 (2C), 147.16 (2C), 160.31 (2C), 161.98. ES-MS m/z 396 ($M^+$H). Anal. Calcd. for $C_{22}H_{29}N_5O_2 \cdot 1.5H_2O \cdot 0.2C_3H_4N_2$: C, 62.24; H, 7.58; N, 17.34. Found: C, 62.34; H, 7.59; N, 17.31.

EXAMPLE 114

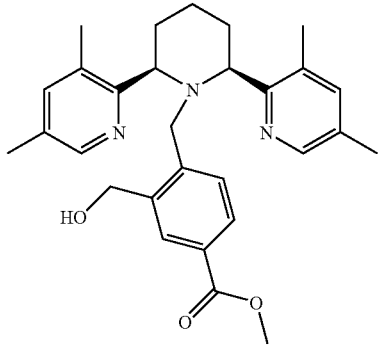

COMPOUND 114: 3-Hydroxymethyl-4-meso-(3,5,3",5"-tetramethyl-3',4',5',6'-tetrahydro-2'H-[2,2';6',2"]terpyridin-1'-ylmethyl)-benzoic acid methyl ester A solution of meso-3,5,3",5"-tetramethyl-1',2',3',4',5',6'-hexahydro-[2,2';6',2"]terpyridine (0.44 g, 1.5 mmol), 2-bromomethyl-5-cyano-benzoic acid methyl ester (0.49 g, 1.9 mmol), and KI (49 mg, 0.30 mmol) in anhydrous DMF (7.5 mL) was treated with DIPEA (0.52 mL, 3.0 mmol) and stirred at 60° C. for 16 hours. The mixture was then concentrated under reduced pressure and the residue dissolved in EtOAc (20 mL). The organic solution was washed with brine (5×15 mL), dried ($MgSO_4$), and concentrated under reduced pressure. This afforded, after purification by column chromatography with silica gel (25:1 $CH_2Cl_2$/MeOH), 5-cyano-2-meso-(3,5,3",5"-tetramethyl-3',4',5',6'-tetrahydro-2'H-[2,2';6',2"]terpyridin-1'-ylmethyl)-benzoic acid methyl ester as a light beige-colored solid (0.60 g, 86%). $^1$H NMR ($CDCl_3$) δ 1.64 (br, 3H), 2.05 (br, 1H), 2.13 (s, 6H), 2.30 (br, 2H), 2.37 (s, 6H), 3.85 (s, 3H), 3.91 (s, 2H), 4.06 (d, 2H, J=12.0 Hz), 6.97 (s, 2H), 7.36 (d, 1H, J=7.5 Hz), 7.56 (s, 1H), 7.90 (d, 1H, J=6.0 Hz), 8.03 (s, 2H).

The alkylated product from above (0.60 g, 1.3 mmol) was dissolved in THF (15 mL) and MeOH (15 mL), cooled to 0° C., and treated with solid $LiBH_4$ (0.33 g, 15.4 mmol). After vigorous bubbling subsided, the mixture was let warm to room temperature over 1 hour while stirring. The excess $LiBH_4$ was quenched with 1N NaOH solution (5 mL) plus brine (25 mL). The aqueous phase was then extracted with $CH_2Cl_2$ (3×30 mL) and the combined organics dried ($Na_2SO_4$) and concentrated under reduced pressure to give, after column chromatographic purification on a silica gel plate (50:1:0.1 $CH_2Cl_2$/MeOH/$NH_4OH$), 3-hydroxymethyl-4-meso-(3,5,3",5"-tetramethyl-3',4',5',6'-tetrahydro-2'H-[2,2';6',2"]terpyridin-1'-ylmethyl)-benzonitrile as a fluffy white solid (0.45 g, 80%).

The compound from above (0.44 g, 1.0 mmol) was dissolved in MeOH (2.5 mL) and water (2.5 mL) and treated with NaOH pellets (0.40 g, 10 mmol) at 100° C. for 16 hours. The reaction was cooled to room temperature and 4N HCl added (~2 mL) until the solution pH=5. Brine (10 mL) was added and the aqueous extracted several times with $CH_2Cl_2$ (5×15 mL). The combined organics were dried ($Na_2SO_4$) and concentrated under reduced pressure to afford the desired 3-hydroxymethyl-4-meso-(3,5,3",5"-tetramethyl-3',4',5',6'-tetrahydro-2'H-[2,2';6',2"]terpyridin-1'-ylmethyl)-benzoic acid plus ~15% of inseparable amide side product (0.37 g, 86%).

The above mixture (0.37 g, 0.8 mmol) was then dissolved in MeOH (9 mL) and treated with c. $H_2SO_4$ (55 µL, 1.0 mmol) at 85° C. for 16 hours. The reaction was cooled to room temperature and 15% NaOH solution added (~1-2 mL) until the solution was basic pH=8-12. Brine (10 mL) was added and the aqueous extracted with $CH_2Cl_2$ (3×15 mL). The combined organics were dried ($Na_2SO_4$) and concentrated under reduced pressure to afford, after column chromatography with silica gel (50:1:0.1 $CH_2Cl_2$/MeOH/$NH_4OH$), COMPOUND 114 as a white solid (0.26 g, 69%). $^1$H NMR ($CDCl_3$) δ 1.64 (br, 3H), 2.08 (s, 6H), 2.11 (br, 1H), 2.38 (m, 2H), 2.46 (s, 6H), 3.68 (br, 2H), 3.81 (s, 3H), 4.03 (d, 2H, J=11.1 Hz), 4.46 (s, 2H), 6.77 (d, 1H, J=7.5 Hz), 7.03 (s, 2H), 7.31 (d, 1H, J=7.5 Hz), 7.59 (s, 1H), 8.00 (s, 2H). $^{13}$C NMR ($CDCl_3$) δ 17.66 (2C), 18.89 (2C), 25.42, 28.73 (2C), 51.80, 62.59 (2C), 66.69 (2C), 127.21, 127.46, 128.57 (2C), 130.13, 130.99 (2C), 131.42, 138.56, 138.72 (2C), 144.76, 146.76 (2C), 156.30 (2C), 167.06. ES-MS m/z 474 ($M^+$H). Anal. Calcd. for $C_{29}H_{35}N_3O_3 \cdot 0.2CH_2Cl_2$; C, 71.49; H, 7.27; N, 8.57. Found: C, 71.76; H, 7.39; N, 8.52.

EXAMPLE 115

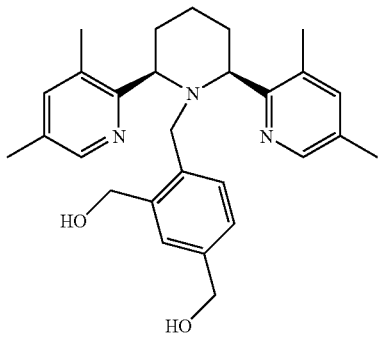

COMPOUND 115: [5-Hydroxymethyl-2-meso-(3,5,3",5"-tetramethyl-3',4',5',6'-tetrahydro-2'H-[2,2';6',2"]terpyridin-1'-ylmethyl)-phenyl]-methanol 3-Hydroxymethyl-4-meso-(3,5,3",5"-tetramethyl-3',4',5',6'-tetrahydro-2'H-[2,2';6',2"]terpyridin-1'-ylmethyl)-benzoic acid methyl ester (0.20 g, 0.42 mmol) was dissolved in THF (4 mL) and treated with solid LiBH$_4$ (0.11 g, 5.1 mmol) stirring at 75° C. for 16 hours. The excess LiBH$_4$ was quenched with 1N NaOH solution (5 mL) plus brine (15 mL). The aqueous phase was then extracted with CH$_2$Cl$_2$ (3×20 mL) and the combined organics dried (Na$_2$SO$_4$) and concentrated under reduced pressure to give, after column chromatographic purification with silica gel (50:1:0.1 CH$_2$Cl$_2$/MeOH/NH$_4$OH), COMPOUND 115 as a white solid (174 mg, 93%). $^1$H NMR (CDCl$_3$) δ 1.64 (br, 3H), 2.02 (m, 1H), 2.11 (s, 6H), 2.34 (m, 2H), 2.45 (s, 6H), 3.62 (br, 2H), 3.97 (d, 2H, J=13.5 Hz), 4.38 (s, 2H), 4.40 (s, 2H), 6.66 (m, 2H), 6.91 (s, 1H), 7.03 (s, 2H), 8.01 (s, 2H). $^{13}$C NMR (CDCl$_3$) δ 17.69 (2C), 18.92 (2C), 25.26, 30.07 (2C), 54.37, 62.34 (2C), 64.59 (2C), 66.60 (2C), 124.89 (2C), 127.57, 128.92, 130.67, 131.06 (2C), 137.65, 138.69 (2C), 138.84, 139.04, 146.69 (2C), 156.74 (2C). ES-MS m/z 446 (M$^+$H). Anal. Calcd. for C$_{28}$H$_{35}$N$_3$O$_2$.0.4CH$_2$Cl$_2$: C, 71.13; H, 7.52; N, 8.76. Found: C, 70.97; H, 7.71; N, 8.84.

EXAMPLE 116

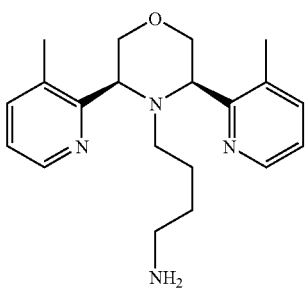

COMPOUND 116: 4-meso-[3,5-bis-(3-methyl-pyridin-2-yl)-morpholin-4-yl]-butylamine (HBr salt)

To a solution of N,N,N$^1$,N$^1$-tetramethylethylenediamine (4.1 mL, 26.93 mmol) in THF (50 mL) at −78° C. was added n-BuLi (12.0 mL, 26.93 mmol) and the reaction mixture was warmed to approximately −55° C. After 30 min, the mixture was re-cooled to −78° C. and a solution of methoxycarbonylmethyoxy-acetic acid methyl ester in THF (10 mL) was added dropwise. After 2 h, the reaction mixture was quenched with water (100 mL) and extracted with CH$_2$Cl$_2$ (3×100 mL). The combined organic layers were dried (MgSO$_4$), filtered, and concentrated to afford a yellow solid. The crude solid was recrystallized from hot EtOAc and the isolated white needles (1.04 g, 31%) were dried in vacuo to give 1-(3-methyl-pyridin-2-yl)-2-[2-(3-methyl-pyridin-2-yl)-2-oxo-ethoxy]-ethanone. $^1$H NMR (CDCl$_3$) δ 2.65 (s, 6H), 5.26 (s, 4H), 7.35 (dd, 2H, J=6.0, 3.0 Hz), 7.60 (dd, 2H, J=9.0, 3.0 Hz), 8.46 (d, 2H, J=3.0 Hz).

To a suspension of the above diketone (750 mg, 2.64 mmol) in MeOH (30 mL) was added NaBH$_4$ (220 mg, 5.80 mmol). After 1 h, the reaction mixture was quenched with water (1 mL), concentrated under reduced pressure, dissolved in CH$_2$Cl$_2$/H$_2$O (1:1) (50 mL), and extracted with CH$_2$Cl$_2$ (3×25 mL). The combined organic layers were dried (MgSO$_4$), filtered, and concentrated to afford 2-[2-hydroxy-2-(3-methyopyridin-2-yl)-ethoxy]-1-(3-methyl-pyridin-2-yl)-ethanol as a pale yellow oil (646 mg).

To a solution of the above diol (646 mg, 2.24 mmol) in CH$_2$Cl$_2$ (30 mL) at −20° C. was added Et$_3$N (0.93 mL, 6.72 mmol) and then MsCl (0.43 mL, 5.60 mmol). After 2 h, the reaction mixture was warmed to 0° C. and quenched with saturated NaHCO$_3$ (25 mL). Then it was extracted with CH$_2$Cl$_2$ (3×25 mL). The combined organic layers were dried (MgSO$_4$), filtered, and concentrated, leaving approximately 5 mL of solvent.

To a solution of the above dimesylate in CH$_2$Cl$_2$ (5 mL) at 0° C. was added allylamine (1.7 mL, 22.40 mmol) and the reaction mixture was slowly warmed to room temperature and stirred overnight. The mixture was quenched with saturated NaHCO$_3$ (20 mL) and extracted with CH$_2$Cl$_2$ (3×20 mL). The combined organic extracts were dried (MgSO$_4$), filtered, and concentrated to afford a yellow oil. Purification by flash column chromatography on silica gel using EtOAc/hexanes (4:1) afforded 4-allyl-meso-3,5-bis-(3-methyl-pyridin-2-yl)-morpholine as a pale yellow oil (166 mg, 24%). $^1$H NMR (CDCl$_3$) δ 2.52 (s, 6H), 2.89 (d, 2H, J=6.0 Hz), 3.82 (dd, 2H, J=9.0, 3.0 Hz), 3.97 (t, 2H, J=16.0 Hz), 4.28 (dd, 2H, J=9.0, 3.0 Hz), 4.45 (d, 1H, J=18.0 Hz), 4.81 (d, 1H, J=12.0 Hz), 5.68-5.77 (m, 1H), 7.09 (dd, 2H, J=7.5, 4.5 Hz), 7.42 (d, 2H, J=6.0 Hz), 8.50 (d, 2H, J=3.0 Hz).

To a solution of the above amine (200 mg, 0.65 mmol) in CH$_2$Cl$_2$ (30 mL) was added 1,3-dimethylbarbituric acid (505 mg, 3.23 mmol) and Pd(PPh$_3$)$_4$ (81 mg, 0.07 mmol) and the reaction mixture was stirred overnight. The reaction mixture was quenched with saturated NaHCO$_3$ (20 mL) and extracted with CH$_2$Cl$_2$ (3×20 mL). The combined organic layers were dried (MgSO$_4$), filtered, and concentrated to afford an orange oil. Purification by radial chromatography on silica gel (1 mm plate; using MeOH/CH$_2$Cl$_2$; 1:100) afforded meso-3,5-bis-(3-methyl-pyridin-2yl)-morpholine as a pale yellow oil (97 mg, 55%).

To a solution of the above amine (97 mg, 0.36 mmol) and 2-(4-bromo-butyl)-isoindole-1,3-dione (203 mg, 0.72 mmol) in DMF (5 mL) was added DIPEA (0.16 mL, 0.90 mmol) and KI (7 mg, 0.04 mmol) according to General Procedure A. Purification by flash column chromatography on silica gel using MeOH/EtOAc (1:9) afforded 2-{4-meso-[3,5-bis-(3-methyl-pyridin-2-yl)-morpholin-4-yl]-butyl}-isoindole-1,3-dione as a pale yellow foam (56 mg, 34%). $^1$H NMR (CDCl$_3$) δ 0.78 (br s, 2H), 1.00-1.10 (m, 2H), 2.31 (t, 2H, J=7.5 Hz), 2.50 (s, 6H), 3.23 (t, 2H, J=7.5 Hz), 3.79 (dd, 2H, J=9.0, 3.0

Hz), 4.08 (t, 2H, J=7.5 Hz), 4.26 (dd, 2H, J=9.0, 3.0 Hz), 7.01 (dd, 2H, J=7.5, 4.8 Hz), 7.35 (d, 2H, J=7.5 Hz), 7.68-7.73 (m, 2H), 7.76-7.80 (m, 2H), 8.41 (d, 2H, J=3.9 Hz).

To a solution of the above amine (56 mg, 0.12 mmol) in EtOH (2 mL) was added hydrazine (30 µL, 0.85 mmol) and the reaction mixture was stirred overnight. The solvent was removed under reduced pressure to afford a pale yellow solid. Purification by radial chromatography on silica gel (1 mm plate; using NH$_4$OH/CH$_3$OH/CH$_2$Cl$_2$; 1:1:25→1:1:10) afforded 4-meso-[3,5-bis-(3-methyl-pyridin-2-yl)-morpholin-4-yl]-butylamine as a pale yellow oil (33 mg, 81%).

To a solution of the above amine (33 mg, 0.10 mmol) in HOAc (2 mL) was added HBr saturated HOAc (2 mL) according to General Procedure B. After drying in vacuo overnight, a pale yellow solid (58 mg) was isolated. $^1$H NMR (D$_2$O) δ 1.24-1.34 (m, 4H), 2.41 (t, 2H, J=8.0 Hz), 2.66 (s, 6H), 2.76 (t, 2H, J=7.8 Hz, 3.55 (t, 2H, J=11.4 Hz), 4.23 (dd, 2H, J=12.0, 3.9 Hz), 4.87 (dd, 2H, J=10.5, 3.9 Hz), 7.97 (dd, 2H, J=7.8, 6.0 Hz), 8.48 (d, 2H, J=7.8 Hz), 8.75 (d, 2H, J=5.7 Hz). $^{13}$C NMR (D$_2$O) δ 17.27, 20.37, 25.04, 39.30, 52.17, 56.52, 69.57, 126.91, 138.53, 140.66, 149.15, 149.66. ES-MS m/z 341 [M$^+$H]$^+$. Anal. Calcd. for C$_{20}$H$_{28}$N$_4$O.3.0HBr.2.2H$_2$O.0.2C$_4$H$_{10}$O: C, 39.18; H, 5.91; N, 8.79; Br, 37.59. Found: C, 39.03; H, 5.78; N, 8.68; Br, 37.88.

EXAMPLE 117

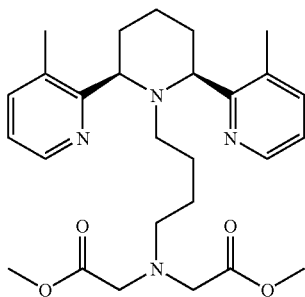

COMPOUND 117: Meso-{[4-(3,3"-dimethyl-3',4',5',6'-tetrahydro-2'H-[2,2';6',2"]terpyridin-1'-yl-buyl]-methoxycarbonylmethyl-amino}-acetic acid methyl ester To a solution of the 4-(3,3"-dimethyl-3',4',5',6',-tetrahydro-2'H-[2,2';6',2"]terpyridin-1'-yl)butylamine (544 mg, 1.61 mmol) in CH$_2$Cl$_2$ (30 mL) was added DIPEA (0.28 mL, 1.61 mmol) and methyl bromoacetate (0.14 mL, 1.45 mmol) according to General Procedure A. Purification by flash column chromatography on silica gel using MeOH/NH$_4$OH/CH$_2$Cl$_2$ (2:1:97) afforded the product as a yellow oil (248 mg, 32%). $^1$H NMR (CDCl$_3$) δ 0.59-0.70 (m, 4H), 1.54-1.63 (m, 3H), 1.96-2.16 (m, 7H), 2.50 (br s, 6H), 3.27 (s, 4H), 3.61 (s, 6H), 4.02 (br s, 2H), 7.03 (t, 2H, J=6.0 Hz), 7.38 (d, 2H, J=6.0 Hz), 8.38 (br s, 2H). $^{13}$C NMR (CDCl$_3$) δ 17.46, 19.07, 23.59, 25.67, 29.48, 30.43, 47.85, 50.62, 51.81, 54.47, 54.85, 60.75, 64.19, 71.45, 122.17, 132.08, 138.53, 139.64, 146.88, 160.55, 171.92. ES-MS m/z 483 [M$^+$H]$^+$. Anal. Calcd. for C$_{27}$H$_{38}$N$_4$O$_4$.0.2CH$_2$Cl$_2$.0.4H$_2$O: C, 64.46; H, 7.80; N, 11.05. Found: C, 64.79; H, 7.81; N, 11.14.

EXAMPLE 118

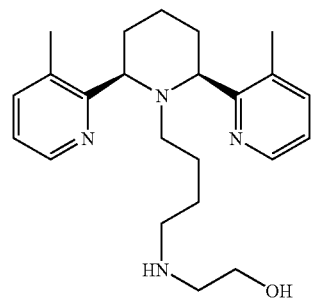

COMPOUND 118: Meso-2-[4-(3,3"-dimethyl-3',4',5',6'-tetrahydro-2'H-[2,2';6',2"]terpyridin-2'-yl)-butylamino]-ethanol To a solution of meso-[4-(3,3"-dimethyl-3',4',5',6',-tetrahydro-2'H-[2,2';6',2"]terpyridin-1'-yl)-butylamino]-acetic acid methyl ester (63 mg, 0.15 mmol) in THF (2 mL) was added LiAlH$_4$ (29 mg, 0.77 mmol). After 1 h, the reaction mixture was quenched with saturated NH$_4$Cl (10 mL) and extracted with 2% MeOH/CH$_2$Cl$_2$ (4×20 mL). The combined organic layers were dried (Na$_2$SO$_4$), filtered, and concentrated to afford a yellow oil. Purification by radial chromatography on silica gel (1 mm plate; using CH$_2$Cl$_2$/MeOH/NH$_4$OH; 50:1:1→25:1:1) afforded the product as a yellow oil (23 mg, 40%). $^1$H NMR (CDCl$_3$) δ 1.54-1.67 (m, 4H), 1.94-2.05 (m, 8H), 2.48 (s, 6H), 2.88-2.95 (m, 4H), 3.48-3.54 (m, 2H), 4.02 (d, 2H, J=12.0 Hz), 7.05-7.09 (m, 2H), 7.42 (d, 2H, J=6.0 Hz), 8.45 (br s, 2H). $^{13}$C NMR (D$_2$O) δ 19.21, 23.05, 25.45, 27.80, 31.49, 48.97, 50.61, 51.04, 53.82, 60.98, 63.54, 71.27, 122.17, 131.32, 138.75, 139.72, 147.21, 160.88. ES-MS m/z 383 [M$^+$H]$^+$. Anal. Calcd. for C$_{23}$H$_{34}$N$_4$O.1.5H$_2$O: C, 67.45; H, 9.1 1; N, 13.68. Found: C, 67.42; H, 8.74; N, 13.89.

EXAMPLE 119

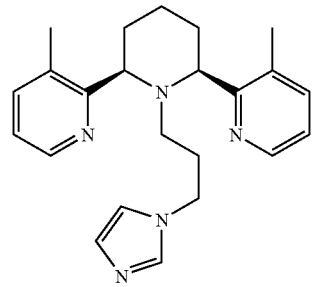

COMPOUND 119: 1'-(2-imidazol-1-yl-ethyl)-3,3"-dimethyl-1',2',3',4',5',6'-hexahydro-[2,2';6',2"]terpyridine (HBr salt)

To a solution of imidazole (1.33 g, 19.54 mmol) in THF (40 mL) was added NaH (60%, 0.94 g, 23.45 mmol) and 1,2- dibromoethane (5.1 mL, 58.61 mmol) and the reaction mixture was stirred overnight. Then the mixture was quenched with H$_2$O (25 mL) and extracted with CH$_2$Cl$_2$ (2×30 mL). The combined organic layers were dried (MgSO$_4$), filtered, and concentrated to afford a pale yellow oil (1.31 g), which was used without any further purification.

A mixture of the above bromide (1.31 g, 7.48 mmol), meso-4-(3,3'-dimethyl-3',4',5',6'-tetrahydro-2'H-[2,2';6',2"]terpyridin-1'-yl)-butylamine (0.67 g, 2.49 mmol), DIPEA (0.65 mL, 3.74 mmol), and KI (41 mg, 0.25 mmol) in DMF (5 mL) were stirred according to General Procedure A. Purification by flash column chromatography on silica gel using MeOH/NH$_4$OH/CH$_2$Cl$_2$ (2:1:97), followed by purification by radial chromatography on silica gel (1 mm plate; using CH$_2$Cl$_2$/MeOH/NH$_4$OH; 50:1:1→25:1:1) afforded 1'-(2-imidazol-1-yl-ethyl)-3,3"-dimethyl-1',2',3',4',5',6'-hexahydro-[2,2';6',2"]terpyridine as a yellow oil (38 mg 1% (over two steps)). $^1$H NMR (CDCl$_3$) δ 1.61-1.73 (m, 2H), 2.22-2.35 (m, 2H), 2.48 (s, 6H), 2.69 (s, 4H, J=9.0 Hz), 2.88 (s, 2H), 4.19 (d, 2H, J=12.0 Hz), 5.90 (s, 1H), 6.52 (s, 1H), 6.67 (s, 1H), 7.14 (dd, 2H, J=7.5, 4.8 Hz), 7.47 (dd, 2H, J=7.7, 0.6 Hz), 8.48 (d, 2H, J=3.9 Hz).

To a solution of the above amine (38 mg, 0.11 mmol) in HOAc (2 mL) was added a HBr saturated solution of HOAc (2 mL) according to General Procedure B. After drying in vacuo overnight, a sticky orange solid (60 mg) was isolated. $^1$H NMR (D$_2$O) δ 1.52-1.64 (m, 2H), 1.71-1.84 (m, 1H), 1.97-2.02 (m, 1H), 2.20 (d, 2H, J=12.0 Hz), 2.61 (s, 6H), 2.89 (t, 2H, J=7.5 Hz), 4.21 (t, 2H, J=7.5 Hz), 4.71 (s, 2H), 7.06 (s, 1H), 7.34 (s, 1H), 7.95 (dd, 2H, J=7.8, 6.0 Hz), 8.47 (s, 1H), 8.50 (d, 2H, J=6.9 Hz), 8.71 (d, 2H, J=5.7 Hz). $^{13}$C NMR (D$_2$O) δ 17.18, 22.15, 32.65, 44.27, 52.06, 58.56, 120.77, 121.79, 126.49, 135.07, 137.21, 140.37, 150.07, 153.40. ES-MS m/z 362 [M$^+$H]$^+$. Anal. Calcd. for C$_{22}$H$_{27}$N$_5$.3.4HBr.3.2H$_2$O.0.5C$_4$H$_{10}$O: C, 39.42; H, 5.76; N, 9.58; Br, 37.15. Found: C, 39.50; H, 5.70; N, 9.66; Br, 37.10.

EXAMPLE 120

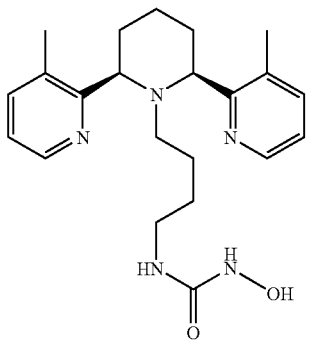

COMPOUND 120: [4-(3,3"-Dimethyl-3',4',5',6'-tetrahydro-2'H-[2,2';6',2"]terpyridin-1'-yl)-butyl]-hydroxyurea To a solution of 4-(3,3"-dimethyl-3',4',5',6'-tetrahydro-2'H-[2,2';6',2"]terpyridine-1'-yl)-butylamine (105 mg, 0.31 mmol) in THF (5 mL) was added 1,1'-carbonyldiimidazole (80 mg, 0.49 mmol) and after 40 min, the mixture was concentrated in vacuo. The residue was re-dissolved in DMF (5 mL) and treated with DIPEA (0.43 mL, 2.45 mmol) and NH$_2$OH.H$_2$O salt (136 mg, 1.96 mmol) and the reaction mixture was stirred overnight. Then the mixture was diluted with CH$_2$Cl$_2$ (25 mL) and washed with brine (5×15 mL). The organic layer was dried (MgSO$_4$), filtered, and concentrated to afford a pale yellow oil. Purification by radial chromatography on silica gel (1 mm plate; using CH$_2$Cl$_2$/MeOH/NH$_4$OH; 25:1:1→10:1:1) afforded the product as a white foam (54 mg, 44%). $^1$H NMR (CDCl$_3$) δ 0.78 (br s, 4H), 1.53-1.68 (m, 3H), 1.92-2.07 (m, 3H), 2.14 (br s, 2H), 2.44 (s, 6H), 2.72 (br s, 3H), 3.96 (d, 2H), J=9.0 Hz), 5.64 (s, 1H), 7.08 (dd, 2H, J=6.0, 3.0 Hz), 7.44 (d, 2H, J=6.0 Hz), 8.46 (s, 3H), 10.35 (s, 1H). $^{13}$C NMR (CDCl$_3$) δ 19.23, 23.18, 25.48, 27.98, 31.87, 39.16, 51.27, 53.81, 64.16, 71.47, 122.42, 131.42, 139.24, 147.06, 160.33, 162.15. ES-MS m/z 398 [M$^+$H]$^+$. Anal. Calcd. for C$_{22}$H$_{31}$N$_5$O$_2$.0.3CH$_2$Cl$_2$: C, 63.32; H, 7.53; N, 16.56. Found: C, 63.13; H, 7.68; N, 16.46.

EXAMPLE 121

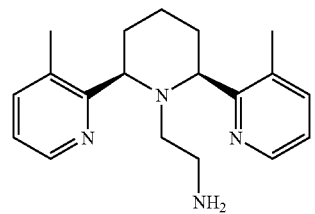

COMPOUND 121: 2-(3,3"-Dimethyl-3',4',5',6'-tetrahydro-2'H-[2,2';6',2"]terpyridin-1'-yl)-ethylamine To a solution of the N-(2-hydroxy-ethyl)-2-nitro-benzenesulfonamide (2.0 g, 8.12 mmol) and Et$_3$N (1.35 mL, 9.74 mmol) in CH$_2$Cl$_2$ (20 mL) at −20° C. was added a solution of MsCl (0.63 mL, 8.12 mol) in CH$_2$Cl$_2$ (5 mL) dropwise (via syringe pump) over 45 min. After addition, the mixture was stirred for 20 min at −20° C. Then the reaction was washed with saturated NH$_4$Cl (2×50 mL) and brine (2×50 mL), dried (MgSO$_4$), filtered, and concentrated to afford a yellow oil (2.0 g, 86%). $^1$H NMR (CDCl$_3$) δ 3.03 (s, 3H), 3.51 (q, 2H, J=6.0 Hz), 4.30 (t, 2H, J=4.5 Hz), 5.82 (t, 1H, J=6.0 Hz), 7.76-7.79 (m, 2H), 7.90-7.91 (m, 1H), 8.13-8.16 (m, 1H).

To a solution of the above methanesulfonic acid 2-(2-nitro-benzenesulfonylamine)-ethyl ester (2.03 g, 6.95 mmol) in benzene (20 mL) was added a solution of KOH (1.95 g, 34.73 mmol) in H$_2$O (8 mL) rapidly. After 2 h, H$_2$O (15 mL) was added and the phases were separated. The organic layer was dried (MgSO$_4$), filtered, and concentrated to afford 1-(2-nitro-benzenesulfonyl)-aziridine as a yellow oil (0.88 g, 55%). $^1$H NMR (CDCl$_3$) δ 2.63 (s, 4H), 7.74-7.80 (m, 3H), 8.20-8.22 (m, 1H).

A solution of meso-4-(3,3'-dimethyl-3',4',5',6'-tetrahydro-2'H-[2,2';6',2"]terpyridin-1'-yl)-butylamine (550 mg, 2.06 mmol), nosyl aziridine (470 mg, 2.06 mmol), and DIPEA (0.57 mL, 3.30 mmol) in THF (10 mL) was stirred at room temperature for 3 d. Then the mixture was concentrated in vacuo, and the residue was dissolved in CH$_2$Cl$_2$ (20 mL) and washed with saturated NaHCO$_3$ (3×20 mL). The organic layer was dried (MgSO$_4$), filtered, and concentrated to afford a yellow solid. Purification by flash column chromatography on silica gel using 5% MeOH/CH$_2$Cl$_2$ afforded the product impurely as a yellow solid (650 mg, 64%), which was used without further purification.

To a solution of the above amine (650 mg, 1.31 mmol) in CH₃CN (13 mL) was added K₂CO₃ (1.09 g, 7.86 mmol) and thiophenol (0.74 mL, 7.21 mmol). After 2 h, the mixture was diluted with CH₂Cl₂ (20 mL) and H₂O (20 mL). The aqueous layer was extracted with CH₂Cl₂ (2×20 mL). The combined organic layers were dried (MgSO₄), filtered, and concentrated to afford a bright yellow oil. Purification by flash column chromatography on silica gel using MeOH/CH₂Cl₂ (2%→5%) afforded the product as a yellow foam (309 mg, 48% (over two steps)). $^1$H NMR (CDCl₃) δ 1.62 (m, 2H), 1.70-1.78 (m, 3H), 1.91-1.93 (m, 1H), 2.15-2.20 (m, 2H), 2.39-2.44 (m, 8H), 4.07 (d, 2H, J=9.0 Hz), 7.18 (dd, 2H, J=6.0, 3.0 Hz), 7.53 (d, 2H, J=6.0 Hz), 8.60 (d, 2H, J=3.0 Hz), 9.36 (br s, 2H). $^{13}$C NMR (CDCl₃) d 19.22, 25.12, 30.06, 34.19, 35.53, 49.86, 66.77, 123.06, 127.53, 127.86, 129.43, 131.37, 139.75, 140.12, 140.48, 147.47, 160.07. ES-MS m/z 311 [M⁺H]⁺. Anal. Calcd. for C₁₉H₂₆N₄.0.8CH₂Cl₂.1.3H₂O: C, 59.19; H, 7.58; N, 13.94. Found: C, 59.46; H, 7.59; N, 14.10.

EXAMPLE 122

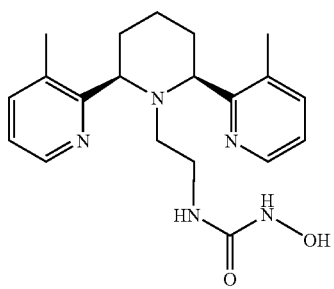

COMPOUND 122: [2-(3,3''-Dimethyl-3',4',5',6'-tetrahydro-2'H-[2,2';6',2'']terpyridin-1'-yl)-ethyl]hydroxyurea To a suspension of 2-(3,3''-dimethyl-3',4',5',6'-tetrahydro-2'H-[2,2';6',2'']terpyridin-1'-yl)-ethylamine (84 mg, 0.27 mmol) in THF (3 mL) was added 1,1'-carbonyldiimidazole (44 mg, 0.27 mmol) and the mixture was heated to 60° C. After 2 h, the mixture was concentrated in vacuo. The residue was re-dissolved in DMF (3 mL) and treated with DIPEA (0.13 mL, 1.35 mmol) and NH₂OH.HCl (75 mg, 1.08 mmol) and the reaction mixture was stirred overnight. Then the mixture was diluted with CH₂Cl₂ (20 mL) and washed with brine (5×15 mL). The organic layer was dried (MgSO₄), filtered, and concentrated to afford a yellow oil. Purification by radial chromatography on silica gel (1 mm plate; using CH₂Cl₂/MeOH/NH₄OH; 25:1:1) afforded the product as a white solid (27 mg, 27%). $^1$H NMR (CDCl₃) δ 1.53-1.57 (m, 1H), 1.70 (d, 2H, J=15.0 Hz), 1.92-2.09 (m, 5H), 2.43-2.45 (m, 8H), 3.86 (d, 2H, J=9.0 Hz), 4.70 (br s, 1H), 6.43 (br s, 1H), 7.09 (dd, 2H, J=6.0, 3.0 Hz), 7.46 (d, 2H, J=9.0 Hz), 8.53 (d, 2H, J=3.0 Hz), 10.07 (br s, 1H). $^{13}$C NMR (CDl₃) δ 19.33, 24.96, 33.13, 38.80, 55.54, 66.00, 122.70, 130.80, 139.36, 147.73, 161.02, 162.06. ES-MS m/z 370 [M⁺H]⁺. Anal. Calcd. for C₂₀H₂₇N₅O₂.0.2CH₂Cl₂: C, 62.78; H, 7.15; N, 18.12. Found: C, 62.86; H, 7.46; N, 17.97.

EXAMPLE 123

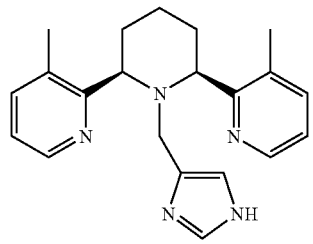

COMPOUND 123: 1'-(1H-imidazol-4-ylmethyl)-3,3''-dimethyl-1',2',3',4',5',6'-hexahydro-[2,2';6',2'']terpyridine To a solution of 4-(hydroxymethyl)imidazole hydrochloride salt (526 mg, 3.91 mmol) in DMF (5 mL) was added DIPEA (2.04 mL, 11.73 mmol) and SEM-chloride (0.82 mL, 4.69 mmol). After 3 h, the reaction mixture was diluted with EtOAc (25 mL) and washed with water (2×20 mL) and brine (2×20 mL). The organic layer was dried (MgSO₄), filtered, and concentrated to afford a yellow oil. Purification by flash column chromatography on silica gel using MeOH/NH₄OH/CH₂Cl₂ (3:1:96) afforded [3-(2-trimethylsilanyloxy-ethoxymethyl)-3H-imidazol-4-yl]-methanol as a yellow oil (354 mg, 40%). $^1$H NMR (CDCl₃) δ −0.01 (s, 9H), 0.88-0.94 (m, 2H), 2.60-2.62 (br m, 1H), 3.45-3.53 (m, 2H), 4.67 (br s, total 2H), 5.23 and 5.36 (s total 2H), 6.99 and 7.04 (s, total 1H), 7.55 and 7.56 (s, total 1H).

To a solution of the above alcohol (354 mg, 1.55 mmol) in CH₂Cl₂ at 0° C. was added Et₃N (0.43 mL, 3.10 mmol) and MsCl (0.13 mL, 2.33 mmol) according to General Procedure F. No further purification afforded a yellow oil (270 mg).

A suspension of the above mesylate (270 mg, 0.88 mmol), meso-4-(3,3'-dimethyl-3',4',5',6'-tetrahydro-2'H-[2,2';6',2''] terpyridin-1'-yl)-butylamine (236 mg, 0.88 mmol), DIPEA (0.23 mL, 1.32 mmol), and KI (15 mg, 0.09 mmol) in DMF (10 mL) was stirred together according to General Procedure A. Purification by flash column chromatography using MeOH/NH₄OH/CH₂Cl₂ (2:1:97) afforded the product as a yellow oil (110 mg).

A solution of the above amine (110 mg, 0.23 mmol) in 6N HCl (10 mL) was stirred at 60° C. After 3 h, the reaction mixture was cooled and basified to pH=10-11 with solid K₂CO₃. Then it was extracted with CH₂Cl₂ (4×30 mL). The combined organic layers were dried (MgSO₄), filtered, and concentrated to afford a pale yellow solid. Purification by radial chromatography on silica gel (1 mm plate; using CH₂Cl₂/MeOH/NH₄OH; 50:1:1→25:1:1) afforded the product as a white solid (34 mg, 43%). $^1$H NMR (CDCl₃) δ 1.44-1.57 (m, 1H), 1.73 (d, 2H, J=12.0 Hz), 1.89-2.04 (m, 3H), 2.47 (br s, 6H), 3.31 (s, 2H), 3.84 (br d, 2H, J=12.0 Hz), 6.02 (br s, 1H), 7.07 (br s, 2H), 7.41-7.43 (m, 3H), 8.42 (d, 2H, J=3.0 Hz). $^{13}$C NMR (CDCl₃) δ 19.34, 25.26, 31.80, 32.36, 46.07, 70.19, 121.87, 122.53, 126.77, 135.13, 137.96, 147.04, 160.63. ES-MS m/z 348 [M⁺H]⁺. Anal. Calcd. for C₂₁H₂₅N₅.0.8H₂O: C, 69.70; H, 7.41; N, 19.35. Found: C, 69.78; H, 7.41; N, 19.01.

EXAMPLE 124

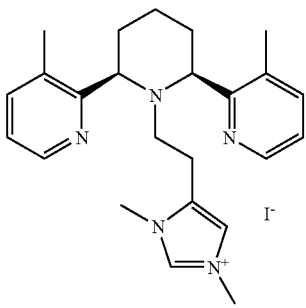

COMPOUND 124: 4-[2-(3,3''-Dimethyl-3',4',5',6',-tetrahydro-2'H-[22 ';6',2'']terpyridin-1'-yl)-ethyl]-1,3-dimethyl-3H-imidazol-1-ium iodide To a solution of 1'-[2-(3H-imidazol-4-yl)-ethyl]-3,3''-dimethyl-1',2',3',4',5',6'-hexahydro-[2,2';6',2'']terpyridine (223 mg, 0.62 mmol) in THF (6 mL) at 0° C. was added NaH (60%, 27 mg, 0.68 mmol) and MeI (40 µL, 0.62 mmol). The reaction mixture was warmed to room temperature and stirred overnight. The mixture was filtered in vacuo and the filtrate was concentrated to afford an orange foam. Purification by radial chromatography on silica gel (2 mm plate; using $CH_2Cl_2$/MeOH/$NH_4OH$; 50:1:1→5:1:1) afforded the product as a yellow oil (103 mg, 32%). $^1$H NMR ($CDCl_3$) δ 1.55-1.66 (m, 2H), 1.79-1.81 (m, 1H), 1.92-2.11 (m, 3H), 2.44 (s, 6H), 3.12 (m, 2H), 3.39 (s 2H), 3.78 (s, 3H), 4.04 (d, 2H, J=9.0 Hz), 6.42 (s, 1H), 7.11-7.15 (m, 2H), 7.49 (d, 2H, J=9.0 Hz), 8.42 (br s, 2H), 9.45 (s, 1H). $^{13}$C NMR ($CDCl_3$) δ 19.36, 23.41, 25.13, 30.22, 33.43, 36.98, 50.01, 65.09, 71.21, 120.00, 122.95, 131.97, 134.07, 137.02, 139.19, 140.60, 146.69, 147.14, 160.05. ES-MS m/z 390 [M-I]$^+$. Anal. Calcd. for $C_{24}H_{33}N_5I.0.9H_2O.0.4CH_2Cl_2$: C, 51.89; H, 6.05; N, 12.30; I, 22.29. Found: C, 52.03; H, 6.45; N, 12.42; I, 22.14.

EXAMPLE 125

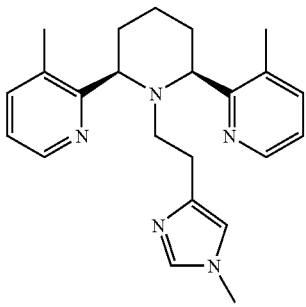

COMPOUND 125: 3,3''-Dimethyl-1'-[2-(1-methyl-1H-imidazol-4-yl)-ethyl]-1',2',3',4',5',6'-hexahydro-[2,2';6',2'']terpyridine To a solution of 1'-[2-(3H-imidazol-4-yl)-ethyl]-3,3''-dimethyl-1',2',3',4',5',6'-hexahydro-[2,2';6',2'']terpyridine (167 mg, 0.46 mmol) in THF (5 mL) at 0° C. was added NaH (60%, 7 mg, 0.17 mmol). After 30 min at 0° C., MeI (10 mL, 0.15 mmol) was added and the reaction mixture was warmed to room temperature and stirred overnight. The next day the mixture was concentrated to afford a yellow foam. Purification by radial chromatography on silica gel (1 mm plate; using $CH_2Cl_2$/MeOH/$NH_4OH$; 50:1:1→10:1:1) afforded the product as a yellow oil (23 mg, 41%). $^1$H NMR ($CDCl_3$) δ 1.57-1.72 (m, 3H), 1.94-2.16 (m, 3H), 2.48-2.53 (m, 8H), 3.41 (s, 3H), 3.71 (s, 2H), 4.13 (d, 2H, J=9.0 Hz), 5.94 (br 2, 1H), 7.02-7.06 (m, 3H), 7.40 (d, 2H, J=9.0 Hz), 8.45 (br s, 2H). $^{13}$C NMR ($CDCl_3$) δ 19.25, 23.34, 25.40, 32.42, 33.46, 50.08, 62.13, 115.93, 122.07, 132.50, 136.91, 138.83, 141.50, 147.32, 160.82. ES-MS m/z 376 [M$^+$H]$^+$. Anal. Calcd. for $C1753H_{29}N_5.1.4H_2O.0.4CH_2Cl_2$: C, 64.65; H, 7.56; N, 16.11. Found: C, 65.01; H, 7.67; N, 15.99.

EXAMPLE 126

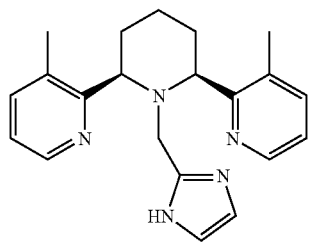

COMPOUND 126: 1'(1H-imidazol-2-ylmethyl)-3,3''-dimethyl-1',2',3',4',5',6'-hexahydro-[2,2';6',2''] terpyridine To a suspension of 2-imidazolecarboxaldehyde (1.01 g, 10.51 mmol) in $CH_2Cl_2$ (25 mL) was added $Et_3N$ (2.9 mL, 21.02 mmol) and tosyl chloride (3.01 g, 15.77 mmol) and the reaction mixture was heated to reflux overnight. Then the mixture was cooled and washed with saturated $NH_4Cl$ (4×30 mL). The organic layer was dried ($MgSO_4$), filtered, and concentrated to afford a dark brown oil. Purification by flash column chromatography on silica gel using 2% MeOH/$CH_2Cl_2$ afforded 1-(toluene-4-sulfonyl)-1H-imidazole-2-carbaldehyde as a yellow oil (1.53 g, 58%). $^1$H NMR ($CDCl_3$) δ 2.45 (s, 3H), 7.31 (s, 1H), 7.49 (d, 2H, J=6.0 Hz), 7.83 (s, 1H), 8.00 (d, 2H, J=7.5 hz), 9.78 (s, 1H).

To a solution of the above aldehyde (1.53 g, 6.11 mmol) in $CH_2Cl_2$ (50 mL) at 0° C. was added TFA (5 mL) as described in *J. Med. Chem.* (1997) 40:2196. Purification by flash column chromatography using EtOAc/hexane (1:1) afforded [1-(toluene-4-sulfonyl)-1H-imidazol-2-yl]-methanol as a white solid (0.55 g, 36%). $^1$H NMR ($CDCl_3$) δ 2.45 (s, 3H), 3.03 (br s, 1H), 4.84 (s, 2H), 6.99 (d, 1H, J=3.0 Hz), 7.35 (s, 1H), 7.39 (d, 2H, J=3.0 Hz), 7.83 (d, 2H, J=9.0 Hz).

To a solution of the above alcohol (0.55 g, 2.17 mmol) and $CBr_4$ (1.08 g, 3.26 mmol) in $CH_2Cl_2$ (25 mL) at 0° C. was added a solution of triphenylphosphine (0.68 g, 2.60 mmol) in $CH_2Cl_2$ (10 mL) as described in *J. Med. Chem.* (1997) 40, 14:2196. Purification by flash column chromatography using 25% EtOAc/hexanes afforded 2-bromomethyl-1-(toluene-4-sulfonyl)-1H-imidazole as a yellow oil (0.31 g, 45%). $^1$H NMR ($CDCl_3$) δ 2.45 (s, 3H), 4.81 (s, 2H), 7.04 (s, 1H), 7.37 (d, 2H, J=9.0 Hz), 7.42 (s, 1H), 7.92 (d, 2H, J=9.0 Hz).

A mixture of the above bromide (310 mg, 0.98 mmol), meso-4-(3,3'-dimethyl-3',4',5',6'-tetrahydro-2'H-[2,2';6',2"]terpyridin-1'-yl)-butylamine (88 mg, 0.33 mmol), DIPEA (0.23 mL, 1.32 mmol), and KI (5 mg, 0.03 mmol) in DMF (5 mL) was stirred together according to General Procedure A. Purification by flash column chromatography on silica gel using MeOH/CH$_2$Cl$_2$ (2%→5%) afforded the product as a yellow oil (76 mg, 46%).

To a solution of the above tosylate (76 mg, 0.15 mmol) in MeOH (1 mL) was added HOBT (82 mg, 0.61 mmol) and the reaction mixture was stirred overnight. Then the mixture was concentrated to afford a brown oil. Purification by radial chromatography on silica gel (1 mm plate; using CH$_2$Cl$_2$/MeOH/NH$_4$OH; 50:1:1→10:1:1) afforded the product as a yellow oil (32 mg, 59%). $^1$H NMR (CDCl$_3$) δ 1.54-1.63 (m, 1H), 1.73 (d, 2H, J=16.0 Hz), 1.91-1.21 (m, 3H), 2.44 (s, 6H), 3.40 (s, 2H), 3.96 (d, 2H, J=9.0 Hz), 6.49 (br s, 1H), 6.67 (br s, 1H), 6.94-6.99 (m, 2H), 7.37 (d, 2H, J=9.0 Hz), 8.35 (d, 2H, J=3.0 Hz). $^3$C NMR (CDCl$_3$) δ 19.42, 20.27, 33.11, 53.77, 65.87, 122.32, 131.49, 139.03, 147.13, 160.37. ES-MS m/z 347 [M$^+$H]$^+$. Anal. Calcd. for C$_{21}$H$_{25}$N$_5$·1.1H$_2$O: C, 68.68; H, 7.46; N, 19.07. Found: C, 68.49; H, 7.37; N, 19.27.

EXAMPLE 127

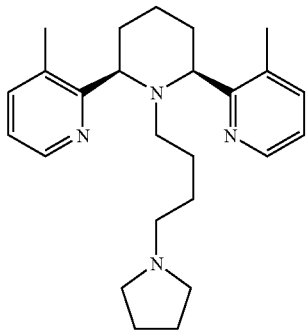

COMPOUND 127: 3,3"-dimethyl-1'-(4-pyrrolidine-1-yl-butyl)-1',2',3',4',5',6'-hexahydro-[2,2';6',2"]terpyridine To a solution of 4-(3,3"-dimethyl-3',4',5',6'-tetrahydro-2'H-[2,2';6'2"]terpyridin-1'-yl)-butyraldehyde (155 mg, 0.46 mmol) and pyrrolidine (50 μL, 0.55 mmol) in MeOH (5 mL), which had been pre-stirred together for 30 min, was added NaBH$_3$CN (58 mg, 0.92 mmol). The reaction mixture was stirred overnight, which was then concentrated in vacuo. The residue was dissolved in CH$_2$Cl$_2$ (20 mL) and washed with saturated NaHCO$_3$ (3×20 mL). The organic layer was dried (MgSO$_4$), filtered, and concentrated to afford a yellow oil. Purification by radial chromatography on silica gel (1 mm plate; using CH$_2$Cl$_2$/MeOH/NH$_4$OH (50:1:1) afforded the product as a yellow oil (34 mg, 19%). $^1$H NMR (CDCl$_3$) δ 0.81 (br s, 3H), 1.54-1.67 (m, 6H), 1.92-2.00 (m, 5H), 2.16-2.22 (m, 6H), 2.47 (br s, 5H), 2.64 (br s, 1H), 3.77 (s, 2H), 4.06 (d, 2H), J=12.0 Hz), 7.06 (dd, 2H, J=6.0, 3.0 Hz), 7.40 (d, 2H, J=6.0 Hz), 8.45(br s, 2H). ES-MS m/z 393 [M$^+$H]$^+$.

EXAMPLE 128

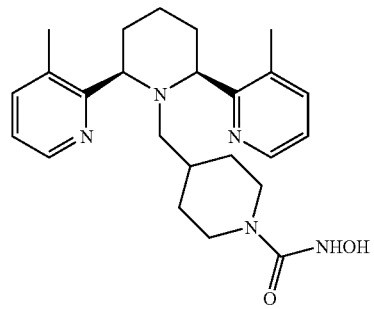

COMPOUND 128: 4-(3,3"-dimethyl-3',4',5',6'-tetrahydro-2'H-[2,2',6',2"]terpyridin-1'-ylmethyl)-piperidine-1-hydroxyurea To a solution of ethyl isonipectotate (2.0 mL, 12.99 mmol) in CH$_2$Cl$_2$ (20 mL) was added Et$_3$N (3.6 mL, 25.98 mmol) and p-toluenesulfonyl chloride (3.71 g, 19.48 mmol) and the reaction mixture was stirred overnight. Then the mixture was diluted with CH$_2$Cl$_2$ (10 mL) and washed with saturated NH$_4$Cl (3×30 mL). The organic layer was dried (MgSO$_4$), filtered, and concentrated to afford a yellow solid. Purification by flash column chromatography on silica gel using hexanes/EtOAc (3:1) afforded 1-(toluene-4-sulfonyl)-piperidine-4-carboxylic acid ethyl ester as a white solid (3.45 g, 85%).

To a solution of the above ester (1.29 g, 4.79 mmol) in CH$_2$Cl$_2$ (20 mL) at 0° C. was added a solution of LiAlH$_4$ in THF (1.0 M, 13.9 mL, 13.87 mmol) and the mixture was heated to reflux. After 1 h, the mixture was cooled back down to 0° C. and quenched with H$_2$O (0.51 mL), 15% NaOH (0.51 mL), and H$_2$O (1.53 mL). After stirring for 30 min, the reaction mixture was dried (MgSO$_4$), filtered, and concentrated to afford [1-(toluene-4-sulfonyl)-piperidin-4-yl]-methanol as a clear oil (1.24 g, 100%). $^1$H NMR (CDCl$_3$) δ 1.31-1.43 (m, 4H), 1.79 (d, 2H, J=12.0 Hz), 2.24 (t, 2H, J=12.0 Hz), 2.43 (s, 3H), 3.47 (d, 2H, J=6.0 Hz), 3.81 (d, 2H, J=12.0 Hz), 7.32 (d, 2H, J=6.0 Hz), 7.64 (d, 2H, J=6.0 Hz).

To a solution of the above alcohol (1.24 g, 4.79 mmol) in CH$_2$Cl$_2$ (20 mL) at 0° C. was added Et$_3$N (1.3 mL, 9.58 mmol) and MsCl (0.56 mL, 7.18 mmol) according to General Procedure F. No further purification afforded a pale yellow solid (1.49 g, 90%).

The above mesylate (485 mg, 1.40 mmol), meso-4-(3,3'-dimethyl-3',4',5',56'-tetrahydro-2'H-[2,2';6',2"]terpyridin-1'-yl)-butylamine (311 mg, 1.16 mmol), DIPEA (0.30 mL, 1.71 mmol), and KI (20 mg, 0.12 mmol) in DMF (5 mL) was stirred together according to General Procedure A. Purification by flash column chromatography on silica gel using MeOH/NH$_4$OH/CH$_2$Cl$_2$ (2:1:97) afforded 3,3"-dimethyl-1'-[1-(toluene-4-sulfonyl)-piperidin-4-ylmethyl]-1',2',3',4',5',6'-hexahydro-[2,2';6',2"]terpyridine as 77%). $^1$H NMR (CDCl$_3$) δ 0.11-0.22 (m, 2H), 1.00 (d, 2H, J=15.0 Hz), 1.51-1.69 (m, 5H), 2.04-2.08 (m, 1H), 2.25-2.36 (m, 4H), 2.45 (s, 3H), 2.50 (s, 6H), 3.18 (d, 2H, J=12.0 Hz), 3.64 (s, 1H), 4.10 (d, 2H, J=12.0 Hz), 7.01 (dd, 2H, J=6.0, 3.0 Hz), 7.25 (d, 2H, J=7.5 Hz), 7.35 (d, 2H, J=7.5 Hz), 7.45 (d, 2H, J=6.0 Hz), 8.33 (d, 2H, J=6.0 Hz).

The above tosylate (348 mg, 0.67 mmol) in HBr saturated HOAc (4 mL) was stirred overnight at 70° C. Then the reaction mixture was cooled and concentrated and the residue was dissolved in a minimum amount of $H_2O$ and basified to pH=11 using 10N NaOH. The aqueous phase was extracted with $CH_2Cl_2$ (5×20 mL). The combined organic layers were dried ($MgSO_4$), filtered, and concentrated to afford a brown oil. Purification by flash column chromatography on silica gel using $MeOH/NH_4OH/CH_2Cl_2$ (2:1:97) afforded 3,3'-dimethyl-1'-piperidin-4-ylmethyl-1',2',3',4',5',6'-hexahydro-[2,2';6',2"]terpyridine as a yellow oil (80 mg, 33%).

To a solution of the above amine (71 mg, 0.19 mmol) in THF (5 mL) was added hydroxyurea 4-nitrol-phenyl ester (46 mg, 0.23 mmol) and the reaction mixture was stirred at 70° C. After 2 h, the reaction was concentrated under reduced pressure. Purification by radial chromatography on silica gel (1 mm plate; using $CH_2Cl_2/MeOH/NH_4OH$; 50:1:1→25:1:1) afforded the product as a white solid (16 mg, 20%). $^1H$ NMR ($CDCl_3$) δ −0.46 (br m, 1H), 0.04 (br m, 1H), 1.07 (d, 2H, J=12.0 Hz), 1.55-1.71 (m, 3H), 2.01-2.35 (m, 12H), 2.50 (s, 6H), 3.45 (d, 2H, J=12.0 Hz), 4.12 (d, 2H, J=9.0 Hz), 6.47 (s, 1H), 7.09 (d, 2H, J=6.0, 3.0 Hz), 7.42 (d, 2H, J=6.0 Hz), 8.41 (d, 2H, J=6.0 Hz), $^{13}C$ NMR ($CDCl_3$) δ 0.39, 19.06, 25.74, 26.56, 29.73, 36.44, 43.64, 44.44, 53.82, 65.60, 122.55, 132.61, 138.26, 146.65, 160.35, 160.85. ES-MS m/z 424 $[M^+H]^+$. Anal. Calcd. for $C_{24}H_{33}N_5O_2 \cdot 1.2CH_2Cl_2$: C, 57.60; H, 6.79; N, 13.33. Found: C, 57.90; H, 6.82; N, 13.40.

EXAMPLE 129

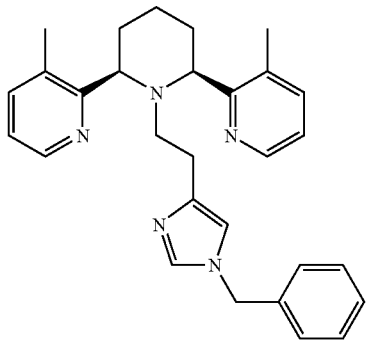

COMPOUND 129: 1'-[2-(1-Benzyl-1H-imidazol-4-yl)-ethyl]-3,3"-dimethyl-1',2',3',4',5',6'-hexahydro-[2,2';6',2"]terpyridine To a solution of 1'-[2-(3H-imidazol-4-yl)-ethyl]-3,3"-dimethyl-1',2',3',4',5',6'-hexahydro-[2,2';6',2"]terpyridine (191 mg, 0.53 mmol) in THF (5 mL) at 0° C. was added NaH (60%, 8 mg, 0.20 mmol). After stirring at 0° C. for 30 min, benzyl bromide (21 μL, 0.18 mmol) was added and the resulting mixture was stirred overnight at room temperature. The next morning the mixture was concentrated under reduced pressure to afford a brown residue. Purification by radial chromatography on silica gel (1 mm plate; using $CH_2Cl_2/MeOH/NH_4OH$; 50:1:1→10:1:1) afforded the product as a yellow oil (39 mg, 48%). $^1H$ NMR ($CDCl_3$) δ 1.57-1.70 (m, 3H), 1.93-2.16 (m, 5H), 2.46 (br s, 8H), 4.12 (d, 2H, J=9.0 Hz), 4.36 (s, 2H), 4.83 (s, 2H), 5.94(s, 1H), 6.99 (br s, 4H), 7.17 (s, 1H), 7.28 (s, 3H), 7.36 (d, 2H, J=9.0 Hz), 8.42 (s, 2H). $^{13}C$ NMR ($CDCl_3$) δ 19.23, 23.41, 25.39, 32.47, 50.23, 50.97, 62.04, 115.12, 122.07, 127.64, 128.49, 129.23, 136.52, 138.84, 147.33, 160.82. ES-MS m/z 452 $[M^+H]^+$. Anal. Calcd. for $C_{29}H_{33}N_5 \cdot 0.5CH_2Cl_2$: C, 71.71; H, 6.94; N, 14,17. Found: C, 71.78; H, 7.23; N, 14.10.

EXAMPLE 130

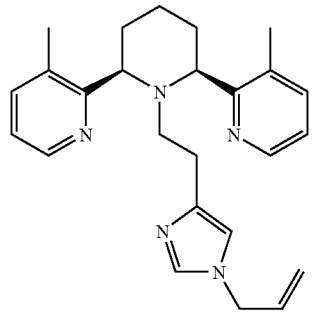

COMPOUND 130: 1'-[2-(1-Allyl-1H-imidazol-4-yl)-ethyl]-3,3"-dimethyl-1',2',3',4',5',6'-hexahydro-[2,2';6',2"]terpyridine To a solution of 1'-[2-(3H-imidazol-4-yl)-ethyl]-3,3"-dimethyl-1',2',3',4',5',6'-hexahydro-[2,2';6',2"]terpyridine (202 mg, 0.56 mmol) in THF (5 mL) at 0° C. was added NaH (60%, 8 mg, 0.21 mmol). After 30 min at 0° C., allyl bromide (16 mL, 0.19 mmol) was added. After 4 h, the reaction mixture was concentrated to afford an orange solid. Purification by radial chromatography on silica gel (2 mm plate; using $CH_2Cl_2/CH_3OH/NH_4OH$; 50:1:1→10:1:1) afforded the product as a pale yellow oil (25 mg, 33%). $^1H$ NMR ($CDCl_3$) δ 1.58-1.73 (m, 3H), 1.95-2.08 (m, 3H), 2.38-2.48 (m, 8H), 2.93 (s, 2H), 4.14 (d, 2H, J=9.0 Hz), 4.27 (d, 2H, J=6.0 Hz), 5.02 (d, 1H, J=18.0 Hz), 5.16 (d, 1H, J=9.0 Hz), 5.71-5.84 (m, 1H), 5.96 (s, 1H), 7.06 (dd, 2H, J=6.0, 3.0 Hz), 7.12 (s, 1H), 7.40 (d, 2H, J=9.0 Hz), 8.46 (s, 2H). $^{13}C$ NMR ($CDCl_3$) δ 19.21, 23.68, 25.45, 30.08, 31.94, 49.56, 62.43, 114.86, 118.69, 122.07, 131.27, 133.15, 136.13, 138.79, 141.84, 147.25, 160.74. ES-MS m/z 402 $[M^+H]^+$. Anal. Calcd. for $C_{25}H_{31}N_5 \cdot 1.5H_2O$: C, 70.06; H, 8.00; N, 16.34. Found: C, 70.19; H, 7.98; N, 16.05.

EXAMPLE 131

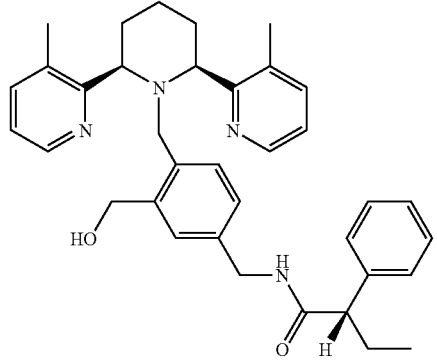

COMPOUND 131: N-[4-(3,3"-dimethyl-3',4',5',6'-tetrahydro-2'H-[2,2';6',2"]-terpyridin-1'-ylmethyl)-3-hydroxymethyl-benzyl]-2-phenyl-butyramide To a solution of 3,3"-dimethyl-1',2',3',4',5',6'-hexahydro-[2,2';6',2"]terpyridine (0.500 g, 1.87 mmol) dissolved in CH₃CN (10 mL) was added 2-bromomethyl-5-cyano-benzoic acid methyl ester (0.500 g, 1.96 mmol) and K₂CO₃ (0.720 g, 5.61 mmol). The mixture was stirred for 15 hours at 80° C. under a positive pressure of N₂. The mixture was concentrated in vacuo, quenched with saturated aqueous NaCl (25 mL) and extracted with CH₂Cl₂ (3×30 mL). The combined organic extracts were dried (Na₂SO₄), filtered, and concentrated in vacuo to give a brown oil which was used without purification.

The brown oil from the previous step was dissolved in MeOH (10 mL) followed by the slow addition of LiBH₄ (0.411 g, 18.7 mmol) to ensure the reaction mixture did not bubble over. The mixture was stirred at room temperature for 16 hours. The mixture was concentrated in vacuo, redissolved in CH₂Cl₂ (30 mL) and quenched with saturated aqueous NaHCO₃ (30 mL). The resulting mixture was extracted with CH₂Cl₂ (3×40 mL) and the combined organic extracts were dried (Na₂SO₄), filtered, and concentrated in vacuo to afford a yellow foam. Purification via column chromatography on silica gel (CH₂Cl₂:MeOH:NH₄OH, 92:5:3, v/v/v) afforded 4-(3,3"-dimethyl-3',4',5',6'-tetrahydro-2'H-[2,2';6',2"]terpyridin-1'-ylmethyl)-3-hydroxymethyl-benzonitrile as a white foam (0.610 g, 80%, 2-steps). ¹H NMR (CDCl₃) δ 1.58-1.69 (m, 3H), 2.05 (m, 1H), 2.29-2.41 (m, 2H), 2.48 (s, 6H), 3.67 (s, 2H), 4.11 (d, 2H, J=12.0 Hz), 4.44 (s, 2H), 5.13 (br s, 1H), 6.85 (dd, 2H, J=6.0, 4.5 Hz), 6.92 (s, 2H), 7.23 (s+d, 3H), 8.16 (d, 2H, J=3.0 Hz).

To a solution of 4-(3,3"-dimethyl-3',4',5',6'-tetrahydro-2'H-[2,2';6',2"]terpyridin-1'-ylmethyl)-3-hydroxymethyl-benzonitrile (0.610 g, 1.48 mmol) dissolved in MeOH (12 mL) ammonia gas was bubbled for 10 minutes. A pre-washed mixture of Raney Nickel (~1.5 grams) was added to the nitrile and the mixture was shaken on the hydrogenator at 45 psi for 2.5 hours. The mixture was filtered through a sintered glass funnel containing a celite plug and the filtrated was concentrated in vacuo to a green foam. Purification by column chromatography on silica gel (CH₂Cl₂:MeOH:NH₄OH, 87:8:5, v/v/v) afforded [5-aminomethyl-2-(3,3"-dimethyl-3',4',5',6'-tetrahydro-2'H-[2,2';6',2"]-terpyridin-1'-ylmethyl)-phenyl]-methanol as a white foam (0.540 g, 88% ). ¹H NMR (CDCl3) δ 1.25 (br s, 1H), 1.62-1.72 (m, 3H), 2.03 (m, 1H), 2.32 (m, 2H), 2H), 2.49 (s, 6H), 2.81 (br s, 1H), 3.55 (s, 2H), 3.62 (s, 1H), 4.01 (d, 2H, J=9.0 Hz), 4.34 (s, 2H), 5.18 (br s, 1H), 6.59 (d, 1H, J=9.0 Hz), 6.72 (d, 1H, J=9.0 Hz), 6.83 (m, 3H), 7.23 (d, 2H, J=9.0 Hz), 8.22 (d, 2H, J=3.0 Hz).

[5-Aminomethyl-2-(3,3"-dimethyl-3',4',5',6'-tetrahydro-2'H-[2,2';6',2"]terpyridin-1'-ylmethyl)-phenyl]-methanol (0.121 g, 0.29 mmol), S-(⁺)-2-phenylbutyric acid (54 μL, 0.35 mmol), HOBT (0.047 g, 0.35 mmol), EDCI (0.067 g, 0.35 mmol) and DIPEA (61 μL, 0.35 mmol) in CH₂Cl₂ (8 mL) were reacted according to General Procedure G. Purification by column chromatography on silica gel (CH₂Cl₂:MeOH: NH₄OH, 94:5:1, v/v/v) afforded N-[4-(3,3"-dimethyl-3',4',5', 6'-tetrahydro-2'H-[2,2';6',2"]-terpyridin-1'-ylmethyl)-3-hydroxymethyl-benzyl]-2-phenyl-butyramide as a white solid (0.120 g, 73%). ¹H NMR (CDCl₃) δ 0.86 (t, 3H, J=7.5 Hz), 1.59-1.76 (m, 3H), 2.04 (m, 1H), 2.32 (m, 2H), 2.49 (s, 6H), 3.62 (s, 2H), 4.00-4.09 (m, 4H), 4.32 (s, 2H), 5.07 (br s, 1H), 5.35 (br s, 1H), 6.44 (d, 1H, J=7.5 Hz), 6.63 (d, 2H, J=9.0 Hz), 6.75 (m, 2H), 7.13-7.33 (m, 7H), 8.22 (d, 2H, J=3.0 Hz). HPLC: 94% . ES-MS m/z 563 [M⁺H]⁺, 585 [M⁺Na]⁺.

EXAMPLE 132

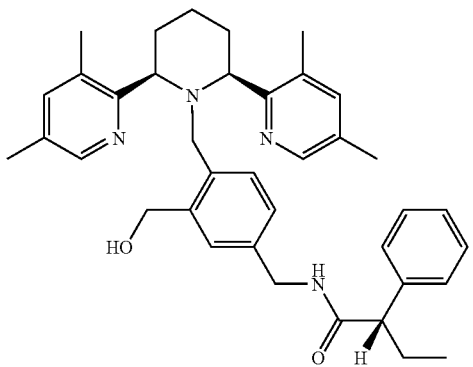

COMPOUND 132: N-[3-hydroxymethyl-4-(3,5,3", 5"-tetramethyl-3',4',5',6'-tetrahydro-2'H-[2,2';6',2"] terpyridin-1'-ylmethyl)-benzyl]-2-phenyl-butyramide To a solution of 3,5,3",5"-tetramethyl-1',2',3',4',5',6'-hexahydro-[2,2';6',2"]-terpyridine (0.130 g, 0.44 mmol) dissolved in CH₃CN (5 mL) was added 2-bromomethyl-5-cyano-benzoic acid methyl ester (0.117 g, 0.46 mmol) and K₂CO₃ (0.169 g, 1.32 mmol). The mixture was stirred for 15 hours at 80° C. under a positive pressure of N₂. The mixture was concentrated in vacuo, quenched with saturated aqueous NaCl (25 mL) and extracted with CH₂Cl₂ (3×30 mL). The combined organic extracts were dried (Na₂SO₄), filtered, and concentrated in vacuo to give a yellow oil which was used without purification.

The yellow oil from the previous step was dissolved in MeOH (5 mL) followed by the slow addition of LiBH₄ (0.097 g, 4.41 mmol) to ensure the reaction mixture did not bubble over. The mixture was stirred at room temperature for 16 hours. The mixture was concentrated in vacuo, redissolved in CH₂Cl₂ (30 mL) and quenched with saturated aqueous NaHCO₃ (30 mL). The resulting mixture was extracted with CH₂Cl₂ (3×40 mL) and the combined organic extracts were dried (Na₂SO₄), filtered, and concentrated in vacuo to afford a yellow oil. Purification via column chromatography on silica gel (CH₂Cl₂:MeOH:NH₄OH, 92:5:3, v/v/v) afforded 3-hydroxymethyl-4-(3,5,3",5"-tetramethyl-3',4',5',6'-tetrahydro-2'H-[2,2';6',2"]terpyridin-1'-ylmethyl)benzonitrile as a yellow oil (0.060 g, 31%, 2-steps. ¹H NMR (CDCl₃) δ 1.58-1.69 (m, 3H), 2.05 (m, 1H), 2.14 (s, 6H), 2.26-2.35 (m, 2H), 2.43 (s, 6H), 3.63 (s, 2H), 4.00 (d, 2H, J=12.0 Hz), 4.44 (s, 2H), 5.26 (br s, 1H), 6.82 (d, 1H, J=9.0 Hz), 6.92 (d, 1H, J=9.0 Hz), 7.05 (s, 2H), 7.26 (s, 1H), 8.01 (s, 2H).

To a solution of 3-hydroxymethyl-4-(3,5,3",5"-tetramethyl-3',4',5',6'-tetrahydro-2'H-[2,2';6',2"]terpyridin-1'-ylmethyl)-benzonitrile (0.060 g, 0.14 mmol) dissolved in MeOH (7 mL) ammonia gas was bubbled for 10 minutes. A pre-washed mixture of Raney Nickel (~0.5 gram) was added to the nitrile and the mixture was shaken on the hydrogenator at 40 psi for 2 hours. The mixture was filtered through a sintered glass funnel containing a celite plug and the filtrated was concentrated in vacuo to give a green foam. Purification by column chromatography on silica gel (CH₂Cl₂:MeOH: NH₄OH, 87:8:5, v/v/v) afforded [5-aminomethyl-2-(3,5,31", 5"-tetramethyl-3',4',5',6'-tetrahydro-2'H-[2,2';6',2"]terpyridin-1'-ylmethyl)-phenyl]-methanol as a pale yellow foam (0.061 g, 99%). $^1$H NMR (CDCl3) δ 1.52-1.62 (m, 3H), 1.98 (m, 1H), 2.10 (s, 6H), 2.20-2.30 (m, 2), 2.37 (s, 6H), 3.50 (s, 2H), 3.57 (s, 1H), 3.88 (d, 2H, J=9.0 Hz), 4.27 (s, 2H), 6.59 (d, 1H, J=9.0 Hz), 6.68 (d, 1H, J=9.0 Hz), 6.89 (s, 1H), 7.03 (s, 2H), 8.03 (s, 2H).

[5-Aminomethyl-2-(3,5,3",5"-tetramethyl-3',4',5',6'-tetrahydro-2'H-[2,2';6',2"]-terpyridin-1'-ylmethyl)-phenyl]-methanol (0.061 g, 0.14 mmol), S-($^+$)-2-phenylbutyric acid (22 µL, 0.16 mmol), HOBT (0.022 g, 0.16 mmol), EDCI (0.032 g, 0.16 mmol) and DIPEA (29 µL, 0.16 mmol) in $CH_2Cl_2$ (8 mL) were reacted according to General Procedure G. Purification by column chromatography on silica gel ($CH_2Cl_2$:MeOH:$NH_4$OH, 94:5:1, v/v/v) afforded N-[3-hydroxymethyl-4-(3,5,3",5"-tetramethyl-3',4',5',6'-tetrahydro-2'H-[2,2';6',2"]terpyridin-1'-ylmethyl)-benzyl]-2-phenyl-butyramide as a white solid (0.045 g, 55% ). $^1$H NMR (CDCl3) δ 0.86 (t, 3H, J=7.5 Hz), 1.66-1.76 (m, 3H), 2.10 (s$^+$m, 7H), 2.32 (m, 2H), 2.42 (s, 6H), 3.65 (br s, 2H), 3.92 (m, 4H), 4.35 (s, 2H), 5.46 (br s, 1H), 6.45 (d, 1H, J=7.5 Hz), 6.60 (d, 1H, J=9.0 Hz), 6.68 (s, 1H), 7.00 (s, 2H), 7.13-7.33 (m, 7H), 8.00 (s, 2H). HPLC: 93%. ES-MS m/z 591 [M$^+$H]$^+$, 613 [M$^+$Na]$^+$.

EXAMPLE 133

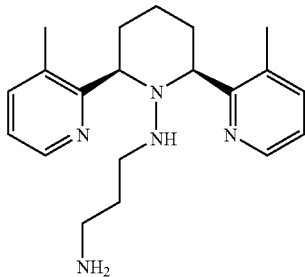

COMPOUND 133: N$^1$-(3,3"-Dimethyl-3',4',5',6'-tetrahydro-2'H-[2,2';6',2"]terpyridin-1'-yl)-propane-1,3-diamine (HBr salt)

To a room temperature solution of 3,3'-dimethyl-1',2',3',4',5',6'-hexahydro-[2,2';6',2"]terpyridine (850 mg, 3.18 mmol) in 1 N HCl (20 mL) was added $NaNO_2$ (658 mg, 9.54 mmol) and the mixture was heated to 70° C. for 2 hours. The mixture was then cooled to room temperature and neutralized with 10 N NaOH. It was extracted with $CH_2Cl_2$ (3×50 mL). The combined organic extracts were dried (MgSO$_4$), filtered and concentrated to give a yellow solid.

3,3"-Dimethyl-1'-nitroso-1',2',3',4',5',6'-hexahydro-[2,2'; 6'2"]tetrapyridine from above was dissolved in EtOH (5 mL) and cooled to 0° C. $NH_4$OH (5 mL), $NH_4$OAc (193 mg, 2.51 mmol) and zinc dust (225 mg, 5.0 mmol) were added and the mixture was stirred at room temperature for 1 hour. Zinc was filtered and rinsed with water (10 mL) and $CH_2Cl_2$ (20 mL). The layers were separated and the organic was dried with mgSO$_4$, was filtered and concentrated. The crude material was purified by column chromatography on silica gel (19:1: 0.2 $CH_2Cl_2$:$CH_3$OH:$NH_4$OH) to provide 3,3"-dimethyl-3',4', 5',6'-tetrahydro-2'H-[2,2';6'2"]terpyridine-1'-ylamine (430 mg, 48%). $^1$H NMR (CDCl$_3$) δ 1.55-1.69 (m, 1H), 1.75-1.95 (m, 3H), 2.01-2.14 (m, 3H), 2.40-2.75 (br m, 8H), 3.65-3.80 (br s, 2H), 7.07 (dd, 2H, J=4.2, 7.5 Hz), 7.43 (d, 2H, J=7.2 Hz), 8.45 (br s, 2H).

3,3"-Dimethyl-3',4 ',5',6'-tetrahydro-2'H-[2,2';6'2"]terpyridine-(1'-ylamine 92.6 mg, 0.328 mmol) and 3-(tert-butoxycarbonylamino)-1-propanal (Bioorg. Med. Chem. Lett. (2000) 10:559-562) (114 mg, 0.64 mmol) were stirred in dry EtOH (10 mL) for 2 hrs. The solvent was removed and dry THF added (10 mL) and the mixture was cooled to 0° C. LiAlH$_4$ (1.0 M in THF/0.48 mmol) was added and the mixture was warmed to room temperature and was stirred for 30 min. Water (10 mL) was added and the mixture was extracted with $CH_2Cl_2$ (2×20 mL) and the combined organic extracts were dried (MgSO$_4$) and concentrated. The crude material was purified by radial chromatography on silica gel (Et$_2$O saturated with $NH_4$OH) to give [3-(3,3"-dimethyl-3',4',5',6'-tetrahydro-2'H-[2,2';6',2"]terpyridin-1'-ylamino)-propyl]-carbamic acid tert-butyl ester (49 mg, 34%).

Following the General Procedure B for salt formation using HBr saturated HOAc [3-(3,3"-dimethyl-3',4',5',6'-tetrahydro-2'H-[2,2';6',2"]terpyridin-1'-ylamino)-propyl]-carbamic acid tert-butyl ester (49 mg, 0.111 mmol) was converted to COMPOUND 133 (67 mg,79%). $^1$H NMR (D$_2$O) δ 1.20-1.29 (m, 2H), 1.54-1.74 (m, 3H), 1.90-1.06 (m, 1H), 2.17-2.23 (m, 2H), 2.30-2.46 (m, 4H), 2.16 (s, 6H), 7.90 (dd, 2H, J=5.7, 7.8 Hz), 8.44 (d, 2H, J=7.8 Hz), 8.67 (d, 2H, J=5.7 Hz); $^{13}$C NMR (D$_2$O) δ 17.0, 22.3, 26.1, 32.6, 37.5, 41.6, 61.4, 125.9, 136.9, 139.5, 149.5, 154.6; ES-MS m/z 340 (M$^+$H). Anal. Calcd. For $C_{20}H_{29}N_5$.2.4H$_2$O.3.8HBr.0.3$C_4H_{10}$O: C, 35.74; H, 5.74; N, 9.83; Br, 42.62. Found: C, 35.83; H, 5.56; N, 9.86; Br, 42.41.

EXAMPLE 134

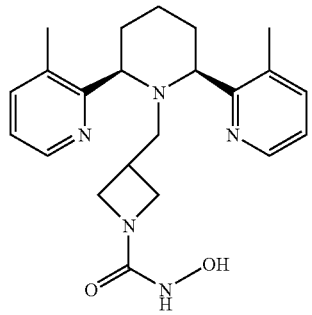

COMPOUND 134: 3-(3,3"-Dimethyl-3',4',5'6'-tetrahydro-2'H-[2,2';6',2"]terpyridin-1'-ylmethyl)-azetidine-1-carboxylic acid hydroxyamide Tert-butyl 3-(aminomethyl)-1-azetidinecarboxylate (J. Med. Chem., (2001) 44:94-104) (441 mg, 2.35 mmol) was dissolved in $CH_2Cl_2$ (2 mL) and TFA (1.5 mL) and the mixture was stirred for 2 hours at room temperature. The volatiles were removed under reduced pressure and the residue was dissolved in dry MeOH (5 mL). Solid NaHCO$_3$ was added (~500 mg) and the mixture was stirred for 17 hours. MeOH was removed, $CH_2Cl_2$ (50 mL) was added and the mixture was filtered through a plug of Celite. The filtrate was concentrated and the residue was dissolved in DMF (15 mL). DIPEA (0.817 mL, 4.70 mmol) and 2-nitrobenzenesulfonyl chloride (580 mg, 2.58 mmol) were added and the mixture was stirred for 2 hours. The mixture was concentrated and the residue was purified by column chromatography on silica gel (100% EtOAc) to provide [1-(2-nitro-benzenesulfonyl)-azetidin-3-yl]-methanol (167 mg, 26%). $^1$H NMR (CDCl$_3$) δ 2.73-2.80 (m, 1H), 3.76 (dd, 2H, J=5.4, 5.7 Hz), 3.90 (dd, 2H, J=5.7, 8.1 Hz), 4.17 (dd, 2H, J=8.1, 8.1 Hz).

To a 0° C. solution of [1-(2-nitro-benzenesulfonyl)-azetidin-3-yl]-methanol (165 mg, 0.606 mmol) in EtOAc (15 mL) was added Et$_3$N (0.101 mL, 0.727 mmol) then mesyl chloride (0.052 mL, 0.666 mmol). The reaction mixture was stirred for 1 hour at room temperature. The precipitate was filtered through a plug of Celite and was washed with EtOAc. The filtrate was concentrated and the crude mesylate was dissolved in DMF (5 mL). To this solution was added DIPEA (0.211 mL, 1.20 mmol) and 3,3'-dimethyl-1',2',3'4',5',6'-hexahydro-[2,2';6',2"]terpyridine (162 mg, 0.606 mmol) and the mixture was heated at 80° C. for 17 hour Saturated NaHCO$_3$ (15 mL) was added and the mixture was extracted with CH$_2$Cl$_2$ (3×30 mL). The combined organic extracts were dried (MgSO$_4$), filtered and concentrated. The crude material was purified by radial chromatography on silica gel (Et$_2$O saturated with NH$_4$OH) to give 3,3'-dimethyl-1'-[1-(2-nitro-benzenesulfonyl)-azetidin-3-ylmethyl]-1',2',3',4',5',6'-hexahydro-[2,2';6',2"]terpyridine (168 mg, 53%).

A mixture of 3,3'-dimethyl-1'-[1-(2-nitro-benzenesulfonyl)-azetidin-3-ylmethyl]-1',2',3'4',5',6'-hexahydro-[2,2';6',2"]terpyridine (168 mg, 0.322 mmol), thiophenol (0.3 mL), K$_2$CO$_3$ (500 mg) in CH$_3$CN (5 mL) were stirred at room temperature for 17 hours. The volatiles were removed under reduced pressure and saturated NaHCO$_3$ (15 mL) was added and the mixture was extracted with CH$_2$Cl$_2$ (3×30 mL). The combined organic extracts were dried (MgSO$_4$), filtered and concentrated. The crude material was subjected to column chromatography on silica gel (10:1:0.1 CH$_2$Cl$_2$:CH$_3$OH:NH$_4$OH; then 10:1:0.5) to provide 1'-azetidin-3-ylmethyl-1',2',3'4',5',6'-hexahydro-[2,2';6',2"]terpyridine (74 mg, 80% pure by LC/MS).

To a 0° C. solution of 1'-azetidin-3-ylmethyl-1',2',3'4',5',6'-hexahydro-[2,2';6',2"]terpyridine from above (74 mg, 0.219 mmol) in toluene (2.5 mL) and DIPEA (0.095 mL, 0.5 mmol) was added phosgene solution in toluene (20 wt %, 0.12 mL, 0.26 mmol). The reaction mixture was warmed to room temperature and was stirred for 1.5 hours. The volatiles were removed under reduced pressure and the remaining yellow solid was dissolved in DMF (5 mL). DIPEA (0.40 mL) and NH$_2$OH.H$_2$O (100 mg, 1.56 mmol) were added and the mixture was stirred for 17 hours at room temperature. Saturated NaHCO$_3$ (15 mL) was added and the mixture was extracted with CH$_2$Cl$_2$ (3×30 mL). The combined organic extracts were dried (MgSO$_4$), filtered and concentrated. The crude material was purified by radial chromatography (10:1:0.2 CH$_2$Cl$_2$:CH$_3$OH:NH$_4$OH) on silica gel to provide COMPOUND 134 (27 mg, 31%) as a clear film. $^1$H NMR (CDCl$_3$) δ 1.16-1.19 (m, 1H), 1.53-1.65 (m, 3H), 1.94-2.11 (m, 3H), 2.42 (s, 6H), 2.41-2.43 (m, 2H), 3.01-3.06 (m, 2H), 3.45 (t, 2H, J=8.4 Hz), 3.60 (br s, 1H), 3.88 (d, 2H, J=10.2 Hz), 7.10 (dd, 2H, J=4.2, 7.5 Hz), 7.45 (d, 2, J=7.5 Hz), 8.41 (d, 2H, J=4.2 Hz); $^{13}$C NMR (CDCl$_3$) δ 19.2, 25.2, 29.2, 30.8, 55.0, 57.4, 65.5, 122.7, 131.4, 139.2, 147.2, 160.6, 163.5; ES-MS m/z 396 (M$^+$H). Anal. Calcd. for C$_{22}$H$_{29}$N$_5$O$_2$.0.1H$_2$O.1.2CH$_2$Cl$_2$: C, 55.82; H, 6.38; N, 14.03. Found: C, 55.75; H, 6.35; N, 14.08.

EXAMPLE 135

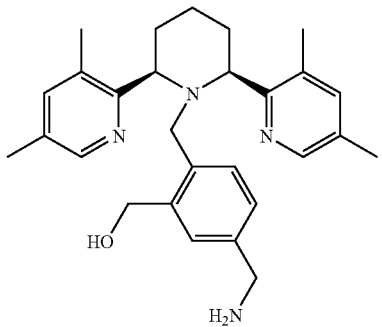

COMPOUND 135: Meso-2'β,6'β-[5-aminomethyl-2-(3,5,3",5"-tetramethyl-3',4',5',6'-tetrahydro-2'H-[2,2';6',2"]terpyridin-1'-ylmethyl)-phenyl]-methanol Following the General Procedure A, meso-2'β,6'β-[3,5,3",5"-tetramethyl-1',2',3',4',5',6'-hexahydro-[2,2';6'2"]terpyridine] (0.1903 g, 0.64 mmol), 2-bromomethyl-5-cyano-benzoic acid methyl ester (0.1630 g, 0.64 mmol), KI (0.0100 g, 0.06 mmol), DIPEA (0.22 mL, 1.29 mmol), and DMF (6.4 mL) were stirred at 60° C. for 17 hours. Purification of the crude material by column chromatography on silica gel (50:1:1 CH$_2$Cl$_2$-MeOH—NH$_4$OH) provided 0.2682 g (89%) of meso-2'β,6'β-[5-cyano-2-(3,5,3",5"-tetramethyl-3',4',5'.6'-tetrahydro-2'H-[2,2';6'2"]terpyridin-1'-ylmethyl)-benzoic acid methyl ester] as a brown oil. $^1$H NMR (CDCl$_3$) δ 1.63-1.67 (m, 3H), 2.00-2.05 (m, 1H), 2.12 (s, 6H), 2.21-2.31 (m, 2H), 2.36 (s, 6H), 3.84 (s, 3H), 3.90-3.94 (m, 2H), 4.05-4.08 (m, 2H), 6.96 (s, 2H), 7.37 (d, 1H, J=9.0 Hz), 7.56 (d, 1H, J=3.0 Hz), 7.90 (s, 1H), 8.02 (s, 2H).

To a solution of meso-2'β,6'β-[5-cyano-2-(3,5,3",5"-tetramethyl-3',4',5',6'-terahydro-2'H-[2,2';6'2"]terpyridin-1'-ylmethyl)-benzoic acid methyl ester] (0.2682 g, 0.57 mmol) in THF (6 mL) at 0° C. under Ar was added dropwise 1.0 M LiAlH$_4$ in THF (5.7 mL, 5.72 mmol). The mixture was stirred at room temperature for 2 hours, then distilled water (0.3 mL) was added, followed by 15% NaOH (1 mL), and distilled water (3 mL), and stirred for 15 minutes. The mixture was filtered through celite with CH$_2$Cl$_2$ and concentrated. Purification of the crude material by column chromatography on silica gel (25:1:1 CH$_2$Cl$_2$-MeOH—NH$_4$OH) provided 0.1435 g (54%) of COMPOUND 135 as a white solid. $^1$H NMR (CDCl$_3$) δ 1.58-1.62 (m, 4H), 2.01-2.07 (m, 2H), 2.10 (s, 6H), 2.31-2.35 (m, 2H), 2.45 (s, 6H), 3.58 (d, 4H, J=10.8 Hz), 4.36 (s, 2H), 6.57-6.67 (m, 2H), 6.85 (s, 1H), 7.02 (s, 2H), 8.01 (s, 2H). $^{13}$C NMR (CDCl$_3$) δ 18.08, 19.26, 25.84, 29.08, 46.30, 52.52, 62.98, 67.18, 125.22, 125.72, 127.84, 129.13, 131.23, 131.41, 138.04, 138.94, 140.91, 146.94, 157.02. ES-MS m/z 445.5 (M$^+$H). Anal. Calcd. for C$_{28}$H$_{36}$N$_4$O.0.2CH$_2$Cl$_2$.0.3H$_2$O: C, 72.53; H, 7.99; N, 12.00. Found: C, 72.91; H, 8.07; N, 11.91.

EXAMPLE 136

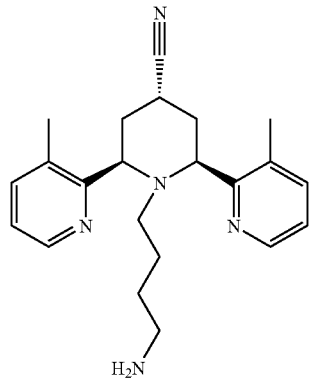

COMPOUND 136: Meso-2'β,4'α,6'β-[1'-(4-aminobutyl)-3,3"-dimethyl-1',2',3',4',5',6-hexahydro-[2,2';6',2"]terpyridine-4'-carbonitrile]

To a solution of meso-2'β,6'β-[3,3"-dimethyl-2',3',5',6'-tetrahydro-1'H-[2,2';6'2"]terpyridin-4'-one] (1.0760 g, 3.8 mmol) in MeOH (38 mL) under Ar was added NaBH$_4$ (0.3631 g, 9.6 mmol), and stirred at room temperature for 3.5 hours. The mixture was then concentrated, and saturated NaHCO$_3$ (40 mL) was added and extracted with CH$_2$Cl$_2$ (3×60 mL). The combined organic extracts were dried (Na$_2$SO$_4$), filtered, and concentrated to provide 1.0466 g (92%) of meso-2'β,4'β,6=β-[3,3"-dimethyl-1',2',3',4',5',6'-hexahydro-[2,2';6'2"]

terpyridin-4'-ol] as a yellow solid. $^1$H NMR (CDCl$_3$) δ1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H), J=6.0 Hz).

To a solution of meso-2'β,4'β,6'β-[3,3"-dimethyl-1',2',3',4',5',6'-hexahydro-[2,2';6'2"]terpyridin-4'-ol] (1.0466 g, 3.48 mmol) in THF (20 mL) were added DIPEA (1.80 mL, 10.44 mmol) and Boc$_2$O (1.5484 g, 6.96 mmol) in THF (15 mL). The mixture was stirred at 50° C. for 16 hours, then concentrated. Saturated NaHCO$_3$ (40 mL) was added and extracted with CH$_2$Cl$_2$ (3×60 mL). The combined organic extracts were washed with brine (2×25 mL), dried (Na$_2$SO$_4$), filtered, and concentrated. Purification of the crude material by column chromatography on silica gel (50:1:1 CH$_2$Cl$_2$-MeOH—NH$_4$OH) provided 0.8317 g (62%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester]. $^1$H NMR (CDCl$_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz).

To a solution of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester] (0.8317 g, 2.17 mmol) and Et$_3$N (0.45 mL, 3.26 mmol) in CH$_2$Cl$_2$ (22 mL) at 0° C. under Ar was added MsCl (0.20 mL, 2.60 mmol). The mixture was stirred at 0° C. for 30 minutes, then at room temperature for 2 hours, and quenched with saturated NaHCO$_3$ (15 mL) and extracted with CH$_2$Cl$_2$ (3×50 mL). The combined organic extracts were dried (Na$_2$SO$_4$), filtered, and concentrated to provide 1.0185 g (100%) of meso-2'β,4=β,6'β-[4'-methanesulfonyloxy-3,3"-dimethyl-3',4',5',6'-tetrahydro-2'H-[2,2';6'2"]terpyridine-1'-carboxylic acid tert-butyl ester] as an orange solid. $^1$H NMR (CDCl$_3$) δ 1.20 (s, 9H), 2.37 (s, 6H), 2.41-2.45 (m, 2H), 2.88-2.99 (m, 2H), 3.07 (s, 3H), 5.07-5.14 (m, 1H), 5.39-5.44 (m, 2H), 6.94-6.98 (m, 2H), 7.33-7.35 (m, 2H), 8.09 (d, 2H, J=6.0 Hz).

To a solution of meso-2=β,4'β,6'β-[4'-methanesulfonyloxy-3,3"-dimethyl-3',4',5',6'-tetrahydro-2'H-[2,2';6'2"]terpyridine-1'-carboxylic acid tert-butyl ester] (1.0185 g, 2.21 mmol) in DMSO (11 mL) was added NaCN (2.2398 g, 44.22 mmol), and stirred at 80° C. for 17 hours. The mixture was concentrated, and saturated NaHCO$_3$ (40 mL) was added and extracted with CH$_2$Cl$_2$ (3×100 mL). The combined organic extracts were washed with brine (3×40 mL), dried (Na$_2$SO$_4$), filtered, and concentrated. Purification of the crude material by column chromatography on silica gel (4:1 hexanes-EtOAc, then 100:1:1 CH$_2$Cl$_2$-MeOH—NH$_4$OH) provided 0.4933 g (57%) of meso-2'β,4'α,6'β-[4'-cyano-3,3"-dimethyl-3',4',5',6'-tetrahydro-2'H-[2,2';6'2"]terpyridine-1'-carboxylic acid tert-butyl ester] as a beige solid. $^1$H NMR (CDCl$_3$) δ 1.56 (s, 9H), 1.97-2.07 (m, 2H), 2.15 (s, 6H), 2.79-2.84 (m, 2H), 5.13-5.23 (m, 1H), 5.74 (s, 2H, J=6.0 Hz), 6.66-6.70 (m, 2H), 7.00 (d, 2H, J=9.0 Hz), 7.94 (d, 2H, J=6.0 Hz).

To a solution of the above nitrile (0.3118 g, 0.79 mmol) in CH$_2$Cl$_2$ (5 mL) was added TFA (5 mL) and stirred at room temperature for 3 hours, then concentrated. Distilled water (5 mL) and 10 N NaOH (3 mL) were added and extracted with CH$_2$Cl$_2$ (3×50 mL). The combined organic extracts were dried (Na$_2$SO$_4$), filtered, and concentrated. Purification of the crude material by column chromatography on silica gel (100:1:1 CH$_2$Cl$_2$-MeOH—NH$_4$OH) provided 0.1304 g (56%) of meso-2'β,4'α,6'β-[3,3"-dimethyl-1',2',3',4',5',6'-hexahydro-[2,2';6'2"]terpyridine-4'-carbonitrile] as an orange oil. $^1$H NMR (CDCl$_3$) δ 1.92-2.02 (m, 4H), 2.43 (s, 6H), 2.80-2.88 (m, 1H), 3.42 (s, 1H), 4.58-4.61 (m, 2H), 6.98-7.09 (m, 2H), 7.42-7.45 (m, 2H), 8.42 (d, 2H, J=6.0 Hz).

Following the General Procedure A, meso-2'β,4'α,6'β-[3,3"-dimethyl-1',2',3',4',5',6'-hexahydro-[2,2';6'2"]terpyridine-4'-carbonitrile] (0.1304 g, 0.45 mmol), 2-(4-bromo-butyl)-isoindole-1,3-dione (0.1383 g, 0.49 mmol), KI (0.0075 g, 0.05 mmol), DIPEA (0.16 mL, 0.90 mmol), and DMF (5 mL) were stirred at 60° C. for 16 hours. Purification of the crude material by column chromatography on silica gel (100:1:1 CH$_2$Cl$_2$-MeOH—NH$_4$OH) provided 0.1064 g (48%) of meso-2'β,4'α,6'β-[1'-[4-(1,3-dioxo-1,3-dihydro-isoindol-2-yl)-butyl]-3,3"-dimethyl-1',2',3',4',5',6'-hexahydro-[2,2'; 6'2"]terpyridine-4'-carbonitrile] as a white solid. $^1$H NMR (CDCl$_3$) δ 0.25-0.27 (m, 2H), 0.77-0.82 (m, 2H), 1.85 (d, 2H, J=14.7 Hz), 2.35 (t, 2H, J=7.5 Hz), 2.50 (s, 6H), 2.54-2.63 (m, 2H), 3.11 (t, 2H, J=7.2 Hz), 3.35-3.36 (m, 1H), 4.57 (d, 2H, J=12.0 Hz), 6.94-6.98 (m, 2H), 7.27-7.29 (m, 2H), 7.71-7.75 (m, 2H), 7.79-7.82 (m, 2H), 8.36 (d, 2H, J=3.0 Hz).

To a solution of meso-2'β,4'α,6'β-[1'-[4-(1,3-dioxo-1,3-dihydro-isoindol-2-yl)-butyl]-3,3"-dimethyl-1',2',3',4',5',6'-hexahydro-[2,2';6'2"]terpyridine-4'-carbonitrile] (0.1064 g, 0.22 mmol) in EtOH (2.2 mL) was added hydrazine monohydrate (0.10 mL, 2.16 mmol) and stirred at room temperature for 16 hours, then concentrated. Purification of the crude material by column chromatography on silica gel (50:1:1, then 30:1:1 CH$_2$Cl$_2$-MeOH—NHOH) provided 0.0313 g (39%) of COMPOUND 136 as a colorless oil. $^1$H NMR (CDCl$_3$) δ 0.46-0.48 (m, 2H), 0.63-0.73 (m, 2H), 1.89 (d, 2H, J=13.8 Hz), 2.12 (t, 2H, J=6.9 Hz), 2.26 (t, 2H, J=7.8 Hz), 2.48-2.52 (m, 2H), 2.53 (s, 6H), 2.90-3.10 (bs, 1H), 3.31-3.33 (m, 1H), 4.55 (d, 2H, J=11.1 Hz), 7.09-7.13 (m, 2H), 7.46 (d, 2H, J=7.5 Hz), 8.44 (d, 2H, J=3.9 Hz). $^{13}$C NMR (CDCl$_3$) δ 18.94, 25.19, 27.10, 29.26, 31.27, 41.77, 45.81, 59.61, 122.46, 122.81, 132.75, 138.64, 146.88, 158.33. ES-MS m/z 364.4 (M$^+$H). Anal. Calcd. for C$_{22}$H$_{29}$N$_5$.0.3CH$_2$Cl$_2$: C, 68.86; H, 7.67; N, 18.00. Found: C, 69.22; H, 7.88; N, 18.15.

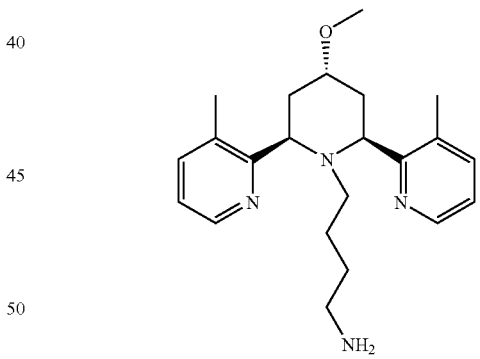

COMPOUND 137: Meso-2'β,4'α,6'β-[4-(4'-methoxy-3,3"-dimethyl-3',4',5',6'-tetrahydro-2'H-[2,2';6',2"]terpyridin-1'-yl)-butylamine To a solution of meso-2'β,6'β-[3,3"-dimethyl-2',3',5',6'-tetrahydro-1'H-[2,2';6'2"]terpyridin-4'-one] (3.5417 g, 12.6 mmol) in THF (90 mL) under Ar at −78° C. was slowly added L-selectride (13.8 mL, 13.8 mmol), and was stirred for 30 minutes (*Tetrahedron: Asymmetry* (1999) 10:2225-2235). MeOH (35 mL) was added, and at room temperature distilled water (70 mL) was added and extracted with CH$_2$Cl$_2$ (3×150 mL). The combined organic extracts were dried (Na$_2$SO$_4$), filtered, and concentrated to provide 5.37 g (100%) of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] as a sticky orange oil. ¹H NMR (CDCl₃) δ 1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44-8.45 (m, 2H).

To a solution of a 1:1 mixture of meso-2'β,4'β,6'β-[3,3"-dimethyl-1',2',3',4',5',6'-hexahydro-[2,2';6'2"]terpyridin-4'-ol] and meso-2'β,4'α,6'β-[3,3"-dimethyl-1',2',3',4',5',6'-hexahydro-[2,2';6'2"]terpyridin-4'-ol] in THF (90 mL) was added DIPEA (4.36 mL, 25.2 mmol) and Boc₂O (3.3407 g, 15.1 mmol) and stirred at 50° C. for 16 hours. The mixture was concentrated, and saturated NaHCO₃ (75 mL) was added and extracted with CH₂Cl₂ (3×100 mL). The combined organic extracts were washed with brine (2×75 mL), dried (Na₂SO₄), filtered, and concentrated. Purification of the crude material by column chromatography on silica gel (1:1 hexanes-EtOAc) provided 1.2984 g (27%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester as a yellow solid and 0.8605 g (18%) of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester a pale yellow solid. ¹H NMR (CDCl₃) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz) and ¹H NMR (CDCl₃) δ 1.50 (s, 9H), 1.67-1.76 (m, 2H), 2.21 (s, 6H), 2.69-2.76 (m, 2H), 5.62-5.67 (m, 1H), 5.80-5.83 (m, 2H), 6.68-6.72 (m, 2H), 6.97-7.05 (m, 2H), 7.99 (d, 2H, J=3 Hz), respectively.

To a solution of meso-2'β,4'β,6'β-[4'-hydroxy-3,3"-dimethyl-3',4',5',6'-tetrahydro-2'H-[2,2';6'2"]terpyridine]-1'-carboxylic acid tert-butyl ester (0.1427 g, 0.37 mmol) in THF (4 mL) was added 60% NaH in mineral oil (0.0224 g, 0.56 mmol) and stirred at room temperature for 1 hour. MeI (0.05 mL, 0.75 mL) was added and stirred for 16 hours, and concentrated. Purification of the crude material by column chromatography on silica gel (NH₄OH saturated Et₂O) provided 0.1034 g (70%) of meso-2'β,4'α,6'β-[4'-methoxy-3,3"-dimethyl-1',2',3',4',5',6'-hexahydro-[2,2';6'2"]terpyridine] as a yellow oil. ¹H NMR (CDCl₃) δ 1.35 (s, 9H), 1.69-1.78 (m, 2H), 2.29 (s, 6H), 2.64-2.72 (m, 2H), 3.44-3.51 (m, 3H), 4.79-4.83 (m, 1H), 5.66 (t, 2H, J=4.5 Hz), 6.78-6.82 (m, 2H), 7.15 (d, 2H, J=9.0 Hz), 8.06 (d, 2H, J=3.0 Hz).

To a solution of meso-2'β,4'α,6'β-[4'-methoxy-3,3"-dimethyl-1',2',3',4',5',6'-hexahydro-[2,2';6'2"]terpyridine] (0.1236 g, 0.31 mmol) in CH₂Cl₂ (3 mL) was added TFA (3 mL), and stirred at room temperature for 2.5 hours. The mixture was concentrated, and distilled water (2 mL) and 10 N NaOH (3 mL) were added and extracted with CH₂Cl₂ (3×15 mL). The combined organic extracts were dried (Na₂SO₄), filtered, and concentrated to provide 0.0666 g (72%) of meso-2'β,4'α,6'β-[4'-methoxy-3,3"-dimethyl-1',2',3',4',5',6'-hexahydro-[2,2';6'2"]terpyridin] as a yellow oil. ¹H NMR (CDC₃) δ 1.73-1.82 (m, 4H), 2.03-2.07 (m, 1H), 2.39 (s, 6H), 3.49 (s, 3H), 3.92-3.94 (m, 1H), 4.61 (d, 2H, J=12.0 Hz), 7.01-7.05 (m, 2H), 7.39 (d, 2H, J=6.0 Hz), 8.44 (d, 2H, J=6.0 Hz).

To a solution of meso-2'β,4'α,6'β-[4'-methoxy-3,3"-dimethyl-1',2',3',4',5',6'-hexahydro-[2,2';6'2"]terpyridin] (0.0666 g, 0.22 mmol), in DMF (3 mL) was added 2-(4-bromo-butyl)-isoindole-1,3-dione, KI (0.0033 g, 0.02 mmol), and DIPEA (0.08 mL, 0.44 mmol), and was stirred at 60° C. for 24 hours. The reaction mixture was concentrated, and saturated NaHCO₃ (5 mL) was added and extracted with CH₂Cl₂ (3×20 mL). The combined organic extracts were washed with brine (2×15 mL), dried (Na₂SO₄), filtered, and concentrated. Purification of the crude material by column chromatography on silica gel (50:1:1 CH₂Cl₂-MeOH—NH₄OH) provided 0.1006 g (92%) of meso-2'β,4'α,6'β-[2-[4-(4'-methoxy-3,3"-dimethyl-3',4',5',6'-tetrahydro-2'H-[2,2';6',2"]terpyridin-1'-yl)-butyl]-isoindole-1,3-dione] as a white sticky foam.

To a solution of meso-2'β,4'α,6'β-[2-[4-(4'-methoxy-3,3"-dimethyl-3',4',5',6'-tetrahydro-2'H-[2,2';6',2"]terpyridin-1'-yl)-butyl]-isoindole-1,3-dione] (0.1006 g, 0.20 mmol) in EtOH (2 mL) was added hydrazine monohydrate (0.1 mL, 2.02 mmol), and stirred at room temperature for 16 hours. The reaction mixture was concentrated, and purification of the crude material by column chromatography on silica gel (50:1:1 then 25:1:1 CH₂Cl₂-MeOH—NH₄OH) provided 0.0471 g (60%) of COMPOUND 137 as a colorless oil. ¹H NMR (CDCl₃) δ 0.40-0.42 (m, 2H), 0.62-0.71 (m, 2H), 1.88 (d, 2H, J=13.5 Hz), 2.09-2.13 (m, 2H), 2.45-2.40 (m, 4H), 2.53 (s, 6H), 3.39 (s, 3H), 3.82 (s, 1H), 4.57 (d, 2H, J=12.0 Hz), 7.04-7.08 (m, 2H), 7.41 (d, 2H, J=7.5 Hz), 8.42 (d, 2H, J=3.9 Hz). ¹³C NMR (CDCl₃) δ 19.07, 25.21, 31.12, 31.36, 41.82, 45.66, 56.39, 57.65, 75.10, 122.26, 132.79, 138.31, 146.69, 160.04. ES-MS m/z 369.4 (M⁺H). Anal. Calcd. for C₂₂H₃₂N₄O.0.1CH₂Cl₂.1.0H₂O: C, 67.20;

EXAMPLE 138

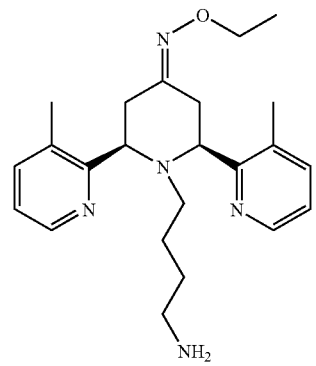

COMPOUND 138: Meso-2'β,6'β-[1'-(4-amino-butyl)-3,3"-dimethyl-2',3',5',6'-tetrahydro-1'H-[2,2'; 6'2"]terpyridin-4'-one O-ethyl-oxime]

To a solution of meso-2'β,6'β-[3,3"-dimethyl-2',3',5',6'-tetrahydro-1'H-[2,2';6'2"]terpyridin-4'-one] (0.3065 g, 1.1 mmol) in MeOH (22 mL) was added O-ethylhydroxylamine hydrochloride and stirred at room temperature for 24 hours. Saturated NaHCO₃ was added, extracted with CH₂Cl₂ (3×30 mL), and the combined organic extracts were dried (Na₂SO₄), filtered, and concentrated to provide 0.4528 g (100%) of meso-2'β,6'β-[3,3"-dimethyl-2',3',5',6'-tetrahydro-1'H-[2,2';6',2"]terpyridin-4'-one O-ethyl-oxime] as a yellow oil. ¹H NMR (CDCl₃) δ 1.27 (t, 3H, J=7.5 Hz), 1.71 (s, 1H), 2.10-2.18 (m, 1H), 2.39 (s, 6H), 2.43-2.53 (m, 2H), 3.30-3.41 (m, 1H), 3.44-3.49 (m, 1H), 4.09-4.16 (m, 2H), 4.28-4.35 (m, 2H), 7.05-7.09 (m, 2H), 7.43 (d, 2H, J=9.0 Hz), 8.46 (d, 2H, J=6.0 Hz).

To a solution of meso-2'β,6'β-[3,3"-dimethyl-2',3',5',6'-tetrahydro-1'H-[2,2';6',2"]terpyridin-4'-one O-ethyl-oxime] (0.4528 g, 1.40 mmol) in DMF (14 mL) was added 2-(4-bromo-butyl)-isoindole-1,3-dione (0.4329 g, 1.54 mmol), KI (0.0232 g, 0.14 mmol), and DIPEA (0.49 mL, 2.80 mmol), and was stirred at 60° C. for 20 hours. The reaction mixture was concentrated, and saturated NaHCO$_3$ (15 mL) was added and extracted with CH$_2$Cl$_2$ (3×40 mL). The combined organic extracts were dried (Na$_2$SO$_4$), filtered, and concentrated. Purification of the crude material by column chromatography on silica gel (4:1 hexanes-EtOAc) provided 0.2813 g of meso-2'β,6'β-[2-[4-(4'-ethoxyimino-3,3"-dimethyl-3',4',5',6'-tetrahydro-2'H-[2,2';6',2"]terpyridin-1'-yl)-butyl]-isoindole-1,3-dione] as a yellow foam.

To a solution of meso-2'β,6'β-[2-[4-(4'-ethoxyimino-3,3"-dimethyl-3',4',5',6'-tetrahydro-2'H-[2,2';6',2"]terpyridin-1'-yl)-butyl]-isoindole-1,3-dione] (0.2813 g, 0.54 mmol) in EtOH (5 mL) was added n-butyl amine (0.53 mL, 5.35 mmol), and was stirred at 80° C. for 16 hours before it was concentrated. Purification of the crude material by column chromatography on silica gel (50:1:1 then 15:1:1 CH$_2$Cl$_2$-MeOH—NH$_4$OH) provided 0.1325 g (23% over 2 steps) of COMPOUND 138 as a pale yellow oil. $^1$H NMR (CDCl$_3$) δ 0.22-0.25 (bs, 2H), 0.58-0.63 (m, 2H), 1.23 (t, 3H, J=6.9 Hz), 2.04 (t, 2H, J=6.6 Hz), 2.33-2.44 (m, 3H), 2.51 (s, 6H), 2.77-2.87 (m, 1H), 3.09-3.29 (m, 2H), 4.04-4.10 (m, 2H), 4.28-4.38 (m, 2H), 7.09-7.11 (m, 2H), 7.43 (d, 2H, J=7.2 Hz), 8.41-8.42 (m, 2H). $^{13}$C NMR (CDCl$_3$) δ 14.88, 18.75, 26.22, 31.04, 32.01, 41.68, 42.60, 63.32, 64.49, 69.00, 122.34, 122.71, 133.11, 133.25, 137.88, 138.25, 146.44, 146.50, 157.83, 157.87, 159.50. ES-MS m/z 396.4 (M$^+$H). Anal. Calcd. for C$_{23}$H$_{33}$N$_5$O.0.7H$_2$O: C, 67.68; H, 8.49; N, 17.16. Found: C, 67.74; H, 8.37; N, 16.98.

EXAMPLE 139

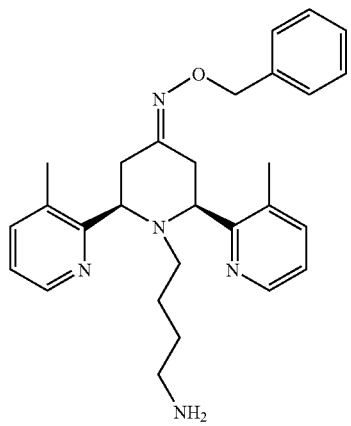

COMPOUND 139: Meso-2'β,6'β-[1'-(4-amino-butyl)-3,3"-dimethyl-2',3',5',6'-tetrahydro-1'H-[2,2';6',2"]terpyridin-4'-one O-benzyl-oxime]

To a solution of meso-2'β,6'β-[3,3"-dimethyl-2',3',5',6'-tetrahydro-1'H-[2,2';6'2"]terpyridin-4'-one] (0.2902 g, 1.0 mmol) in MeOH (20 mL) was added O-benzylhydroxylamine hydrochloride (0.1811 g, 1.1 mmol) and stirred at room temperature for 22 hours. Saturated NaHCO$_3$ (15 mL) was added, extracted with CH$_2$Cl$_2$ (3×40 mL), and the combined organic extracts were dried (Na$_2$SO$_4$), filtered, and concentrated to provide 0.4358 g (100%) of meso-2'β,6'β-[3,3"-dimethyl-2',3',5',6'-tetrahydro-1'H-[2,2';6',2"]terpyridin-4'-one O-benzyl-oxime] as a yellow oil. $^1$H NMR (CDCl$_3$) δ 2.13-2.21 (m, 1H), 2.37 (s, 6H), 2.40-2.59 (m, 2H), 3.22 (bs, 1H), 3.49-3.54 (m, 1H), 4.30 (d, 2H, J=22.8 Hz), 5.13 (s, 2H), 7.06-7.09 (m, 2H), 7.32-7.43 (m, 7H), 8.45 (d, 2H, J=6.0 Hz).

To a solution of meso-2'β,6'β-[3,3"-dimethyl-2',3',5',6'-tetrahydro-1'H-[2,2';6',2"]terpyridin-4'-one O-benzyl-oxime] (0.4358 g, 1.13 mmol) in DMF (11 mL) was added 2-(4-bromo-butyl)-isoindole-1,3-dione (0.3498 g, 1.24 mmol), KI (0.0188 g, 0.11 mmol), and DIPEA (0.39 mL, 2.26 mmol), and was stirred at 60° C. for 19 hours. The reaction mixture was concentrated, and saturated NaHCO$_3$ (15 mL) was added and extracted with CH$_2$Cl$_2$ (3×40 mL). The combined organic extracts were dried (Na$_2$SO$_4$), filtered, and concentrated. Purification of the crude material by column chromatography on silica gel (4:1 hexanes-EtOAc) provided 0.4436 g of meso-2'β,6'β-[2-[4-(4'-benzyloxyimino-3,3"-dimethyl-3',4',5',6'-tetrahydro-2'H-[2,2';6',2"]terpyridin-1'-yl)-butyl]-isoindole-1,3-dione] as an orange foam.

To a solution of meso-2'β,6'β-[2-[4-(4'-benzyloxyimino-3,3"-dimethyl-3',4',5',6'-tetrahydro-2'H-[2,2';6',2"]terpyridin-1'-yl)-butyl]-isoindole-1,3-dione] (0.4436 g, 0.75 mmol) in EtOH (8 mL) was added n-butyl amine (0.75 mL, 7.55 mmol), and was stirred at 80° C. for 16 hours before it was concentrated. Purification of the crude material by column chromatography on silica gel (50:1:1 then 20:1:1 CH$_2$Cl$_2$-MeOH—NH$_4$OH) provided 0.1276 g (24% over 2 steps) of COMPOUND 139 as a pale yellow oil. $^1$H NMR (CDCl$_3$) δ 0.19-0.22 (bs, 2H), 0.56-0.66 (m, 2H), 2.04 (t, 2H, J=6.9 Hz), 2.36-2.46 (m, 3H), 2.51 (s, 6H), 2.87 (t, 1H, J=13.2 Hz), 3.16 (t, 1H, J=13.8 Hz), 3.32 (d, 1H, J=14.4 Hz), 4.27-4.39 (m, 2H), 5.08 (s, 2H), 7.08-7.12 (m, 2H), 7.28-7.44 (m, 7H), 8.41 (d, 2H, J=4.2 Hz). $^{13}$C NMR (CDCl$_3$) δ 18.83, 25.75, 27.15, 31.14, 32.76, 41.75, 43.58, 62.91, 64.20, 75.69, 122.78, 127.97, 128.44, 128.63, 130.31, 132.91, 133.01, 138.41, 146.66, 146.71, 157.95, 160.30. ES-MS m/z 458.4 (M$^+$H). Anal. Calcd. for C$_{28}$H$_{35}$N$_5$O.0.9H$_2$O: C, 70.98; H, 7.83; N, 14.78. Found: C, 70.87; H, 7.62; N, 14.58.

EXAMPLE 140

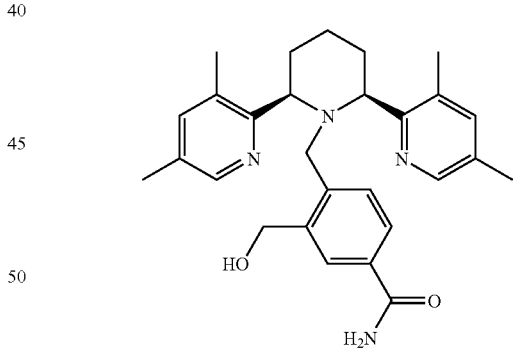

COMPOUND 140: Meso-2'β,6'β-[3-hydroxymethyl-4-(3,5,3",5"-tetramethyl-3',4',5',6'-tetrahydro-2'H-[2,2';6',2"]terpyridin-1'-ylmethyl)-benzamide To a solution of meso-2'β,6'β-[5-cyano-2-(3,5,3",5"-tetramethyl-3',4',5',6'-tetrahydro-2'H-[2,2';6'2"]terpyridin-1'-ylmethyl)-benzoic acid methyl ester] (0.4541 g, 0.97 mmol) in MeOH (5 mL) and THF (5 mL) was added at 0° C. LiBH$_4$ (0.1053 g, 4.84 mmol). The reaction was stirred at room temperature for 4 hours, then 1N NaOH (20 mL) and CH$_2$Cl$_2$ (30 mL) were added and stirred for 10 minutes. The phases were separated, and the aqueous phase was extracted with $CH_2Cl_2$ (3×20 mL). The combined organic extracts were dried ($Na_2SO_4$), filtered, and concentrated to provide 0.4030 g (94%) of meso-2'β,6'β-[3-hydroxymethyl-4-(3,5,3",5"-tetramethyl-3',4',5',6'-tetrahydro-2'H-[2,2';6'2"]terpyridin-1'-ylmethyl)-benzonitrile] as a yellow solid. $^1$H NMR ($CDCl_3$) δ 1.58-1.69 (m, 2H), 2.13 (s, 6H), 2.45 (s, 6H), 2.88-2.91 (m, 2H), 3.66 (s, 2H), 4.01-4.05 (m, 2H), 4.46 (s, 2H), 5.22 (s, 1H), 6.82-6.84 (m, 1H), 6.92-6.94 (m, 1H), 7.05 (s, 2H), 7.23 (s, 1H), 8.00 (s, 2H).

To a solution of meso-2'β,6'β-[3-hydroxymethyl-4-(3,5,3",5"-tetramethyl-3',4',5',6'-tetrahydro-2'H-[2,2';6'2"]terpyridin-1'-ylmethyl)-benzonitrile] (0.4030 g, 0.91 mmol) in MeOH (9 mL) and water (6 mL) was added sodium perborate tetrahydrate (0.2815 g, 1.83 mmol), and stirred at 50° C. for 16 hours. The mixture was concentrated, and purification of the crude material by column chromatography on silica gel (100:1:1 then 20:1:1 $CH_2Cl_2$-MeOH—$NH_4OH$), followed by another column (50:1:1 $CH_2Cl_2$-MeOH—$NH_4OH$) provided 45.3 mg (9%) of COMPOUND 140 as a white solid. $^1$H NMR ($CDCl_3$) δ 1.59-1.68 (m, 3H), 2.03-2.08 (m, 1H), 2.09 (s, 6H), 2.30-2.37 (m, 2H), 2.45 (s, 6H), 3.64 (s, 2H), 4.99 (d, 2H, J=11.1 Hz), 4.47 (s, 2H), 5.68 (s, 1H), 6.21 (s, 1H), 6.77 (d, 1H, J=7.5 Hz), 7.04 (s, 2H), 7.21 (d, 1H, J=7.8 Hz), 7.35 (s, 1H), 8.00 (s, 2H). $^{13}$C NMR ($CDCl_3$) 18.07, 19.30, 25.69, 30.26, 54.42, 62.49, 67.02, 126.23, 127.20, 127.64, 129.31, 131.14, 131.83, 139.13, 139.25, 143.24, 147.18, 156.82, 169.70. ES-MS m/z 459.5 ($M^+H$). Anal. Calcd. for $C_{28}H_{34}N_4O_2 \cdot 1.1CH_2Cl_2 \cdot 0.2H_2O$: C, 62.91; H, 6.64; N, 10.08. Found: C, 62.66; H, 6.64; N, 9.95.

EXAMPLE 141

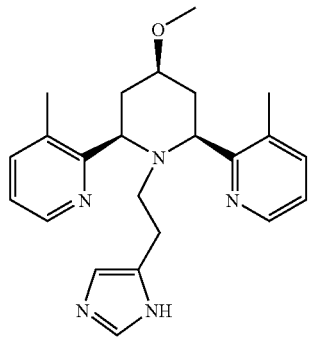

COMPOUND 141: Meso-2'β,4'β,6'β-{1'-[2-(3H-imidazol-4-yl)-ethyl]-4'-methoxy-3,3"-dimethyl-1',2',3',4',5',6'-hexahydro-[2,2';6'2"]terpyridine To a solution of meso-2'β,6'β-[3,3"-dimethyl-2',3',5',6'-tetrahydro-1'H-[2,2';6'2"]terpyridin-4'-one] (1.0760 g, 3.8 mmol) in MeOH (38 mL) under Ar was added $NaBH_4$ (0.3631 g, 9.6 mmol), and stirred at room temperature for 3.5 hours. The mixture was then concentrated, and saturated $NaHCO_3$ (40 mL) was added and extracted with $CH_2Cl_2$ (3×60 mL). The combined organic extracts were dried ($Na_2SO_4$), filtered, and concentrated to provide 1.0466 g (92%) of meso-2'β,4'β,6'β-[3,3"-dimethyl-1',2',3',4',5',6'-tetrahydro-[2,2';6'2"]terpyridin-4'-ol] as a yellow solid. $^1$H NMR ($CDCl_3$) δ1.43-1.55 (m, 2H), 1.81-1.97 (m, 2H), 2.14-2.18 (m, 2H), 2.36 (s, 6H), 3.97-4.07 (m, 1H), 4.19-4.20 (m, 2H), 7.00-7.07 (m, 2H), 7.38-7.42 (m, 2H), 8.44 (d, 2H), J=6.0 Hz).

To a solution of meso-2β',4β',6'β-[3,3"-dimethyl-1',2',3',4',5',6'-hexahydro-[2,2';6'2"]terpyridin-4'-ol] (1.0466 g, 3.48 mmol) in THF (20 mL) were added DIPEA (1.80 mL, 10.44 mmol) and $Boc_2O$ (1.5484 g, 6.96 mmol) in THF (15 mL). The mixture was stirred at 50° C. for 16 hours, then concentrated. Saturated $NaHCO_3$ (40 mL) was added and extracted with $CH_2Cl_2$ (3×60 mL). The combined organic extracts were washed with brine (2×25 mL), dried ($Na_2SO_4$), filtered, and concentrated. Purification of the crude material by column chromatography on silica gel (50:1:1 $CH_2Cl_2$-MeOH—$NH_4OH$) provided 0.8317 g (62%) of meso-2'β,4'β,6'β-[4'-hydroxy-3,3"-dimethyl-3',4',5',6'-tetrahydro-2'H-[2,2';6'2"]terpyridine-1'-carboxylic acid tert-butyl ester]. $^1$H NMR ($CDCl_3$) δ 1.17 (s, 9H), 2.19 (t, 4H, J=6.6 Hz), 2.40 (s, 6H), 4.17-4.20 (m, 1H), 5.38 (t, 2H, J=6.3 Hz), 6.05 (d, 1H, J=10.2 Hz), 6.94-6.98 (m, 2H), 7.34-7.36 (m, 2H), 8.11 (d, 2H, J=3.9 Hz).

To a solution of meso-2'β,4'α,6'β-[4'-hydroxy-3,3"-dimethyl-3',4',5',6'-tetrahydro-2'H-[2,2';6'2"]terpyridine]-1'-carboxylic acid tert-butyl ester (0.5194 g, 1.36 mmol) in DMF (5 mL) was added 60% NaH in mineral oil (0.0816 g, 2.04 mmol) and stirred at room temperature for 1 hour. MeI (0.17 mL, 2.72 mL) was added and stirred for 3.5 hours, and concentrated. Purification of the crude material by column chromatography on silica gel (50:1:1 $CH_2Cl_2$-MeOH—$NH_4OH$) provided 0.4289 g (79%) of meso-2'β,4'β,6'β-[4'-methoxy-3,3"-dimethyl-1',2',3',4',5',6'-hexahydro-[2,2';6'2"]terpyridine] as a beige solid. ES-MS m/z 398.3 ($M^+H$).

To a solution of the above material (0.2435 g, 0.82 mmol) in DMF (8 mL) were added 5-(2-chloro-ethyl)-1H-imidazole (0.1606 g, 1.23 mmol), DIPEA (0.29 mL, 1.64 mmol), and KI (0.0133 g, 0.08 mmol) and stirred at 80° C. for 48 hours. The mixture was concentrated and saturated $NaHCO_3$ (15 mL) was added and extracted with $CH_2Cl_2$ (3×30 mL). The combined organic extracts were washed with brine (2×30 mL), dried ($Na_2SO_4$), filtered, and concentrated. Purification of the crude material by column chromatography on silica gel (25:1:1 $CH_2Cl_2$-MeOH—$NH_4OH$) followed by another column (50:1:1 $CH_2Cl_2$-MeOH—$NH_4OH$) provided 39.9 mg (11%) of COMPOUND 141 as a light beige solid. $^1$H NMR ($CDCl_3$) δ 1.74 (s, 1H), 2.03-2.05 (m, 4H), 2.41 (s, 6H), 2.50-2.52 (m, 2H), 2.63 (s, 1H), 3.35 (s, 3H), 3.49-3.50 (m, 1H), 4.04-4.05 (m, 2H), 6.11 (s, 1H), 7.04-7.06 (m, 2H), 7.33 (s, 1H), 7.39 (d, 2H, J=6.9 Hz), 8.35-8.36 (m, 2H). $^{13}$C NMR ($CDCl_3$) 19.08, 23.69, 36.45, 49.86, 55.70, 62.59, 68.86, 118.64, 122.62, 131.69, 134.50, 139.08, 140.32, 147.05, 159.35. ES-MS m/z 392.2 ($M^+H$). Anal. Calcd. for $C_{23}H_{29}N_5O \cdot 0.4CH_2Cl_2$: C, 66.06; H, 7.06; N, 16.46. Found: C, 66.38; H, 7.31; N, 16.32.

EXAMPLE 142

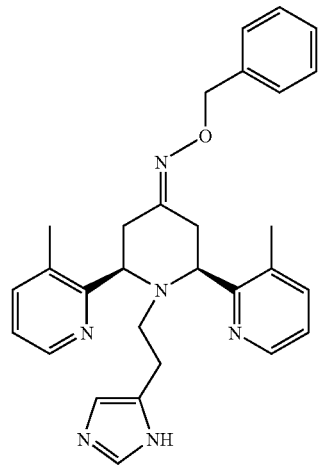

COMPOUND 142: Meso-2'β,6'β-{1'-[2-(3H-imidazol-4-yl)-ethyl]-3,3"-dimethyl-2',3',5',6'-tetrahydro-1'H-[2,2';6',2"]terpyridin-4'-one O-benzyl-oxime}

To a solution of meso-2'β,6'β-[3,3"-dimethyl-2',3',5',6'-tetrahydro-1'H-[2,2';6',2"]terpyridin-4'-one O-benzyl-oxime]

(0.1449 g, 1.11 mmol) in DMF (7 mL) was added 5-(2-chloro-ethyl)-1H-imidazole (0.0966 g, 0.74 mmol), KI (0.0123 g, 0.07 mmol), and DIPEA (0.25 mL, 1.48 mmol), and was stirred at 80° C. for 19 hours. The reaction mixture was concentrated, and saturated NaHCO$_3$ (15 mL) was added and extracted with CH$_2$Cl$_2$ (3×30 mL). The combined organic extracts were washed with brine (2×25 mL), dried (Na$_2$SO$_4$), filtered, and concentrated. Purification of the crude material by column chromatography on silica gel (100:1:1 then 10:1:1 CH$_2$Cl$_2$-MeOH—NH$_4$OH) followed by radial chromatography (25:1:1 CH$_2$Cl$_2$-MeOH—NH$_4$OH) provided 19.6 mg (5%) of COMPOUND 142 as a yellow oil. $^1$H NMR (CDCl$_3$) δ 1.58-1.59 (m, 1H), 2.39-2.43 (m, 2H), 2.44 (s, 6H), 2.68 (t, 2H, J=7.5 Hz), 2.84 (t, 1H, J=12.3 Hz), 3.10 (t, 1H, J=12.3 Hz), 3.30 (d, 1H, J=14.7 Hz), 4.22-4.33 (m, 2H), 5.08 (s, 2H), 6.13 (s, 1H), 7.09 (t, 2H, J=6.3 Hz), 7.27-7.34 (m, 7H), 7.42 (d, 2H, J=7.5 Hz), 8.40-8.41 (m, 2H). $^{13}$C NMR (CDCl$_3$) δ 18.94, 25.27, 28.56, 34.04, 46.33, 63.05, 64.34, 75.79, 119.70, 122.96, 128.07, 128.46, 128.69, 132.54, 132.68, 134.42, 138.37, 138.83, 146.90, 158.01, 159.27. ES-MS m/z 481.5 (M$^+$H). Anal. Calcd. for C$_{29}$H$_{32}$N$_6$O.0.4H$_2$O.0.3CH$_2$Cl$_2$: C, 68.56; H, 6.56; N, 16.37. Found C, 68.87; H, 6.53; N, 16.65.

EXAMPLE 143

Assay for Inhibition of HIV-1 (NL4.3) Replication in PBMC's

Inhibition of HIV-1 NL4.3 replication assays in PBMC's (peripheral blood mononuclear cells) are performed as previously described (De Clercq, et al., *Proc. Natl. Acad. Sci.* (1992) 89:5286-5290; De Clercq, et al., *Antimicrob. Agents Chemother.* (1994) 38:668-674; Schols, D., et al., *J. Exp. Med.* (1997) 186:1383-1388). Briefly, PBMC's from healthy donors are isolated by density gradient centrifugation and stimulated with PHA at 1 μg/ml (Sigma Chemical Co., Bornem, Belgium) for 3 days at 37° C. The activated cells (PHA-stimulated blasts) are washed three times with PBS, and viral infections are performed as described by Cocchi et al. (Science 1995, 270, 1811-1815). HIV-infected or mock-infected PHA-stimulated blasts are cultured in the presence of 25 U/mL of IL-2 and varying concentrations of test compounds. Supernatant is collected at days 6 and 10, and HIV-1 core antigen in the culture supernatant is analyzed by the p24 ELISA kit (DuPont-Merck Pharmaceutical Co, Wilmington, Del.). The 50% inhibitory concentration (IC$_{50}$) is defined as the concentration of test compound required to inhibit p24 antigen production by 50%.

When tested in the assay described above, the compounds of the invention exhibit IC$_{50}$'s in the range 0.5 nM-5 μM.

EXAMPLE 144

Assay for Inhibition of SDF-1α Induced Ca Flux in CEM Cells

Inhibition of SDF-1 induced calcium flux is assayed using CCRF-CEM cells, a T-lymphoblastoid cell line which expresses CXCR4. CCRF-CEM cells (5×10$^6$ cells/mL in RPMI 1640 medium containing 2% fetal bovine serum) are pre-loaded with 1 μM Fluo-4 fluorescent calcium indicator dye and incubated at 37° C. for 40 minutes. The loaded cells are washed and resuspended in buffer containing 20 mm HEPES pH 7.4, 1× Hanks Balanced Salt Solution (HBSS), 0.2% bovine serum albumin, 2.5 mm probenecid and plated out in 96 well tissue culture plates at 3.5×10$^5$ cells per well. The cells are incubated with test compound, or buffer control, for 15 minutes at 37° C. Calcium flux is stimulated by addition of 25 nM SDF-1 and fluorescence measured using a FLEXstation fluorescence plate reader (Molecular Devices). Ionomycin is added 80 seconds after addition of SDF-1 in order to measure total calcium loading. Compounds are tested at a concentration range of 2000-0.128 nM. Fluorescence measurements are normalized with respect to untreated controls. The 50% inhibitory concentration (IC$_{50}$ value) is defined as the concentration of test compound required to inhibit SDF-1-induced calcium flux by 50% relative to untested controls.

When tested in the assay described above, the compounds of the invention exhibit IC$_{50}$s in the range 0.5 nM -5 μM.

EXAMPLE 145

Elevation of Mouse Progenitor Cell Levels

The effects of subcutaneous (s.c.) administration of 1,1'-[1,4-phenylene -bis(methylene)]-bis-1,4,8,11-tetraazacyclotetradecane (AMD3100) to C3H/H3 J mice on numbers of granulocyte macrophage (CFU-GM), erythroid (BFU-E), and multipotential (CFU-GEMM) progenitor cells per mL of blood were measured. Progenitors were stimulated to form colonies in vitro with the combination of 1 U/ml rhu Epo, 50 ng/ml rhu SLF, 5% Vol/Vol pokeweed mitogen mouse spleen cell conditioned medium (PWMSCM), and 0.1 mm hemin. Plates were scored 7 days after incubation.

The time dependent effects on the number of progenitors mobilized with AMD3100 are for a single s.c. injection of 5 mg/Kg and are shown in Table 1.

TABLE 1

| | Absolute Progenitors Per ML Blood Methylcellulose Culture | | |
|---|---|---|---|
| | CFU-GM | BFU-E | CFU-GEMM |
| Control | 289.8 | 49.4 | 25.8 |
| AMD3100: 15" | 791.6 | 134.5 | 90.4 |
| AMD3100: 30" | 1805.5 | 209.3 | 113.5 |
| AMD3100: 120" | 828.7 | 102.3 | 47.6 |

To measure the dose-dependent effects, AMD3100 was administered at 1, 2.5, 5 and 10 mg/Kg via a single s.c. injection and the number of progenitors per mL of blood was measured at 1 hour post administration, and the results are shown in Table 2.

TABLE 2

| | Absolute Number Progenitors Per ML Blood Methylcellulose Culture | | |
|---|---|---|---|
| | CFU-GM | BFU-E | CFU-GEMM |
| Saline | 188.1 | 16 | 19 |
| AMD3100: 10 mg/kg | 825.6 | 120.5 | 79.8 |
| AMD3100: 5 mg/kg | 608.4 | 92.8 | 69.5 |
| AMD3100: 2.5 mg/kg | 687.6 | 98.9 | 70.6 |
| AMD3100: 1 mg/kg | 424 | 62 | 27.1 |

Fold Change Compared to Time 0

| | Progenitors Methylcellulose Culture | | |
|---|---|---|---|
| Time | GM | BFU-E | CFU-GEMM |
| 15" | 2.73 | 2.72 | 3.51 |
| 30" | 6.23 | 4.24 | 4.41 |
| 2' | 2.86 | 2.07 | 1.85 |

Maximum mobilization of mouse progenitors is achieved at a dose of 2.5 to 10 mg/kg AMD3100, approximately 0.5 to 1 hour after injection, as shown in Table 3. The compounds of the invention behave in a manner similar to AMD3100.

EXAMPLE 146

Mobilization of Mouse Progenitor Cells in Combination with MIP-1α and G-CSF

The progenitor cell mobilization capacity of AMD3100 in combination with mouse (mu) macrophage inflammatory protein (MIP-1α) was tested with or without prior administration of rhu G-CSF. MIP-1α has been previously shown to mobilize progenitor cells in mice and humans (Broxmeyer, H. E., et al., *Blood Cells, Molecules, and Diseases* (1998) 24(2): 14-30).

Groups of mice were randomized to receive control diluent (saline) or G-CSF at a dose of 2.5 µg per mouse, twice a day, for two days via s.c. injection. Eleven hours after the final injection of saline or G-CSF, the mice were divided into groups to receive MIP-1α administered I.V. at a total dose of 5 µg, AMD3100 administered s.c. at a dose of 5 mg/Kg, or a combination of both MIP-1α and AMD3100 at the same doses. One hour later, the mice were sacrificed and the number of progenitor cells per mL of blood were measured. These data are summarized in FIG. 1.

AMD3100 acts in an additive to greater than additive manner for mobilization of progenitor cells when used in combination with mouse (mu) macrophage inflammatory protein (MIP)-1α, each given 11 hours after the addition of rhu G-CSF or control diluent (saline) and 1 hour prior to assessing the blood. The compounds of the invention behave in a manner similar to AMD3100.

EXAMPLE 147

Clinical Elevation of Progenitor Cell Levels

Five healthy human volunteers having initial white blood cell counts of 4,500-7,500 cells/mm$^3$ were used in the study. Each patient was given a single subcutaneous (s.c.) injection of 80 µg/kg AMD3100 (i.e., 1,1'-[1,4-phenylene-bis(methylene)]-bis-1,4,8,11-tetraazacyclotetradecane) in 0.9% saline, from a stock solution of 10 mg/mL AMD3100 in saline, under sterile conditions. Blood samples were obtained via catheter prior to the dose, and at various times up to 24 hours after dosing.

The blood samples were evaluated for total white blood cells, CD34 positive progenitor cells (via FACS analysis) as a percentage of total white blood cells, as well as the absolute numbers per mL and cycling status of granulocyte macrophage (CFU-GM), erythroid (BFU-E), and multipotential (CFU-GEMM) progenitor cells.

As shown in Tables 3 and 4, administration of AMD3100 caused an elevation of the white blood cell count and of CD34 positive progenitor cells in human volunteers which maximized at 6 hours post-administration.

TABLE 3

AMD3100 induced mobilization of white blood cells in individual volunteers (×10$^3$ WBC's).

| | | | TREATMENT | | | | | | |
|---|---|---|---|---|---|---|---|---|---|
| ID | Screen | Base-line | 30 Min | 1 Hr | 2 Hr | 4 Hr | 6 Hr | 9 Hr | Day 2 |
| P1 | 7.4 | 6.41 | 8.02 | 14.8 | 21.4 | 23.2 | 26.2 | 22.3 | 7.07 |
| P2 | 6.04 | 5.45 | 6.53 | 8.93 | 13.5 | 18.00 | 19.2 | 19.6 | 8.03 |
| P3 | 4.38 | 5.8 | 7.14 | 9.28 | ND | 18.10 | 17.9 | 18.4 | 4.98 |
| P4 | 5.08 | 5.31 | 4.37 | 7.38 | 12.4 | 14.6 | 15.8 | 13.9 | 4.98 |
| P5 | 4.53 | 5.02 | 6.08 | 8.43 | ND | 16.90 | 19.3 | 19.00 | 4.57 |

TABLE 4

AMD3100 induced mobilization of CD34 positive cells, expressed as the percentage of the total WBC's in individual volunteers.

| | | TREATMENT | | | | |
|---|---|---|---|---|---|---|
| ID | Baseline | 1 Hr | 3 Hr | 6 Hr | 9 Hr | Day 2 |
| P1 | .07 | .04 | .07 | .11 | .11 | .08 |
| P2 | .08 | .06 | .08 | .13 | .11 | .12 |
| P3 | .07 | .16 | .06 | ND | .11 | .07 |
| P4 | .05 | .07 | .09 | .09 | .1 | .1 |
| P5 | .12 | .12 | .13 | .2 | .2 | .16 |

The blood was also analyzed for AMD3100 mobilized these progenitors.

Absolute numbers of unseparated and low density (Ficohypaque separated) nucleated cells per mL of blood, as well as the absolute numbers per mL and cycling status of granulocyte macrophage (CFU-GM), erythroid (BFU-E), and multipotential (CFU-GEMM) progenitor cells were measured in normal donors injected s.c. with AMD3100. The above parameters were assessed prior to injection and at 1, 3, 6, 9 and 24 hours after injection of AMD3100. All progenitor cell results are based on the scoring of 3 culture plates per assay per point.

For the progenitor cell numbers and cycling status, the numbers of CFU-GM, BFU-E and CFU-GEMM in methylcellulose cultures by stimulation of the cells with 1 Unit (U)/ml recombinant human (rhu) erythropoietin, 100 U/ml rhu granulocyte-macrophage colony stimulating factor (GM-CSF), 100 U/ml rhu interleukin-3 (IL-3) and 50 ng/ml rhu steel factor (SLF=stem cell factor (SCF)). The CFU-GM were also evaluated in agar cultures stimulated with 100 U/ml rhu GM-CSF and 50 ng/ml rhu SLF. For both types of assays, colonies were scored after 14 day incubation in a humidified atmosphere with 5% $CO_2$ and lowered (5%) $O_2$ tension. Cell cycling status of progenitors was measured using a high specific activity tritiated thymidine kill technique as previously described (Broxmeyer, H. E., et al., *Exp. Hematol.* (1989) 17:455-459).

The results are given first, as the mean fold change in absolute numbers of nucleated cells and progenitors at 1, 3, 6, 9 and 24 hours compared to the preinjection (=Time (T) 0) counts for all five donors, as seen in Tables 5-7.

In the tables below,
STD—Standard deviation
STE—Standard error
PBL-US—peripheral blood-unseparated
PBL-LD—peripheral blood-low density (Ficoll Separated)
P—Significance using a 2 tailed t test

TABLE 5

Fold Change Compared to TIME = 0 (Average of 5 donors)

NUCLEATED CELLULARITY

| | PBL-US | | | | | PBL-LD | | | | |
|---|---|---|---|---|---|---|---|---|---|---|
| | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | |
| T = 1 | 1.69 | 0.00 | 0.00 | 68.6% | 0.017 | 1.86 | 0.00 | 0.00 | 86.2% | 0.000 |
| T = 3 | 2.80 | 0.51 | 0.23 | 180.2% | 0.000 | 2.86 | 0.28 | 0.12 | 185.6% | 0.000 |
| T = 6 | 3.26 | 0.61 | 0.27 | 225.8% | 0.000 | 3.66 | 0.43 | 0.19 | 266.3% | 0.001 |
| T = 9 | 3.09 | 0.69 | 0.31 | 209.4% | 0.000 | 3.64 | 1.18 | 0.53 | 264.3% | 0.001 |
| T = 24 | 1.07 | 0.65 | 0.29 | 7.0% | 0.553 | 1.05 | 1.19 | 0.53 | 4.6% | 0.815 |

TABLE 6

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | MEAN | STD | STE | % CHG | P | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | | 1.00 | 0.00 | 0.00 | 0.0% | |
| T = 1 | 4.77 | 0.00 | 0.00 | 376.7% | 0.001 | 1.99 | 0.00 | 0.00 | 98.9% | 0.002 | 2.32 | 0.00 | 0.00 | 131.8% | 0.000 |
| T = 3 | 13.66 | 1.56 | 0.70 | 1266.5% | 0.001 | 3.21 | 0.50 | 0.22 | 221.3% | 0.004 | 4.33 | 0.44 | 0.20 | 332.5% | 0.000 |
| T = 6 | 21.71 | 5.78 | 2.58 | 2070.6% | 0.000 | 6.01 | 1.25 | 0.56 | 500.5% | 0.006 | 10.07 | 0.59 | 0.27 | 907.2% | 0.002 |
| T = 9 | 10.47 | 5.09 | 2.28 | 947.3% | 0.000 | 4.34 | 2.99 | 1.34 | 334.4% | 0.000 | 5.25 | 4.54 | 2.03 | 425.4% | 0.014 |
| T = 24 | 1.56 | 3.01 | 1.34 | 55.5% | 0.005 | 1.26 | 1.02 | 0.45 | 26.3% | 0.194 | 1.53 | 3.04 | 1.36 | 53.2% | 0.199 |

TABLE 7

AGAR CULTURE
CFU-GM

| | MEAN | STD | STE | % CHG | P |
|---|---|---|---|---|---|
| T = 0 | 1.00 | 0.00 | 0.00 | 0.0% | |
| T = 1 | 2.81 | 0.00 | 0.00 | 180.8% | 0.001 |
| T = 3 | 8.54 | 0.75 | 0.34 | 754.1% | 0.000 |
| T = 6 | 17.93 | 1.62 | 0.72 | 1692.8% | 0.000 |
| T = 9 | 10.25 | 4.57 | 2.04 | 924.9% | 0.000 |
| T = 24 | 2.08 | 2.06 | 1.03 | 108.3% | 0.073 |

The results are then shown as a fold change from T=0 levels for each individual donor, as shown in Tables 8-10.

TABLE 8

FOLD CHANGE COMPARED TO TIME = 0 for each individual patient [P]

NUCLEATED CELLULARITY

| | PBL-US | | | | | PBL-LD | | | | |
|---|---|---|---|---|---|---|---|---|---|---|
| | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 9

PROGENITORS

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.48 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

TABLE 10

AGAR CULTURE
CFU-GM

| | P1 | P2 | P3 | P4 | P5 |
|---|---|---|---|---|---|
| T = 0 | 1.00 | 1.00 | 1.00 | 1.00 | 1.00 |
| T = 1 | 3.05 | 3.74 | 1.67 | 2.71 | 2.87 |
| T = 3 | 8.88 | 9.49 | 7.47 | 10.46 | 6.40 |
| T = 6 | 17.77 | 24.01 | 14.04 | 13.07 | 20.75 |
| T = 9 | 10.28 | 7.72 | 10.22 | 12.78 | |
| T = 24 | 3.69 | 1.13 | 1.30 | 2.20 | |

*Note: T=9 and T=24 rows appear in TABLE 10-continued; columns shown are P1, P2, P3, P4, P5 but only four values are listed.*

The actual nucleated cell and progenitor cell numbers per mL of blood and the cycling status (=% progenitors in DNA synthesis (S) phase of the cell cycle) of progenitors for each of the five donors (#'s P1, P2, P3, P4, and P5) is shown in Tables 11 and 12.

TABLE 11

| | CFU-GM P1 | | BFU-E P1 | | CFU-GEMM P1 | | CFU-GM P2 | | BFU-E P2 | | CFU-GEMM P2 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 247 | 6% | 261 | 0% | 127 | 6% | 273 | 0% | 410 | 2% | 120 | 0% |
| T = 1 | 1259 | 1% | 674 | 0% | 264 | 0% | 1455 | 0% | 608 | 3% | 272 | 6% |
| T = 3 | 1760 | 1% | 1340 | 13% | 540 | 7% | 4646 | 2% | 809 | 0% | 418 | 0% |
| T = 6 | 3624 | 0% | 2388 | 0% | 949 | 0% | 6540 | 0% | 1502 | 0% | 1126 | 0% |
| T = 9 | 1547 | 2% | 1418 | 11% | 335 | 0% | 3416 | 0% | 1886 | 0% | 854 | 4% |
| T = 24 | 271 | 0% | 278 | 0% | 142 | 0% | 521 | 3% | 768 | 2% | 316 | 0% |

| | CFU-GM P3 | | BFU-E P3 | | CFU-GEMM P3 | | CFU-GM P4 | | BFU-E P4 | | CFU-GEMM P4 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 281 | 0% | 351 | 0% | 140 | 0% | 138 | 0% | 460 | 0% | 101 | 0% |
| T = 1 | 1040 | 0% | 806 | 0% | 312 | 0% | 947 | 0% | 672 | 0% | 199 | 0% |
| T = 3 | 4233 | 1% | 915 | 0% | 610 | 0% | 2857 | 5% | 1195 | 9% | 519 | 0% |
| T = 6 | 5895 | 0% | 1593 | 0% | 916 | 0% | 3936 | 0% | 1533 | 0% | 920 | 8% |
| T = 9 | 2647 | 0% | 1302 | 0% | 347 | 0% | 1942 | 0% | 1348 | 0% | 457 | 0% |
| T = 24 | 402 | 0% | 402 | 0% | 97 | 0% | 208 | 5% | 362 | 3% | 99 | 0% |

TABLE 11-continued

|  | CFU-GM | | BFU-E P5 | | CFU-GEMM | |
| --- | --- | --- | --- | --- | --- | --- |
|  | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 169 | 0% | 343 | 1% | 55 | 0% |
| T = 1 | 481 | 0% | 730 | 0% | 169 | 0% |
| T = 3 | 1423 | 5% | 1288 | 3% | 244 | 0% |
| T = 6 | 3454 | 0% | 3208 | 1% | 987 | 0% |
| T = 9 | 1710 | 0% | 1731 | 0% | 526 | 0% |
| T = 24 | 310 | 0% | 495 | 0% | 124 | 0% |

TABLE 12

|  | AGAR Culture CFU-GM P1 | | AGAR Culture CFU-GM P2 | | AGAR Culture CFU-GM P3 | | AGAR Culture CFU-GM P4 | | AGAR Culture CFU-GM P5 | |
| --- | --- | --- | --- | --- | --- | --- | --- | --- | --- | --- |
|  | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 233 | 6% | 100 | 0% | 140 | 0% | 124 | 0% | 104 | 0% |
| T = 1 | 710 | 0% | 376 | 0% | 234 | 0% | 336 | 0% | 298 | 3% |
| T = 3 | 2070 | 0% | 953 | 1% | 1049 | 0% | 1299 | 0% | 664 | 0% |
| T = 6 | 4142 | 0% | 2409 | 3% | 1972 | 3% | 1623 | 0% | 2153 | 1% |
| T = 9 |  |  | 1032 | 0% | 1085 | 0% | 1268 | 0% | 1326 | 0% |
| T = 24 |  |  | 371 | 0% | 159 | 0% | 162 | 0% | 229 | 0% |

The results for all five donors were very consistent with maximal fold increases in circulating levels of progenitor cells seen 6 hours after injection of AMD3100 into the human donor subjects. Progenitors were in a slow or non-cycling state prior to and 1, 3, 6, 9 and 24 hours after injection of AMD3100. The compounds of the invention behave in a manner similar to AMD3100.

EXAMPLE 148

Mobilized Bone Marrow Stem Cells for Myocardial Repair

Adult rats are anesthetized and a thoracotomy is performed. The descending branch of the left coronary artery is ligated and not reperfused. Within 4 to 6 hours after ligation the animals are injected with limit dilution AMD3100 or AMD3100 plus rhG-CSF. Control rats are not treated with the reagents. The animals are monitored at one-week intervals by echocardiography and MRI. The experiment is terminated at 2, 6 to 12 weeks post-surgery. On the day of sacrifice, the hemodynamic functions are analyzed for left ventricle-end diastolic pressure, left ventricle-developed pressure and the rate of rise and fall of left ventricle pressure. The heart is then arrested in diastole and perfused via the abdominal aorta to flush residual blood from the vascular network of the myocardium. This is followed by perfusion of the heart with 10% formalin. Several slices are made through the fixed heart and these are embedded in paraffin and sections. The sections are stained and analyzed by light microscopy to determine the size of the infarct in the treated and control animals. Tissue sections from hearts taken at 2 weeks after surgery are stained with antibodies specific for immature, developing myocyte and blood vessel proteins and analyzed by confocal microscopy. The immunohistochemical analysis involves the identification of transcription factors and surface markers expressed in early stages of myocyte development. The results of this experiment will show that when the reagent AMD3100 is administered within hours after induction of cardiac ischemia, together with or without rhG-CSF, this reagent mobilizes bone marrow stem cells rapidly, and will result in a block to cardiac remodeling and scar formation and will lead to regeneration of the dead myocardium. The compounds of the invention behave in a manner similar to AMD3100.

EXAMPLE 149

Clinical Elevation of WBC Levels—Healthy Volunteers

Eleven human patients having initial white blood cell counts of 4,000-6,500 cells/mm$^3$ were used in the study. An intravenous dosing solution of AMD3100 (i.e., 1,1'-[1,4-phenylene-bis(methylene)]-bis-1,4,8,11-tetraazacyclotetradecane) were prepared from a stock solution which is a 1 mg/ml 1:10 dilution of a concentrate in 0.9% saline (normal saline) under sterile conditions. Aliquots from this stock solution were added to 50-ml bags of 0.9% saline for intravenous injection in amounts to achieve the desired dosage levels (10 µg/kg-80 µg/kg).

The subjects described in this Example already contained an indwelling peripheral intravenous catheter. The prescribed amount of AMD3100 was administered over 15 minutes by intravenous fusion in a single dose. Blood samples were obtained prior to the dose, and at various times up to 24 hours after dose administration.

Eleven human subjects received intravenous administration of AMD3100 at doses 10, 20, 40, and 80 μg/kg. Five subjects also received a single subcutaneous injection of AMD3100 at doses of 40 and 80 μg/kg. The effect of AMD3100 given intravenously in these 11 human subject is shown in FIG. 1. Three patients were administered dosages of 10 μg/kg (open circles); 3 patients were administered dosages of 20 μg/kg (solid circles); 3 patients were administered 40 μg/kg (open triangles); and 2 patients were administered 80 μg/kg (closed triangles).

Figure 2:
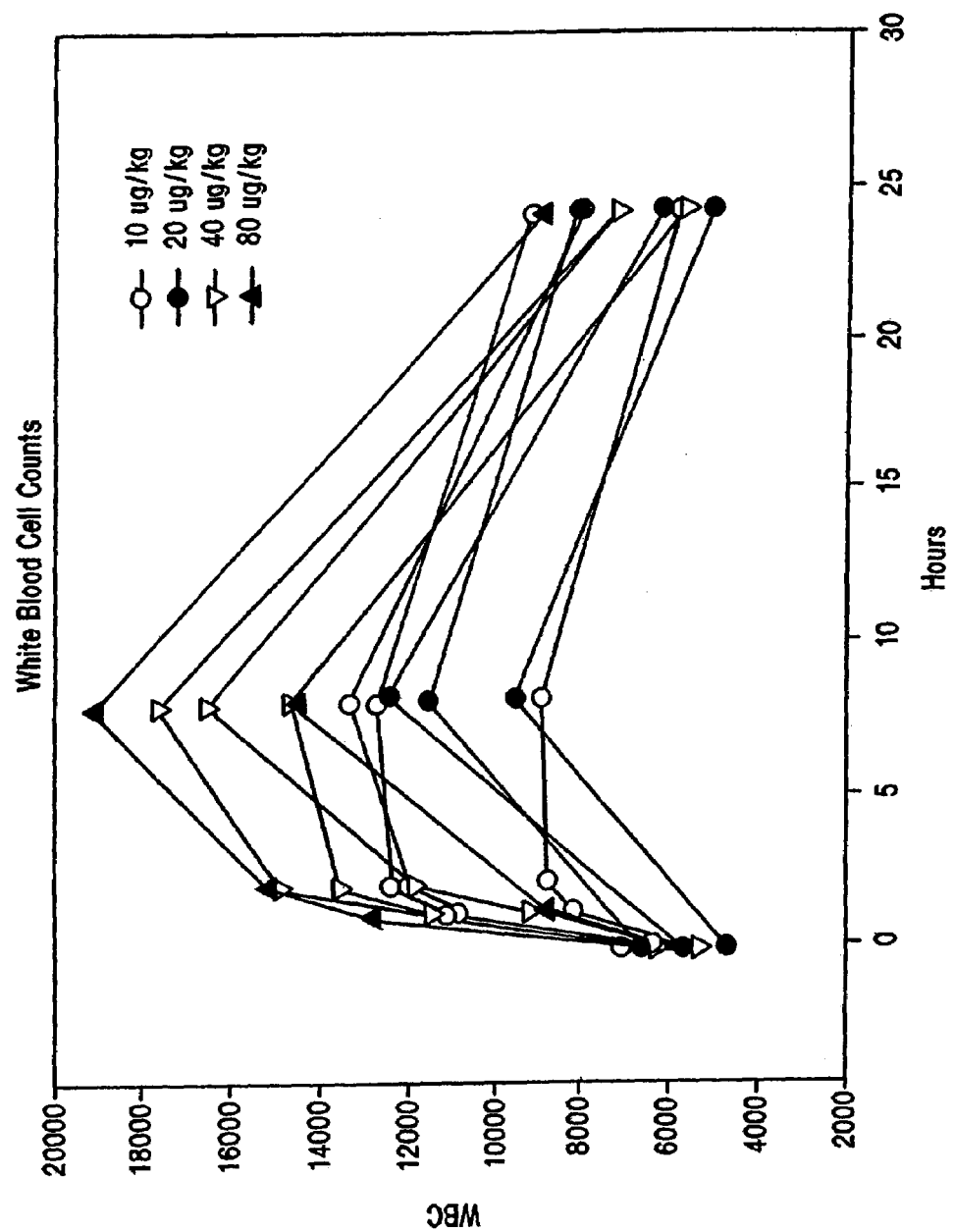
FIG. 2 shows the response in elevation of WBC counts observed in HIV-infected patients who received AMD3100 by continuous infusion for up to 10 consecutive days.

As shown in FIG. 2, all of the patients at all levels of administration showed a marked increase in white blood cell count over the succeeding 5-10 hours after administration which WBC count tapered off after about 24 hours, although not, in any case, returning to the original level. Generally, the levels of WBC correlate with the concentration levels of the compound in the bloodstream. For Example, one patient who received 80 μg/kg experienced an enhancement of white blood cell count from 6,000 cells/mm$^3$ to a peak value of 19,000 cells/mm$^3$. Even the patient showing the least response, who was given 20 μg/kg, experienced an increase from about 6,300 cells/mm$^3$ to about 9,000 cells/mm$^3$.

Thus, it appears that AMD3100 is consistently able to enhance WBC count in human patients. The compounds of the invention behave in a manner similar to AMD3100.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR4, and thus to inhibit entry of the virus into the cell. These particular receptors appear homologous throughout a wide range of species, including mouse, rat, cat and man.

EXAMPLE 150

Clinical Elevation of WBC Levels—HIV-Infected Patients

Elevations in WBC counts have also been observed in HIV-infected patients who received AMD3100 by continuous infusion for up to 10 consecutive days (FIG. 3). Eight patients received AMD3100 at infusion dose rates of 2.5 μg/kg/hr (patients 1-4) and 5.0 μg/kg/hr (patients 5-8). Elevations relative to the baseline were noted in samples taken on days 2, 6, and 11 (immediately prior to end of infusion) of the infusion period. Elevations in WBC count ratios (day 11 samples) ranged from 1.4 to 2.8 times the baseline. WBC counts returned to baseline 7 days after discontinuation of the infusion. Thus, it appears that AMD3100 is consistently able to enhance WBC count following single dose or with continuous infusion in human patients. The compounds of the invention behave in a manner similar to AMD3100.

While not intending to be bound by any theory, the ability to enhance WBC count across various species and the use of various compounds of formula (1) is believed due to the similarity of action of this compound in its antiviral applications and a possible mechanism for enhancing WBC count. The compounds of the invention are believed to exert their antiviral effects by inhibiting the binding of the second receptor for the HIV virus, CXCR4, and thus to inhibit entry of the virus into the cell. These particular receptors appear homologous throughout a wide range of species, including mouse, rat, cat and man.

It is understood that the foregoing detailed description and accompanying Examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:
1. A compound of the formula

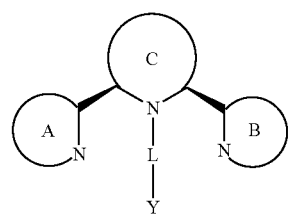

(1)

or the pharmaceutically acceptable salts thereof;
wherein each of rings A and B is independently a pyridinyl optionally substituted with one or more substituents selected from the group consisting of alkyl ($C_{1-10}$), alkenyl ($C_{2-10}$), and alkynyl ($C_{2-10}$);
ring C is an unsubstituted piperidine or is piperidine substituted only at position 4 with OH, OMe, CN, OBz, =NOEt, or =NOBz;
wherein Y is phenyl, benzimidazole or imidazole; or is selected from the group consisting of,
—$(CH_2)_m NH_2$,
—$(CH_2)_m NHCH_3$,
—$(CH_2)_m NH(CH_2)_m NH_2$,
—$(CH_2)_m NH(CH_2)_m NH(CH_2)mNH_2$,
—$(CH_2)_m OH$,
—$(CH_2)_m CO(CH_2)_m OH$,
—$(CH_2)_m CO(CH_2)_m NH_2$,
—$(CH_2)_m CO(CH_2)_m NH(CH_2)_m NH_2$,
—$(CH_2)_m NHCO(CH_2)_m NH_2$,
—$(CH_2)_m NH (CH_2)_m CO_2H$,
—$(CH_2)_m NH (CH_2)_m SO_2H$,
—$(CH_2)_m NHCO(CH_2)_m NH(CH_2)_m NH_2$,
—$(CH_2)_m NHCO(CH_2)_m NH(CH_2)_m NH(CH_2)_m NH(CH_2)_m NH_2$,
—$(CH_2)_m NH(CH_2)_m OH$,
—$(CH_2)_m CH=NOH$,
—$(CH_2)_m CONH(CH_2)_m OH$,
—$(CH_2)_m N[(CH_2)_m CO_2H]_2$,
—$(CH_2)_m NHCOZ$ and
—$(CH_2)_m NH—(CH_2)_m Z$,
wherein each m is independently 0-4; and Z is an optionally substituted aromatic or heteroaromatic moiety containing 5-12 ring members;
L is $(CR^3_2)_l$ where each $R^3$ is H or alkyl wherein a single bond in alkyl may be replaced with a double or triple bond and wherein l is 1-6.
2. The compound of claim 1, wherein Y is $(CH_2)_m NH_2$ wherein m is 1-4.
3. The compound of claim 1, wherein each of rings A and B contain a single substituent at the position adjacent to the bond linking the rings to ring C.

4. The compound of claim 3, wherein said substituents are identical on rings A and B.

5. A pharmaceutical composition which comprises as active ingredient the compound of claim 1 or a pharmaceutically acceptable salt thereof along with at least one excipient.

6. The compound of claim 1 selected from the group consisting of 4-(3,3"-dimethyl-3',4',5',6'-tetrahydro-2'H-[cis-2,2';6',2"] terpyridin-1'-yl) -butylamine;

4-(3,3"-diisopropyl-3',4',5',6'-tetrahydro-2'H-[cis-2,2';6', 2"]terpyridin-1'-yl)-butylamine;

(2'R,6'S)-1'-[3-(1H-Imidazol-4-yl)-propyl ]-3,3"-dimethyl-1',2',3',4',5',6'-hexahydro-cis- [2,2';6',2"]terpyridine;

[4-(3,3"-dimethyl-3',4',5',6'-tetrahydro-2 'H-cis-[2,2';6', 2"]terpyridin-1'-yl) -butyl]-urea;

N-[4-(3,3"-dimethyl-3',4',5',6'-tetrahydro-2 'H-cis-[2,2';6', 2"]terpyridin-1'-yl) -butyl]-6-hydroxy-nicotinamide;

meso-2'β,6'β-[3-(3,3"-dimethyl-3',4',5',6'-tetrahydro-2'H-cis-[2,2';6',2"]terpyridin-1'-yl)-propylamine];

3,5-dichloro-N-[4-(3,3"-dimethyl-3',4',5',6'-tetrahydro-2'H-cis-[2,2';6',2"]terpyridin-1'-yl)-butyl]-isonicotinamide;

4-meso-[2,7-Bis-(3-methyl-pyridin-2-yl)-2,3,6,7-tetrahydroazepin-1-yl]butylamine;

meso-cis-2',5'-[4-(2,5-di-pyridin-2-yl-pyrrolidin-1-yl)-butylamine];

(2'R,6'S)-1'-(1H-benzoimidazol-4-ylmethyl)-3,3"-dimethyl-1',2',3',4',5',6'-hexahydro-[2,2';6',2"]terpyridine;

meso-2',6'-[3-(3,3"-dimethyl-3',4',5',6'-tetrahydro-2'H-cis-[2,2';6',2"]terpyridin-1'-yl)-propyl]-urea;

meso-2',6'-N-[3-(3,3"-dimethyl-3',4',5',6'-tetrahydro-2'H-cis-[2,2';6',2"]terpyridin-1'-yl)-propyl]-6-hydroxy-nicotinamide;

meso-2',6'-[4-(3,5,3",5"-tetramethyl-3',4',5',6'-tetrahydro-2'H-cis-[2,2';6',2"]terpyridin-1'-yl)-butylamine];

meso-2'β,4'α,6'β-[1'-(4-amino-butyl)-3,3'-dimethyl-1',2', 3',4',5',6'-hexahydro-[2,2';6',2']terpyridin-4'-ol];

meso-2',6'-[4-(3,3'-dichloro-3',4',5',6'-tetrahydro-2'H-cis-[2,2';6',2"]terpyridin -1'-yl)-butylamine];

a 1:1 mixture of meso-2'13,4'α,6'β-[1'-(4-amino-butyl)-3, 4',3"-trimethyl-1',2',3',4',5',6'-hexahydro-[2,2';6',2"] terpyridin-4'-ol] and meso-2'β,4'β,6'β-[1'-(4-amino-butyl)-3,4',3"-trimethyl-1',2',3',4',5',6'-hexahydro-[2,2';6', 2"]terpyridin-4'-ol];

meso-2'β,4'α,6'β-[1'-(4-amino-butyl)-3,3"-dimethyl-1',2', 3',4',5',6'-hexahydro-[2,2';6',2"]terpyridin-4'-ol];

meso-2'β,4'α,6β-[4-(4'-fluoro-3,3"-dimethyl-3',4',5',6'-tetrahydro-2'H-[2,2';6',2"]terpyridin-1'-yl)-butylamine];

meso-2'β,4'β,6'β-[4'-benzyloxy-1'-[2-(3H-imidazol-4-yl)-ethyl]-3,3"-dimethyl -1',2',3',4',5',6'-hexahydro-[2,2';6', 2"]terpyridine;

5-((2'R,6'S)-3,3"-dimethyl-3',4',5',6'-tetrahydro-2'H-[2,2'; 6',2"]terpyridin-1'-yl)-pentanoic acid hydroxyamide;

6-((2'R,6'S)-3,3"-dimethyl-3',4',5',6'-tetrahydro-2'H-[2,2'; 6',2"]terpyridin-1'-yl)-hexanoic acid hydroxyamide;

Methyl-[4-(3,5,3",5"-tetramethyl-3',4',5',6'-tetrahydro-2'H-[2,2';6',2"]terpyridin-1'-yl)-butyl]-amine;

4-(3,3"-dimethyl-3',4',5',6'-tetrahydro-2'H-cis-[2,2';6',2"] terpyridin-1'-yl)-butyramide;

[4-(3,3"-dimethyl-3',4',5',6'-tetrahydro-2'H-cis-[2,2';6',2"] terpyridin-1'-yl)-butyl]-pyridin-2-ylmethyl-amine;

4-(3,3"-dimethyl-3',4',5',6'-tetrahydro-2'H-cis-[2,2';6',2"] terpyridin-1'-yl) -N-hydroxy-butyramide;

4-(3,3"-dimethyl-3',4',5',6'-tetrahydro-2'H-cis-[2,2';6',2"] terpyridin-1'-yl)-butyric acid hydrazide;

4-(3,3"-dimethyl-3',4',5',6'-tetrahydro-2'H-cis-[2,2';6',2"] terpyridin-1'-yl)-butan-1 -ol;

4-(3,3"-dimethyl-3',4',5',6'-tetrahydro-2'H-cis-[2,2';6',2"] terpyridin-1'-yl) -N-(2-hydroxy-ethyl)-butyramide;

(2'S,6'R)- 1'-[3-(1H-benzoimidazol-2-yl)-propyl]-3,3"-dimethyl-1',2',3',4',5',6'-hexahydro-cis-]2,2';6',2"] terpyridine;

[4-(3,3"-dimethyl-3',4',5',6'-tetrahydro-2'H-cis-[2,2';6',2"] terpyridin-1'-yl)-butyl]-(1H-imidazol-2-yl)-amine;

1'-(3-imidazol-1-yl-propyl)-3,3"-dimethyl-1,',2',3',4',5', 6'-hexahydro-[2,2';6',2"]terpyridine;

1'-(4-imidazol-1-yl-butyl)-3,3"-dimethyl-1',2',3',4',5',6'-hexahydro-[2,2';6',2"]terpyridine;

1'-[2-(3H-imidazol-4-yl)-ethyl]-3,3"-dimethyl-1',2',3',4', 5',6'-hexahydro-[2,2';6',2"]terpyridine;

[4-meso-(3,5,3",5"-tetramethyl-3',4',5',6'-tetrahydro-2'H-[2,2';6',2"]terpyridin-1'-yl)-butyl]-urea;

4-meso-[3,5-bis-(3-methyl-pyridin-2-yl)-morpholin-4-yl]-butylamine;

meso-2-[4-(3,3"-dimethyl-3',4',5',6'-tetrahydro-2'H-[2,2'; 6'2"]terpyridin-2'-yl) -butylamino]-ethanol;

1'-(2-imidazol-1-yl-ethyl)-3,3"-dimethyl-1',2',3',4',5',6'-hexahydro-[2,2';6',2"]terpyridine;

2-(3,3"-dimethyl-3',4',5',6'-tetrahydro-2'H-[2,2';6',2"] terpyridin-1'-yl)-ethylamine;

1'-(1H-imidazol-4-ylmethyl)-3,3"-dimethyl-1',2',3',4',5', 6'-hexahydro-[2,2';6',2"]terpyridine;

1'(1H-imidazol-2-ylmethyl)-3,3"-dimethyl-1',2',3',4',5',6'-hexahydro-[2,2';6',2"]terpyridine;

meso-2'β,4'α,6'β-[1'-(4-amino-butyl)-3,3"-dimethyl-1',2', 3',4',5',6'-hexahydro-[2,2';6',2"]terpyridine-4'-carbonitrile];

meso-2'β,4'α,6β-[4-(4'-methoxy-3,3"-dimethyl-3',4',5',6'-tetrahydro-2'H-[2,2';6',2"]terpyridin-1'-yl)-butylamine;

meso-2'β,6'β-[1'-(4-amino-butyl)-3,3"-dimethyl-2',3',5', 6'-tetrahydro-1'H-[2,2';6',2"]terpyridin-4'-one O-ethyl-oxime];

meso-2'β,6'β-[1'-(4-amino-butyl)-3,3"-dimethyl-2',3',5', 6'-tetrahydro-1'H-[2,2';6',2"]terpyridin-4'-one O-benzyl-oxime];

meso-2'β,4'β,6'β-{1'-[2-(3H-imidazol-4-yl)-ethyl]-4'-methoxy-3,3"-dimethyl -1',2',3',4',5',6'-hexahydro-[2, 2';6',2"]terpyridine; and meso-2'β,6'β-{1'-[2(3H-imidazol-4-yl)-ethyl]-3,3"-dimethyl-2',3',5',6'-tetrahydro -1'H-[2,2';6',2"]terpyridin-4'-one O-benzyl-oxime}; and the pharmaceutically acceptable salts thereof.

7. A pharmaceutical composition comprising as active ingredient the compound of claim 6 or a pharmaceutically acceptable salt thereof along with at least one excipient.

8. The compound of claim 6 which is 4-(3,3",-dimethyl-3', 4',5',6'-tetrahydro-2'H-cis-[2,2';6',2"]terpyridin-1'-yl)-butylamine or a pharmaceutically acceptable salt thereof.

9. A pharmaceutical composition comprising as active ingredient the compound of claim 8 or a pharmaceutically acceptable salt thereof along with at least one excipient.

10. The compound of claim 6 which is N-[4-meso-(3,5,3", 5"-tetramethyl-3',4',5',6'-tetrahydro-2'H-[2,2';6',2"]terpyridine-1'-yl)-butyl]-N'-hydroxyurea or a pharmaceutically acceptable salt thereof.

11. A pharmaceutical composition comprising as active ingredient the compound of claim 10 or a pharmaceutically acceptable salt thereof along with at least one excipient.

* * * * *